(12) United States Patent
Krichevsky

(10) Patent No.: US 9,506,075 B2
(45) Date of Patent: Nov. 29, 2016

(54) BIOLUMINESCENT PLANTS COMPRISING BACTERIAL LUX OPERON AND METHODS OF MAKING SAME

(75) Inventor: Alexander Krichevsky, Centereach, NY (US)

(73) Assignee: BioGlow, LLC, St. Louis, MO (US)

( * ) Notice: Subject to any disclaimer, the term of this patent is extended or adjusted under 35 U.S.C. 154(b) by 1651 days.

(21) Appl. No.: 12/670,340

(22) PCT Filed: Jul. 31, 2008

(86) PCT No.: PCT/US2008/009310
§ 371 (c)(1),
(2), (4) Date: Jan. 22, 2010

(87) PCT Pub. No.: WO2009/017821
PCT Pub. Date: Feb. 5, 2009

(65) Prior Publication Data
US 2010/0192262 A1 Jul. 29, 2010

Related U.S. Application Data

(60) Provisional application No. 60/953,337, filed on Aug. 1, 2007.

(51) Int. Cl.
*C12N 15/82* (2006.01)

(52) U.S. Cl.
CPC ......... *C12N 15/8214* (2013.01); *C12N 15/825* (2013.01); *C12N 15/8212* (2013.01); *C12N 15/8213* (2013.01); *C12N 15/8242* (2013.01)

(58) Field of Classification Search
None
See application file for complete search history.

(56) References Cited

U.S. PATENT DOCUMENTS

| | | | | |
|---|---|---|---|---|
| 5,576,198 | A | * | 11/1996 | McBride et al. ............ 435/91.3 |
| 5,877,402 | A | * | 3/1999 | Maliga et al. ................ 800/298 |
| 6,620,601 | B1 | * | 9/2003 | Yamaguchi et al. .......... 435/135 |
| 6,686,516 | B2 | * | 2/2004 | Lebel et al. ................... 800/298 |
| 7,049,483 | B1 | | 5/2006 | Hudkins |
| 7,129,392 | B2 | * | 10/2006 | Hahn et al. ................... 800/282 |
| 7,294,506 | B2 | * | 11/2007 | Daniell et al. ............ 435/320.1 |
| 7,663,022 | B1 | * | 2/2010 | Hudkins ........................ 800/282 |
| 7,994,396 | B2 | * | 8/2011 | Hudkins ........................ 800/282 |
| 2004/0002148 | A1 | | 1/2004 | Gupta et al. |
| 2004/0126883 | A1 | | 7/2004 | Liu |
| 2005/0081268 | A1 | | 4/2005 | Kay et al. |
| 2006/0117400 | A1 | | 6/2006 | Herz et al. |
| 2006/0253916 | A1 | | 11/2006 | Biesgen |

FOREIGN PATENT DOCUMENTS

WO 2007136432 A1 11/2007

OTHER PUBLICATIONS

Swartzman et al (1990, J. Biol. Chem. 265:3513-3517).*
Zhou et al. (2007), "Identification of a plastid intercistronic expression element (IEE) facilitating the expression of stable translatable monocistronic mRNAs from operons", The Plant Journal 52:961-72.*
Hirose et al. (1999) "The chloroplast infA gene with a functional UUG initiation codon", FEBS Lett. 445:169-72.*
Drechsel et al. (2011) "Selection of Shine-Dalgarno sequences in plastids", Nucleic Acids Res. 39 (4):1427-38.*
Meyers et al. (2010) "Nuclear and plastid genetic engineering of plants: comparison of opportunities and challenges." Biotechnol Adv. 28(6):747-56.*
Waheed et al. (2011) "Plastid expression of a double-pentameric vaccine candidate containing human papillomavirus-16 L1 antigen fused with LTB as adjuvant: transplastomic plants show pleiotropic phenotypes", Plant Biotechnol. J. 9(6):651-60, Abstract Only.*
Meighen (1993) "Bacterial bioluminescence: organization, regulation, and application of the lux genes." FASEB J., 7:1016-22.*
Krichevsky et al. (2010) "Autoluminescent Plants", PLoS ONE 5(11):e15461. doi: 10.1371/j ournal.pone. 0015461.*
Francis et al. (2000) "Monitoring bioluminescent *Staphylococcus aureus* infections in living mice using a novel luxABCDE construct", Infect. Immun. 68(6):3594-600.*
Bock, R. (2007) In: Topics in Current Genetics, Cell and Molecular Biology of Plastids, Springer-Veflag Berlin Heidelberg 19.*
Sakamoto, W. (2006) "Protein degradation machineries in plastids", Annu. Rev. Plant Biol. 57: 599-621.*
Zerges 2000 Biochimie 82:583-601.*
Schuler et al, 1982 Nuc. Acids Res. 24:8245-8261.*
Arai et al 2004 Plant cell Physiol. 45:1176-1184.*
Maliga 2003 Trends Biotechnol. 21:20-28.*
Beachy 1984, Proceedings of the Stadlers genetics Symposium, Ed. P Gustafson. Plenum Press, Inc. pp. 605-626.*
Daniell 2006 Biotechnol. J. 1:1071-1079.*
Koop et al (2007) The genetic transformation of plastids In: Topics in Current Genetics, Cell and Molecular Biology of Plastids, Ed: Bock, R. Springer-Veflag Berlin Heidelberg 19, p. 457-510.*
Swartzman et al., "Delineation of the Transcriptional Boundaries of the lux Operon of Vibrio harveyi Demonstrates the Presence of Two New lux Genes," J. Biol. Chem. 265 (6):3513-3517 (Feb. 1990).
Meighen, Edward A., "Bacterial bioluminescene: organization, regulation, and application of the lux genes," The FASEB Journal 7:1016-1022 (Aug. 1993).
Lee et al, "Riboflavin Synthesis Genes are Linked with the lux Operon of Photobacterium phosphoreum," J. Bacteriology 176 (7):2100-2104, (Apr. 1994).
Diaz et al., "Biodegradation of Aromatic Compounds by *Escherichia coli*," Microbiology and Molecular Biology Reviews 65 (4): 523-569 (Dec. 2001).

* cited by examiner

Primary Examiner — Anne Kubelik
(74) Attorney, Agent, or Firm — Dennis A. Bennett

(57) ABSTRACT

In one aspect, the invention relates to a transgenic bioluminescent plant including an expressible heterologous nucleotide sequence comprising a bacterial LUX operon, which includes LUX A, LUX B, LUX C, LUX D, LUX E, and LUX G genes, wherein the heterologous nucleotide sequence is expressed to render the plant bioluminescent.

13 Claims, 22 Drawing Sheets

A pCas-3 digested with AgeI/NcoI

Prrn promoter

FIG. 14

```
Vh    CAAAAGAGAAGCTCTTGATATGGAAAAACACTTACCTTTAATAATAAATGGGCAAAT---  57
X1    CATTAAATGGATGGCTAATATGACTAAAAAAATTTCATTCATTATTAACGGCCAGGTTGA  60
P1    --CCAAAGGAG---ATTACATGATTAAGAAGATCCCAATGATTATTGGGGGTGTAGTTCA  55
           *  *     *  ***  **  *    *  *  **  **    **       *

Vh    AGTTTCTACTAAAGAAAATCGATTTGAG------ATCAGTTTTGAAGAAAAAAAAGTTAA  111
X1    AATTTTTCCCGAAAGTGATGATTTAGTGCAATCCATTAATTTTGGTGATAATAGTGTTTA  120
P1    AAACACGTCTGGATATGGCATGCGTGAAC------TAACGCTCAACAATAATAAAGTGAA  109
       *     *   *             *       *  *    *  **  *  **     *

Vh    GATTGATTCCTTTAATCATTTTCATTTAATCCAGATGGTGACTCATGATTATTTAAATGA  171
X1    CCTGCCAATATTGAATAATTCTCATGTAAAAAACATTATTGATTATAATGAAAATAATAA  180
P1    TATCCCTATCATCACCCAAAGTGATGTTGAAGCTATTCAATCACTAAATATAGAAAACAA  169
          *       *     *     *  *       **       **       **    *

Vh    TCTAAATATTAATAACATCATCAATTTTCTTTATACAACGGGGCAGCGTTGGAAGAGCGA  231
X1    ATTACGGTTGCATAATATTGTCAATTTTCTCTATACGGTAGGGCAAAGATGGAAAAATGA  240
P1    ATTGACTATAAATCAGATAGTTAATTTCTTATATACAGTGGGACAAAAATGGAAGAGCGA  229
        *    *   **  *  **   *  ***** *  *****     **  **  ***** *  **

Vh    AGAATATTCAAGAAGAAGGGCATATATTCGGTCTCTTATTACTTATTTGGGGTATTCACC  291
X1    AGAATATTCAAGACGCAGGACATACATTCGTGATTTAAAAAAATATATGGGATATTCAGA  300
P1    AACTTACAGCCGACGACTCACTTATATTCGAGATCTTATTAAGTTCCTCGGTTACTCACA  289
      *   **      **  *    *  **  *****    *  *   *       *  **  **  ***

Vh    ACAAATGGCGAAACTAGAAGCAAATTGGATTGCAATGATCCTTTGCTCTAAGAGTGCGCT  351
X1    AGCAATGGCCAAGTTAGAGGCCAACTGGATATCTATGATTTTATGTTCTAAAGGTGGCCT  360
P1    AGAGATGGCAAAACTTGAAGCTAACTGGATCTCAATGATTCTGTGTAGCAAAAGTGCGTT  349
       *  *****  **  *  **  **  **  *****  * *****  *  **      **  ***  *

Vh    CTACGACATTATTGATACCGAGCTTGGCTCAACGCATATACAAGATGAATGGCTACCGCA  411
X1    TTATGATGTTGTAGAAAATGAACTTGGTTCTCGCCATATCATGGATGAATGGCTACCTCA  420
P1    GTACGATATTGTTGAGAATGATCTTAGCTCACGGCATATTATTGATGAGTGGATCCCCCA  409
       **  **    **  **  *  **  **  **    *****      *****  ***  *  **  **

Vh    GGGTGAGTGTTATGTGAGGGCTTTTCCTAAAGGACGCACGATGCATTTGCTTGCGGGGAA  471
X1    GGATGAAAGTTATATTAAGGCTTTTCCGAAAGGTAAGTCTATACATCTGTTGGCAGGTAA  480
P1    AGGTGAATGTTATGTCAAAGCGCTCCCAAAAGGAAAATCTGTACACCTATTAGCTGGTAA  469
        *  ***  *****  **  **  *  **  * *****     *  *  **  **  **  **  **

Vh    TGTTCCTCTCTCCGGTGTGACCTCAATACTACGAGGCATACTGACGAGAAATCAATGTAT  531
X1    TGTTCCATTATCTGTGATCATGTCTATATTACGCGCAATTTTAACCAAGAATCAGTGTAT  540
P1    CGTACCACTATCTGGTGTGACTTCTATTCTTCGTGCGATTTTGACCAAAAACGAGTGCAT  529
       **  **    *  **    *    **    *    **    *  *    **    *  **  **

Vh    TGTGAGAATGTCAGCATCGGATCCTTTTACTGCCCACGCGCTAGCGATGAGCTTTATTGA  591
X1    TATAAAAACATCGTCAACCGATCCCTTTACCGCTAATGCATTAGCGTTAAGCTTTATCGA  600
P1    CATAAAAACGTCATCAGCTGATCCTTTTACAGCTACTGCGCTAGTTAATAGTTTTATCGA  589
       *  *  **    **  **   *****  *****  **       **  ***      **  *****  **

Vh    CGTCGATCCGAATCATCCAATTTCTCGTTCTATCTCCGTATTGTATTGGCCTCATGCATC  651
X1    TGTAGACCCTAATCATCCGATAACGCGCTCTTTGTCTGTTGTATATTGGCCACACACCAAGG  660
P1    TGTAGATGCAGAACACCCGATCACACGTTCAATCTCAGTTATGTATTGGTCACATAGCGA  649
       **  **    *    *  **  **  **  **    *  **  **  ***  **      * **

Vh    GGATACGACACTCGCTGAAGAGTTACTCAGTCATATGGATGCAGTGGTTGCTTGGGGGGG  711
X1    TGATACATCACTCGCAAAAGAAATTATGCAACATATGGATGTTATTGTCGCTTGGGGAGG  720
P1    GGATCTTGCTATTCCAAAACAAATAATGAGCTGTGCTGATGTGGTTATTGCATGGGGTGG  709
      ***     *      *  ** *  *     *    **  ****  *  *  **  ***** **

Vh    GGCGGGATGCCATTGATTGGGCGGTTAAGCATTCTCCTTCACATATCGATGTTTTGAAGT  771
X1    GG-AAGATGCGATTAATTGGGCTGTAGAACATGCACCACCCTATGCTGACGTGATTAAAT  779
```

FIG. 14 (CONT.)

```
P1      TG-ATGATGCAATTAAATGGGCTACAGAACATGCACCATCACACGCAGATATTCTAAAAT  768
           *  ***** *** * *****   * *** ** ** * *    ** *  * ** *

Vh      TTGGTCCAAAGAAGAGTTTTTACCGTGTTAGACCATCCAGCCGATCTAGAAGAAGCCGCCT  831
X1      TTGGCTCTAAAAAGAGTTTTTTGCATTATTGATAATCCAGTTGATTTAACGTCAGCAGCTA  839
P1      TTGGTCCCAAAAAGAGTATATCCATTGTTGACAACCCAACAGATATTAAGGCTGCTGCTA  828
        ****  * ** ******  * *  * ** * ***   *** *    ** **

Vh      CGGGTGTTGCCCATGATATTTGCTTTTATGACCAAAATGCCTGCTTTTCTACTCAGAATA  891
X1      CCGGTGCGGCTCATGATATTTGTTTTTACGATCAGCGCGCTTGTTTTTCTGCCCAAAACA  899
P1      TCGGTGTAGCACATGATATCTGTTTTTACGATCAGCAAGCATGTTTCTCCACCCAAGATA  888
         ****  **  ********* ** ***** ** **    ** ** ** ** *  **   * *

Vh      TTTACTTTTCTGGAGATAAGTATGAAGAATTTAAATTAAAACTTGTTGAAAAACTGAATC  951
X1      TATATTACATGGGAAATCAGTATGAGGAATTTAAGTTAGCGTTGATAGAAAAACTTAATC  959
P1      TTTATTATATTGGCGATAGCATAGACATATTTTTTGATGAATTAGCTCAGCAATTAAATA  948
         * ** *   ** **    ** **    **  ****      *  *  ** * ***

Vh      TCTATCAAGAAGTTTTACCAAAATCAAAACAAAGTTTTGATGACGAAGCTTTATTTTCTA 1011
X1      TATATGCGCATATATTACCAAACGCCAAAAAAGATTTTGATGAAAAGGCGGCCTATTCTT 1019
P1      AATATAAAGACATATTGCCTAAAGGTGAGCGGAATTTTGATGAAAAAGCAGCTTTTTCTT 1008
         *** *   *  *    ** ** **  *   ******** *  **  *  ****

Vh      TGACTCGTCTTGAGTGTCAATTTTCTGGGTTGAAAGTTATATCAGAACCGGAAAATAACT 1071
X1      TAGTCCAAAAAGAGAGCTTATTTGCTGGATTAAAAGTAGAGGTGGATGTTCATCAACGTT 1079
P1      TAACGGAAAGAGAATGTTTGTTTGCCAAATATAAAGTTCAAAAAGGTGAAAGCCAATCTT 1068
        *     **  *    *** *  *   *  * *****  *   *   *   *  *

Vh      GGATGATCATCGAGTCAGAGCCCGGGGTTGAATATAACCATCCATTAAGTCGTTGCGTTT 1131
X1      GGATGATTATTGAGTCAAATGCGGGTGTGGAATTTAATCAACCACTTGGCAGATGTGTGT 1139
P1      GGTTATTAACGCAATCACCTGCGGGATCATTTGGTAATCAGCCGTTATCACGCTCGGCTT 1128
        **  *   *  * *     * ***    * **  *** **  *   *    *   *

Vh      ATGTCCACAAAATAAATAAGGTTGATGATGTTGTTGAATATATAGAAAAACATCAAACAC 1191
X1      ATCTTCATCACGTCGATAATATTGAGCAAGTATTGCCTTATGTTCAAAAAAATAAGACAC 1199
P1      ATATTCATCAAGTAAATGACATTTCAGAAGTCATTCCATTCGTGCATAAGGCGGTAACGC 1188
        ** * **  *  *  *  ** **   *    * * *  *  *    ***     ** *

Vh      AAACGATTTCTTTTTATCCATGGGAATCTTCCAAGAAATATCGAGATGCATTCGCCGCAA 1251
X1      AAACCATATCTATTTTTCCTTGGGAATCCGCATTTAAGTATCGAGATGCGTTGGCATTAA 1259
P1      AAACCGTCGCAATAGCGCCGTGGGAGTCGTCTTTCAAATATAGAGATATATTAGCAGAAC 1248
        ****  *  *  *   ** ***** **  *    ** *** ***** ** ** *

Vh      AAGGGGTAGAAAGAATCGTTGAATCTGGGATGAATAATATATTTAGAGCTGGTGGCGCAC 1311
X1      GAGGTGCGGAAAGGATTGTAGAAGCAGGAATGAATAATATATTTCGAGTTGGTGGATCTC 1319
P1      ATGGTGCAGAACGAATTATAGAAGCCGGAATGAATAATATATTTCGAGTAGGTGGCGCCC 1308
        * ** *  *** ** * ** ** *  **  ***************** *** ***** *  *

Vh      ATGATGCAATGCGCCCACTTCAACGTTTAGTTCGATTTGTTTCTCATGAAAGACCATATA 1371
X1      ATGACGGAATGAGGCCGTTACAACGATTAGTGACATATATTTCTCATGAGAGGCCATCTC 1379
P1      ATGATGGGATGCGTCCCCCTTCAACGGCTTGTTAACTATATATCACATGAAAGGCCGTCAA 1368
        ****  * *** *  ** * *****   * **    * * ***  ***** ** ** **

Vh      ACTTCACCACTAAGGATGTATCTGTCGAAATAGAGCAAACCCGCTTTCTTGAAGAAGATA 1431
X1      ATTATACTGCTAAGGATGTTGCGGTTGAAATAGAACAGACTCGATTCCTGGAAGAAGATA 1439
P1      CATATACCACTAAAGATGTCTCGGTGAAAATCGAACAGACTCGTTATCTTGAGGAAGATA 1428
          * **  ****  ***** *  ** ***** ** **  ** ** ** * ** *******

Vh      AATTCTTGGTTTTCGTCCCTTAAATAAGGAAA-ATTACAATGAATAA---TCAATGCAAG 1487
X1      AGTTCCTTGTATTTGTCCCGTAAATAGGTAAAA-AGTATGGAAAATAAATCCAAATATAAA 1498
P1      AGTTCCTCGTATTTGTACCGTAGAAAGAGATATATCATGGAAAATACACAACATTCATTA 1488
        * *** * * * *  ** ** *  **  *    * * *      ****    *  *

Vh      ACTATTGCACACGTGTTACGCGTGAACAATGGTCAGGAACTTCACGTCTGGGAAACGCCC 1547
X1      ACCATCGACCATGTTCTTTGTGTTGAAGGAAATAAAAAAAATTCATGTTTGGGAAACGCTG 1558
P1      CCTATTGATCACGTAATTGATATTGGTGATAACCGTTATATTCGAGTATGGGAAACCAAG 1548
          * ** ** **  **  *     *     *      *   ***  ** *******

Vh      CCAAAAGAAAATGTGCCTTCTAAAAATAACACCATTTTAATTGCTTCTGGTTTTGCCAGA 1607
X1      CCAGAAGAAACCAGCCCAAAGAGAAAGAATCCCATTATTATTGCGTCGGGTTTTGCCCGA 1618
P1      CCGAAAAATAAAGAAACCAAGCGTAATAATACCATCGTTATCGCCTCAGGCTTTGCTCGA 1608
        **  **  *     *         ** ** *** * * ** ** ** *  ***** **
```

FIG. 14 (CONT.)

```
Vh    AGAATGGATCACTTTGCTGGGTTGGCCGAGTATCTATCTGAAAATGGTTTCCATGTGTTC  1667
X1    AGGATGGATCATTTTGCTGGTTTAGCGGAATATTTATCGCGGAATGGGTTTCATGTGATT  1678
P1    CGCATGGATCATTTTGCTGGTCTTGCCGAATATTTAGCAAATAATGGTTTTCGTGTTATT  1668
      * ******** *******  *  ** ** ***  **  *     ***** ** * ***    *

Vh    CGTTATGACTCTCTTCATCATGTGGGGCTCAGCTCGGGTTCGATTGATGAATTCACCATG  1727
X1    CGCTATGATTCACTTCACCACGTTGGGTTGAGTTCAGGGACAATTGATGAATTTACAATG  1738
P1    CGTTATGATTCGTTAAATCATGTCGGTCTTAGTAGCGGAGAGATCAAACAGTTCTCGATG  1728
      ** *****  **  *  * ** ** ** ***    **     **  *   * **  * ***

Vh    ACGACGGGCAAAAATAGTTTGTGCACTGTTTATCACTGGCTGCAGACCAAGGGCACACAA  1787
X1    TCTATAGGAAAACAGAGCCTATTAGCCGTGGTTGATTGGTTAAATACACGAAAAATAAAT  1798
P1    TCAGTAGGTAAACACAGTTTGCTAACTGTTATTGATTGGCTAAAAGAACGAAATATTAAC  1788
              *  ** *** * **   *    * **  * **  ***  *           *   *

Vh    AACATTGGCTTGATTGCGGCAAGTCTCTCAGCTCGTGTCGCCTATGAAGTTATCTCTGAT  1847
X1    AACCGTGGTATTTTGGCTTCAAGCTTATCTGCACGGATAGTTTATGCAAGTCTATCTGAA  1858
P1    AATATAGGTCTTATTGCTTCGAGTCTTTCTGCTCGAATTGCTTATGAAGTGGCAGCAGAA  1848
      **    **     **  ** * **  **  ** **   *  ****  *      * **

Vh    CTGGAGCTGTCTTTTCTGATTACTGCGGTTGGTGTGGTGAACTTGCGTGACACACTAGAA  1907
X1    ATTAATGTTTCATTTTTAATCACCGCAGTCGGTGTTGTTAACTTAAGATATACGCTTGAA  1918
P1    ATTGATTTGTCATTTTTAATTACCGCCGTCGGTGTTGTCAATTTAAGAAGTACGCTAGAA  1908
       *  *  * ** *** ***  ** ** ** ***** **  * **      ** ** ***

Vh    AAAGCGCTTGGTTTTGATTACCTCAGTTTGCCTATCGATGAGCTACCAAACGATCTTGAT  1967
X1    AGAGCTTTAGGATTTGATTATCTCAGTTTACCCATTAATGAATTGCCGAATAATTTGGAT  1978
P1    AAAGCACTGAAATATGATTATCTACAAATGGAAGTAAATACTATTCCTGAAGATTTAATT  1968
      * ***  *     * *****  * ** * *  *      *  *      *  **  * *

Vh    TTTGAAGGTCATAAGCTTGGTTCTGAAGTGTTCGTTCGCGACTGCTTCGAGCATCACTGG  2027
X1    TTTGAAGGCCATAAATTGGGTGCTGAAGTCTTTGCGAGAGATTGCCTTGATTTTGGCTGG  2038
P1    TTTGAAGGACACAATCTAGGTTCAAAAGTCTTTGTGACAGATTGTTTTGAAAATAATTGG  2028
      ********  **  **  ** *  *  *** **      **  ** *  *    *  ***

Vh    GATACCTTAGATTCTACTCTCGACAAAGTAGCCAATACCTCGGTTCCTTTAATCGCCTTT  2087
X1    GAAGATTTAACTTCTACAATCAATAGCATGATGTATCTTGATATACCGTTTATTGCTTTT  2098
P1    GACTCATTAGATTCGACAATAAATAAAATTTGTGAACTAGATATTCCATTTATTGCTTTC  2088
      **    *** *** **   *  *  * *   *       *    ** ** ** ** **

Vh    ACCGCTAACAACGATGATTGGGTTAAGCAAGAAGAAGTCTATGACAT-GTTAGCGCATAT  2146
X1    ACTGCAAATAACGACAATTGGGTAAAGCAAGATGAAGT-TATCACATTGTTATCAAATAT  2157
P1    ACTTCAGATGGCGATGATTGGGTTTGCCAACATGAAGTAAAAACATTTAGTCAGTA-ACGT  2147
      **  **   *   *** ******  *  **      ***     * **   *    *  *

Vh    CCGCACTGGGCATTGCAAGCTCTACTCCTTGCTTGGTAGCTCTCATGACTTGGGCGAAAA  2206
X1    TCGTAGTAATCGATGCAAGATACATTCTTTGTTAGGAAGTTCGCATGACTTGTGTGTTTT  2217
P1    TAAATCTGACAAAAAGAAAATTTACTCACTCGTTGGCTCATCTCATGATTTGGGCGAAAA  2207
       *                    **  **  *  * *  * *   **** ***  *

Vh    CTTGGTCGTGTTACGTAATTTTTACCAATCCGTCACCAAAGCCGCCATCGCAATGGATGG  2266
X1    CTTAGTGGTCCTGCGCAATTTTTATCAATCGGTTACGAAGGCTGCTATCGCGATGGATAA  2277
P1    CCTAGTGGTGCTTCGTAACTTCTATCAATCAATGACGAAAGCTGCTGTGAGCCTTAGATCG  2267
      * * **  **  *   ** ** ** ***** *   **  *** ** **    *** ***

Vh    AGGCAGCTTAGAAATCGACGTCGACTTTATCGAGCCTGATTTTGAACAACTCACCATCGC  2326
X1    TGATCGTCTGGATATTGATGTTGATATTATTGAACATCATTCGAACATCTAACTATTGC  2337
P1    TCAATTAGTAGAGCTTGTTGATGAAATTATTGAACCAAATTTTGAAGACCTAACAGTTAT  2327
      *  **   *  *  *     **   ****** **  **  *** **  ** **  *

Vh    GACTGTGAATGAACGTCGCTTGAAAGCGGAAATTGAAAGCCGTACGCCAGAAATGGCTTA  2386
X1    GACAGTCAATGAACGTCGAATGAAAATTGAGATTGAAAATCAAGCGATTTCGCTGTCTTA  2397
P1    TACGGTAAATGAACGGCGCCTCAAAAATAAAATCGAAAATGAAAT--TATTAATAGATTA  2385
       **  *  *******  **  * ***  *   * **** *         *   ***

Vh    GGTCTCATCGTAATA-------------------------------------------  2401
X1    AAACCTATTGGGATAGATATTACCCTATAGATTTCAAGATGGATCGCGACGGCAAGGGAG  2457
P1    GCTGATCGCGTATTGGCTAGTGTCTAAATAGTACTTACCTAAGT---------------  2429
                    *  *

Vh    ------------------------------------------CCAATAAATAA  2412
```

FIG. 14 (CONT.)

```
X1          CGAATCCCGGGAGCATAGCAAACTATGTGACCGGGGTGAGTGAGTGCAGCCAACAAAGAA 2517
P1          ----------------------------------------------ACAGCCAAAAG 2440
                                                            ** ** *

Vh          G------GAAATGT-------------------------------------------TATG 2424
X1          GCAACTTGAAAGATAACGGGTATAGTTAATTCTATCACTCAAATATAAGGGCTCTCTATG 2577
P1          G------AAGAAATA--------------------------------------------ATG 2452
            *       * * *                                               ***

Vh          AAATTTGGAAACTTCCTTCTCACTTATCAGCCACCTGAGCTATCTCAGACCGAAGTGATG 2484
X1          AAATTTGGAAACTTTTTTGCTTACATACCAACCCCCCCAATTTTCTCAAACAGAAGTAATG 2637
P1          AAAATTAGTAATATCTGTTTCTCATACCAACCACCAGGTGAATCACATCAAGAGGTAATG 2512
            *** ** * **   *    * * ** ** ** **         ** **    ** ** ***

Vh          AAGCGATTGGTTAATCTGGGCAAAGCGTCTGAAGGTTGTGGTTTCGACACTGTTTGGTTA 2544
X1          AAACGTTTGGTTAAATTAGGTCGTATTTCTGAGGAGTGTGGTTTTGATACTGTATGGTTA 2697
P1          GAGCGCTTTATTCGTTTAGGCGTTGCATCAGAAGAGCTCAACTTTGATGGTTTCTATACA 2572
            * ** ** **   * **          ** **  *      ** **    * ** *  *

Vh          CTAGAGCACCACTTCACTGAATTTGGGTTGTTAGGGAATCCTTATGTTGCTGCCGCACAT 2604
X1          CTGGAGCATCATTTCACGGAGTTTGGTTTGCTTGGTAACCCTTATGTCGCTGCTGCATAT 2757
P1          CTTGAACACCATTTCACTGAGTTTGGTATTACAGGTAACCTTTATATTGCCTGTGCCAAT 2632
            **  ** ** ** ***** **  *****  *    * **  ** ** *     **  **

Vh          CTATTAGGTGCGACAGAAAAGCTCAATGTTGGCACCGCAGCCATTGTATTGCCGACTGCC 2664
X1          TTACTTGGTGCAACCAAAAAATTGAATGTAGGGACTGCGGCTATTGTTCTTCCCACCGCT 2817
P1          ATTCTTGGTCGAACCAAAAGGATCCAAGTCGGTACCATGGGGATAGTGTTACCGACAGAG 2692
              * * *** *    * *  *   * ** *  **  **   ** ***  *  ** ** *

Vh          CATCCGGTTCGACAAGCAGAAGACGTAAACCTACTGGATCAAATGTCGAAAGGACGATTC 2724
X1          CATCCAGTGCGCCAACTTGAAGATGTGAATTTATTGGATCAAATGTCAAAAGGACGATTT 2877
P1          CACCCAGCACGACATGTAGAAAGTCTTCTCGTTTTAGATCAACTGTCTAAAGGGCGCTTT 2752
            ** ** *  **  *   **  *     *     * * ****** * *** *** ** **

Vh          CGTTTTGGGATTTGTCGCGGTTTGTACGACAAAGATTTCCGTGTCTTTGGTACAGACATG 2784
X1          CGGTTTGGTATTTGTCGGGGGCTTTACAATAAAGACTTTCGCGTATTTGGCACGGATATG 2937
P1          AACTACGGTACTGTTCGCGGACTCTACCATAAAGATTTTCGTGTTTTTGGTACATCACAG 2812
              * ** * *  ** *** **    ** * ***** ** ** ** *** ***    * *

Vh          GATAACAGCCGAGCCTTAATGGACTGTTGGTATGACTTGATGAAAGAAGGCTTCAATGAA 2844
X1          AATAACAGTCGCGCTTTAACGGAGTGCTGGTACGGGTTGATAAAAAATGGCATGACAGAG 2997
P1          GAAGATTCTCGTAAGACCGCAGAAAATTTCTACTCTATGATCTTGGATG-CATCAAAAAC 2871
             *  *   **  *     *  ** *  * * *   **** * *  * *   * * *

Vh          GGCTATATCGCG-GCGGATAACGAACATATTAAGTTCCCGAAAATCCAACTGAATCCATC 2903
X1          GGATATATGGAA-GCTGATAATGAACATATCAAGTTCCATAAGGTAAAAGTAAACCCGAC 3056
P1          AGGTGTGCTACATACTGACGGTGAAGTAGTAGAGTTCCCAGATGTCAATGTTTATCCAGA 2931
             *  *       *  **    ***   **  *****  *  *     **    **

Vh          GGCTTACACACAAGGTGGCGCTCCTGTTTATGTCGTCGCGGAGTCAGCATCAACGACAGA 2963
X1          AGCATATAGTAAAGGTGGAGCCCCTGTTTATGTGGTTGCTGAATCAGCCTCGACAACTGA 3116
P1          AGCTTACAGCAAAAAACAA---CCCACCTGCATGACAGCCGAATCATCCGAGACCATCAC 2988
            ** ** *   **      **     * *  *  *   ** ** ** ***   **  *

Vh          ATGGGCTGCAGAGCGTGGCCTACCAATGATTCTAAGCTGGATCATCAATACTCACGAGAA 3023
X1          ATGGGCCGCTCAATTTGGTTTACCGATGATATTAAGTTGGATTATAAATACTAACGAAAA 3176
P1          TTATTTAGCTGAACGTGGTTTACCAATGGTGTTAAGTTGGATTATTCCGGTCAGTGAGAA 3048
              *   **  *  * ****  *** *** * **** *****  **    * ** ** **

Vh          GAAAGCGCAGCTTGATCTTTACAATGAAGTCGCGACTGAACATGGCTACGATGTGACTAA 3083
X1          GAAAGCACAGCTTGAGCTTTATAACGAGGTGGCTCAAGAATATGGGCACGATATTCATAA 3236
P1          AGTCTCACAAATGGAATTGTACAATGAAGTTGCGGCAGAGCATGGTCATGACATTAACAA 3108
             *  *   *   **   ** * ** ** ** **      ** **   * ** *   **

Vh          GATTGACCACTGTTTGTCTTACATCACCTCCGTCGATCATGACTCAAATAAAGCCAAAGA 3143
X1          TATCGACCATTGCTTATCATATATAACATCTGTAAATTATGACTCAAATAAAGCGAAAGA 3296
P1          CATTGAACATATCCTAACTTTCATTTGCTCTGTAAATGAAGACGGTGAAAAAGCAGACAG 3168
             ** ** **     *  *  * *     **    * **   *    **   * * * *

Vh          TATTTGCCGCAACTTCTTGGGTCATTGGTACGACTCATACGTGAATGCCACCAAGATTTT 3203
X1          GATTTGTCGGAAATTTCTAGGGCATTGGTATGATTCTTATGTGAATGCCACGACCATTTT 3356
P1          CGTATGCCGTAATTTCCTAGAAAATTGGTACGACTCTTACAAAAATGCAACCAACATCTT 3228
```

FIG. 14 (CONT.)

```
                    *  **  **  **  **   *  *    *******  **  **  **         *****  **  *    **  **
Vh      TGACGACTCTGACCAAACAAAAGGCTACGACTTCAATAAAGGCCAATGGCGCGATTTTGT  3263
X1      TGATGATTCAGACAAAACAAGAGGTTATGATTTCAATAAAGGGCAGTGGCGTGACTTTGT  3416
P1      CAACGACAGTAACCAAACTCGTGGCTACGATTACCTCAAAGCTCAGTGGCGTGAGTGGGT  3288
            *  **         **  ****        **  **  **  *  *       ****    **  *****  **   *   **

Vh      GTTGAAAGGCCACAAAGATACCAACCGCCGAATTGATTACAGCTACGAAATCAACCCAGT  3323
X1      ATTAAAGGGACATAGAGATACTAATCGCCGCATTGATTACAGTTACGAAATCAATCCCGT  3476
P1      AATGAAGGGGTTGGCTGATCCTCGTCGCCGACTTGATTACAGTAACGAATTAAACCCTGT  3348
            *  **  **            ***  *       *****   **********    *****  *  **  **  **

Vh      AGGGACGCCTGAAGAGTGTATCGCGATTATCCAGCAAGATATCGATGCAACGGGTATTGA  3383
X1      GGGAACCCCGCAGGAATGCATTGACATAATTCAAAAAGACATTGATGCCACGGGAATATC  3536
P1      CGGCACGCCAGAACGATGCATTGAGATCATTCAAAGTAATATTGATGCCACTGGAATTAA  3408
            **  **  **       *        **  **  **         *   **  *****  **  **  **

Vh      CAATATTTGTTGTGGTTTTGAAGCAAACGGTTCTGAAGAAGAAATTATCGCATCTATGAA  3443
X1      AAATATCTGTTGTGGGTTTGAAGCGAATGGAACAGTAGACGAAATTATTGCTTCCATGAA  3596
P1      GCATATTACTGTTGGATTTGAAGCGAATGGTTCTGAACAAGAAATTCGTGAATCCATGGA  3468
            ****     *   ***  ********  **   *  *  *   **  ******    **   **   ***   **

Vh      GCTATTCCAGTCCGATGTGATGCCATATCTCAAAGAAAAACAGTAATTAATATTTTCTAA  3503
X1      GCTCTTCCAGTCTGATGTCATGCCGTTTCTTAAAGAAAAACAACGTTCGCTATTATAGTA  3656
P1      GCTATTTATGGAAAAAGTAGCGCCACACTTAAAAGATCCTCAGTAAGCTGTTCTTTTTAA  3528
            ***  **       *  ***   ***          *  *****          **           *  *  *        *

Vh      ------------------AAGGAAAGAGACATGAAATTTGGATTATTCTTCCTCAATT  3543
X1      GCT---------------AAGGAAAAAGAAATGAAATTTGGATTGTTCTTCCTTAACT  3699
P1      ACTATTCAATATCAAGGCATAAGGAATAAAATATGAATTTCGGGTTATTTTTCCTAAATT  3588
                                       ******  *  *  *****  **  **  **  **      *****  **  *

Vh      TTATGAATTCAAAGCGTTCTTCTGATCAAGTCATCGAAGAAATGTTAGATACCGCACATT  3603
X1      TCATCAATTCAACAACTGTTCAAGAACAAAGTATAGTTCGCATGCAGGAAATAACGGAGT  3759
P1      TCCAGCCTGAAGGTATGACTTCAGAAATGGTTTTAGACAACATGGTAGATACTGTCGCAT  3648
            *          *  *         *  **            *  **           *  *       ***     **  **          *

Vh      ACGTAGATCA-GTTGA-----AGTTTGACACGTTGGCTGTTTACGAAAACCATTTCTCGA  3657
X1      ATGTTGATAA-GTTGA-----ATTTTGAACAGATTTTGGTGTATGAAAATCATTTTTCAG  3813
P1      TAGTGGATAAAGATGATTACCACTTTAAAAGAGTGCTCGTCAGCGAGCATCATTTTTCTA  3708
            **  ***   *  *  ***       *  ***  *       *         *  **       **  *  *****  **

Vh      ACAATGGTGTGGTTGGTGCCCCATTAACAGTGGCTGGTTTTTTACTTGGTATGACAAAGA  3717
X1      GTAATGGTGTTGTCGGTGCTCCTCTGACTGTTTCTGGTTTTTTGCTCGGTTTAACAGAAA  3873
P1      AAAACGGCATTATCGGAGAACCTTTGACAGCGATTAGCTTCTTACTTGGTTTGACTAAAC  3768
            **  **     *   *  **     *  **   *  **   *   **  **  **  **  ***  *  **        *

Vh      ACGCCAAAGTGGCTTCGTTGAATCACGTTATTACAACACATCATCCAGTACGTGTGGCGG  3777
X1      AAATTAAAATTGGCTCATTGAATCACATCATTACAACTCATCATCCTGTCCGAATAGCGG  3933
P1      GTATAGAAATTGGTTCTTTAAATCAAGTGATTACCACCCATCATCCTGTACGTATCGGAG  3828
            **  *  *     **  **  *****  *  *****   **  ********  **  **       *  *  *

Vh      AAGAAGCGTGTCTACTCGACCAAATGAGTGAAGGCCGTTTTGTCTTTGGCTTTAGTGATT  3837
X1      AGGAGGCTTGCTTACTGGATCAATTAAGCGAAGGGAGATTTATTTTAGGGTTTAGTGATT  3993
P1      AACAAACGGGCTTACTTGATCAAATGTCTTACGGTCGTTTCGTTTTAGGCTTAAGTGACT  3888
            *    *    *    *   ****  **  ***   *        *  **    *   **  **  **  **  ******    *

Vh      GTGAAAAGAGTGCAGATATGCGCTTCTTTAATCGACCAACGGATTCTCAGTTTCAGTTGT  3897
X1      GTGAAAAAAAGATGAAATGCGTCTTTTTTAATCGCCCTGTTGAATATCAACAGCAACTAT  4053
P1      GTGTCAATGACTTCGAAATGGATTTCTTTAAGAGAAAACGTAGCTCTCAACAGCAACAAT  3948
            ***  **         **  ***           *  *****   *            *  ***       **        *

Vh      TCAGTGAGTGTCACAAGATCATCAATGATGCATTCACTACTGGGTACTGCCATCCAAACA  3957
X1      TTGAAGAGTGTTATGAAATCATTAACGATGCTTTAACAACAGGCTATTGTAATCCCGATA  4113
P1      TCGAAGCATGTTACGAAATTTTAAATGAAGCGCTGACGACAAACTATTGTCAGGCAGATG  4008
            *  *     ***      **  *  **  *  *  **  **  **   **  **   **  **  *    *   *

Vh      ATGATTTTTATAGTTTTCCTAAAATCTCTGTTAACCCACACGCTTACACTGAAGGCGGTC  4017
X1      ATGATTTTTATAGTTTCCCTAAAATATCGGTAAACCCCACGCTTATACCCAAGGCGGGC  4173
P1      ATGACTTCTTTAACTTCCCACGTATTTCTGTTAACCCGCA---TTGTATT---AGCGAAG  4062
            ****  **  *  **  **  **   **  **  **  **  ******  **    **  *             ***
```

FIG. 14 (CONT.)

```
Vh      CTGCGCAATTTGTGAATGCGACGAGCAAAGAAGTGGTTGAATGGGCGGCTAAGTTAGGGC    4077
X1      CTCGGAGATATATTACAGCAACCAGTCATCATATTGTTGAATGGGCGGCTAAAAAAGGCA    4233
P1      TAAAACAATATATTTTAGCTTCAAGCATGGGCGTGGTTGAATGGGCAGCAAGAAAAGGAT    4122
                **  *  *  **     *  ************  **  *   ***

Vh      TTCCACTCGTGTTTAAATGGGACGACTCAAACGCGCAAAGAAAAGAATACGCCGGTTTGT    4137
X1      TTCCTCTCATCTTTAAGTGGGATGACTCCAATGATGTTAGATATGAATATGCTGAAAGGT    4293
P1      TGCCACTCACTTACCGCTGGAGTGACAGCCTAGCAGAAAAAGAAAAATACTATCAGCGTT    4182
         *  ** ***       ***   ***    ***         *   *   ****       *

Vh      ACCACGAAGTTGCTCAGGCACATAGTGTCGATGTTAGTCAGGTTCGA-CACAAGCTGACG    4196
X1      ATAAAGCCGTTGCTGCTGATAAATATGGCATTGAC-TTATCAGCGATAGATCATCAGTTAATG    4352
P1      ATCTCGCTGTTGCTAAAGAGAATAATATTGAT-GTATCAAATATTGACCACCAATTCCCA    4241
         *    *  ******     **     *  **   **        *  **  **   *    *

Vh      CTGTTGGTCAACCAAAATGTAGATGGTGAAGCAGCAAGGGCAGAAGCACGCCTGTATTTG    4256
X1      GTATTGGTTAACTATAACGAAGATAGTCACAAAGCTAAACAAGAGACGCGTGCATTTATC    4412
P1      CTGCTCGTTAATATCAATGAAAATCGTCGTATTGCTCGAGATGAAGTAAGGGAGTATATA    4301
         *  * ** **      **  ** * **    **        **    **    *  * **

Vh      GAAGAGTTTGTCCGTGAATCTTACCCAAATA---CCGAATTTGAGCAAAAAATGGCAGAG    4313
X1      CGTGATTATGTTCTTGAAATGTATCCTAATG---AAAATCTCGAAAATAAACTTGAAGAG    4469
P1      CAAAGTTATGTGAGTGAAGCCTACCCTACTGACCCCAACATTGAGCTAAGAGTAGAAGAG    4361
         *  ***  ****    ** ***     **            *  **   *   * ****

Vh      CTGTTGTCAGAAAATGCCATCGGTACTTATGAAGAAAGTACTCAGGCAGCGCGAGTTGCG    4373
X1      ATAATCACAGAAAACGCTGTCGGAGATTATACGGAATGTATAGCTGCGGCTAAGCTGGCA    4529
P1      CTTATTGAGCAGCATGCTGTCGGCAAAGTGGATGAGTACTACGACTCAACAATGCACGCA    4421
         *   *     *    **  ** ***          **   **     *   *    **

Vh      ATTGAGTGTTGTGGTGCCGCGGACCTATTGATGTCTTTTGAGTCGATGGAAGATAAAGCG    4433
X1      ATTGAAAAGTGCGGTGCAAAAAGGGTATTATTATCCTTTGAACCAATGAATGACTTGATG    4589
P1      GTAAAAGTTACAGGTTCAAAAAATTTATTACTCTCTTTTGAATCAATGAAAAATAAAGAC    4481
         *  *    *** *        ****  *  **  ***** * *** *   *

Vh      CAGCAAAGAGCGGTTATCGATGTGGTAAACGCCAACATCGTCAAATACCACTCGTAACGT    4493
X1      CACCAAAAAAATGTAATCAATATTGTTGATGATAATATTAAAAAGTACCACATGTAGTA-    4648
P1      GATGTTACCAAGCTTATAAATATGTTTAATCAAAAAATCAAAGATAACCTTATTAAATAA    4541
         *      *   **  **  *   *   *  *     ** **    ***   *

Vh      TT-------AACTGATGCTGAAGGGGCAGCGA--------TGCCCCTTATAT-------    4530
X1      ---------AAAGAATAT------GGCAGCAA--------CGCT---------------    4669
P1      TTTAATTACGGATAGATATTTTCGATATATCTAAGTCTTACTACCATTTATATAAACTAT    4601
                  *  **        ***  *        *

Vh      ---------CACCATTCTTTTCGCGCGA-------------TAGCGCTAACTAATAG---    4565
X1      ---------GCCATATTCTCTA----------------------AATTATTTG---    4691
P1      TTATACAGATAACGTTTCATTTGATTAAGTCAGTAAATAATTGCCATTAATTAATGGCAG    4661
                  *   *   *                                 ** **  *  *

Vh      ------------------------------AGGCATTTATATGGACGTACTTTCAG    4591
X1      ------------------------------GAGGGGTAAAACAGGTATGACTTCAT    4717
P1      TGCAGATCCTTACACTGCCATTTATAAATTAAATAAGGGTTAACATGTCAACATTATTAA    4721
                                        *   *  *           * *

Vh      CGGTTAAGCAGGAAAATATCGCAGCGAGCACAGAAATCGATGACTTGATTTTCATGGAA    4651
X1      ATGTTGATAAACAAGAGATCATAGCAAGCTCAGAAATTGATGATTTGATTTTTTCCAGCG    4777
P1      ATATAGATGCAACTGAAATTAAGGTGAGTACAGAAATAGATGATATTATTTTTTACATCAT    4781
         *  *     *  **    *  **  * *** ***** *****  *  * ****

Vh      CTCCTCAGCAATGGTCATTGCAGGAACAAAAACAGCTGACATCTCGCCTTGTTAAAGGGG    4711
X1      ATCCATTAGCTTGGTCTTACGATGAACAGGAAAAAAATCAGAAACAAATTTGTTCTTGATG    4837
P1      CACCGCTAACGTTACTATTTGAAGATCAAGAAAAAAATACAGAAAGAACTTTATTTTGGAGT    4841
          **       *    *     *  *   *   **   *   *       ** *     *

Vh      CATATCAATACCATTACCACAATAATGATGACTATCGTCAGTTCTGCCAAAGGCTGGGAG    4771
X1      CATTTCGTAATCACTATAAACATTGTCAAGAATACCGTCACTACTGTCAGGTACACAAAG    4897
P1      CTTTCCATTATCATTACAATCATAATAAAGATTATAAGTACTATTGTAATATACAAGGCG    4901
         *  *    *  ** ** *  **  *    **   **     *   **  *      *

Vh      TCGGAGAGGAGGTCGAAGATCTCAATGAGATCCCCGTTTTCCCTACTTCTATTTTTAAGT    4831
X1      TAGACGACAATATTACGGAAATTGATGACATACCTGTATTCCCAACATCAGTTTTTAAGT    4957
```

FIG. 14 (CONT.)

```
P1    TAGATGAGAATATACAGTCCATTGACGATATTCCTGTTTTTCCTACTTCAATGTTCAAGT 4961
      *  *  **   *  *       *  *  **  **  **  **  **  **  **   *  **  ****

Vh    TGAAGACCCTATTAACACTTGACGATGAAGAGGTAGAGAATCGCTTTACTAGCAGCGGTA 4891
X1    TTACTCGCTTATTAACTTCTCAGGAGAACGAGATTGAAAGTTGGTTTACCAGCAGCGGCA 5017
P1    ACTCAAGATTACATACTGCTGATGAATCAAATATTGAAAATTGGTTTACTAGTAGTGGTA 5021
      **    **   *  *  **      *   *  **  **  **  *****  **  **  **  **   *

Vh    CTAGTGGCATCAAAAGTATTGTCGCACGAGATAGACTCAGTATTGAGCGACTTCTTGGCT 4951
X1    CGAGTGGTTTAAAAAGTCAGGTGGCGCGTGACAGACTAAGTATTGAGAGACTCTTAGGCT 5077
P1    CAAAGGGAGTCAAAAGTCATATAGCTCGAGATCGGCAGAGTATTGAACGCTTGCTAGGTT 5081
      *  *  **   *  ******    *  **  **  **    *  *  ********   *   *   *  **  *

Vh    CAGTAAATTTCGGTATGAATTACGTTGGTGATTGGTTTGACCATCAGATGGAGTTGGTGA 5011
X1    CTGTGAGTTATGGCATGAAATATGTTGGTAGTTGGTTTGATCATCAAATAGAGTTGGTCA 5137
P1    CTGTTAATTACGGCATGAAATACTTGGGTGAATTTCACGAGCATCAATTAGAACTAGTGA 5141
      *  **   *  **   **  *****  **   *  ***    *    **  *****   *  **   *  **   *

Vh    ACTTAGGCCCAGATCGCTTTAATGCCAACAATATTTGGTTCAAGTACGTCATGAGCTTAG 5071
X1    ACTTAGGGCCAGATAGATTTAATGCTCATAACATTTGGTTTAAATATGTTATTAGTTTGG 5197
P1    ATATGGGGCCAGATCGTTTCAGTGCGTCAAATGTTTGGTTTAAATATGTAATGAGCTTAG 5201
      *   *  **  ******   *  **  *  ***        **  *******  **  **  **  **  **  *

Vh    TCGAGCTCCTTTATCCGACCGCATTTACTGCCACTGAGGATGAGATCGACTTTGAGGCGA 5131
X1    TAGAATTATTATATCCCACGACATTTACCGTAATGGAAGAACGAATAGATTTTGTTAAGA 5257
P1    TTCAATTACTTTACCCAACAACATTTACCGTTGAAAACGATGAAATCGATTTTGAACAAA 5261
      *   *   *   *  **  **  **   *******  *     *  **   **  **  ****        *

Vh    CGCTAGCTAATATGAATCG-TATTAAGCAGTCTGGTAAAACCATTTGTCTTATCGGCCCT 5190
X1    CATTGAATAGCCTTGAGCG-AATAAAAAATCAAGGGAAAGATATTTGTCTTATCGGCTCA 5316
P1    CCATC-TTAGCGTTAAAAGCAATTCAGCGTAAAGGAAAAGGAATTTGTTTAATTGGCCCT 5320
      *    *   **   *   *  *   **  *     **  ***   ******   *  **  ***   *

Vh    CCTTATTTTATCTATCTACTGTGCTGTTTCATGCGCGAGCAAGGTCAAACTTTCAATGGT 5250
X1    CCATACTTTATTTATTTGCTCTGCCAGTATATGAAAGATAAAAACATCTCATTTTATGGG 5376
P1    CCGTATTTTATTTATTTGTTATGCCACTACATGAAAGAGCATAATATCGAATTTAATGCT 5380
      **  **  *****  ***  *  *  ***   *  ***   **   *        **   ***

Vh    GGTCGCGATCTTTACATCATCACTGGCGGCGGCTGGAAAAAACATCAGGATCAATCGCTC 5310
X1    GATAAAAACCTTTATATCATAACGGGGGGCGGCTGGAAAAAGTTATGAAAAAGAGTCCCTA 5436
P1    GGTGCACATATGTTTATCATTACAGGTGGGGGATGGAAAAACCAAACAAAAAGAAGCGCTA 5440
      * *      *   ****   **  **  **  *******     *  *   *    *  **

Vh    GATAGAGACGAGTTCAACCAGCTTTTGTGTGAGACTTTTACCTTAGAAAGCGCAGAGCAG 5370
X1    AAACGCGATGATTTCAATCATCTTTTATTCGACACGTTCAACCTCAATAATATTAGTCAA 5496
P1    AACCGACAAGATTTCAATCAACTATTGATGGAGACTTTTAGCCTTTTCCATGAAAGTCAA 5500
      *   *   *  **  *****  **  **    **  **  **  *****       **

Vh    ATTCGAGACACATTTAATCCAGTTGAACTGAACACCTGCTTTTTTGAAGATACAGAACAC 5430
X1    ATCGCGATATATTTAATCAAGTTGAACTCAACACTTGTTTCTTTGAGGATGAAATGCAA 5556
P1    ATTCGAGATATCTTTAACCAAGTAGAGCTAAACACTTGTTTCTTTGAAGACAGCCTACAG 5560
      **  **  **   *  *****   *  ***  **  **  *****  **  **  *****  **   **

Vh    AAAAAGCGTGTACCGCCCTGGGTCTTTGCAAGAGCTCTGGATCCTAAAACATTAAAGCCG 5490
X1    CGTAAACGTGTTCCGCCGTGGGTATATGCGCGAGCACTTGATCCTGAAACATTGAAACCT 5616
P1    CGTAAACATGTACCACCGTGGGTATATGCTCGTGCGCTTGATCCTGTCACTTTAACGCCC 5620
      **  *  ***  **  **  ****** *  ***   *  **  **  ******   **  **   *   **

Vh    CTTCCGCATGGCCAGCCAGGACTGATGAGCTATATGGATGCCTCGGCGGTCAGCTATCCA 5550
X1    GTACCTGATGGAATGCCGGGTTTGATGAGTTATATGGATGCGTCATCAACGAGTTATCCG 5676
P1    GTAGAAGATGGCCAAGAGGGCTTGATGAGTTATATGGATGCCTCATCTACCAGCTACCCG 5680
      *      ****     **  ******   ***********   **    *    **  **   **

Vh    TGTTTTCTAGTGACGGATGACATCGGCATCGTGCG------AGAAGAAGAAGGCGATCGC 5604
X1    GCATTTATTGTTACCGATGATGTCGGGATAATGAG------CAGAGAATATGGTCAATAT 5730
P1    ACATTTATTGTTACCGACGATATTGGTATTGTTCGCCATCTAAAAGAACCAGATCCATTC 5740
      ***  *  **  **  **  **    *  **  **   *   *            ****    *

Vh    CCGGGAACCACTGTTGAGATCGTTAGAAGAGTTAAGACGCGGGGTATGAAGGGGTGTGCT 5664
X1    CCTGGTGTACTTGTTGAGATTTTACGTCGCGTCAATACGAGGGCACAGAAAGGGTGTGCT 5790
P1    CAAGGAACAACGGTTGAAATTGTTCGTCGTTTAAATACGCGAGAACAAAAAGGATGTTCA 5800
      *   **       *****  **    *    *    *  **  ***  * *        **  **  ***   *
```

FIG. 14 (CONT.)

```
Vh    CTCAGTATGTCTCAAGCATTTA-CAGCTAAGAATGAAGGAGGCAACTGACATGTTAT-GT   5722
X1    TTAAGCTTAAACCAAGCATTTAATAGTTGA------------------------------   5820
P1    CTCTCAATGG-CCACGAGCCTG--AAATAAAAGCAGGGCTTAATCATGATTTTTAATTGC   5857
       *    *   ** *    *    *  *

Vh    TCGATAGAAAAAATTGAGCCGTTAACTAACCTCATATTCCGAGTATTGCTCAAGCCAGAT   5782
X1    ------------------------------------------------------------
P1    AAGGTTAAAAAAGTCGAAGCATCTGACAGCCATATTTACAAAGTGTTTATTAAGCCTGAC   5917

Vh    CAGCCTTTTGAATTTAGGGCAGGGCAGTACATTAACGTCAGTTTAAGCTTTGGTAGTTTA   5842
X1    ------------------------------------------------------------
P1    AAATGCTTTGATTTTAAAGCGGGTCAATATGTAATTGTGTATCTCAATGGAAAAAATTTG   5977

Vh    CCGTTTTCTATAGCCTCATGTCCTTCTAATGGTGCGTTTTTAGAACTCCATATTGGTGGC   5902
X1    ------------------------------------------------------------
P1    CCGTTTTCTATTGCTAACTGCCCAACTTGTAATGAGCTCCTTGAATTACATGTAGGAGGT   6037

Vh    TCAGATATCAGCAAGAAAAATACGCTTGTGATGGAAGAACTCACCAATTCATGGGCTGC    5962
X1    ------------------------------------------------------------
P1    TCGG---TAAAAGAATCCGCCATTGAAGCTATTTCGCACTTTATTAATGCATTTATTTAT   6094

Vh    GGCAACATGGTTGAAGTCAGTGAGGCGCGAGGTGAGGCTTGGTTGCGTGATGAGAGTGTC   6022
X1    ------------------------------------------------------------
P1    CAAAAAGAATTTACAATCGATGCACCACACGGTGATGCATGGCTGAGAGATGAAAGCCAA   6154

Vh    AAACCCTTGTTATTGGTCGCAGGCGGGACGGGAATGTCATACACCCTAAGTATTTTGAAA   6082
X1    ------------------------------------------------------------
P1    TCACCTTTACTACTTATAGCAGGAGGGACAGGTTTATCATATATCAATAGCATTTTAAGT   6214

Vh    AATAGCTTGGAGCAAGGGTTTACCCAGCCGATTTACGTCTATTGGGCGCCAAGGATATG    6142
X1    ------------------------------------------------------------
P1    TGTTGTATTAGTAAACAGTTATCTCAGCCTATCTATCTTTATTGGGGAGTAAATAACTGT   6274

Vh    GATAACCTGTATGTACATGACGAACTGGTGGATATTGCGCTTGAAAACAAAAACGTCAGT   6202
X1    ------------------------------------------------------------
P1    AATTTACTCTATGCTGATCAACAACTAAAAACACTCGCCGCACAATACAGAAATATAAAT   6334

Vh    TACGTGCCAGTCACTGAAATATCAACCTGTCCCCAATACGCTAAGCAAGGAAAGGTGTTG   6262
X1    ------------------------------------------------------------
P1    TATATTCCTGTGGTAGAGAATTTAAATACTGACTGGCAGGGAAAAATTGGTAATGTTATT   6394

Vh    GAGTGTGTGATGAGTGATTTCCGTAACTTATCTGAGTTCGATATCTACTTGTGTGGTCCT   6322
X1    ------------------------------------------------------------
P1    GACGCGGTTATTGAAGATTTTTTCAGATTTATCTGACTTTGATATCTATGTCTGCGGGCCA   6454

Vh    TGCAAAATGGTTGAAGTGGCTCGTGATTGGTTCTGTGACAAAAGAGGGGCAGAACCAGAG   6382
X1    ------------------------------------------------------------
P1    TTTGGTATGAGCCGGACTGCGAAAGATATTCTGATCTCACAGAAAAAGGCGAATATAGGA   6514

Vh    CAACTTTACGCGGACGCGTTCGCTTATTTGTAATCATTATCAAGGAGAAGAAACTATGAG   6442
X1    ------------------------------------------------------------
P1    AAAATGTATTCTGATGCATTTAGCTATACGTAA---------------------------   6547

Vh    CTCAACGTCACTACTAGATGAGTTTGGCACTCCAGTACAAAGGGTAGAAAGAGCGATTGA   6502
X1    ------------------------------------------------------------
P1    ------------------------------------------------------------

Vh    GGCTCTGAAAAATGGCCTTGGTGTTCTATTAATGGATGATGAGGATCGCGAGAACGAAGG   6562
```

FIG. 14 (CONT.)

```
Vh        CGACCTTATCTTCTCTGCACAGCATCTTACCGAAGCGCAAATGGCACTCATGATTCGTGA  6622
X1        ------------------------------------------------------------
P1        ------------------------------------------------------------

Vh        ATGCAGTGGTATCGTGTGTTTGTGCTTAACGGAGGAACGCGCCAATTGGTTAGAGCTTCC  6682
X1        ------------------------------------------------------------
P1        ------------------------------------------------------------

Vh        TCCTATGGTGAAAGATAATCGCAGTAAAAACCAGACCGCTTTTACGGTTTCGATTGAAGC  6742
X1        ------------------------------------------------------------
P1        ------------------------------------------------------------

Vh        GAAAGAAGGGGTGACGACAGGAGTCTCTGCGAAAGATCGCGTTACAACGGTTAAAACGGC  6802
X1        ------------------------------------------------------------
P1        ------------------------------------------------------------

Vh        TACTTATTTTGATGCTCAACCAGAAGATTTAGCAAGACCAGGCCATGTTTTTCCGCTGGT  6862
X1        ------------------------------------------------------------
P1        ------------------------------------------------------------

Vh        TGCGAAAACAAATGGCGTGTTGGCCCGTCGAGGTCATACCGAAGGTACGATCGATTTGAT  6922
X1        ------------------------------------------------------------
P1        ------------------------------------------------------------

Vh        GTATCTAGCAAACTTAGTCCCATCAGGGATCCTTTGCGAACTGACTAACCGTGATGGAAC  6982
X1        ------------------------------------------------------------
P1        ------------------------------------------------------------

Vh        CATGGCGAAACTACCAGAAACCATTGAGTTTGCAAGACGTCATGGAATGCCAGTGCTCAC  7042
X1        ------------------------------------------------------------
P1        ------------------------------------------------------------

Vh        TATTGAAGATATCGTCGATTATCGGACGGTAATTGAACTGAGAAATGAATATGAGAGTGG  7102
X1        ------------------------------------------------------------
P1        ------------------------------------------------------------

Vh        CTTAGTGTGTGAAGTGAGTTGGTCTTAG  7130      (SEQ ID NO: 4)
X1        ----------------------------            (SEQ ID NO: 5)
P1        ----------------------------            (SEQ ID NO: 6)
```

BIOLUMINESCENT PLANTS COMPRISING BACTERIAL LUX OPERON AND METHODS OF MAKING SAME

CROSS-REFERENCE TO RELATED APPLICATION

This application is a U.S. National Phase Application of International Application No. PCT/US2008/009310 filed on Jul. 31, 2008. The specification of International Application No. PCT/US2008/009310 is hereby incorporated by reference in its entirety.

This application claims the benefit of U.S. Provisional Application No. 60/953,337, filed Aug. 1, 2007, which is incorporated herein by reference in its entirety.

BACKGROUND OF THE INVENTION

The phenomenon of light emission by living organisms, known as bioluminescence, is a characteristic of different species including, for example, insects and bacteria. Most of the world's luminescent bacteria are represented by marine species, including Vibrio, Photobacterium, Photorhabdus and Shewanella families. Some of these organisms live as free water-born bacteria, while others as symbionts in light organs of marine animals.

Non-bacterial organisms such as plants that are capable of bioluminescence would be useful for many purposes, such as for environmental and aesthetic applications. However, such organisms have not been readily achieved for many reasons. For example, the genes and mechanisms responsible for bioluminescence are complex.

Genetic engineering of plants has been typically limited to introduction of one or two new genes into plant genome. This limitation prevents incorporation of complex metabolic pathways, such as those involved in light emission, into transgenic plant organisms.

Conventionally constructed genetic transformation vectors are made using "regular" restriction endonucleases with average recognition site length of six nucleotides. Such construction is a laborious and time consuming process, which involves sequential cloning of different functional plasmid elements (e.g., promoters, terminators, and integration sequences) by a series of multiple cloning steps.

After cloning several vector segments, commonly used restriction endonucleases sites will be present in the newly inserted DNA fragments (due to high statistical probability of occurrence of a six base pair sequence in an extended DNA fragment). The presence of such sites significantly limits the number and size of additional DNA sequences that may need to be added to achieve a desired biological property such as bioluminescence. Moreover, if initially cloned DNA elements are required to be exchanged to yield another property, the entire vector typically must be reconstructed. It is often impossible to remove previously cloned genetic elements without affecting later cloned sequences.

Incorporation of multiple transgenes into a single plant organism has been attempted using standard breeding techniques. However, such an approach is time consuming and largely ineffective. Accordingly, a genetic vectors system allowing for efficient incorporation of multiple transgenes is needed. An approach for allowing rapid exchange of multiple transgenes in the genome of any selected plant species (especially the plastid genome) is also needed.

SUMMARY OF THE INVENTION

The present invention addresses these and other objectives.

In one aspect, the invention relates to a transgenic bioluminescent plant that includes an expressible heterologous nucleotide sequence comprising a bacterial LUX operon, comprising LUX A, LUX B, LUX C, LUX D, LUX E, and LUX G genes, wherein the heterologous nucleotide sequence is expressed to render the plant bioluminescent.

In another aspect, the invention relates to a method for producing a transgenic bioluminescent plant. The method includes transfecting a plant cell with a vector that includes an expressible heterologous nucleotide sequence including a bacterial LUX operon, comprising LUX A, LUX B, LUX C, LUX D, LUX E, and LUX G genes.

The present invention provides methods for producing luminescence in plants comprising transfection of a plant cell with genes corresponding to the LUX operon. In one embodiment of the invention, the transfected genes comprise the genes from the LUX operon which encode for bacterial luciferase, i.e., the LUX A and B genes; the genes related to production of substrates required for the bacterial luciferase luminescent reaction, i.e., LUX genes: C, D, and E; and LUX G.

In one aspect, the present invention provides methods of producing luminescence in plants comprising transfection of a plant cell with genes encoding for bacterial luciferase encoded by LUX A and B genes and any other gene related to production of substrates required for the bacterial luciferase luminescent reaction including, but not limited to LUX genes: C, D, E, G, H, F, as well as any component of the RIB operon (such as LS or RS) involved in riboflavin synthesis and donors of fatty acids for the aldehyde synthesis, such as bacterial or plant acyl carrier protein (ACP). In another aspect, the invention provides corresponding transgene expression in all and any part of the plant cell from nuclear, chloroplast, plasmid or any other plant genetic sequences, as well as means of regulation for the genes expression, such as inducible promoters, etc. In a further aspect, the invention provides transfection of at least one plant cell with at least one vector encoding for the luciferase system mentioned herein and growing at least one plant cell into plant.

In yet another aspect, the invention relates to a vector for transforming a plastid. The vector includes a first and a second homologous recombination site, wherein each of said homologous recombination site is flanked by a unique rare cutting enzyme sequence; and a multiple cloning site comprising at least one unique rare cutting enzyme sequences.

In a further aspect, the invention relates to a method for producing a vector for transforming a plastid. The method includes providing an acceptor vector, which includes (i) a first and a second homologous recombination site, wherein each of said homologous recombination site is flanked by a unique rare cutting enzyme sequence; and (ii) a multiple cloning site that includes at least one unique rare cutting enzyme sequence. The method further includes providing at least one donor vector, wherein the donor vector includes a heterologous nucleotide sequence flanked by a rare cutting enzyme sequence that is sufficiently identical to the at least one unique rare cutting enzyme sequence of the multiple cloning site of the acceptor vector. The method further includes sequentially subcloning the heterologous nucleotide sequence from the donor vector into the acceptor vector, wherein a vector for transforming a plastid is produced.

In yet another aspect, the invention relates to a vector system kit. The kit includes an acceptor vector that includes (i) a first and a second homologous recombination site, wherein each of said homologous recombination site is flanked by a unique rare cutting enzyme sequence; and (ii) a multiple cloning site comprising at least one unique rare cutting enzyme sequence. The kit further includes at least one donor vector, wherein the donor vector comprises a heterologous nucleotide sequence flanked by a rare cutting enzyme sequence that is sufficiently identical to the at least one unique rare cutting enzyme sequence of the multiple cloning site of the acceptor vector.

BRIEF DESCRIPTION OF DRAWINGS

FIG. 2(B): Schematic illustration example of a pCas vector: use of photosystem II (psbA) regulatory elements for transgene expression (PI-PspI-PpsbA-LpsbA-MCS-TpsbA-PI-PspI (SEQ ID NO: 1). Abbreviations: PpsbA is a psbA promoter; LpsbA is a psbA leader; TpsbA is a psbA terminator.

FIG. 14: Alignment of LUX operons from three major luminescent bacteria families, namely *Photobacterium, Vibrio* and *Xenorhabdus* (aka *Photorhabdus*). Sequence comparison produced using ClustalW software (EBI) of three luminescent bacteria species: *Photobacterium leiognathi* (abbreviated as P1), *Vibrio harveyi* (abbreviated as Vh) and *Xenorhabdus* (aka *Photorhabdus*) *luminescens* (abbreviated as Xl).

DETAILED DESCRIPTION OF THE INVENTION

In the present invention, bacterial luminescence machinery is exploited for the production of bioluminescent reactions in plants. The metabolically engineered plants preferably produce high levels of luminescence which is detectable by a human eye.

The invention is useful: (1) as a commodity product for ornamental flowers and horticultural markets, (2) as an environmental pollution control tool and (3) for basic research, e.g., as an improved reporter system.

The following abbreviations are used throughout the specification. PCR—polymerase chain reaction; RB—right border; LB—left border (note: the DNA sequence located between right and left borders of the binary plasmid is integrated into host plant nuclear genome); MCS—multiple cloning site; pSAT vectors—series of vectors used for subcloning of cassettes, carrying genetic sequences, into binary PZP-RCS plasmid; PZP-RCS plasmid—binary vector used for plant transformation; pLDCtV—chloroplast transformation vector (Ref: De Cosa et al, 2001.); pUniPlast—a plastid transformation system developed by BioGlow Inc; HE—homing endonuclease; ZNF—zinc finger nuclease.

Figure 1:
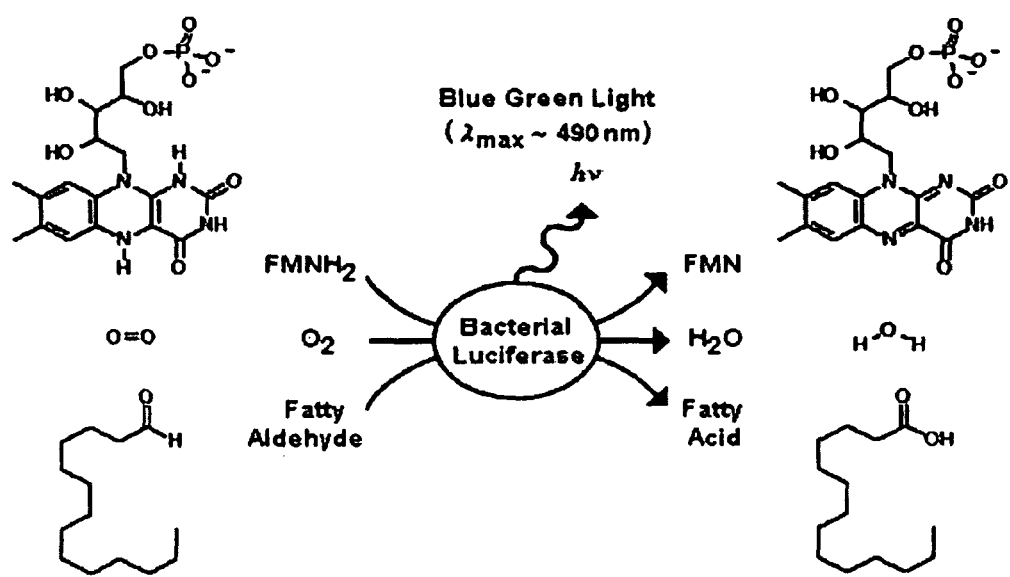
FIG. 1: Schematic illustration of the biochemistry of a bacterial luminescence reaction.
Figure 2:
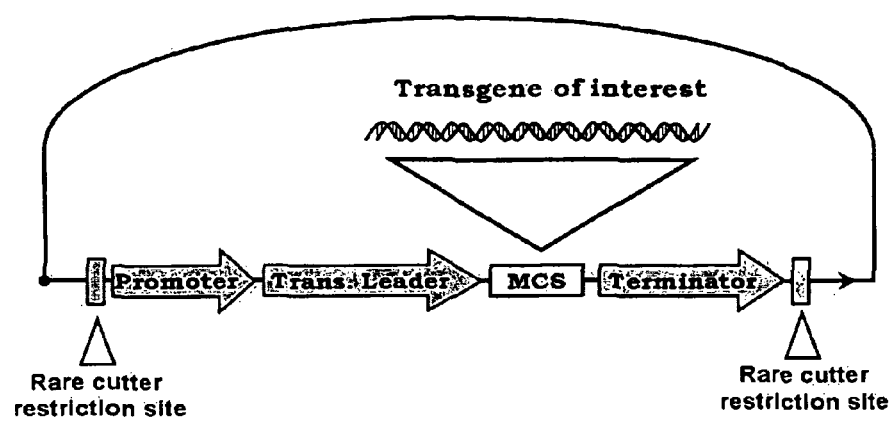
FIG. 2: (A) Schematic illustration of a transgene cloned into a donor vector, pCas vector. The region from the 5'-end of the leftmost rare cutter restriction site to the 3'-end of the rightmost rare cutter restriction site (or rare cutting enzyme sequence) represents an expression cassette to be introduced into plastid genome.
Figure 2:
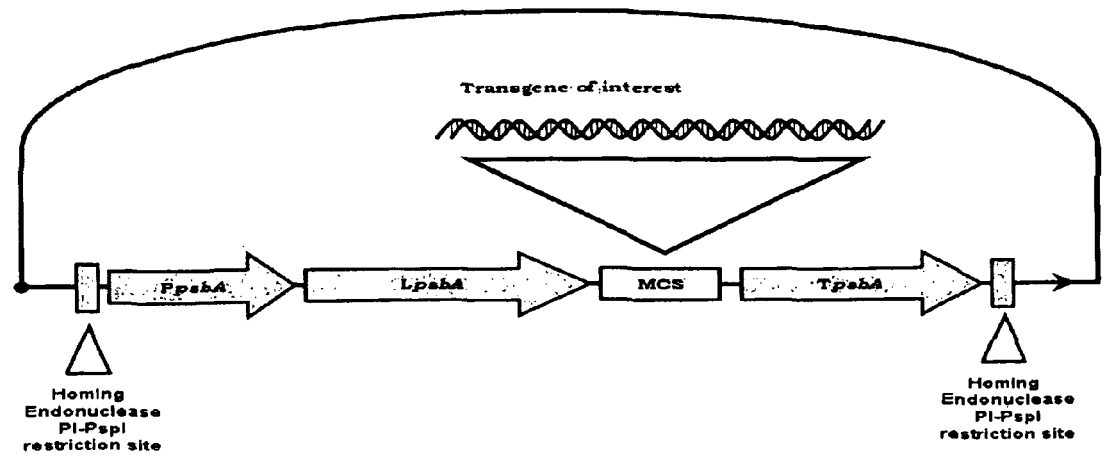

Biochemistry of Bacterial Luminescence:

The bacterial luminescence reaction involves bacterial luciferase; two substrates, i.e., reduced flavin mononucleotide (FMNH$_2$) and a long-chain aldehyde; and oxygen. See FIG. 1.

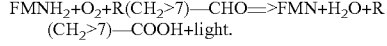

Flavin mononucleotide (FMNH$_2$) cannot be substituted by another type of nucleotide (such as NADH). However, the aldehyde specificity is much less restricted. It has been shown that a wide range of aldehydes with chain length longer then seven carbon atoms, including palmitaldehyde (derived from kidney cortex), tetradecanal (the original bacterial substrate) or decanal, can produce strong luminescence. (Meighen et al. *Adv. Microb. Physiol.,* 34:1-67 (1993); Meighen E. A *FASEB,* 7: 1016-22 (1993).) This was demonstrated in so-called "Standard Assay," where FMNH$_2$ is injected into solution containing an aldehyde and bacterial luciferase, resulting in rapid light emission.

Related Plant Biochemistry

Precursors of fatty acyl acids, such as acyl-ACP, are produced in both prokaryotes and eukaryotes. However, Vitamin B2 is naturally produced only in bacteria and plants, but not animals, which receive it from their diet. Intriguingly, biochemical pathways of Vitamin B2 and fatty acids synthesis are very strongly conserved amongst plants and eubacteria. (Fischer et al., *JBC,* 279:36299-36308 (2004); Slabas et al., *Biochemical Society Transactions,* 30, part 6 (2002).) Therefore, similarly to bacteria, plants possess all the basic components for bioluminescent reaction based on bacterial luciferase system. Also, transgenic plants expressing bacterial luciferase subunits A and B have been shown to produce low levels of luminescence, detectable with low-light imaging equipment (X-ray film or photomultiplier), when exposed to a substrate supplied from an external source. (Greer III L F and Szalay *Luminesc.,* 17:43-74 (2002)).

Transgenic Bioluminescent Plant

In one aspect, the invention relates to a transgenic bioluminescent plant. The plant includes an expressible heterologous nucleotide sequence, which includes a bacterial LUX operon. The LUX operon includes LUX A, LUX B, LUX C, LUX D, LUX E, and LUX G genes ("the six LUX genes"). The heterologous nucleotide sequence is expressed to render the plant cell bioluminescent.

The terms "transgenic," "transformed," "transfected" as used herein includes any cell, cell line, callus, tissue, plant tissue, or plant into which a nucleic acid heterologous to the host cell has been introduced. The term "transgenic" as used herein does not encompass an alteration of the genome (chromosomal or extra-chromosomal) by conventional plant breeding methods or by naturally occurring events, such as random cross-fertilization, non-recombinant viral infection, non-recombinant bacterial transformation, non-recombinant transposition, or spontaneous mutation. The term "transgenic plant" refers to a plant or plant tissue that contains an inheritable heterologous nucleotide sequence.

The term "bioluminescent" as used herein refers to luminescence that occurs in a plant or plant tissue, in which energy from a chemical reaction is transformed into light energy. The term "bioluminescent" further refers to the production of light in a recombinant plant or plant tissue engineered to contain chemical compounds necessary for bioluminescence in the plant or plant tissue. Preferably, the transgenic plant is "stably" bioluminescent, which refers to the introduction and integration of a heterologous nucleotide sequence for bioluminescence into the genome of a transfected cell.

An example of a bioluminescent chemical reaction is a reaction in which a chemical substrate, such as luciferin, reacts with oxygen in the presence of an enzyme, such as luciferase. See the above description of bacterial luminescence.

The term "plant" is used broadly herein to refer to a eukaryotic organism containing plastids, particularly chloroplasts, and includes any such organism at any stage of development. The term "plant" as used herein refers to a whole plant or a part of a plant (e.g., a plant cutting, a plant cell, a plant cell culture, a plant organ, a plant seed, and a plantlet), a seed, a cell- or a tissue-culture derived from a plant, plant organ (e.g., embryos, pollen, ovules, seeds, leaves, flowers, branches, fruit, kernels, ears, cobs, husks, stalks, roots, root tips, anthers, etc.).

Any plant may be used for the invention. For example, *Nicotiniana benthamiana, Arabidopsis thaliana,* or *Nicotiana tabacum* (tobacco) can be used, as they are frequently employed as model organisms in plant research and a large amount of data regarding their biology has been accumulated. Also, a good model organism for the bioluminescent plants of the present invention are plants which intrinsically express large amounts of Vitamin B2, such as, for example, asparagus or chard. To minimize costs, the luminescent system from several highly luminescent bacterial species, such as *Photobacterium leiognathi* or *Vibrio harveyi*, as well as *Shewanella hanedai*, is transferred into several plant species. Since this approach requires application of essentially same technology in parallel on several gene transfers, this strategy does not significantly increase costs. Other preferred plants include ornamental plants, useful or ornamental trees, flowers, cut flowers, shrubs, or turf.

The transgenic bioluminescent plant, as used herein, includes at least one plant cell. A "plant cell" refers to any cell of a plant, either taken directly from a seed or plant, or derived through culture from a cell taken from a plant. A plant cell includes, for example, cells from undifferentiated tissue (e.g., callus), plant seeds, propagules, gametophytes, sporophytes, pollen, microspores, and embryos. A plant cell typically contains a "plastid," which refers to an organelle with its own genetic machinery in a plant cell. Examples of a plastid include chloroplasts, chromoplasts, etioplasts, gerontoplasts, leucoplasts, proplastids, etc.

The transgenic bioluminescent plant further includes an expressible heterologous nucleotide sequence. The term "expressible," "expressed," and variations thereof refer to the ability of a cell to transcribe a nucleotide sequence to mRNA and translate the mRNA to synthesize a peptide that provides a biological or biochemical function. Preferably, the cell is a plant cell.

As used herein, "heterologous" refers to that which is foreign or non-native to a particular host or genome. Accordingly, a "heterologous nucleotide sequence" or "transgene" refers to a nucleotide sequence that originates from a species foreign to the host organism, or if the nucleotide sequence originates from the same species as the host, the nucleotide sequence is substantially modified from its native form in composition and/or genomic locus by deliberate genetic manipulation. The term "nucleotide sequence" refers to a sequence of two or more nucleotides, such as RNA or DNA. A "heterologous protein" refers to a protein that is foreign or non-native to a host cell and is typically encoded by a heterologous nucleotide sequence.

The LUX Operon

The luminescence in bacteria is based on a functional LUX operon, highly conserved amongst different bacterial families. The bacteria do not constantly emit light and the operon is induced by different physiological conditions, such as quorum sensing in light organs of marine animals. LUX contains 6 basic luminescence genes in the following order: C-D-A-B-E-G.

The LUX A and B genes encode luciferase subunits. The LUX C, D and E genes encode fatty-reductase complex which produces aldehyde for the reaction. The LUX G gene encodes an exchange factor, facilitating $FMNH_2$ turnover at the enzyme active site. (Lin et al., *BBRC*, 246(2):446-52 (1998)). LUX G is the "molecular switch" for $FMNH_2$ turnover. Preferably, the heterologous nucleotide sequence does not include a gene encoding *Vibrio harveyi* FRP.

The LUX CDE enzymatic complex diverts a range of fatty-acyl acids, such as acyl-CoA, acyl-ACP and others from the basic fatty acids biosynthesis cycle, converts them to the aldehyde substrate and channels them to the luminescence reaction. The other substrate, the $FMNH_2$, is naturally produced in bacteria. One of the pathways for $FMNH_2$ production in the luminescent bacteria is encoded by the RIB operon, immediately adjacent to the LUX operon. (Lee et al., *Journal of Bacteriology* 176(7):2100-2104 (1994); Jones et al. *Biochem. J.*, 347:205-209 (2000).)

In one embodiment, the heterologous nucleotide sequence includes a bacterial LUX operon. Use of the complete bacterial LUX operon allows for intrinsic bioluminescence, which refers to the ability of a cell to contain all of the required elements for production of light in the transgenic cell, without the requirement for exogenous addition of chemical compounds. Preferably, the cell is a cell from a plant.

The term "operon" refers to a nucleotide sequence which codes for a group of genes transcribed together. The term "gene" refers to chromosomal DNA, plasmid DNA, cDNA, synthetic DNA, or other DNA that encodes a peptide, polypeptide, protein, or RNA molecule, and regions flanking the coding sequence involved in the regulation of expression. Some genes can be transcribed into mRNA and translated into polypeptides (structural genes); other genes can be transcribed into RNA (e.g., rRNA, tRNA); and other types of genes function as regulators of expression (regulator genes).

The term "LUX operon" as used herein refers to an operon that includes at least six genes for intrinsic bioluminescence. The six genes include LUX A, LUX B, LUX C, LUX D, LUX E, and LUX G genes.

For purposes of the invention, the genes corresponding to the LUX operon, and any other gene required for proper functioning of LUX luciferase in a plant, are isolated from the genome of luminescent bacteria. For example, the LUX operon and LUX A, LUX B, LUX C, LUX D, LUX E, and LUX G genes may be derived from any bioluminescent bacteria that express the LUX operon or six LUX genes to generate bioluminescence.

Examples of a nucleotide sequence encoding the full LUX operon is presented in GenBank under accession numbers AY341062 (*Vibrio fischeri* [*Vibrio fischeri* strain ATCC 7744 lux operon, complete sequence](SEQ ID NO: 7); EU192082 (*Vibrio harveyi* [*Vibrio harveyi* BCB440 lux operon, complete sequence]) (SEQ ID NO: 8); AF403784 (*Photorhabdus luminescens*, (formally referred as *Xenorhabdus luminescens* [*Photorhabdus luminescens* lux operon, complete sequence]) (SEQ ID NO: 9); and AB261992 (*Shewanella hanedai* [*Shewanella hanedai* lux operon (luxC, luxD, luxA, luxB, luxE, luxG) genes and flanking regions, strain: NCIMB 2157]) (SEQ ID NO: 10); and M63594 (*Photobacterium leiognathi* [*Photobacterium leiognathi* lux operon (luxC, luxD, luxA, luxB, luxE, luxG) genes, complete cds]) (SEQ ID NO: 11); and DQ988873 (*Photobacterium phosphoreum* [*Photobacterium phosphoreum* strain ATCC 11040, complete LUX and RIB operons]) (SEQ ID NO: 12).

Examples of a nucleotide sequence encoding LUX A, LUX B, LUX C, LUX D, LUX E, and LUX G genes are included in the nucleotide sequences encoding the full LUX operon, listed above. For example, the following LUX genes were derived from GenBank accession number M63594 (*Photobacterium leiognathi* [*Photobacterium leiognathi* lux operon (luxC, luxD, luxA, luxB, luxE, luxG) genes, complete cds]) (SEQ ID NO: 11): LUX A (SEQ ID NO: 13), LUX B (SEQ ID NO: 14), LUX C (SEQ ID NO: 15), LUX D (SEQ ID NO: 16), LUX E (SEQ ID NO: 17), and LUX G (SEQ ID NO: 18) genes.

Further examples of a LUX E gene is presented in GenBank accession number M62812 for *Vibrio fischeri* [*Vibrio fischeri* LuxE (luxE) gene, partial cds; and LuxG (luxG) gene, complete cds]) (SEQ ID NO: 19). Further examples of a LUX G gene is presented in the sequences of SEQ ID NO: 53 (*Photobacterium leiognathi* (derived from GenBank #M63594); SEQ ID NO: 54 (*Photobacterium*

*phosphoreum* (derived from DQ988873); SEQ ID NO: 55 (*Vibrio harveyi* (derived from EU192082); SEQ ID NO: 56 (*Vibrio fischeri* (derived from M62812); and SEQ ID NO: 57 (*Shewanella hanedai* (derived from AB261992).

The polymerase chain reaction can be used to amplify the isolated LUX genes. Such genes may be cloned into a vector, such as a donor or acceptor vector described below.

The nucleotide sequence of the LUX operon and LUX A, LUX B, LUX C, LUX D, LUX E, and LUX G genes may be derived from wild-type organisms. Wild-type refers to the normal gene or organism found in nature without any known mutation. Other nucleotide sequences within the invention include a nucleotide sequence that encodes variants of LUX A, LUX B, LUX C, LUX D, LUX E, and LUX G proteins, and a nucleotide sequence that encodes mutant forms, recombinant forms, or non-naturally occurring variant forms of these proteins.

In some additional preferred embodiments, the heterologous nucleotide sequence (the transfected gene) includes additional genes related to production of substrates, such as, for example, LUX H, LUX F, LUX Y, and/or LUX L. In another embodiment, the heterologous nucleotide sequence further includes a LUX H, LUX F, LUX Y, and/or a LUX L gene, or combinations thereof. In some species, an additional gene not conserved amongst other luminescent bacteria, such as LUX F or LUX H, can be present but is not directly related the luminescence. These genes mainly encode for proteins with support function, such as luminescence wave length shift. (Karatani et al., *Photochemistry and Photobiology* 71(2): 230-236 (2000)).

LUX Y encodes a Yellow Fluorescent Protein (YFP). LUX Y can be isolated from, for example, *Vibrio fischeri* strain Y-1. LUX L gene codes for a lumazine protein with an amino acid identity of riboflavin synthase, and is located upstream of LUX C gene in some *Photobacterium* species. An example of a nucleotide sequence encoding *Photobacterium leiognathi* LUX F gene is presented at EBI #CAA30833 (SEQ ID NO: 20). An example of nucleotide sequence encoding *Aliivibrio fischeri* yellow fluorescent protein LUX Y is presented at EBI #AAA27544 (SEQ ID NO: 21). An example of a nucleotide sequence encoding *Vibrio* sp. BCB494 LUX H is presented at UniProtKB/TrEMBL entry B0F6S8, EBI #ABY56819 (SEQ ID NO: 22).

In another embodiment, the heterologous nucleotide sequence includes a plastid targeting sequence. A "plastid targeting sequence" as used herein refers to a nucleotide sequence that encodes a polypeptide sequence, which can direct a second polypeptide to a plastid of the plant cell. Preferably, the plastid targeting sequence is a chloroplast targeting sequence.

It is known in the art that non-chloroplast proteins may be targeted in vivo and in vitro to the chloroplast by use of protein fusions with a peptide encoded by a chloroplast targeting sequence. For example, luciferase genes of a heterologous nucleotide sequence may be fused with a plastid targeting sequence. When the luciferase gene is expressed, the targeting sequence is included in the translated polypeptide. The targeting sequence then directs the polypeptide into a plastid, such as a chloroplast.

Typically, the chloroplast targeting sequence encodes a polypeptide extension (called a chloroplast transit peptide (CTP)). The polypeptide extension is linked to the N-terminus of the heterologous peptide encoded by the heterologous nucleotide sequence.

Those skilled in the art will appreciate that there are a variety of known targeting sequences that can be added to the expressed polypeptide. (See, for example, Gnanasambandam A, Polkinghorne IG, and Birch RG. "Heterologous signals allow efficient targeting of a nuclear-encoded fusion protein to plastids and endoplasmic reticulum in diverse plant species." *Plant Biotechnol J.*, 2007 5(2):290-6; and Rensink W A, Pilon M, and Weisbeek P. "Domains of a transit sequence required for in vivo import in *Arabidopsis* chloroplasts." *Plant Physiol.* 1998 118(2):691-9).

Examples of a chloroplast targeting sequence include a sequence that encodes the *Arabidopsis thaliana* EPSPS chloroplast transit peptide, the *Petunia hybrida* EPSPS chloroplast transit peptide, and the rice rbcS gene chloroplast targeting sequence.

Further examples of a chloroplast target peptide include the small subunit (SSU) of ribulose-1,5,-biphosphate carboxylase, and the light harvesting complex protein I and protein II. Incorporation of a suitable chloroplast target (transit) peptide has been shown to target heterologous protein sequences to chloroplasts in transgenic plants. Those skilled in the art will recognize that various chimeric constructs can be made, if needed, that utilize the functionality of a particular CTP to import a given gene product into a chloroplast.

Other CTPs that may be useful in practicing the present invention include PsRbcS-derived CTPs (*Pisum sativum* Rubisco small subunit CTP); AtRbcS CTP (*Arabidopsis thaliana* Rubisco small subunit 1A CTP; CTP1); AtShkG CTP (CTP2); AtShkGZm CTP (CTP2synthetic; codon optimized for monocot expression); PhShkG CTP (*Petunia hybrida* EPSPS; CTP4; codon optimized for monocot expression); TaWaxy CTP (*Triticum aestivum* granule-bound starch synthase CTPsynthetic, codon optimized for corn expression): OsWaxy CTP (Oryza sativa starch synthase CTP); NtRbcS CTP (*Nicotiana tabacum* ribulose 1,5-bisphosphate carboxylase small subunit chloroplast transit peptide); ZmAS CTP (*Zea mays* anthranilate synthase alpha 2 subunit gene CTP); and RgAS CTP (Ruta graveolens anthranilate synthase CTP). Other transit peptides that may be useful include maize cab-m7 signal sequence and the pea (*Pisum sativum*) glutathione reductase signal sequence.

Additional examples of such targeting sequences may include: spinach lumazine synthase (SEQ ID NO: 23), *Chlamydomonas* ferredoxin (SEQ ID NO: 24), and Rubisco activase (SEQ ID NO: 25) transit peptides, and others.

The chloroplast targeting sequence may be used to target any peptide encoded by a heterologous nucleotide sequence to the chloroplast or other plastid. In one embodiment, the chloroplast targeting sequence is linked to a 5'- or a 3'-end of the LUX A, LUX B, LUX C, LUX D, LUX E, or LUX G genes. In another embodiment, the chloroplast targeting sequence is linked to a 5'- or a 3'-end of a gene encoding a fluorescent protein.

In one embodiment, the heterologous nucleotide sequence can be placed in a single vector. For example, the heterologous nucleotide sequence can include the six LUX genes in a single vector. See FIG. 10. In another embodiment, a heterologous nucleotide sequence encoding one of the six LUX genes can be placed in a different vector for each LUX gene, resulting in multiple different vectors. See FIG. 9. The heterologous nucleotide sequence can additionally include at least one gene encoding a cofactor for enhancing bioluminescence.

The term "vector" as used herein refers to a vehicle used for introduction of a nucleotide sequence into a host. A vector may be a plasmid, cosmid, phage, transposon, virus, or any other suitable vehicle. Preferably, the vector is a plasmid. A vector may include regulatory sequences useful for expression of a gene product in a host, including but not limited to a promoter, ribosomal binding site, and termination sequences. In one preferred embodiment, the vector is a vector for transforming a plastid as described below in another aspect of the invention.

Numerous vectors are suitable for stable transformation of a plant cell or a plastid. Accordingly, the LUX genes may be delivered into nuclear or chloroplast genomes.

In one embodiment, the vector is a binary vector. A "binary vector" refers to a vector that includes a modified T-region from Ti plasmid, which allows replication in *E. coli* and in *Agrobacterium* cells, and usually includes selection marker genes. Preferably, the vector is a binary pPZP-RCS vector (Goderis et al, 2002), assembled employing expression cassettes derived from the pSAT vectors (Tzfira et al., (2005) "pSAT vectors: a modular series of plasmids for autofluorescent protein tagging and expression of multiple genes in plants." *Plant Mol. Biol.*, 57(4):503-16 (2005)).

The pSAT vectors contain a plant promoter, an MCS and a plant terminator, which allows for subcloning and expression of one transgene. Cassettes, containing promoter/gene of interest/terminator sequence are derived from pSAT vectors using homing endonucleases and subcloned into the same sites of the pPZP-RCS vector. The pPZP-RCS is a binary vector that includes homing endonuclease enzyme recognition sites in its MCS and allows for cloning of multiple (from 6 or more) pSATs derived cassettes into it, thus serving as a single binary (acceptor) vector. This vector system allows for multiple nuclear transgene expression without requiring bicistronic RNAs or internal ribosome binding sites (IRES). Accordingly, use of pSAT vectors allows introduction of multiple genes into a single acceptor vector. The single pPZP-RCS acceptor vector containing the multiple genes may then be introduced in a single transformation event into a plant, without requiring three or more subsequent plant transformations.

The specific pSATs and GeneBank accession numbers are: pSAT1-EGFP-C1 (SEQ ID NO: 26), pSAT2-EGFP-C1 (SEQ ID NO: 27), pSAT3-EGFP-C1 (SEQ ID NO: 28), pSAT4-EGFP-C1 (SEQ ID NO: 29), pSAT5-EGFP-C1 (SEQ ID NO: 30), pSAT6-EGFP-C1 (SEQ ID NO: 31) and pSAT7-EGFP-C1 (SEQ ID NO: 32), respective NCBI numbers are: AY818363 (SEQ ID NO: 26), AY818365 (SEQ ID NO: 27), AY818366 (SEQ ID NO: 28), AY818367 (SEQ ID NO: 29), AY818368 (SEQ ID NO: 30), AY818377 (SEQ ID NO: 31) and AY818384 (SEQ ID NO: 32).

In another embodiment, the vector is a plastid (chloroplast) transformation vector. Typically, a transgene in a chloroplast transformation vector is flanked by a "homologous recombination site," which is a DNA region that is homologous to a region of the plastome. The "plastome" refers to the genome of a plastid. The homologous recombination site enables site-specific integration of a transgene construct into the plastome by the process of homologous recombination. Homologous recombination is a process that naturally occurs in plastids. Homologous recombination differs from random transgene integration into plant nuclear genome. An example of a chloroplast transformation vector is pLDCtV (See De Cosa, B., Moar, W., Lee, S. B., Miller, M., and Daniell, H. (2001) "Overexpression of the Bt cry2Aa2 operon in chloroplasts leads to formation of insecticidal crystals". *Nature Biotechnol.*, vol. 19, pp. 71-74).

In a preferred embodiment of the invention, the full or partial LUX operon is directly expressed from the chloroplast genome. Insertion of the genes into chloroplast genome is done by cloning the whole LUX operon into a chloroplast transformation vector. Such a method of cloning may include transforming chloroplasts with the vector, and bringing the population of chloroplast genomes copies to homogenicity using standard methods. (See De Cosa, B., Moar, W., Lee, S. B., Miller, M., and Daniell, H. (2001) "Overexpression of the Bt cry2Aa2 operon in chloroplasts leads to formation of insecticidal crystals". *Nature Biotechnol.*, vol. 19, pp. 71-74.)

In another preferred embodiment, the vector is derived from the pUniPlast vector system, which is a plastid transformation vector system developed by BioGlow Inc.

The heterologous nucleotide sequence or vector described herein may include regulatory sequences useful for expression of a gene product in a host, such a promoter. The term "promoter" refers to a nucleotide sequence capable of controlling the expression of a coding sequence. A promoter drives expression of an operably linked nucleotide sequence. The term "operably linked" as used herein refers to linkage of a promoter to a nucleotide sequence such that the promoter mediates transcription of the nucleotide sequence. A "coding sequence" refers to a nucleotide sequence that encodes a specific amino acid sequence. A promoter is typically located upstream (5') to a coding sequence.

A wide variety of promoters is known in the art and may be used to facilitate expression of a gene in the heterologous nucleotide sequence. Examples of suitable promoters include constitutive promoters, plant tissue-specific promoters, plant development-specific promoters, inducible promoters, circadian cycle promoters, viral promoters, male germline-specific promoters, female germline-specific promoters, flower-specific promoters, and vegetative shoot apical meristem-specific promoters.

A "constitutive" promoter refers to a promoter that causes a gene to be expressed in all cell types at all times. An example of a constitutive plastid promoter is psbA, photosystem II reaction center promoter (derived from pCLT146, GeneBank #DQ463359; and rrn, chloroplast 16S rRNA gene promoter (derived from pN-IC101, GeneBank #AY442171.

Examples of nuclear genomic constitutive plant promoters include the cauliflower mosaic virus (CaMV) 35S promoter, which confers constitutive, high-level expression in most plant cells; the nopaline synthase promoter; the octopine synthase promoter; cauliflower mosaic virus 19S promoter; rice actin 1 promoter; manopine synthase promoter; and a histone promoter. Further suitable constitutive promoters include the Rubisco small subunit (SSU) promoter, leguminB promoter, TR dual promoter, ubiquitin promoter, and Super promoter. Different heterologous nucleotide sequences or vectors may contain different promoters to prevent gene silencing when several consecutive genes on a chromosome are expressed from the same promoter.

An "inducible" promoter refers to a promoter that is regulated in response to a stress or stimuli. Examples of inducible promoters include a tetracycline repressor system, Lac repressor system, copper-inducible system, salicylate-inducible system (such as the PR1a system), and alcohol-inducible system. Further examples include inducible promoters that are regulated in response to environmental, hormonal, chemical, and/or developmental stress or stimuli. Such stress or stimuli include heat (e.g., tomato hsp70 promoter or hsp80 promoter); light; hormones (e.g., steroid-inducible MMTV LTR promoter), such as abscisic acid; chemicals, such as methyl jasmonate, salicylic acid; increased salinity; drought; pathogen (e.g., promoter of the PRP1 gene); heavy metals (e.g., heavy metal-inducible metallothionein I promoter and the promoter controlling expression of the tobacco gene cdiGRP; and wounds (e.g., pinII promoter). Preferably, the promoter is a promoter induced by heavy metals.

A "tissue-specific" promoter as used herein refers to a promoter that drives expression of an operably linked nucleotide sequence to a particular tissue. A tissue-specific promoter drives expression of a gene in one or more cell types in a specific organ (such as leaves, or seeds), specific tissues (such as embryo or cotyledon), or specific cell types (such as seed storage cells or leaf parenchyma). Examples include *Gentiana triflora* promoter for chalcone synthase (NCBI accession AB005484), a seed-specific promoter, such as β-conglycinin, napin promoter, and phaseolin; mature leaves-specific promoter, such as the SAG promoter from *Arabidopsis*.

Promoters responsible to the circadian cycle can also be used in the heterologous nucleotide sequence or vector. Such promoters include the native ELF3 promoter and the promoter from the chlorophyll a/b binding protein (CAB2 promoter).

The heterologous nucleotide sequence or vector may also include leader sequences, such as; rbcL, ribulose-bisphosphate carboxylase gene leader sequence (derived from pCLT516, GeneBank #DQ882177: (SEQ ID NO: 33); and Shine-Dalgarno consensus ribosome binding sequence (AG-GAGG); and terminators, such as psbA, which is a photosystem II reaction center terminator (derived from pCLT146, GeneBank #DQ463359: (SEQ ID NO: 34); and rps16 gene rps16 terminator (derived from pL3 vector series, GeneBank #EU520589, EU520588, EU520587: (SEQ ID NO: 35).

In addition, the heterologous nucleotide sequence or vector may include a nucleotide sequence for a selectable and/or screenable marker. A "selection marker" refers to a protein necessary for survival or growth of a transformed plant cell grown in a selective culture regimen. Typical selection markers include sequences that encode proteins, which confer resistance to selective agents, such as antibiotics, herbicides, or other toxins. Examples of selection markers include genes for conferring resistance to antibiotics, such as spectinomycin, streptomycin, tetracycline, ampicillin, kanamycin, G 418, neomycin, bleomycin, hygromycin, methotrexate, dicamba, glufosinate, or glyphosate.

Various other selection markers confer a growth-related advantage to the transformed cells over the non-transformed cells. Examples include selection markers for β-glucuronidase (in conjunction with, for example, cytokinin glucuronide), mannose-6-phosphate isomerase (in conjunction with mannose), and UDP-galactose 4-epimerase (in conjunction with, for example, galactose).

Preferably, the selection marker is functional in plastids. Such selection markers include those which confer resistance to spectinomycin (e.g., encoded by the resistance gene, aadA), streptomycin, kanamycin, lincomycin, gentamycin, hygromycin, methotrexate, bleomycin, phleomycin, blasticidin, sulfonamide, phosphinothricin, chlorsulfuron, bromoxynil, glyphosate, 2,4-D, atrazine, 4-methyltryptophan, nitrate, S-aminoethyl-L-cysteine, lysine/threonine, aminoethyl-cysteine or betaine aldehyde. Especially preferred are the genes aadA (GeneBank NC_009838), nptII (GeneBank FM177583), BADH (GeneBank AY050316), aphA-6 (GeneBank X07753).

After a heterologous nucleotide sequence has been introduced into a host cell, it may be advantageous to remove or delete certain sequences from the plastome or genome of the plant or cell. For example, it may be advantageous to remove a selection marker gene that has been introduced into a genome if the selection marker is no longer necessarily required after the selection phase. Methods for directed deletion of sequences are known in the art. For example, the nucleotide sequence encoding a selection marker preferably includes a homology-based excision element, such as Cre-lox and attB/attP recognition sequences, which allow removal of the selection marker genes using phage site-specific recombinases.

In one embodiment, the heterologous nucleotide sequence or vector includes reporter genes. Reporter genes encode readily quantifiable proteins which, via their color or enzyme activity, allow an assessment of the transformation efficiency, the site or time of expression or the identification of transgenic plants. Examples of reporter genes include green fluorescent protein (GFP), luciferase, β-Galactosidase, β-Glucuronidase (GUS), R-Locus gene product, β-Lactamase, xy1E gene product, Alpha-amylase, and Tyrosinase.

The heterologous nucleotide sequence or vector may include sequences encoding a fluorescent protein that are excited or fluoresce at different wavelengths, at different periods of time, or under different conditions. Such a fluorescent protein is DsRed (GeneBank #EU827527, DsRed-Monomer gene, synthetic construct)(SEQ ID NO: 129), which can fluoresce and emit light at red wavelengths.

The heterologous nucleotide sequence or vector may also include functional elements, which influence the generation, multiplication, function, use or value of the heterologous nucleotide sequence or vector used within the scope of the present invention. Examples of functional elements include replication origins (ORI), which make possible an amplification of the heterologous nucleotide sequence or vector according to the invention in, for example, *E. coli* or in plastids; multiple cloning sites (MCSs), which permit and facilitate the insertion of one or more nucleic acid sequences; homologous recombination sites, allowing stable recombination of transgenes into plastid genome; and border sequences, which make possible *Agrobacterium*-mediated transfer of the heterologous nucleotide sequence or vector into plant cells for the transfer and integration into the plant genome, such as, for example, the right or left border of the T-DNA or the vir region.

The heterologous nucleotide sequence or vector may optionally include RNA processing signals, e.g., introns, which may be positioned upstream or downstream or within a polypeptide-encoding sequence in the heterologous nucleotide sequence. Intron sequences are known in the art to aid in the expression of heterologous nucleotide sequences in plant cells.

The heterologous nucleotide sequence or vector described herein preferably includes a rare cutting enzyme sequence. A "rare cutting enzyme" refers to an enzyme that cleaves a nucleotide sequence at a recognition site of eight or more nucleotide base pairs characteristic to the particular enzyme. The frequency of cutting for a particular rare cutting enzyme is determined in part by the length of the recognition sequence, and the distribution of bases and motifs in the target DNA. Examples of rare cutting enzymes include endonucleases, homing endonucleases, and zinc finger nucleases.

Homing endonucleases are double stranded DNases with large and extremely rare recognition sites that are longer than eight base pairs long, usually 12-40 base pairs long. Homing endonuclease I-SceI has an 18 base pair long recognition sequence, which statistically may only occur once in every $7 \times 10^{10}$ base pairs, which is equivalent in length to 20 mammalian-sized genomes. On the other hand, a "regular" restriction enzyme, such as EcoRI having a six base pair recognition site, appears on average every 4×10³ bp, and thus on average 10⁶ times in a single mammalian genome. Thus, on average, homing endonucleases are approximately 20 million times less likely to cut a given DNA sequence than a "regular" DNA restriction enzyme. This property of rare-cutting enzymes allows for their use in engineering of long DNA sequences and assembly of transformation vectors from pre-arranged expression cassettes.

Examples of homing endonucleases include F-SceI, F-SceII, F-SuvI, F-TevI, F-TevII, I-AuraI, I-AniI, I-CeuI, I-CeuAIIP, I-ChuI, I-CmoeI, I-CpaI, I-CpaII, I-CreI, I-CrepsbIP, I-CrepsbIIP, I-CrepsbIIIP, I-CrepsbIVP, I-CsmI, I-CvuI, I-CvuAIP, I-DdiII, I-DirI, I-DmoI, I-HspNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PpbIP, I-PpoI, I-SP-BetaIP, I-ScaI, I-SceI, I-SceII, I-SceIII, I-SceIV, I-SceV, I-SceVI, I-SceVII, I-SexIP, I-SneIP, I-SpomCP, I-SpomIP, I-SpomIIP, I-SquIP, I-Ssp6803I, I-SthPhiJP, I-SthPhiST3P, I-SthPhiS3bP, I-TdeIP, I-TevI, I-TevII, I-TevIII, I-UarAP, I-UarHGPAIP, I-UarHGPAI3P, I-VinIP, I-ZbiIP, PI-MtuI, PI-MtuHIP, PI-MtuHIIP, PI-PfuL PI-PfuII, PI-PkoI, PI-PkoII, PI-PspI, PI-Rma438121P, PI-SPBetaIP, PI-SceI, PI-TfuI PI-TfuII, PI-ThyI, PI-TliI, PI-TliII.

A "zinc finger nuclease" or "ZFN" refers to a chimeric protein molecule that includes at least one zinc finger DNA binding domain operably linked to at least one nuclease capable of cleaving DNA. A zinc finger nuclease is capable of directing targeted genetic recombination or targeted mutation in a host cell by causing a break at a target site. A zinc finger typically includes a DNA-binding domain and a DNA-cleavage domain, wherein the DNA binding domain includes at least one zinc finger and is operably linked to a DNA-cleavage domain. A preferred example of a zinc finger nuclease is ZFN QQR (TTCTTCCCCGAAT-TCGGGGAAGAA)(SEQ ID NO: 36)

A "rare cutting enzyme sequence" refers to a nucleotide sequence in a target DNA that is a recognition site for a rare cutting enzyme to cut the target DNA at the recognition site. The rare cutting enzyme sequences are typically 10 or more base pairs in length and occur rarely, if at all, in a host cell.

Examples of preferred rare cutting enzyme sequences include the following:

```
PI-PspI;                    (SEQ ID NO: 37)

I-CeuI;                     (SEQ ID NO: 38)

I-SceI;                     (SEQ ID NO: 39)

I-PpoI;                     (SEQ ID NO: 40)
and

AscI; FseI; and ZFN QQR.
```

Any combination of rare cutting enzyme sequences can be included in the heterologous nucleotide sequence or vector of the invention. In the embodiments described herein, rare cutting enzymes (e.g., endonucleases, homing endonucleases and gateway technology) may be used to clone LUX genes into any vector, or plant cellular vectors, or chloroplast expression vectors.

Preferably, a rare cutting enzyme sequence flanks a gene in the heterologous nucleotide sequence or vector. The rare cutting enzyme sequence may flank either the 5'-end, the 3'-end, or both the 5'- and 3'-end of a given sequence or gene.

More preferably, a unique rare cutting enzyme sequence flanks each gene. For example, in one embodiment, a unique rare cutting enzyme sequence flanks a reporter gene, another unique rare cutting enzyme sequence flanks a selection marker gene, yet another unique rare cutting enzyme sequence flanks a multiple cloning site, and a further unique rare cutting enzyme sequence flanks a regulatory sequence. A first nucleotide sequence "flanks" a second nucleotide sequence if the two sequences are adjacent to one another, or if the two sequences are separated by no more than about 100 nucleotides, preferably by no more than about 50 nucleotides.

A first nucleotide sequence is "adjacent" to a second nucleotide sequence if the two sequences are attached to or positioned next to one another, having no intervening nucleotides. By way of example, the first nucleotide sequence 5'-AAAAA-3' is adjacent to the second nucleotide sequence 5'-TTT-3' when the two are connected thus: 5'-AAAAATTT-3' or 5'-TTTAAAAA-3', but not when the two are connected thus: 5'-AAAAACTTT-3'.

In another embodiment, the heterologous nucleotide sequence or vector includes at least one gene encoding a cofactor for enhancing bioluminescence. As used herein, the term "cofactor" refers to an organic molecule, an inorganic molecule, a peptide, or a protein required for enzyme activity. The protein products encoded by the LUX genes may require the cofactors for regenerating and enhancing $FMNH_2$ pool, and fatty acid precursors in order to induce bioluminescence. These cofactors are typically synthesized in the chloroplasts.

In some applications of the present invention, the level of luminescence may be enhanced by additional transfection of a riboflavin operon (RIB operon) and/or genes encoding for fatty acid donors (i.e. genes belonging to the Fatty Acids Synthase [either FASI or FASII] pathway). In particular, in some embodiments, a component of the RIB operon (such as, for example, ribE and ribH (encoding riboflavin synthase or lumasine synthase, respectively)) involved in riboflavin synthesis and/or donors of fatty acids for the aldehyde synthesis, such as bacterial or plant acyl carrier protein (ACP), can be transfected into a plant cell as part of a heterologous nucleotide sequence or vector. In plants, ACP exists as a small cofactor protein that participates in reactions of fatty acid biosynthesis and metabolism. Addition of these genes strongly boosts substrate production and increases bioluminescence levels.

Specific examples of suitable cofactors for enhancing bioluminescence include a polypeptide encoded by a RIB operon (GeneBank accession AF364106) (SEQ ID NO: 41) or RIB genes, bacterial acyl carrier protein, plant acyl carrier protein, transcriptional activators, and FRE flavin reductases enzymes from either luminescent (*P. luminescens* (GeneBank #D17745) (SEQ ID NO: 42) and *V. fischeri* (GeneBank #D17744) (SEQ ID NO: 43) or other bacteria (*E. coli* FRE, GeneBank #NC_010473) (SEQ ID NO: 44). Further examples of suitable cofactors include riboflavin kinases (RFK) such as plant *Arabidopsis thaliana* RFK (GeneBank #NC_003075) (SEQ ID NO: 45) or bacterial *E. coli* RFK (GeneBank #NC_009801) (SEQ ID NO: 46).

As used herein, "enhancing" bioluminescence refers to increased bioluminescent intensity or brightness that is greater than that without the cofactor. Enhancing bioluminescence may further include replenishing exhausted luciferin or other substrate or cofactor or other protein in order to continue or revive the reaction for bioluminescence.

The term "RIB operon" refers to an operon containing genes coding for proteins essential to production of riboflavin (commonly known as VitaminB2). The RIB operon in the bacteria belonging to the genus *Bacillus* includes following genes: ribO gene coding for control element, ribG gene coding for deaminase/reductase, ribB gene coding for riboflavin synthase (a-subunit), ribA gene coding for GTP-cyclohydrolase/3,4-dihydroxy-2-butanon-4-phosphate synthase, ribH gene coding for lumasine synthetase, and ribT gene coding for a protein with unknown function. Nucleotide sequences of ribG, ribB, ribA, ribH and ribH genes of *Bacillus subtilis* are presented in GenBank under accession numbers X51510 (*B. subtilis* riboflavin biosynthesis operon ribG, ribB, ribA, ribH, and ribT genes) (SEQ ID NO: 47). The rib genes for *Escherichia coli* include rib, ribA, and ribE code for GTP cyclohydrolase II, 3,4-dihydroxy-2-butanone 4-phosphate (DHBP) synthetase, and riboflavin synthetase, respectively. Nucleotide sequences of rib, ribA, and ribE genes of *E. coli* are presented in EBI under accession numbers ABV 17158 (SEQ ID NO: 48) and CAA48861 (SEQ ID NO: 49), respectively. Similarly, *Photobacterium leiognathi*, strain PL741, RIB operon, encoding for rib E, H, B and A genes can be found at the GeneBank under accession number AF364106 (SEQ ID NO: 50).

The term "plant acyl carrier protein" or "bacterial acyl carrier protein" refer to any acyl carrier protein having the essential functional characteristics of naturally occurring ACP molecules found in plants or bacteria. Nucleotide sequences encoding a plant or bacterial acyl carrier protein include those presented in GenBank such as *Arabidopsis thaliana* ACP (EBI#X13708) (SEQ ID NO: 51) and *Photobacterium* sp. ACP (EBI #: EAR53459) (SEQ ID NO: 52).

Figure 7:
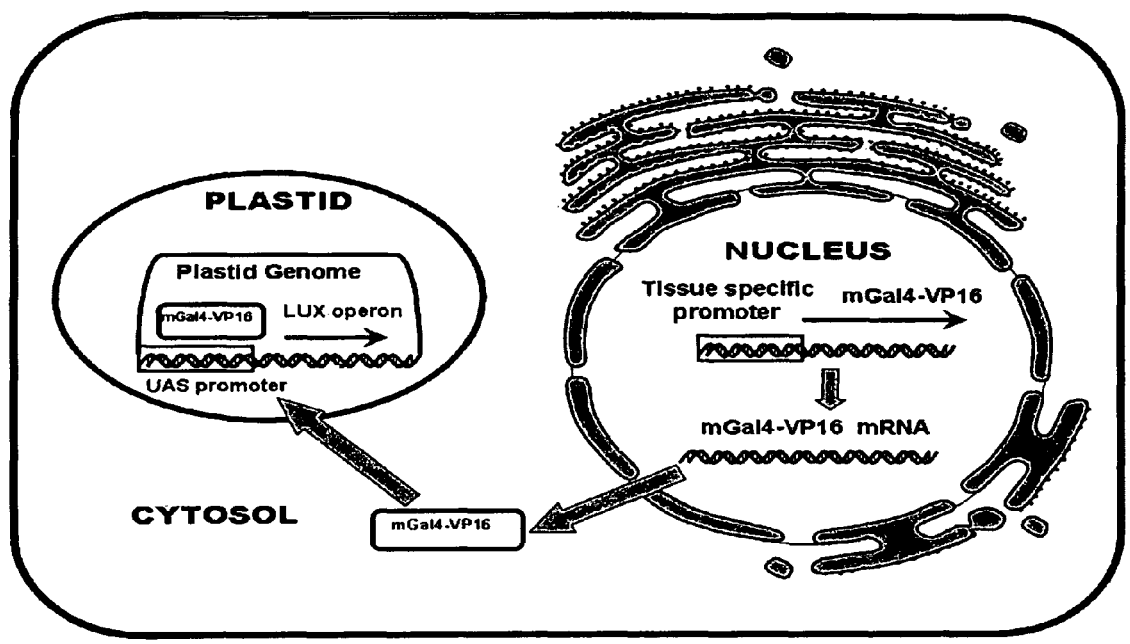
FIG. 7: Schematic illustration of a chimeric transcriptional activator containing the yeast GAL4 DNA binding domain [mGal4, modified for optimal activity in *Arabidopsis*] fused to the VP16 transcriptional activator from Herpes simplex virus. This mGal4-VP16 transcription factor expression will be controlled by an inducible promoter, such as a tissue-specific or circadian or otherwise inducible (stress, heavy metal, etc) promoter in the nucleus. When the tissue-specific promoter is activated, the mGal4-VP16 protein will transcribed and be targeted to a plastid (e.g., a chloroplast) using N-terminally fused plastid transit peptide. The LUX genes in the chloroplast will be driven by an mGal4-VP16-inducible Gal4-UAS promoter (http://www-.plantsci.cam.ac.uk/Haseloff/Home.html), to which mGal4-VP16 binds and thus activates LUX transcription. Thus, activation of the LUX operon is indirect.
Figure 12:
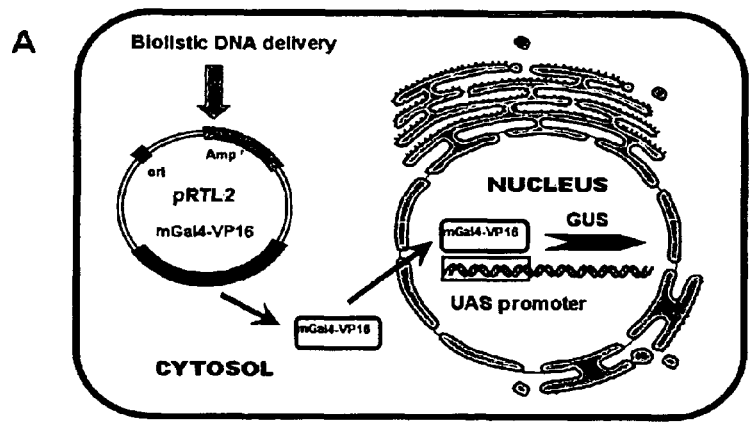
FIG. 12: Remote activation of an inducible promoter in-planta. (A) Schematic representation of beta-glucuronidase (GUS) activation by plasmid-borne mGal4-VP16. (B). mGal4-VP16 expressed from transient plant expression vector pRTL2 was biolistically delivered into leaves of an *Arabidopsis* plant carrying UAS driven, genome-integrated GUS reporter gene. Transient expression of mGal4-VP16 resulted in activation of GUS expression and was detected by histochemical staining (C) Specificity of UAS promoter activation has been confirmed when similar biolistic delivery has been made into a wild-type *Arabidopsis* plants, carrying no UAS driven GUS gene. Krichevsky et al unpublished and Developmental Biology (2007).
Figure 12:
Figure 12:

In one embodiment, a transgenic bioluminescent plant as described above is provided in which a first heterologous nucleotide sequence includes, for example, a LUX operon and an inducible promoter. The plant also includes a second heterologous nucleotide sequence that includes a gene encoding a promoter and a gene encoding a transcription factor. In the present embodiment, activation of transcription of the LUX genes is indirect. See FIGS. 7 and 12.

Preferably, the promoter for the first heterologous nucleotide sequence is inducible by a transcription factor in order to activate transcription of the LUX operon. A preferred example of such a promoter is a Gal4-UAS promoter, which is inducible by mGal4-VP16 chimeric transcription factor. See FIGS. 7 & 12.

Preferably, the promoter for the second heterologous nucleotide sequence is an inducible promoter, such as a heavy metal sensitive promoter from tobacco cdiGRP gene, or a tissue-specific promoter. Preferably, the second heterologous nucleotide sequence further includes a plastid targeting sequence and/or a reporter gene (e.g., a gene that encodes a fluorescent protein).

The term "transcription factor" refers to any protein that is involved in the initiation of transcription, but which is not itself a part of the polymerase. Transcription factors interact preferentially with specific nucleotide sequences, i.e., regulatory sequences, and which in appropriate conditions stimulate transcription ("transcriptional activator") or repress transcription ("transcriptional repressor"). Preferably, the transcription factor sequence includes an mGal4 binding domain, which is modified for optimal activity in *Arabidopsis* and a VP16 domain from Herpes simplex virus. Such a sequence encodes a chimeric transcriptional activator mGal4-VP16.

Any combination of various sequences may be included in the heterologous nucleotide sequence or vector of the invention, such as sequences encoding a promoter, transcriptional leader, terminator element; sequences encoding a selectable and/or screenable marker; reporter genes; functional elements, such as an origin of replication, multiple cloning sites, border sequences; RNA processing signals; rare cutting enzyme sequences; sequences encoding a cofactor, and/or transcription factor, etc.

Figure 3:
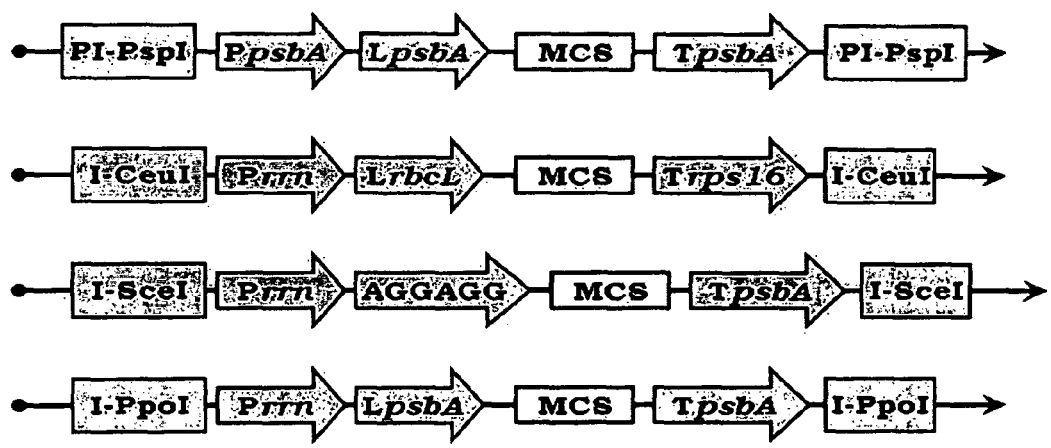
FIG. 3: Schematic illustration of four different examples of a heterologous nucleotide sequence in a pCas (donor vector) expression cassette.
Figure 4:
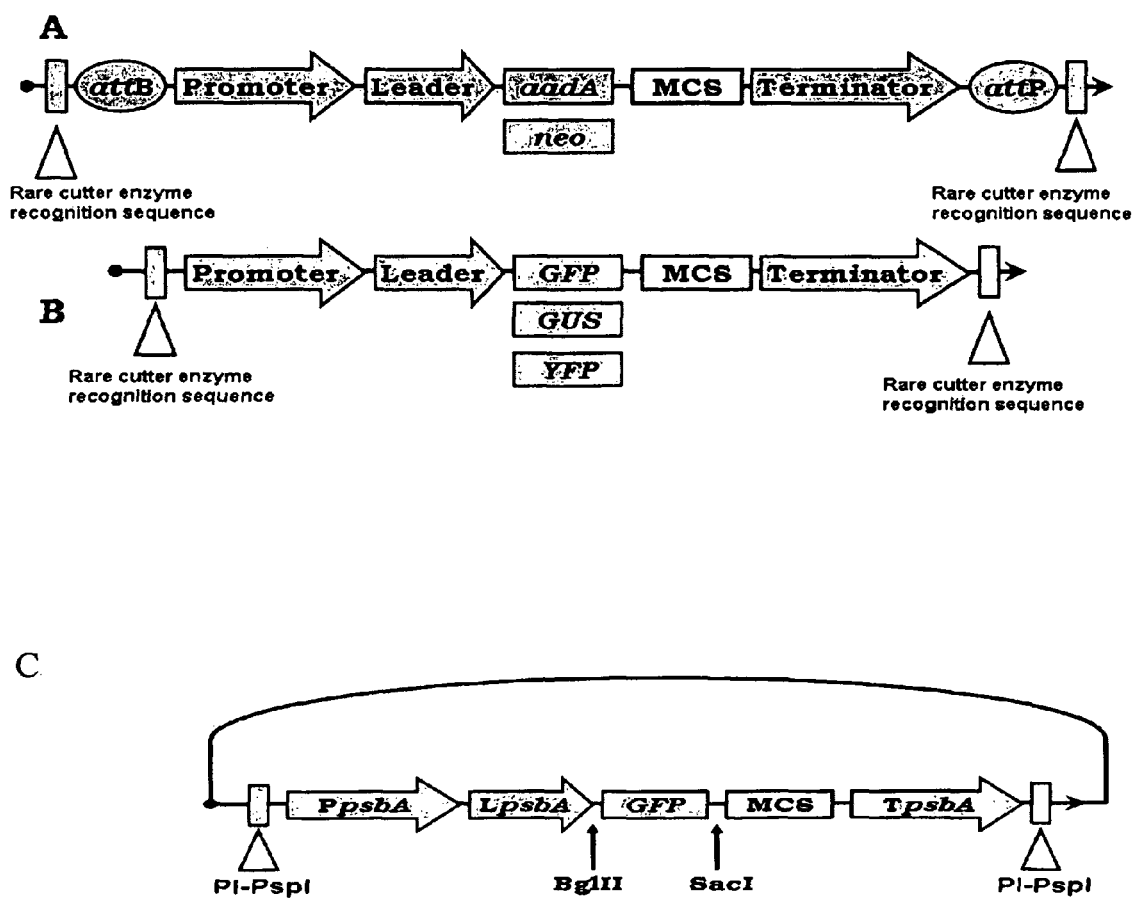
FIG. 4: Schematic illustration of pCas expression cassettes with pre-cloned antibiotic resistance and marker genes. MCS located past marker/selection genes is used to express inserted transgenes of interest on one polycistronic mRNA or as translational fusions with marker/selection genes. (A) attB/attP recombination sites flanking, selection marker expression cassette, are aimed for removal of antibiotic resistance genes from the final transgenic crop product. Spectinomycin resistance gene (aadA) and phiC31 phage site-specific recombinase attachment (attP/attB) are illustrated. phiC31 phage recombinase attachment sequences can be used to flank the selection marker gene for its future removal from commercial crops (not illustrated). (B) MCS located past reporter gene is used to express inserted transgenes of interest on one polycistronic mRNA or as translational fusions with reporter gene. (C) Schematic illustration example of fluorescent marker gene (GFP) incorporated into pre-cloned pCas expression vector. The gene encoding for Green Fluorescent Protein has been inserted using BglII and SacI restriction enzymes. Additional genes can be cloned downstream of GFP and, upon incorporation of a ribosome binding site, translationally co-expressed as a single operon unit (PI-PspI-PpsbA-LpsbA-BglII-GFP-SacI-MCS-TpsbA-PI-PspI (SEQ ID NO: 2). Abbreviations: aadA—spectinomycin resistance gene; neo—kanamycin resistance gene; GFP—green fluorescent protein; YFP—yellow fluorescent protein; GUS—beta-glucuronidase; attB/attP—selection marker excision recombination sites; HE—homing endonuclease recognition site; MCS—multiple cloning site.

See, for example, FIG. 3, which is a schematic illustration of four different examples of a heterologous nucleotide sequence in a pCas (donor vector) expression cassette. From top to bottom the examples include:
PI-PspI-PpsbA-LpsbA-MCS-TpsbA-PI-PspI;
I-CeuI-Prrn-LrbcL-MCS-Trps16-I-CeuI;
I-SceI-Prrn-AAGGAGG-MCS-TpsbA-I-SceI; and
I-PpoI-Prrn-LpsbA-MCS-TpsbA-I-PpoI. Combinations of various promoter, transcriptional leader and terminator elements can be used to produce pCas vectors with different transcription regulation elements, and thus adjustable levels of transgene expression. Different homing endonucleases used to create a number of expression cassettes to be inserted in a single pUniPlast vector.

Method for Producing a Transgenic Bioluminescent Plant

In another aspect, the invention relates to a method for producing a transgenic bioluminescent plant. The method includes transfecting at least one plant cell with a vector, growing the at least one plant cell into a mature plant, and providing a means for regulating expression of the gene. The vector includes a heterologous nucleotide sequence that includes a bacterial LUX operon. The LUX operon includes LUX A, LUX B, LUX C, LUX D, LUX E, and LUX G genes ("the six LUX genes").

The term "transfecting" or "transforming" refers to introducing a nucleotide sequence into a host cell or into plastids of the cell. The nucleotide sequence that is being introduced to the host cell or plastid of the cell may include a heterologous nucleotide sequence or a vector, as described above.

Transfection of the heterologous nucleotide sequences and plant genomic sequences is achieved by methods known to a skilled artisan. Any method that permits the introduction of a nucleotide sequence into a plant cell or a plastid of a cell is suitable. Examples of such methods include microinjection, electroporation, bombardment with DNA-coated microparticles, permeabilizing a cell with polyethylene glycol, fusion with other DNA-comprising units such as minicells, cells, lysosomes, or liposomes. Preferred methods include, for example, biolistic gene delivery and *Agrobacterium* mediated transformation.

In one embodiment, the heterologous nucleotide sequence that is being transfected is integrated in nuclear DNA of the plant cell. Typically, expression of a foreign gene in a plant is achieved by integration of the foreign gene into nuclear DNA. However, the number of copies of the foreign gene integrated into the transformed plant nuclear genome may be low and the expression levels may also be low. The term "nuclear DNA" refers to the part of the plant genome that is located in the nucleus of a plant cell. Preferably, the heterologous nucleotide sequence that is integrated in nuclear DNA of the plant cell also includes a chloroplast targeting sequence, as described above.

A suitable and well-known method for nuclear transformation or integrating the heterologous nucleotide sequence into nuclear DNA of the plant cell includes the natural transformation system of *Agrobacterium*. The Ti and Ri plasmids of *A. tumefaciens* and *A. rhizogenes*, respectively, carry genes responsible for genetic transformation of the plant. Other bacteria such as *Sinorhizobium, Rhizobium*, and *Mesorhizobium* that interact with plants naturally can be modified to mediate gene transfer to a number of diverse plants. These plant-associated symbiotic bacteria can be made competent for transfecting (gene transfer) by acquisition of both a disarmed Ti plasmid and a suitable binary vector. The heterologous nucleotide sequences to be transferred via an *Agrobacterium*-mediated transformation method may include one or more "border" sequences, such as right border (RB) and left border (LB) sequences that usually define the extent of the transferred DNA (T-DNA) containing one or more genes to be expressed in a plant cell, and may further include an enhancer sequence such as an overdrive sequence or a plurality of overdrive sequences.

In preferred embodiment, heterologous nucleotide sequence that is being transfected is integrated in plastid DNA of the plant cell. "Plastid DNA" refers to that portion of the plant genome located in a plastid of a plant cell. Preferably, the heterologous nucleotide sequence is integrated in plastid DNA by homologous recombination. Once the heterologous nucleotide sequence is integrated in plastid DNA of the plant cell, it is preferable to avoid creating any double stranded breaks or digestion of the heterologous nucleotide sequence in the plastid. In addition, once the heterologous nucleotide sequence is integrated in plastid DNA, there is no need to remove a rare cutting enzyme sequence from the plastid genome.

Any method for stable transformation of a plastid is suitable. Such methods are well known in the art. Examples include use of a particle bombardment using "genegun" and insertion into the plastidic genome by homologous recombination. Other examples include electroporation, direct DNA transfer into plastids of protoplasts using polyethylene glycol. A preferred method is a biolistic transformation method, in which the nucleotide sequence to be transformed is applied to, for example, gold or tungsten particles, and accelerated towards the cell to be transformed. For purposes of the invention, the rare cutting enzymes are not used to transform a plastid.

The method for producing a transgenic bioluminescent plant further includes growing the plant cell into a mature plant. The term "mature plant" refers to a plant in which normal development of all vegetative and reproductive organs has occurred. After the above-mentioned heterologous nucleotide sequence or vector constructs are delivered into plant genomes by the methods described above, the transformed cells are regenerated into fully grown plants using standard hormone and antibiotic-supplemented media by methods known to a skilled artisan. (See Dandekar A M, and Fisk H J. "Plant transformation: *Agrobacterium*-mediated gene transfer." *Methods Mol Biol.* 286:35-46 (2005)). The plants are then propagated either through seeds or clonal expansion.

The method further includes a means for regulating expression of the heterologous nucleotide sequence. Such means include adding a regulatory sequence or sequences encoding a transcription factor to the heterologous nucleotide sequence that is transfected into the plant cell. Regulatory sequences include those described above, such as promoters, ribosomal binding sites, and termination sequences.

Vector for Transforming a Plastid

In another aspect, the invention relates to a vector for transforming a plastid. The vector includes a first and a second homologous recombination sequence, wherein each of the homologous recombination sequences is flanked by a unique rare cutting enzyme sequence. The vector further includes a multiple cloning site that includes at least one unique rare cutting enzyme sequence.

Suitable homologous recombination sequences typically vary depending on the plant species of the host cell or plastid. Examples of suitable pairs of a first and a second homologous recombination site include trnI/trnA; trnV/rps12; trnfM/trnG, derived from pPRV312L (GeneBank accession number DQ489715), pPRV111A (GeneBank accession number U12812) and pRB94 (GeneBank accession number AJ312392), respectively.

Preferably, each of the homologous recombination sites is flanked by a unique rare cutting enzyme sequence. The term "unique" with reference to a rare cutting enzyme sequence refers to a rare cutting enzyme sequence which occurs only once in a given nucleotide sequence.

In one embodiment, each gene in the heterologous nucleotide sequence or vector is flanked by a unique rare cutting enzyme sequence on both the 5'- and 3'-ends of the homologous recombination sites. For example, a homologous recombination site of trnI is preferably flanked by two rare cutting enzyme sequences, e.g., AscI/I-CeuI, and a homologous recombination site of trnA is preferably flanked by two rare cutting enzyme sequences, e.g., I-SceI/FseI, which will maintain proper directionality of the heterologous nucleotide sequence when it is transfected in a plant cell. In addition, those skilled in the art can appreciate that flanking the homologous recombination site with a unique rare cutting enzyme sequence allows for efficient deletion and replacement of the homologous recombination site with another homologous recombination site without affecting the remaining heterologous nucleotide sequence. This allows rapid adaptation of such plastid transformation vector (e.g. pUniPlast) for the use with any plant species of choice.

Figure 6:
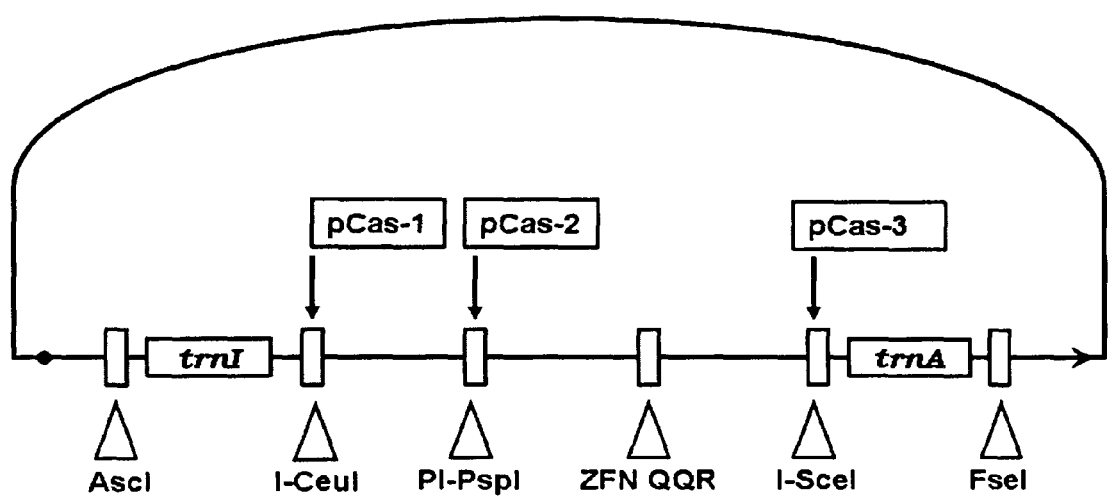
FIG. 6: Schematic illustration of pUniPlast MCS detailed. Homologues recombination sequences—such as trnI and trnA—are flanked by a pair of rare-cutter nuclease sites, allowing sustaining directionality of the cloned insert, as well as easy exchange with sequences from different species, and thus rapid adaptation of pUniPlast for use in any plant species. pUniPlast MCS can be expended by insertion of additional rare-cutter cloning sites, such as those of homing endonucleases (HE) or zinc finger nucleases (ZFN).

The term "multiple cloning site" refers to a nucleotide sequence that contains one or a number of different enzyme recognition sites to permit insertion of a nucleotide sequence at a defined locus (i.e., the enzyme recognition site) on a vector. Preferably, the multiple cloning site is flanked by a unique rare cutting enzyme sequence. In one embodiment, the multiple cloning site includes more than one unique rare cutting enzyme sequence. See FIG. 6.

The multiple cloning site may permit the introduction of a heterologous nucleotide sequence containing a gene into a vector. In one embodiment, the multiple cloning site includes a full length LUX operon. In a further embodiment, the multiple cloning site includes at least the LUX A, LUX B, LUX C, LUX D, LUX E, and LUX G genes. In another embodiment, the multiple cloning site also includes at least one gene encoding a cofactor for enhancing bioluminescence as described above.

Method for Producing a Vector for Transforming a Plastid

In another aspect, the invention relates to a method for producing a vector for transforming a plastid. The method includes providing an acceptor vector, which includes (i) a first and a second homologous recombination site, wherein each of said homologous recombination site is flanked by a unique rare cutting enzyme sequence; and (ii) a multiple cloning site comprising at least one unique rare cutting enzyme sequence. The method further includes providing at least one donor vector, wherein the donor vector comprises a heterologous nucleotide sequence flanked by a rare cutting enzyme sequence that is sufficiently identical to the at least one unique rare cutting enzyme sequence of the multiple cloning site of the acceptor vector. The method also includes sequentially subcloning the heterologous nucleotide sequence from the donor vector into the acceptor vector, whereby a vector for transforming a plastid is produced.

The method allows for multiple rounds of gene transfer by sequentially subcloning a gene from multiple, different donor vectors into an acceptor vector. The multiple donor vectors will be used in different sequential rounds of cloning to allow sequential insertion of genes or heterologous nucleotide sequences into the acceptor vector.

The term "acceptor vector" refers to a vector that is a recipient of a heterologous nucleotide sequence from a donor vector. The acceptor vector is characterized by having a first and a second homologous recombination site, as described above. Accordingly, an acceptor vector is capable of integrating into the genome of a plant or plastid. In addition, the acceptor vector includes a multiple cloning site, as described above. Preferably, the acceptor vector includes unique rare cutting enzyme sequences throughout the vector, including in the multiple cloning site, so that integrity of a heterologous nucleotide sequence or the acceptor vector is maintained during genetic manipulation protocols.

In a preferred embodiment, the acceptor vector is derived from the pUniPlast vector system, which is a plastid transformation vector system developed by BioGlow Inc. In another preferred embodiment, the acceptor vector is a binary pPZP-RCS vector, described above (Goderis, 2002 and Tzfira, 2005). Preferably, the acceptor vector is introduced or transfected into a host cell or into a plastid in vivo.

The term "donor vector" refers to a vector containing a heterologous nucleotide sequence that is transferred to an acceptor vector through gene recombination. Preferably, the donor vector is not introduced into a host cell or into a plastid in vivo. The heterologous nucleotide sequence from the donor vector is preferably transferred to an acceptor vector in vitro. In a preferred embodiment, the donor vector is a pCas vector, developed by BioGlow Inc, and pSAT vectors (Tzfira, 2005).

The heterologous nucleotide sequence of the donor vector is preferably flanked by a rare cutting enzyme sequence that is sufficiently identical to the at least one unique rare cutting enzyme sequence of the multiple cloning site of the acceptor vector. A first rare cutting enzyme sequence is sufficiently identical to a second rare cutting enzyme sequence if one or the same rare cutting enzyme is capable of recognizing and cleaving both the first and the second rare cutting enzyme sequences.

The term "sufficiently identical" as used herein refers to a first nucleotide sequence that contains a sufficient or minimum number of identical or equivalent nucleotides to a second nucleotide sequence, such that the first and second nucleotide sequences share common structural domains or motifs and/or a common functional activity. For example, nucleotide sequences that share common structural domains having at least 80%, 85%, 90%, 91%, 92%, 93%, 94%, 95%, 96%, 97%, 98%, 99%, or more identity across the sequences, and share a common functional activity are defined herein as sufficiently identical.

To determine percent identity of two nucleic acid sequences, the sequences are aligned for optimal comparison purposes (e.g., gaps can be introduced in one or both of a first and second nucleotide sequence for optimal alignment). For example, when aligning a first rare cutting enzyme sequence to a second rare cutting enzyme sequence having 10 nucleotides, at least 70%, preferably at least 80%, more preferably at least 90% of the 10 nucleotides between the first and second sequences are aligned. When a position in the first sequence is occupied by the same nucleotide as the corresponding position in the second sequence, then the molecules are identical at that position. The percent identity between the two sequences is a function of the number of identical positions shared by the sequences, taking into account the number of gaps, the length of the sequences, and the length of each gap that need to be introduced for optimal alignment of the two sequences. An algorithm known in the art may be used to determine percent identity between two sequences.

Conventional cloning or subcloning techniques, reagents, conditions, enzymes may be used to introduce, clone, or subclone the heterologous nucleotide sequence into the multiple cloning site of the acceptor or donor vector. One or more genes may be cloned or subcloned as a group into the acceptor or donor vector.

The term "subcloning" refers to a transfer of a nucleotide sequence from an initial vector to a more specialized vector. For example, subcloning refers to a transfer of a nucleotide sequence from a donor vector to an acceptor vector. Typically, subcloning includes removing the nucleotide sequence from the initial vector with suitable nucleases and then inserting the removed nucleotide sequence into another vector. Preferably, rare cutting enzymes are used in the subcloning.

The term "sequentially" subcloning refers to transferring a nucleotide sequence from a donor vector to an acceptor vector in a stepwise manner. Sequentially subcloning allows for repeated cycles of subcloning until all of the heterologous nucleotide sequences from a donor vector are delivered into the acceptor vector, while maintaining integrity of the acceptor vector and/or the heterologous nucleotide sequences inserted in the acceptor vector from a previous cycle of subcloning.

In a further embodiment, the method includes a second donor vector that includes a heterologous nucleotide sequence. Preferably, the heterologous nucleotide sequence of the second donor vector is flanked by a rare cutting enzyme sequence that is unique from a rare cutting enzyme sequence of the first donor vector.

Figure 5:
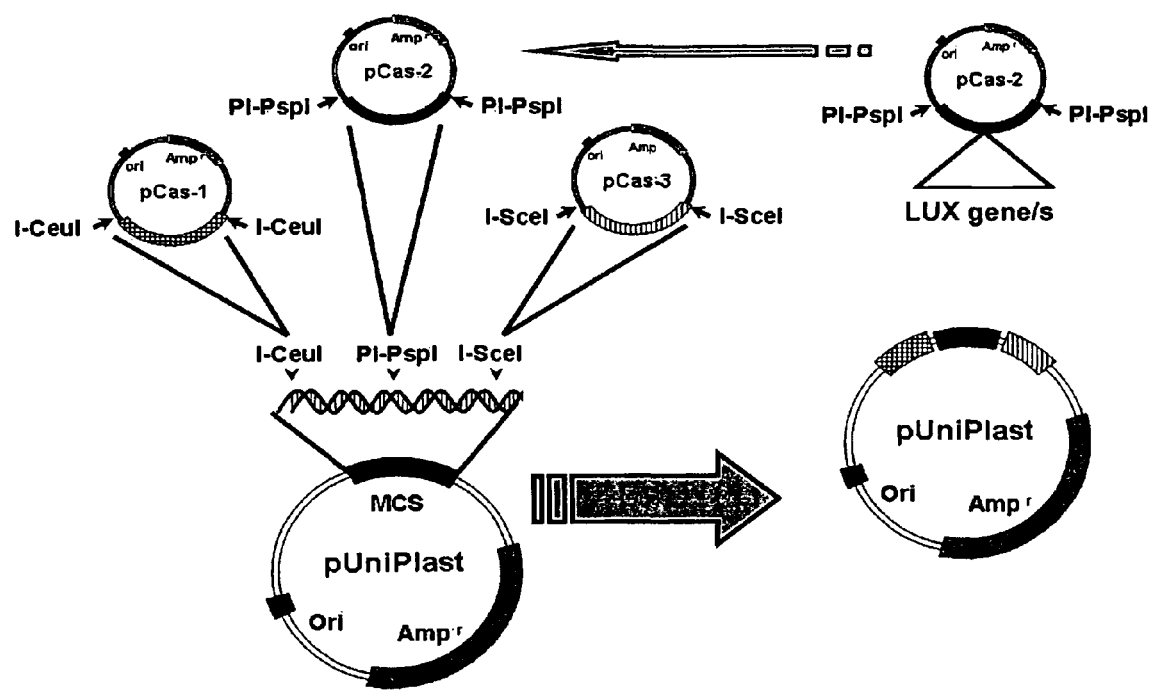
FIG. 5: Schematic illustration of an assembly of modular pUniPlast vector using expression cassettes derived from pCas vectors. pCas vector containing single expression cassette; restriction sites for the homing endonuclease PI-PspI indicated by arrows. Fully assembled pUniPlast vector containing three independent expression cassettes also shown in far right bottom corner.

For example, at least two donor vectors may be used to express multiple genes in plastids. See FIG. 5, for example. A first donor vector may be used to subclone a LUX operon into an acceptor vector and a second donor vector may be used to subclone a RIB operon into the same acceptor vector. Accordingly, the resulting acceptor vector can include more than one operon. The resulting acceptor vector may then be transfected into a plant or plastid for simultaneous transformation of the LUX and RIB operons.

In yet another embodiment, the method for producing a vector for transforming a plastid further includes subjecting a host cell containing the acceptor or donor vector to drug selection or other form of screening/selection.

Other possible modifications and variations can be made to the method, which may include the number of donor vectors; the number and/or arrangements of the rare cutting enzyme sequences; the number and/or arrangements of the heterologous nucleotide sequences, etc. For example, three or more donor vectors with different heterologous nucleotide sequences can be sequentially subcloned into the acceptor vector.

Vector System Kit

In another aspect of the invention, a vector system kit is provided. The kit includes an acceptor vector comprising (i) a first and a second homologous recombination site, wherein each of said homologous recombination site is flanked by a unique rare cutting enzyme sequence; and (ii) a multiple cloning site comprising at least one unique rare cutting enzyme sequence. The kit further includes at least one donor vector, wherein the donor vector comprises a heterologous nucleotide sequence flanked by a rare cutting enzyme sequence that is sufficiently identical to the at least one unique rare cutting enzyme sequence of the multiple cloning site of the acceptor vector.

The kit can further include reagents, buffers, and materials related to any of the nucleotide sequences and proteins described above. In addition, the kit can include a plant or plant cell produced by the invention.

Variants

The present invention further relates to variants of the nucleotide sequences described herein. Variants may occur naturally, such as a natural allelic variant. Other variants include those produced by nucleotide substitutions, deletions, or additions. The substitutions, deletions, or additions may involve one or more nucleotides. These variants may be altered in coding regions, non-coding regions, or both. Alterations in the coding regions may produce conservative or non-conservative amino acid substitutions, deletions, or additions. Preferably, the variant is a silent substitution, addition, or deletion, which does not alter the properties and activities of the peptide encoded by the nucleotide sequence described herein. Conservative substitutions are also preferred.

Further embodiments of the invention include variant nucleotide sequences comprising a sequence having at least 90% identical, and more preferably at least 95%, 96%, 97%, 98%, or 99% identical to a nucleotide sequence described herein. The nucleotide sequences described herein are the "reference" sequences.

For example, a variant nucleotide sequence that is at least 95% identical to a reference nucleotide sequence (e.g., the LUX operon) described herein is identical to sequence described herein except that the variant nucleotide sequence may include up to five point mutations per each 100 nucleotides of the reference nucleotide sequence (e.g., the LUX operon) sequence described herein.

In other words, to obtain a variant nucleotide sequence that is at least 95% identical to a reference nucleotide sequence described herein, up to 5% of the nucleotides in the reference sequence may be deleted or substituted with another nucleotide, or a number of nucleotides up to 5% of the total nucleotides in the reference sequence may be inserted into the reference sequence.

These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

Uses

Environmental Safety:

In some embodiments of the present invention, one or both of the luciferase subunits, for example subunit A, can be controlled by a promoter sensitive to heavy metals, such as cadmium, a known carcinogen heavily used in industry. Specific promoter that may be used is one controlling the expression of tobacco cdiGRP gene in tobacco. (Ueki et al., "Identification of an interactor of cadmium ion-induced glycine-rich protein involved in regulation of callose levels in plant vasculature," *PNAS* 102(34):12089-94 (2005)). This type of transgenic crop starts glowing if exposed to heavy metals. Such embodiment is highly beneficial for monitoring of industrial waste, by simply planting these crops in the area where pollution may occur, and it will become literarily visible within a few hours.

Ornamental Applications:

The glowing plants can be used in ornamental applications. In 1992, the global flower trade was estimated at one hundred billion U.S. dollars. In recent years, the floral industry has grown six percent annually, while the global trade volume in 2003 was 101.84 billion U.S. dollars. In the U.S. alone, floral industry at 2006 was estimated at approximately twenty-one billion U.S. dollars, representing a considerable market (http://www.aboutflowers.com/press_b1.html). Although it is hard to estimate market share of a product which has not existed before, taking to the consideration a novel and appealing appearance of this metabolically engineered plants, one may reasonably suggest that initial market share can be somewhere between 5-10%, representing one to two billion dollars in the U.S. and five to ten billion dollars worldwide.

In some embodiments of the present invention, plants are engineered in such way that the luminescence color is modified by shifting wavelength of the emitted light either by luciferase mutagenesis or simply co-expressing with other fluorescent proteins. In some embodiments of the present invention, plants are engineered in such way that organs of the plant where the luminescence is produced is directed by expressing system components under organ-specific promoters. These embodiments allow production of multiple product lines, enabling market share increase.

Basic Research:

The present invention is a new step in reporter gene technology, as it allows detection of gene expression without need of any type of additional equipment or reagents, just by observation. For example, it will simplify the procedure of identification of new promoters: leaving one of the genes in the system promoter-less (for instance, luciferase A subunit) thus allowing cloning of a genomic library upstream to it. Simple observation of growing plants allows determination of where cloned promoters are expressed and at which plant life stages.

Incorporation of Sequence Listing

Incorporated herein by reference in its entirety is the Sequence Listing for the application. The Sequence Listing is disclosed on a computer-readable ASCII text file titled, "sequence_listing.txt", created on Jul. 31, 2008. The sequence_listing.txt file is 205 kb in size.

EXAMPLES

Example 1

Cloning pUniPlast Vector

A donor vector, pSat1 vector (vector used for genomic plant DNA transformation (Tzfira, et al. 2005), is digested with AscI restriction enzyme. Blunt ends are then created with Mung Bean nuclease (New England Biolabs). A pUniPlast (acceptor vector) multiple cloning site is blunt cloned with annealed primers BG-1 and BG-2. The resulting construct is then sequenced with primers BG-3 and 4.

The trnI (approx. 1,240 bp) homologues recombination targeting sequence is amplified by polymerase chain reaction (PCR) using Pfu polymerase (Stratagene), tobacco plastid DNA as a template and primers BG-5 and 6. The trnI is then cloned with AscI/I-CeuI to maintain insert directionality (double digest in NEB buffer 4).

The trnA (approx. 830 bp) homologues recombination targeting sequence is amplified by polymerase chain reaction (PCR) using Pfu polymerase, tobacco plastid DNA as a template and primers BG-7 and 8. The trnA sequence is then cloned with FseI/I-SceI to maintain insert directionality (double digest in NEB buffer 4).

Sequences for BG primers can be found in Table 1 below.

TABLE 1

BC Primers List

| Primer # | Sequence |
| --- | --- |
| BG-1 | GGCGCGCCTAACTATAACGGTCCTAAGGTAGCGATGGCAAACAGCTATTATGGGTATTATGGGTTTAATTAATAGGGATAACAGGGTAATGGCCGGCC (SEQ ID NO: 58) |
| BG-2 | GGCCGGCCATTACCCTGTTATCCCTATTAATTAAACCCATAATACCCATAATAGCTGTTTGCCATCGCTACCTTAGGACCGTTATAGTTAGGCGCGCC (SEQ ID NO: 59) |
| BG-3-seq | CTTCGCTATTACGCCAGCTGG (SEQ ID NO: 60) |
| BG-4-seq | GTTAGCTCACTCATTAGGCAC (SEQ ID NO: 61) |
| BG-5-AscI-trnI | CTGGCGCGCCGCCTTGTACACACCGCCCGTCAC (SEQ ID NO: 62) |
| BG-6-CeuI-trnI | TCGCTACCTTAGGACCGTTATAGTTAGCAGCTGGGCCATCCTGGACTTG (SEQ ID NO: 63) |
| BG-7-SceI-trnA | AATAGGGATAACAGGGTAATCTCCACTTGGCTCGGGGGATATAG (SEQ ID NO: 64) |
| BG-8-FseI-tmA | TATGGCCGGCCAGCTTTGTATCGGCTAAGTTCACG (SEQ ID NO: 65) |
| BG-9-AgeI-PpsbA | TCACCGGTGGGCAACCCACTAGCATATCG (SEQ ID NO: 66) |
| BG-10-NcoI-PpsbA | AACCATGGTAAAATCTTGGTTTATTTAATC (SEQ ID NO: 67) |
| BG-11-XbaI-TpsbA | CCTCTAGAGATCCTGGCCTAGTCTATAGG (SEQ ID NO: 68) |
| BG-12-NotI-TpsbA | TTATGCGGCCGCTCGAATATAGCTCTTCTTTCTTATTTC (SEQ ID NO: 69) |
| BG-13-aadPsbA | AACCATGGGGGAAGCGGTGATCGCCGAAG (SEQ ID NO: 70) |
| BG-14-BglII-aadA | TGGAGATCTTTATTTGCCGACTACCTTGGTGATC (SEQ ID NO: 71) |
| BG-15-AgeI-Prrn | TCACCGGTCGCCGTCGTTCAATGAGAATGG (SEQ ID NO: 72) |
| BG-16-NcoI-Prrn | AACCATGGATATTCGCCCGGAGTTCGCTC (SEQ ID NO: 73) |
| BG-17-XbaI-Trps16 | CCTCTAGAACCGAAATTCAATTAAGGAAAT (SEQ ID NO: 74) |
| BG-18-EcoRIrem | TTATGCGGCCGCAGAACACGCATTTCAATGGAAGC (SEQ ID NO: 75) |
| BG-19-XhoGFPfw | CCACTCGAGAGGAGGGATTTATGGTGAGCAAGGGCGAGGAGC (SEQ ID NO: 76) |
| BG-20-EcoRI-GFP | GGGAATTCTTACTTGTACAGCTCGTCCATGCCGAG (SEQ ID NO: 77) |
| BG-21-NcoI-GFP | TTCCATGGAGTTGTAGGGAGGGATTTATGGTGAGCAAGGGCGAGGAGC (SEQ ID NO: 78) |

TABLE 1-continued

BC Primers List

| Primer # | Sequence |
| --- | --- |
| BG-22-fwLUX | ACAGAATTCCCAAAGGAGATTACATGATTAAG (SEQ ID NO: 79) |
| BG-23-revLUX | TTGGAATTCTTACGTATAGCTAAATGCATCAG (SEQ ID NO: 80) |
| BG-24-GUSXhoI | CCACTCGAGAGGAGGGATTTATGTTACGTCCTGTAGAAACC (SEQ ID NO: 81) |
| BG-25-rrnaadA | AACCATGGAGTTGTAGGGAGGGATTTATGGGGGAAGCGGTGATCGCC (SEQ ID NO: 82) |
| BG-26-aadXho | TTGCTCGAGTTATTTGCCGACTACCTTGGTGATC (SEQ ID NO: 83) |
| BG-27-GUSEcoRI | GGGAATTCTCATTGTTTGCCTCCCTGCTGC (SEQ ID NO: 84) |

Example 2

Preparing a pCas-1 Vector Containing I-CeuI Derived PpsbA/LpsbA/TpsbA Expression Cassette A PpsbA promoter (approx. 230 bp) is amplified by PCR using Pfu polymerase, using tobacco plastid DNA as a template and primers BG-9 and 10. The PCR product is then digested with AgeI/NcoI enzymes.

The pSat5 (vector used for genomic plant DNA transformation, see Tzfira et al (2005) (donor vector) is then digested with AgeI/NcoI to remove a 35S promoter. The backbone of the vector and the PpsbA promoter is then ligated using T4 DNA ligase (New England Biolabs).

A TpsbA terminator (approx. 400 bp) is amplified by PCR using Pfu polymerase, tobacco plastid DNA as a template, and primers BG-11 and 12. The PCR product is then digested with NotI/XbaI.

The pSat5—PpsbA promoter is digested with NotI/XbaI to remove a 35S terminator (note: may need to use INV110 to prevent XbaI site methylation). The TpsbA terminator is then cloned into the pSAT5-PpsbA promoter vector. From now on this vector is referred as pCas-1 (donor vector).

A aadA gene (spectinomycin selection marker; approx. 800 bp) is PCR amplified using Pfu polymerase, binary plasmid pPZP-RCS1 as a template (vector used for genomic plant DNA transformation, see Tzfira et al (2005), and primers BG-13 and BG-26 primer. The aadA PCR product is then digested using NcoI/XhoI.

The pCas-1 vector is digested with NcoI/XhoI. The aadA product is ligated into the pCas-1 using T4 DNA ligase. The resulting vector is further referred as pCas-1-aadA.

pCas vectors contain pre-cloned expression cassettes, including promoter and terminator sequences, as well as selection and fluorescent/enzymatic markers, if required. These cassettes to be excised from the pCas vectors using rare-cutter enzymes and introduced into plastid transformation pUniPlast vector, containing homologues recombination plastid targeting sequences for creation of transgenic plants. Specifically, if transgene expression is not satisfactory, it can be re-cloned in a single cloning step into another pCas vector with desired regulatory elements (i.e. strong or weak promoter, etc) and subcloned in a second step into an existing pUniPlast vector, creating desired expression vector in two cloning steps.

Certain pCas vectors have an array of pre-arranged autofluorescent and enzymatic tags, such as green fluorescent protein (GFP) and beta-glucuronidase (GUS), which can either be fused or co-expressed on the same polycistronic mRNA with the transgene of interest. The transgene of interest can be rapidly reshuffled between different tags in a single cloning step and further be assembled into a single vector pUniPlast vector, allowing rapid autofluorescent or enzymatic tagging.

Similarly, to exchange fluorescent and enzymatic tags, different pCas-1 vectors contain different selection markers, such as spectinomycin resistance encoded by the aadA gene or kanamycin resistance encoded by the neo gene, or fluorescent protein markers, such as GFP. Expression cassettes containing these resistance markers can be easily reshuffled within the pUniPlast vector, without affecting the other sequences cloned, and allowing for plant recovery on different selective media. Extended MCS allows expression of the transgenes on the same polycistronic mRNA with the selection marker. Furthermore, selected pCas vectors bearing selection markers contain pre-engineered homology-based excision elements, such as Cre-lox and attB/attP recognition sequences, allowing removal of the antibiotic resistance genes using phage site-specific recombinases.

Figure 8:
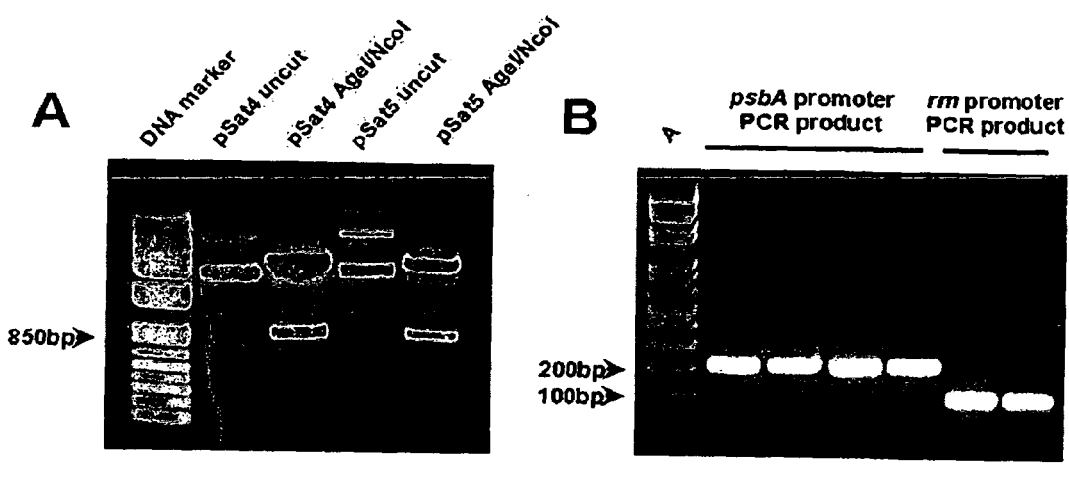
FIG. 8: Agarose gel prepared for DNA analysis. Cloning plastid promoters into pSat plasmids (Tzfira et al, 2005) to create pCas vectors.
Figure 8:
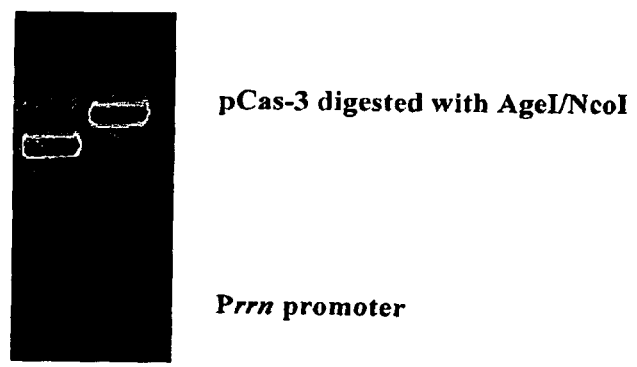

See FIG. 8 (A) Plasmids pSat4 and pSat5 have been digested with AgeI/NcoI to remove the 35S promoter (approx. 900 bp). FIG. 8(B) psbA (approx. 230 bp) and rrn (approx. 100 bp) promoters were PCR amplified from plastid DNA of Nicotiana tabacum. The PCR fragments to be digested with AgeI/NcoI and ligated into the same sites of pSat4 and pSat5 to replace 35S promoter and convert the pSat plasmids to pCas vectors, suitable for use in plastids. FIG. 8 (C) rrn promoter cloned into pCas vector. Lane 1: undigested pCas-3 vector; Lane 2: pCas-3 vector digested with AgeI/NcoI, showing presence of the Prrn.

Example 3

Preparing pCas-2 Vector Containing PI-PspI Derived PpsbA/LpsbA/TpsbA Expression Cassette A pCas-2 vector (donor vector) is made following the same steps above as for pCas-1 vector. Plasmid pSat6 (vector used for genomic plant DNA transformation, see Tzfira et al (2005)) (donor vector) is used as a basis vector to create pCas-2.

Several different expression cassettes may be required to express multiple genes in plastids, and thus several different pCas vectors (donor vectors) must be made. For example, pCas-1 will be employed to subclone LUX operon (NCBI accession: M63594) into pUniPlast (acceptor vector) for generation of bioluminescent transgenic plants.

However, if additional genes need to be introduced into the same pUniPlast (acceptor) vector for simultaneous transformation into plastid genome, an additional pCas vector (donor vector), such as pCas-2 or pCas-3, might be required.

For example, RIB operon genes (GeneBank accession AF364106) encoding for the synthesis of riboflavin, one of the substrates derivatives required for the luminescent reaction, might need to be introduced into plant simultaneously with LUX operon to increase bioluminescence level. In this case, pCas-2 or pCas-3 vectors can be used to introduce RIB operon into an existing pUniPlast vectors containing LUX operon introduced using pCas-1.

Example 4

Preparing pCas-3 Donor Vector Containing I-SceI Derived Prrn/LrbcL/Trps16 Expression Cassette The Prrn promoter (approx 100 bp) is PCR amplified using Pfu polymerase, tobacco plastid DNA as a template and primers BG-15 and 16. The Prrn PCR product is then digested with AgeI/NcoI.

The pSat4 (vector used for genomic plant DNA transformation, see Tzfira et al)(donor vector) is digested with AgeI/NcoI to remove 35S promoter. The donor vector backbone and the Prrn promoter are ligated using T4 DNA ligase.

The Trps16 terminator is PCR amplified using Pfu polymerase, tobacco plastid DNA as a template and primers BG-17 and primer BG-18. The PCR product (approx. 170 bp) is digested with NotI/XbaI.

The pSat4-Prrn promoter is digested with NotI/XbaI to remove 35S terminator (note: may need to use INV110 to prevent XbaI site methylation). The Trps16 terminator is then ligated into pSat4-Prrn promoter using T4 DNA ligase. From now on this vector is referred as pCas-3 (donor vector).

The aadA gene (spectinomycin selection marker; approx. 800 bp) is PCR amplified using Pfu polymerase, binary plasmid pPZP-RCS1 as a template (vector used for genomic plant DNA transformation, see Tzfira et al (2005)), and primers BG-14 and BG-25. The aadA PCR product is digested using NcoI/BglII. The pCas-3 vector is then digested with NcoI/BglII. The aadA product is ligated into pCas-3 using T4 DNA ligase. The resulting vector is further referred as pCas-3-aadA (donor vector).

Figure 13:
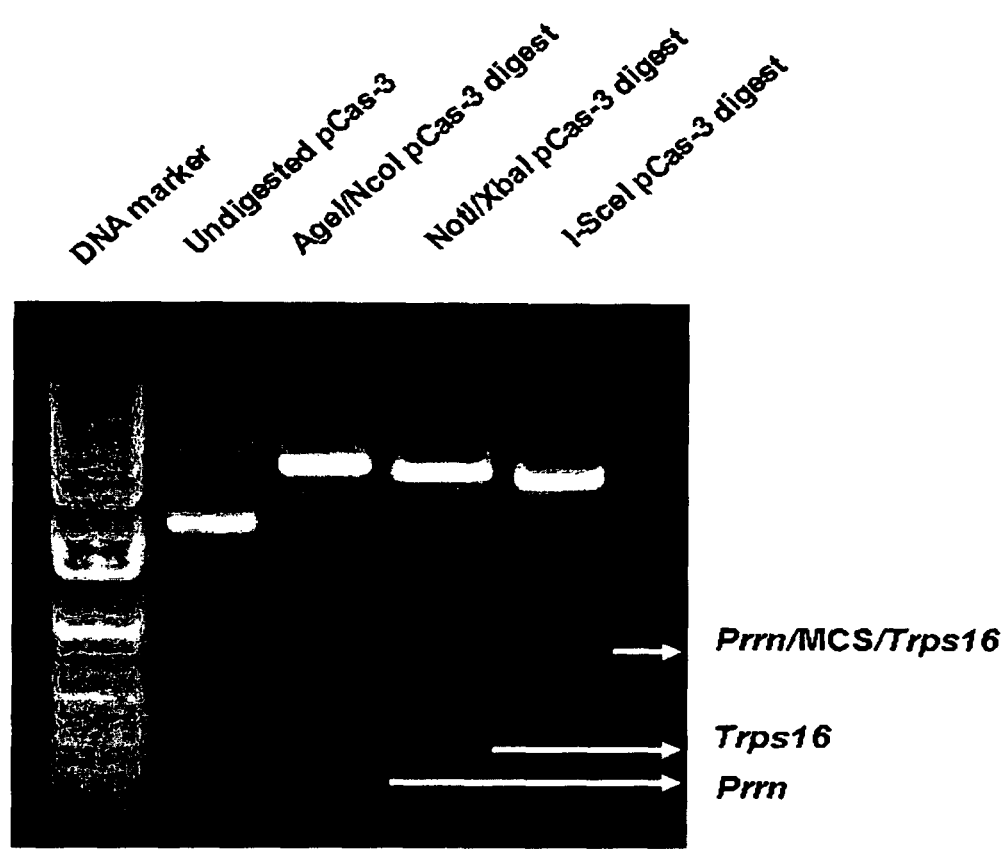
FIG. 13: pCas-3 donor vector prepared by BioGlow Inc. pCas-3 enzymatic digest displays presence of Prrn (AgeI/NcoI fragment), Trps16 (NotI/XbaI fragment) and the whole Prrn/MCS/Trps16 cassette (I-SceI fragment), showing that a complete pCas-3 has been constructed (BioGlow Inc, unpublished).

See FIG. 13. pCas-3 donor vector was prepared by BioGlow Inc. pCas-3 vector, containing rrn promoter (Prrn), multiple cloning site (MCS) and rps16 terminator (Trps16) has been prepared by BioGlow Inc. Transgenes of interest is cloned into pCas-3 multiple cloning site and the cassette comprised of Prrn/Transgene of interest/Trps16 is excised using I-SceI homing endonuclease and subcloned into pUniPlast acceptor vector for generation of transgentic plants.

In FIG. 13, pCas-3 enzymatic digest displays presence of Prrn (AgeI/NcoI fragment), Trps16 (NotI/XbaI fragment) and the whole Prrn/MCS/Trps16 cassette (I-SceI fragment), showing that a complete pCas-3 has been constructed (BioGlow Inc, unpublished).

Cloning of Pre-Arranged Fluorescent and Enzymatic Marker Into pCAS Cassettes

Example 5

Cloning of Green Fluorescent Protein (GFP) into Pre-Arranged pCas Vector for Expression in a Single Operon with the aadA Selection Marker Green fluorescent protein (GFP) is PCR amplified using Pfu polymerase, pSat6-EGFP (Tzfira et al, 2005) as a template, and primers BG-19 and primer BG-20. The PCR product (approx. 700 bp) is digested with XhoI/EcoRI. The PCR product is then cloned into the same sites (XhoI/EcoRI) in pCas-1-aadA and pCas-3-aadA. The resulting vectors are further referred as pCas-1-aadA-GFP and pCas-3-aadA-GFP (donor vectors).

The aadA-GFP cassette is then subcloned into I-CeuI site of pUniPlast (acceptor vector). The resulting pUniPlast-GFP operon construct GFP expressing transgenic plants (see below for plant transformation protocol) are then used.

Example 6

Cloning of Beta-Glucuronidase (GUS) into Pre-Arranged pCas Vector for Expression in a Single Operon with the aadA Selection Marker Beta-Glucuronidase (GUS) (approx. 1,800 bp) is PCR amplified using Pfu polymerase, pSat6-GUS (Tzfira et al, 2005) as a template, and primers BG-24 and BG-27. The PCR product is digested with XhoI/EcoRI. The PCR product is then cloned into the same sites (XhoI/EcoRI) in pCas-1-aadA. The resulting vectors are further referred as pCas-1-aadA-GUS (donor vector).

Example 7

Cloning of the LUX Operon from *Photobacterium leiognathi* into pUNIPLAST Vectors to Create Bioluminescent Plants The full length LUX operon is PCR amplified from *P. leioganthi* using Pfu polymerase, *P. leioganthi* genomic DNA as a template, and primers primers BG-22 and BG-23. EcoRI is then used to digest the LUX operon PCR fragment. The fragment is then cloned into the same sites (EcoRI) in pCas-1-aadA.

The aadA-LUX operon cassettes from pCas1-aadA-LUX operon are excised using I-CeuI homing endonuclease. The aadA-LUX operon is then subcloned into I-CeuI site of pUniPlast. The resulting pUniPlast-LUX operon construct is then used to produce bioluminescent transgenic plants.

To create bioluminescent plants, LUX operon from a variety of luminescent bacteria can be used, for example, the LUX operon from *Photobacterium leiognathi*., American Tissue Culture Collection strain #25521; NCBI accession: M63594.

Example 8

Assessment of pUNIPLAST System Workability in Plants Using Transient Gene Expression Assay A transient gene expression assay in chloroplasts is used to assess effectiveness of transgene expression from pCas cassettes. pCas-1-aadA-GFP and pCas-1-aadA-GUS will be employed for transient expression of GFP and GUS, respectively, in tobacco leaves by the means of biolistic gene delivery. Shortly, 25 μg DNA of each of the constructs expressing the aadA-GFP or aadA-GUS transcriptional fusions is to be adsorbed onto 10 mg of 1-μm gold particles (Bio-Rad, CA) and bombarded at 150-200 psi into the leaf epidermis of greenhouse-grown *Nicotiniana tobaccum* plants using a Helios gene gun (PDS-1000/He, Bio-Rad). After incubation for 24 h at 22-24° C., the bombarded tissues are to be viewed under a Zeiss LSM 5 Pascal confocal laser scanning microscope (for GFP) or stained with GUS substrate X-Gluc (for GUS activity).

Example 9

Creation of Bioluminescent Transgenic Plants

The pUniPlast LUX operon is used to produce transgenic bioluminescent plants. *Nicotiniana tobaccum* plants will be used as a model organism. The following is a preferred protocol for stable expression of LUX operon in the transgenic plants:

Tobacco leaves are harvested at five- to seven-leaf stage of plant growth. An autoclaved Whatman 70-mm circle filter disk is placed on RMOP medium in a deep Petri dish. The leaf on filter disk is placed with its adaxial side facing the medium. The expression vectors are then biolistically delivered into plant tissue (see above). Parafilm is then used to seal the Petri dish.

After 2 days in dark at 24-26° C., 5-mm pieces of bombarded leaves are cut and placed on RMOP selection medium (bombarded side in contact with medium) for the first round of selection. Parafilm is then used to seal the Petri dish. Spectinomycin (500 μg/ml) is used for effective selection of transformants in tobacco. In a culture room, the Petri dishes are sealed with parafilm under white fluorescent lamps (1,900 lux) with 16 h light/8 h dark cycle at 24-26° C. After 4-8 weeks, putative transgenic shoots appear. The putative transplastomic shoots are then screened for transgene integration by PCR; LUX operon primers might be used (BG 22, 23).

For the second round of selection, 2-mm pieces of leaves are cut from the first round plants and are then placed on RMOP selection medium. The leaf sections are then grown in a culture room under white fluorescent lamps (1,900 lux) with 16 h light/8 h dark cycle at 24-26° C. These leaf sections produce transgenic shoots in 3-4 weeks.

The regenerated shoots are then excised and transferred to MSO medium containing the appropriate antibiotic. The shoots are grown in culture room under white fluorescent lamps (1,900 lux) with 16 h light/8 h dark cycle at 24-26° C. This step is termed the third round of selection, where rooting occurs in 3-4 weeks. Southern blot analysis can be carried out to confirm integration and determine, as known in the art.

RMOP Medium

| Material | Amount per 1 liter |
|---|---|
| MS (Murashige and Skoog salts) | according to manufacturer's instructions |
| myo-inositol | 100 mg |
| thiamine HCl | 1 mg |
| BAP (6-Benzylamino purine) | 1 mg |
| NAA (1-Naphthaleneacetic acid) | 0.1 mg |
| Sucrose | 30 g |
| BactoAgar | 6 g |

Adjust pH to 5.8

| Material | Amount per 1 liter |
|---|---|
| MS (Murashige and Skoog salts) | according to manufacturer's instructions |
| Sucrose | 30 g |
| BactoAgar | 6 g |

Adjust pH to 5.8

Example 10

Vector for Nuclear Expression of LUX Genes

Endonucleases, homing endonucleases or gateway technology is used to clone LUX genes into either plant cellular or chloroplast expression vectors. The LUX genes are then delivered into nuclear or chloroplast genomes by methods known to a skilled artisan and expression is governed by corresponding regulatory sequences. In particular, the LUX operon is transferred into a plant, which can be preferably achieved by the use of recently developed pSAT vector system (Tzfira et al., (2005) "pSAT vectors: a modular series of plasmids for autofluorescent protein tagging and expression of multiple genes in plants." *Plant Mol. Biol.,* 57(4): 503-16 (2005)), allowing simultaneous transfer of 12-15 (or more) genes into the same organism, or by direct delivery of the operon into chloroplast genome.

For example, LUX genes are PCR amplified and subcloned into MCS of pSAT vectors (one gene per one vector), under plant-specific regulatory promoter and terminator sequences, such as 35S promoter and terminator. Different pSAT vectors can contain different promoters (such as 35S, nopaline synthase (NOS), manopine synthase (MAS), etc., to prevent gene silencing when several consecutive genes on the chromosome are expressed from the same promoter. Further, the cassettes containing promoter, lux gene and a terminator are subcloned from the SAT vectors into PZP-RCS binary vector using homing endonucleases, such as PI-PspI or I-CeuI. The resulting single binary PZP-RCS-Lux plasmid is used for plant transformation.

The following procedure is used to clone individual LUX genes into expression cassettes of vecors, e.g., pSAT.

A restriction map of the sequence to be cloned (i.e. specific LUX gene) is generated using appropriate software, such as "DNA Strider". The restriction enzymes which do not have restriction sites within a given gene are identified. These enzymes can be used to clone the LUX gene into a cloning vector. For instance, LUX A of *P. leiognathi* is has no restriction sites for enzymes BglII and EcoRI.

Design of the Forward (Fw) Primer.

Primer's gene specific sequence should be 20-25 bp long, in order to anneal to the target sequence. A restriction enzyme polynucleotide sequence is to be added to the gene specific sequence. Gene specific forward sequence used for the LUX A gene is: ATGAAAATTAGTAATATCTG (SEQ ID NO: 85). Since BglII restriction site is located closer to promoter then EcoRI in the pCAS/pSAT multiple cloning site, this enzyme is used with the forward primer to keep the directionality of the gene correct, i.e. 5' of the gene directly following the promoter sequence. NOTE: several nucleotides (underlined) must be added at the 5' of the primer for efficient digest of the PCR fragment. For instance, BglII requires 3 nt to be added. Thus, final 5' primer for cloning of LUX A into a cloning vector using BglII will be: GAAGATCTATGAAAATTAGTAATATCTG (SEQ ID NO: 86) (BglII restriction site in bold).

Design of the Reverse (Rev) Primer.

Primer's gene specific sequence should be 20-25 bp long, in order to anneal to the target gene. A restriction enzyme polynucleotide sequence is to be added to the gene specific sequence. Gene specific reverse primer sequence used for the LUX A gene is: ACTTAAAAGATCCTCAGTAA (SEQ ID NO: 87). Since EcoRI site is located closer to terminator then BglII within the pSAT/pCAS multiple cloning sites, we will use EcoRI enzyme with the LUX A reverse primer to keep the directionality of the gene correct, i.e. 3' of the LUX A gene directly preceding the terminator. NOTE: several nucleotides (underlined) must be added at the 5' end of the primer for efficient digest of the PCR fragment. For instance, EcoRI requires 1-2 nt to be added. Thus, reverse primer for cloning of LUX A into a cloning vector using EcoRI will be: ACTTAAAAGATCCTCAGTAAGAATTCCG (SEQ ID NO: 88). Finally, the reverse primer sequence is reversed in order to constitute a compatible pair with the forward primer (i.e. both sequences must allow DNA replication in opposite direction to one another), and thus the final LUX A reverse primer is:

```
CGGAATTCTTACTGAGGATCTTTTAAGT.      (SEQ ID NO: 89)
```

LUX genes A, B, D, E and G is cloned with BglII at the forward primer (5' of the gene, promoter's end) and with EcoRI at the reverse primer (gene's 3' end and terminator's beginning).

LUX C will be cloned with XhoI at the forward primer (5' of the gene, promoter's end), since there is a BglII restriction site within native LUX C sequence, and with EcoRI at the reverse primer (gene's 3' end and terminator's beginning). Using same restriction sites with different primer pairs intended to facilitate cloning into standartisized pSAT vectors and to simplify overall cloning strategy.

The aforementioned primers are to be used in a polymerase chain reaction to amplify the LUX genes to be cloned, using *Photobacterium leiognathi* genomic DNA as a template. PCR conditions, including melting temperature (Tm, dependent on primer's length and AT/GC content) and elongation time (2 min/kbp for Pfu polymerase) are specific for each given pair of primers. Proofreading Pfu polymerase must be used to decrease probability of point mutations.

LUX A (Length: 1065 bp; SwissProt #P29238)

```
Forward primer:
ATGAAAATTAGTAATATCTG              (SEQ ID NO: 90)
Length-20; GC-4; AT-16; Tm = 53

Addition of BglII restriction site (in bold):
GAAGATCTATGAAAATTAGTAATATCTG      (SEQ ID NO: 91)

Reverse primer:
ACTTAAAAGATCCTCAGTAA              (SEQ ID NO: 92)
Length-20; GC-6; AT-14; Tm = 56

Addition of EcoRI restriction site (in bold):
ACTTAAAAGATCCTCAGTAAGAATTCCG      (SEQ ID NO: 93)

Reverse sequence to be used as final primer:
CGGAATTCTTACTGAGGATCTTTTAAGT      (SEQ ID NO: 94)
```

PCR Parameters:
Tm for PCR=54 C.
Elongation time using Pfu: 2.5 mins.
LUX B (Length: 981 bp; SwissProt #: P29239)

```
Forward primer:
ATGAATTTCGGGTTATTTTCC             (SEQ ID NO: 95)
Length-22; GC-7; AT-15; Tm = 61.

Addition of BglII restriction site (in bold):
GAAGATCTATGAATTTCGGGTTATTTTCC     (SEQ ID NO: 96)

Reverse primer:
CAAAGATAACCTTATTAAATAA            (SEQ ID NO: 97)
Length-22; GC-4; AT-18; Tm = 56.

Addition of EcoRI restriction site (in bold):
CAAAGATAACCTTATTAAATAAGAATTCCG    (SEQ ID NO: 98)

Reverse sequence to be used as final primer:
CGGAATTCTTATTTAATAAGGTTATCTTTG    (SEQ ID NO: 99)
```

PCR Parameters:
Tm for PCR=58 C.
Elongation time using Pfu: 2 mins.

LUX C-(Length: 1437 bp; SwissProt #: P29236)

Forward primer:
ATGATTAAGAAGATCCCAATGA            (SEQ ID NO: 100)
Length-22; GC-7; AT-15; Av. Tm = 61.

Addition of XhoI restriction site (in bold):
CCGCTCGAGATGATTAAGAAGATCCCAATGA   (SEQ ID NO: 101)

Reverse primer:
GTTCCTCGTATTTGTACCGTAG            (SEQ ID NO: 102)
Length-22; GC-10; AT-12; Tm = 66.

Addition of EcoRI restriction site (in bold):
GTTCCTCGTATTTGTACCGTAGGAATTCCG    (SEQ ID NO: 103)

Reverse sequence to be used as final primer:
CGGAATTCCTACGGTACAAATACGAGGAAC    (SEQ ID NO: 104)

PCR Parameters:
Tm for PCR=63 C.
Elongation time using Pfu: 3 mins.

LUX D (Length: 948 bp; SwissProt #: P21309)

Forward primer:
ATGGAAAATACACAACATTC              (SEQ ID NO: 105)
Length-20; GC-6; AT-14; Tm = 56.

Addition of BglII restriction site (in bold):
GAAGATCTATGGAAAATACACAACATTC      (SEQ ID NO: 106)

Reverse primer:
GCGTATTGGCTAGTGTCTAA              (SEQ ID NO: 107)
Length-20; GC-9; AT-11; Tm = 61.

Addition of EcoRI restriction site (in bold):
GCGTATTGGCTAGTGTCTAAGAATTCCG      (SEQ ID NO: 108)

Reverse sequence to be used as final primer:
CGGAATTCTTAGACACTAGCCAATACGC      (SEQ ID NO: 109)

PCR Parameters:
Tm for PCR=58 C.
Elongation time using Pfu: 2 mins.

LUX E (length: 1122 bp; SwissProt #: P29334)

Forward primer:
ATGTCAACATTATTAAATATAG            (SEQ ID NO: 110)
Length-22; GC-4; AT-18; Tm = 56.

Addition of BglII restriction site (in bold):
GAAGATCTATGTCAACATTATTAAATATAG    (SEQ ID NO: 111)

Reverse primer:
AATGGCCACGAGCCTGAAATAA            (SEQ ID NO: 112)
Length-22; GC-10; AT-12; Tm = 66.

Addition of EcoRI restriction site (in bold):
AATGGCCACGAGCCTGAAATAAGAATTCCG    (SEQ ID NO: 113)

Reverse sequence to be used as final primer:
CGGAATTCTTATTTCAGGCTCGTGGCCATT    (SEQ ID NO: 114)

PCR Parameters:
Tm for PCR=61 C.
Elongation time using Pfu: 2.5 mins.

LUX G (length: 705 bp; SwissProt #: P29237)

Forward primer:
ATGATTTTTAATTGCAAGGTTAA           (SEQ ID NO: 115)
Length-23; GC-5; AT-18; Tm = 59.

Addition of BglII restriction site (in bold):
GAAGATCTATGATTTTTAATTGCAAGGTTAA   (SEQ ID NO: 116)

Reverse primer:
GATGCATTTAGCTATACGTAA             (SEQ ID NO: 117)
Length-21; GC-7; AT-15; Tm = 59.

Addition of EcoRI restriction site (in bold):
GATGCATTTAGCTATACGTAAGAATTCCG     (SEQ ID NO: 118)

Reverse sequence to be used as final primer:
CGGAATTCTTACGTATAGCTAAATGCATC     (SEQ ID NO: 119)

PCR Parameters:
Tm for PCR=59 C.
Elongation time using Pfu: 1.5 mins.

Primers' Summary:

| Primer's name | Sequence |
| --- | --- |
| LUX A fw | GAAGATCTATGAAAATTAGTAATATCTG (SEQ ID NO: 91) |
| LUX A rev | CGGAATTCTTACTGAGGATCTTTTAAGT (SEQ ID NO: 94) |
| LUX B fw | GAAGATCTATGAATTTCGGGTTATTTTCC (SEQ ID NO: 96) |
| LUX B rev | CGGAATTCTTATTTAATAAGGTTATCTTTG (SEQ ID NO: (99) |
| LUX C fw | CCGCTCGAGATGATTAAGAAGATCCCAATGA (SEQ ID NO: 101) |
| LUX C rev | CGGAATTCCTACGGTACAAATACGAGGAAC (SEQ ID NO: 104) |
| LUX D fw | GAAGATCTATGGAAAATACACAACATTC (SEQ ID NO: 106) |
| LUX D rev | CGGAATTCTTAGACACTAGCCAATACGC (SEQ ID NO: 109) |
| LUX E fw | GAAGATCTATGTCAACATTATTAAATATAG (SEQ ID NO: 111) |
| LUX E rev | CGGAATTCTTATTTCAGGCTCGTGGCCATT (SEQ ID NO: 114) |
| LUX G fw | GAACATCTATGATTTTTAATTGCAAGGTTAA (SEQ ID NO: 116) |
| LUX G rev | CGGAATTCTTACGTATAGCTAAATGCATC (SEQ ID NO: 119) |

Example 11

Generation of Transgenic Plant Lines

Figure 9:
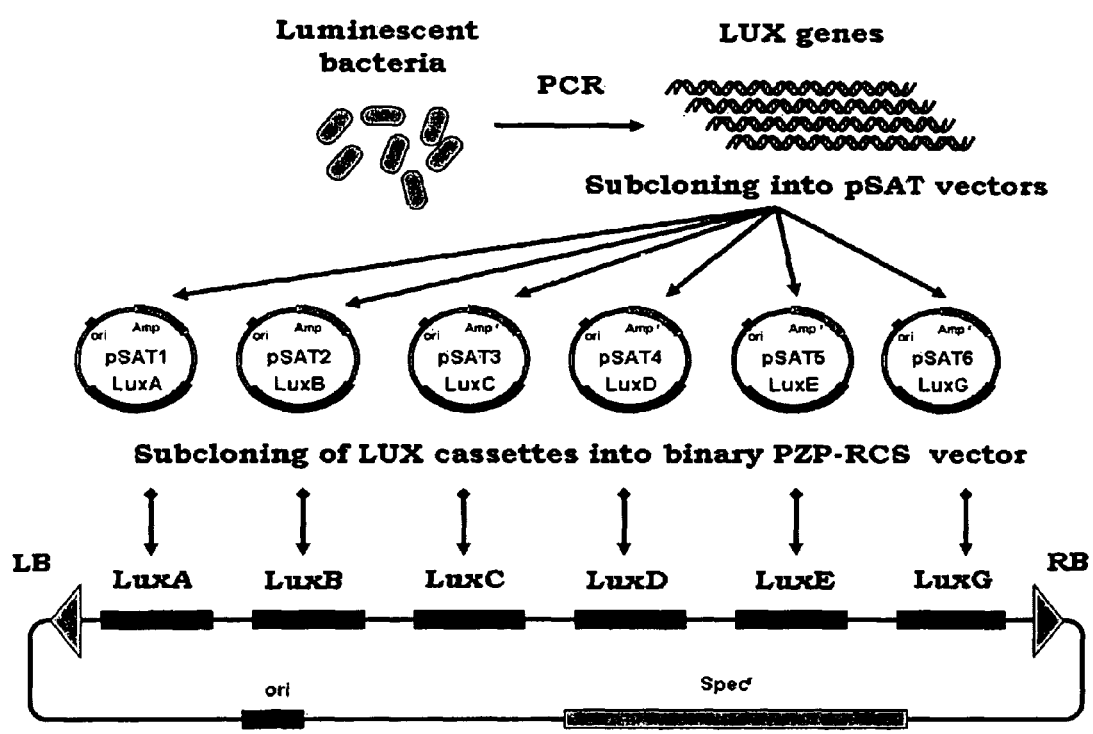
FIG. 9: Vector for nuclear expression of LUX genes. Separate LUX genes are PCR amplified and subcloned into MCS of pSAT vectors (one gene per one vector), under plant-specific regulatory promoter and terminator sequences, such as 35S promoter and terminator. Further, the cassettes containing promoter, lux gene and a terminator are subcloned from the SAT vectors into PZP-RCS binary vector (Tzfira et al, 2005) using homing endonucleases, such as PI-PspI or I-CeuI. The resulting binary PZP-RCS-Lux plasmid is used for plant transformation.
Figure 10:
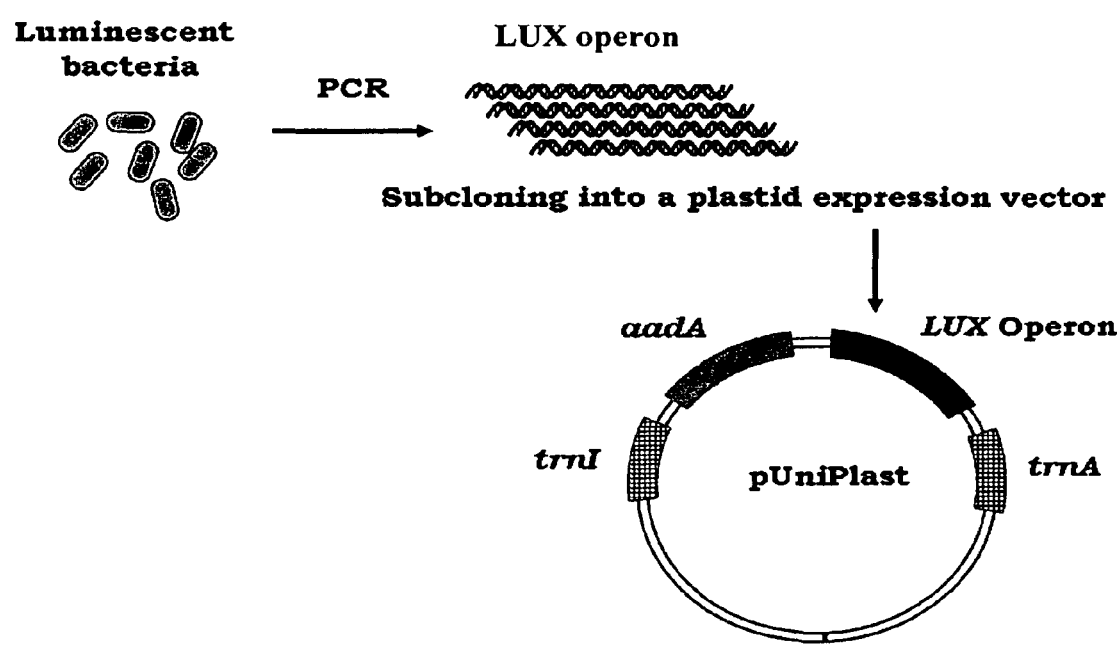
FIG. 10: Vector for expression of LUX operon from chloroplast genome. LUX operon as a whole is PCR amplified and subcloned, under chloroplast specific promoter and terminator, into vector suitable for transformation of chloroplasts, such as pLDCtV (ref: De Cosa, B., Moar, W., Lee, S. B., Miller, M., and Daniell, H. (2001) "Overexpression of the Bt cry2Aa2 operon in chloroplasts leads to formation of insecticidal crystals". Nature Biotechnol., vol. 19, pp. 71-74). Vector elements: aadA: selection marker conferring spectinomycin resistance; trnI/trnA: targeting homologues recombination elements; pUniPlast: Universal Plastid transformation vector.

Preparation of transgenic LUX genes expressing plants involve the following steps: (A) Preparation of gold particles coated with the plant transformation vectors, for either nuclear or chloroplast transformation, as shown in FIGS. 9 and 10, respectively; (B) Biolistic delivery of the DNA into plant tissue; (C) Placing transformed plant tissue on regeneration medium, containing appropriate antibiotics and hormones, and (D) Regenerated transgenic plants appear within several weeks. (adopted from: http://www.ag.usask.ca)

Example 12

Generation of Transgenic Tobacco Plants

Figure 11:
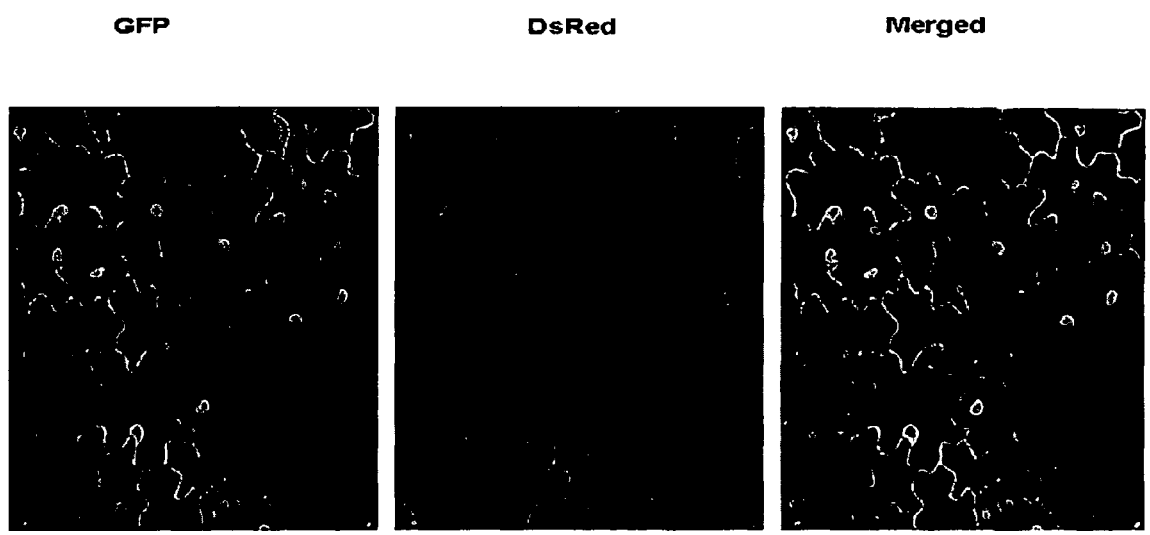
FIG. 11: Generation of transgenic tobacco plants. Transgenic tobacco plants are resistant to kanamycin (through incorporation of nptII gene) and are expressing free DsRed and GFP. Photographs made using fluorescent confocal microscope.

Transgenic tobacco plants expressing free DsRed and GFP have been generated using tobacco leaf disk transformation method and selection on kanamycin supplemented media. The use of pPZP-RCS2 binary vector with subcloned GFP, DsRed and ntpII cassettes, derived from pSAT vectors (Tzfira et al, 2005), resulted in high expression levels of both markers in certain progeny plants selected on kanamycin supplemented media (Krichevsky et al, unpublished). See FIG. 11.

Example 13

Remote Activation of an Inducible Promoter in-Planta

Gal4 DNA binding domain (mGal4) fused to transcriptional activator from the Herpes Simplex Virus (VP16) was cloned under constitutive 35S promoter into transient plant expression vector pRTL2 and biolistically delivered into leaves of an *Arabidopsis* plant carrying UAS driven, genome-integrated GUS reporter gene. Transient expression of mGal4-VP16 resulted in activation of GUS expression and was detected by histochemical staining. See FIGS. 12 (A) and (C). Specificity of UAS promoter activation has been confirmed when similar biolistic delivery has been made into a wild-type *Arabidopsis* plants, carrying no UAS driven GUS gene. See FIG. 12 C.

Example 14

LUX Operons Alignment

Alignment of LUX operons from three major luminescent bacteria families, namely *Photobacterium, Vibrio* and *Xenorhabdus* (aka *Photorhabdus*). A sequence comparison was produced using ClustalW software (EBI) of three luminescent bacteria species: *Photobacterium leiognathi* (abbreviated as Pl), *Vibrio harveyi* (abbreviated as Vh) and *Xenorhabdus* (aka *Photorhabdus*) *luminescens* (abbreviated as Xl). See FIG. 14. These 3 species have been selected because they are representative example of the largest and most prominent luminescent bacteria families, namely *Photobacterium Vibrio* and *Xenorhabdus* (aka *Photorhabdus*).

Conserved nucleotides shown by asterisks. Accordingly, variant nucleotide sequences of the LUX operon preferably do not include a variation of the conserved nucleotides shown in asterisks. Overall conservation between all three families approximates 60%, showing high degree of homology between luminescent bacteria from the three major luminescent bacteria families and suggesting strong conservation of the LUX operon amongst various luminescent bacteria species.

Primers for cloning LUX operons of these 3 bacterial species were designed. Sequence-specific part of the forward primer for individual gene normally starts from gene's first codon, namely ATG. In case of the whole operon cloning, the forward primer will start approx. 15-20 bp downstream of the first ATG of the first gene in the operon in order to include ribosome binding site allowing transcription of the first gene in the operon (each consecutive gene in the operon has its own ribosome binding site preceding its ATG). Further, sequence-specific part of the reverse primer for individual gene normally ends with this particular gene's stop codon (TAA, TAG, etc). Sequence specific primer aimed to amplify the whole operon ends with the last stop codon of the last gene in the operon, allowing to amplify by PCR and further subclone whole operon as a single unit into an expression vector (i.e. pCas/pUniPlast).

The following are examples of primers designed to clone the LUX operon.

Full LUX Operon Sequence for *Photobacterium leiognathi*, GeneBank #M63594:

Primers and Cloning Strategy:

This LUX operon will be cloned as EcoRI PCR fragment (restriction site underlined) directly into the same sites of a pCas vector and further subcloned into pUniPlast for making of transgenic plants.

```
P1 forward primer:
ACAGAATTCCCAAAGGAGATTACATGATTAAG    (SEQ ID NO: 120)

P1 reverse primer:
CTGATGCATTTAGCTATACGTAAGAATTCCAA    (SEQ ID NO: 121)

Final reverse primer:
TTGGAATTCTTACGTATAGCTAAATGCATCAG    (SEQ ID NO: 122)
```

PCR Conditions:

Primers Tm=over 60.

Expected fragment: approx. 6,550 bp.

Full LUX Operon Sequence for *Vibrio harvevi*, GeneBank #EU192082:

Primers and Cloning Strategy:

This LUX operon will be cloned as XhoI PCR fragment directly into the same sites of a pCas vector and further subcloned into pUniPlast for making of transgenic plants.

```
Vh forward primer:
AACTCGAGCAAAAGAGAAGCTCTTGATATGG     (SEQ ID NO: 123)

Vh reverse primer:
GTGTGAAGTGAGTTGGTCTTAGCTCGAGAA      (SEQ ID NO: 124)

Final reverse primer:
TTCTCGAGCTAAGACCAACTCACTTCACAC      (SEQ ID NO: 125)
```

PCR Conditions:

Primers Tm=over 60 C.

Expected fragment: approx. 7,130 bp.

Full LUX Operon Sequence for *Xenorhabdus* (aka *Photorhabdus*) *luminescens*, GeneBank #AF403784:

Primers and Cloning Strategy:

This LUX operon will be cloned as BamHI PCR fragment (restriction site underlined) directly into the same sites of a pCas vector and further subcloned into pUniPlast for making of transgenic plants.

```
Xl forward primer:
ATGGATCCCATTAAATGGATGGCTAATATGAC    (SEQ ID NO: 126)

Xl reverse primer:
CTTAAACCAAGCATTTAATAGTTGAGGATCCAT   (SEQ ID NO: 127)

Final reverse primer:
ATGGATCCTCAACTATTAAATGCTTGGTTTAAG   (SEQ ID NO: 128)
```

PCR Conditions:

Primers Tm=over 60 C.

Expected fragment: approx. 5,820 bp.

Primers' Summary

| Primer's name | Sequence |
|---|---|
| P1 forward primer | ACAGAATTCCCAAAGGAGATTACATGATTAAG (SEQ ID NO: 120) |
| P1 reverse primer | TTGAATTCTTACGTATAGCTAAATGCATCAG (SEQ ID NO: 122) |
| Vh forward primer | AACTCGAGCAAAAGAGAAGCTCTTGATATGG (SEQ ID NO: 123) |
| Vh reverse primer | TTCTCGAGCTAAGACCAACTCACTTCACAC (SEQ ID NO: 125) |
| X1 forward primer | ATGGATCCCATTAAATGGATGGCTAATATGAC (SEQ ID NO: 126) |
| X1 reverse primer | ATGGATCCTCAACTATTAAATGCTTGGTTTAAG (SEQ ID NO: 128) |

What is claimed is:

1. A transgenic bioluminescent plant, comprising:
an expressible heterologous nucleotide sequence comprising a bacterial LUX operon, which comprises LUX A, LUX B, LUX C, LUX D, LUX E, and LUX G genes, wherein the heterologous nucleotide sequence is expressed to render the plant bioluminescent; and
wherein the heterologous nucleotide sequence is integrated in a plastid genome.

2. The plant of claim 1, wherein the plastid is a chloroplast.

3. The plant of claim 1, wherein the heterologous nucleotide sequence further comprises at least one gene encoding a cofactor for enhancing bioluminescence.

4. The plant of claim 3, wherein the cofactor comprises a polypeptide encoded by a LUX H gene and/or a riboflavin (RIB) operon.

5. The plant of claim 3, wherein the cofactor comprises a bacterial or plant acyl carrier protein.

6. The plant of claim 3, wherein the cofactor comprises a flavin reductase enzyme.

7. The plant of claim 1, further comprising a second heterologous nucleotide sequence that comprises a gene encoding a fluorescent protein.

8. A kit, comprising:
a) a seed for generating a transgenic bioluminescent plant having an expressible heterologous nucleotide sequence comprising a bacterial LUX operon, which comprises LUX A, LUX B, LUX C, LUX D, LUX E, and LUX G genes, wherein the heterologous nucleotide sequence is integrated in a plastid genome; and
b) a plant transformation vector.

9. A vector system, comprising:
a) a plastid transformation vector having a first heterologous nucleotide sequence, which comprises LUX A, LUX B, LUX C, LUX D, LUX E, and LUX G genes operably linked to a first promoter, wherein the first heterologous nucleotide sequence is integratable in a plastid genome; and
b) a vector having a second heterologous nucleotide sequence operably linked to a second promoter.

10. The vector system of claim 9, wherein the vector having the second heterologous nucleotide sequence is a binary vector.

11. The vector system of claim 9, wherein the first promoter is an inducible promoter that is inducible by a protein encoded by the second heterologous nucleotide sequence.

12. The vector system of claim 10, wherein the second heterologous nucleotide sequence further comprises a plastid targeting sequence.

13. The vector system of claim 9, wherein the first promoter is a constitutive promoter and the second heterologous nucleotide sequence further comprises a plastid targeting sequence.

* * * * *

SEQUENCE LISTING

<160> NUMBER OF SEQ ID NOS: 129

<210> SEQ ID NO 1
<211> LENGTH: 763
<212> TYPE: DNA
<213> ORGANISM: Artificial Sequence
<220> FEATURE:
<223> OTHER INFORMATION: Synthetic nucleotide sequence

<400> SEQUENCE: 1

```
tggcaaacag ctattatggg tattatgggt gggcaaccca ctagcatatc gaaattctaa      60
ttttctgtag agaagtccgt atttttccaa tcaacttcat taaaaatttg aatagatcta     120
catacaccct ggttgacacg agtatataag tcatgttata ctgttgaata acaagccttc     180
cattttctat tttgatttgt agaaaactag tgtgcttggg agtccctgat gattaaataa     240
accaagattt taccccatgg tccggactca gatctcgagc tcaagcttcg aattctgcag     300
tcgacggtac cgcgggcccg ggatccacct agtctagaga tcctggccta gtctatagga     360
ggttttgaaa agaaaggagc aataatcatt ttcttgttct atcaagaggg tgctattgct     420
cctttctttt tttcttttta tttatttact agtattttac ttacatagac ttttttgttt     480
acattataga aaagaaggaa gaggttattt tcttgcattt attcatgatt gagtattcta     540
ttttgatttt gtatttgttt aaaattgtag aaatagaact tgtttctctt cttgctaatg     600
ttactatatc ttttttgattt ttttttttcca aaaaaaaaat caaattttga cttcttctta     660
tctcttatct ttgaatatct cttatctttg aaataataat atcattgaaa taagaaagaa     720
gagctatatt cgatggcaaa cagctattat gggtattatg ggt                       763
```

<210> SEQ ID NO 2
<211> LENGTH: 1464
<212> TYPE: DNA
<213> ORGANISM: Artificial Sequence
<220> FEATURE:
<223> OTHER INFORMATION: Synthetic nucleotide sequence: GFP pre-cloned
    pCas vector

<400> SEQUENCE: 2

```
tggcaaacag ctattatggg tattatgggt gggcaaccca ctagcatatc gaaattctaa      60
ttttctgtag agaagtccgt atttttccaa tcaacttcat taaaaatttg aatagatcta     120
catacaccct ggttgacacg agtatataag tcatgttata ctgttgaata acaagccttc     180
cattttctat tttgatttgt agaaaactag tgtgcttggg agtccctgat gattaaataa     240
accaagattt taccagatct atgagtaaag gagaagaact tttcactgga gttgtcccaa     300
ttcttgttga attagatggt gatgttaatg ggcacaaatt ctctgtcagt ggagagggtg     360
aaggtgatgc aacatacgga aaacttaccc ttaaatttat ttgcactact ggaaagctac     420
```

```
ctgttccatg gccaacactt gtcactactt tctcttatgg tgttcaatgc ttttcaagat      480
acccagatca tatgaaacag catgactttt tcaagagtgc catgcccgaa ggttatgtac      540
aggaaagaac tatattttac aaagatgacg ggaactacaa atcacgtgct gaagtcaagt      600
ttgaaggtga taccctcgtt aatagaattg agttaaaagg tattgatttt aaagaagatg      660
gaaacattct tggacacaaa atggaataca actataactc acacaatgta tacatcatgg      720
cagacaaaca aaagaatgga atcaaagtta acttcaaaat tagacacaac attgaagatg      780
gaagcgttca actagcagac cattatcaac aaaatactcc aattggcgat ggccctgtcc      840
ttttaccaga caaccattac ctgtccacac aatctgccct tccaaagat cccaacgaaa       900 agagagatca catgatcctt cttgagtttg taacagctgc tgggattaca catggcatgg      960
atgaactata caaataagag ctcaagcttc gaattctgca gtcgacggta ccgcgggccc     1020
gggatccacc tagtctagag atcctggcct agtctatagg aggttttgaa agaaaggag      1080 caataatcat tttcttgttc tatcaagagg gtgctattgc ccctttctttt ttttcttttt     1140 atttatttac tagtatttta cttacataga cttttttgtt tacattatag aaaaagaagg     1200
agaggttatt tcttgcatt tattcatgat tgagtattct attttgattt tgtatttgtt      1260
taaaattgta gaaatagaac ttgtttctct tcttgctaat gttactatat cttttgatt      1320 ttttttttcc aaaaaaaaa tcaaattttg acttcttctt atctcttatc tttgaatatc      1380
tcttatcttt gaataataa tatcattgaa ataagaaaga agagctatat tcgatggcaa      1440
acagctatta tgggtattat gggt                                            1464

<210> SEQ ID NO 3
<211> LENGTH: 2180
<212> TYPE: DNA
<213> ORGANISM: Artificial Sequence
<220> FEATURE:
<223> OTHER INFORMATION: Synthetic nucleotide sequence: pUniPlast MCS

<400> SEQUENCE: 3
ggcgcgccgg gccttgtaca caccgcccgt cacactatgg gagctggcca tgcccgaagt       60
cgttacctta accgcaagga gggggatgcc gaaggcaggg ctagtgactg gagtgaagtc      120
gtaacaaggt agccgtactg gaaggtgcgg ctggatcacc tccttttcag ggagagctaa     180
tgcttgttgg gtattttggt ttgacactgc ttcacacccc caaaaaaaag aagggagcta     240
cgtctgagtt aaacttggag atggaagtct tctttccttt ctcgacggtg aagtaagacc     300
aagctcatga gcttattatc ctaggtcgga acaagttgat aggacccccct tttttacgtc     360 cccatgttcc ccccgtgtgg cgacatgggg gcgaaaaaag gaaagagagg gatggggttt     420
ctctcgcttt tggcatagcg ggccccccagt gggaggctcg cacgacgggc tattagctca     480
gtggtagagc gcgcccctga taattgcgtc gttgtgcctg gctgtgagg gctctcagcc      540 acatggatag ttcaatgtgc tcatcggcgc ctgaccctga tgtggatc atccaaggca       600 cattagcatg gcgtactcct cctgttcgaa ccggggtttg aaaccaaact cctcctcagg     660
aggatagatg gggcgattcg ggtgagatcc aatgtagatc caactttcga ttcactcgtg     720
ggatccgggc ggtccggggg gaccaccac ggctcctctc ttctcgagaa tccatacatc      780
ccttatcagt gtatggacag ctatctctcg agcacaggtt tagcaatggg aaaataaaat     840
ggagcaccta caacgcatc ttcacagacc aagaactacg agatcgcccc tttcattctg      900
gggtgacgga gggatcgtac cattcgagcc gttttttttct tgactcgaaa tgggagcagg      960
tttgaaaaag gatcttagag tgtctagggt tgggccagga gggtctctta acgccttctt     1020
```

-continued

```
ttttcttctc atcggagtta tttcacaaag acttgccagg gtaaggaaga aggggggaac    1080
aagcacactt ggagagcgca gtacaacgga gagttgtatg ctgcgttcgg gaaggatgaa    1140
tcgctcccga aaaggaatct attgattctc tcccaattgg ttggaccgta ggtgcgatga    1200
tttacttcac gggcgaggtc tctggttcaa gtccaggatg gcccagctgc taactataac    1260
ggtcctaagg tagcgatggc aaacagctat tatgggtatt atgggtttct tccccgaatt    1320
cggggaagaa tagggataac agggtaatct ccacttggct cggggggata tagctcagtt    1380
ggtagagctc cgctcttgca attgggtcgt tgcgattacg ggttggatgt ctaattgtcc    1440
aggcggtaat gatagtatct tgtacctgaa ccggtggctc acttttttcta gtaatgggg    1500 aagaggaccg aaacgtgcca ctgaaagact ctactgagac aaagatgggc tgtcaagaac    1560
gtagaggagg taggatgggc agttggtcag atctagtatg gatcgtacat ggacggtagt    1620
tggagtcggc ggctctccca gggttccctc atctgagatc tctggggaag aggatcaagt    1680
tggcccttgc gaacagcttg atgcactatc tcccttcaac cctttgagcg aaatgcggca    1740
aaagaaaagg aaggaaaatc catggaccga ccccatcatc tccacccccgt aggaactacg    1800 agatcacccc aaggacgcct tcggcatcca ggggtcacgg accgaccata gaaccctgtt    1860
caataagtgg aacgcattag ctgtccgctc tcaggttggg cagtcagggt cggagaaggg    1920
caatgactca ttcttagtta gaatgggatt ccaactcagc accttttgag tgagattttg    1980
agaagagttg ctctttggag agcacagtac gatgaaagtt gtaagctgtg ttcgggggg    2040 agttattgtc tatcgttggc ctctatggta gaatcagtcg ggggacctga gaggcggtgg    2100
tttaccctgc ggcggatgtc agcggttcga gtccgcttat ctccaactcg tgaacttagc    2160
cgatacaaag ctggccggcc                                                2180
```

<210> SEQ ID NO 4
<211> LENGTH: 6547
<212> TYPE: DNA
<213> ORGANISM: Photobacterium leiognathi

<400> SEQUENCE: 4

```
ccaaaggaga ttacatgatt aagaagatcc caatgattat tgggggtgta gttcaaaaca      60
cgtctggata tggcatgcgt gaactaacgc tcaacaataa taaagtgaat atccctatca     120
tcacccaaag tgatgttgaa gctattcaat cactaaatat agaaaacaaa ttgactataa     180
atcagatagt taatttctta tatacagtgg gacaaaaatg gaagagcgaa acttacagcc     240
gacgactcac ttatattcga gatcttatta agttcctcgg ttactcacaa gagatggcaa     300
aacttgaagc taactggatc tcaatgattc tgtgtagcaa aagtgcgttg tacgatattg     360
ttgagaatga tcttagctca cggcatatta ttgatgagtg gatcccccaa ggtgaatgtt     420
atgtcaaagc gctcccaaaa ggaaaatctg tacacctatt agctggtaac gtaccactat     480
ctggtgtgac ttctattctt cgtgcgattt tgaccaaaaa cgagtgcatc ataaaaacgt     540
catcagctga tccttttaca gctactgcgc tagttaatag ttttatcgat gtagatgcag     600
aacacccgat cacacgttca atctcagtta tgtattggtc acatagcgag gatcttgcta     660
ttccaaaaca aataatgagc tgtgctgatg tggttattgc atggggtggt gatgatgcaa     720
ttaaatgggc tacagaacat gcaccatcac acgcagatat tctaaaattt ggtcccaaaa     780
agagtatatc cattgttgac aacccaacag atattaaggc tgctgctatc ggtgtagcac     840
atgatatctg ttttttacgat cagcaagcat gtttctccac ccaagatatt tattatattg     900
```

```
gcgatagcat agacatattt tttgatgaat tagctcagca attaaataaa tataaagaca    960
tattgcctaa aggtgagcgg aatttttgatg aaaaagcagc ttttttctttta acggaaagag   1020 aatgtttgtt tgccaaatat aaagttcaaa aaggtgaaag ccaatcttgg ttattaacgc   1080
aatcacctgc gggatcattt ggtaatcagc cgttatcacg ctcggcttat attcatcaag   1140
taaatgacat ttcagaagtc attccattcg tgcataaggc ggtaacgcaa accgtcgcaa   1200
tagcgccgtg ggagtcgtct ttcaaatata gagatatatt agcagaacat ggtgcagaac   1260
gaattataga agccggaatg aataatatat ttcgagtagg tggcgcccat gatgggatgc   1320
gtccccttca acggcttgtt aactatatat cacatgaaag gccgtcaaca tataccacta   1380
aagatgtctc ggtgaaaatc gaacagactc gttatcttga ggaagataag ttcctcgtat   1440
ttgtaccgta gaaagagata tatcatgaaa aatacacaac attcattacc tattgatcac   1500
gtaattgata ttggtgataa ccgttatatt cgagtatggg aaaccaagcc gaaaaataaa   1560
gaaaccaagc gtaataatac catcgttatc gcctcaggct ttgctcgacg catggatcat   1620
tttgctggtc ttgccgaata tttagcaaat aatggttttc gtgttattcg ttatgattcg   1680
ttaaatcatg tcggtcttag tagcggagag atcaaacagt tctcgatgtc agtaggtaaa   1740
cacagtttgc taactgttat tgattggcta aagaacgaa atattaacaa tataggtctt   1800
attgcttcga gtctttctgc tcgaattgct tatgaagtgg cagcagaaat tgatttgtca   1860
tttttaatta ccgccgtcgg tgttgtcaat ttaagaagta cgctagaaaa agcactgaaa   1920
tatgattatc tacaaatgga agtaaatact attcctgaag atttaatttt tgaaggacac   1980
aatctaggtt caaaagtctt tgtgacagat tgttttgaaa ataattggga ctcattagat   2040
tcgacaataa ataaaatttg tgaactagat attccattta ttgctttcac ttcagatggc   2100
gatgattggg tttgccaaca tgaagtaaaa catttagtca gtaacgttaa atctgacaaa   2160
aagaaaattt actcactcgt tggctcatct catgatttgg gcgaaaacct agtggtgctt   2220
cgtaacttct atcaatcaat gacgaaagct gctgtgagct tagatcgtca attagtagag   2280
cttgttgatg aaattattga accaaatttt gaagacctaa cagttattac ggtaaatgaa   2340
cggcgcctca aaaataaaat cgaaaatgaa attattaata gattagctga tcgcgtattg   2400
gctagtgtct aaatagtact tacctaagta cagccaaaag gaagaaataa tgaaaattag   2460
taatatctgt ttctcatacc aaccaccagg tgaatcacat caagaggtaa tggagcgctt   2520
tattcgttta ggcgttgcat cagaagagct caactttgat ggtttctata cacttgaaca   2580
ccatttcact gagtttggta ttacaggtaa cctttatatt gcctgtgcca atattcttgg   2640
tcgaaccaaa aggatccaag tcggtaccat ggggatagtg ttaccgacag agcacccagc   2700
acgacatgta gaaagtcttc tcgtttttaga tcaactgtct aaagggcgct ttaactacgg   2760
tactgttcgc ggactctacc ataaagattt tcgtgttttt ggtacatcac aggaagattc   2820
tcgtaagacc gcagaaaatt tctactctat gatcttggat gcatcaaaaa caggtgtgct   2880
acatactgac ggtgaagtag tagagttccc agatgtcaat gtttatccag aagcttacag   2940
caaaaaacaa cccacctgca tgacagccga atcatccgag accatcactt atttagctga   3000
acgtggttta ccaatggtgt taagttggat tattccggtc agtgagaaag tctcacaaat   3060
ggaattgtac aatgaagttg cggcagagca tggtcatgac attaacaaca ttgaacatat   3120
cctaactttc atttgctctg taaatgaaga cggtgaaaaa gcagacagcg tatgccgtaa   3180
tttcctagaa aattggtacg actcttacaa aaatgcaacc aacatcttca acgacagtaa   3240
ccaaactcgt ggctacgatt acctcaaagc tcagtggcgt gagtgggtaa tgaaggggtt   3300
```

```
ggctgatcct cgtcgccgac ttgattacag taacgaatta aacccgtgtcg gcacgccaga    3360 acgatgcatt gagatcattc aaagtaatat tgatgccact ggaattaagc atattactgt    3420
tggatttgaa gcgaatggtt ctgaacaaga aattcgtgaa tccatggagc tatttatgga    3480
aaaagtagcg ccacacttaa aagatcctca gtaagctgtt cttttaaac tattcaatat     3540 caaggcataa ggaataaaat atgaatttcg ggttattttt cctaaatttc cagcctgaag    3600
gtatgacttc agaaatggtt ttagacaaca tggtagatac tgtcgcatta gtggataaag    3660
atgattacca ctttaaaaga gtgctcgtca gcgagcatca ttttctaaa aacggcatta     3720 tcggagaacc tttgacagcg attagcttct tacttggttt gactaaacgt atagaaattg    3780
gttctttaaa tcaagtgatt accacccatc atcctgtacg tatcggagaa caaacgggct    3840
tacttgatca aatgtcttac ggtcgtttcg ttttaggctt aagtgactgt gtcaatgact    3900
tcgaaatgga tttctttaag agaaaacgta gctctcaaca gcaacaattc gaagcatgtt    3960
acgaaatttt aaatgaagcg ctgacgacaa actattgtca ggcagatgat gacttcttta    4020
acttcccacg tatttctgtt aacccgcatt gtattagcga agtaaaacaa tatatttag    4080 cttcaagcat gggcgtggtt gaatgggcag caagaaaagg attgccactc acttaccgct    4140
ggagtgacag cctagcagaa aaagaaaaat actatcagcg ttatctcgct gttgctaaag    4200 agaataaat tgatgtatca aatattgacc accaattccc actgctcgtt aatatcaatg     4260
aaaatcgtcg tattgctcga gatgaagtaa gggagtatat acaaagttat gtgagtgaag    4320
cctaccctac tgaccccaac attgagctaa gagtagaaga gcttattgag cagcatgctg    4380
tcggcaaagt ggatgagtac tacgactcaa caatgcacgc agtaaaagtt acaggttcaa    4440
aaaatttatt actctctttt gaatcaatga aaaataaaga cgatgttacc aagcttataa    4500
atatgtttaa tcaaaaaatc aaagataacc ttattaaata atttaattac ggatagatat    4560
tttcgatata tctaagtctt actaccattt atataaacta tttatacaga taacgtttca    4620
tttgattaag tcagtaaata attgccatta attaatggca gtgcagatcc ttacactgcc    4680
atttataaat taaataaggg ttaacatgtc aacattatta aatatagatg caactgaaat    4740
taaggtgagt acagaaatag atgatattat ttttacatca tcaccgctaa cgttactatt    4800
tgaagatcaa gaaaaaatac agaaagaact tattttggag tctttccatt atcattacaa    4860
tcataataaa gattataagt actattgtaa tatacaaggc gtagatgaga atatacagtc    4920
cattgacgat attcctgttt ttcctacttc aatgttcaag tactcaagat tacatactgc    4980
tgatgaatca aatattgaaa attggtttac tagtagtggt acaaagggag tcaaaagtca    5040
tatagctcga gatcggcaga gtattgaacg cttgctaggt tctgttaatt acggcatgaa    5100
atacttgggt gaatttcacg agcatcaatt agaactagtg aatatggggc cagatcgttt    5160
cagtgcgtca aatgtttggt ttaaatatgt aatgagctta gttcaattac tttacccaac    5220
aacatttacc gttgaaaacg atgaaatcga ttttgaacaa accatcttag cgttaaaagc    5280
aattcagcgt aaaggaaaag gaatttgttt aattggccct ccgtatttta tttatttgtt    5340
atgccactac atgaaagagc ataatatcga atttaatgct ggtgcacata tgtttatcat    5400
tacaggtggg ggatgaaaaa ccaaacaaaa agaagcgcta aaccgacaag atttcaatca    5460
actattgatg gagacttta gccttttcca tgaaagtcaa attcgagata tctttaacca    5520
agtagagcta aacacttgtt tctttgaaga cagcctacag cgtaaacatg taccaccgtg    5580
ggtatatgct cgtgcgcttg atcctgtcac tttaacgccc gtagaagatg gccaagaggg    5640
```

```
cttgatgagt tatatggatg cctcatctac cagctacccg acatttattg ttaccgacga    5700
tattggtatt gttcgccatc taaaagaacc agatccattc caaggaacaa cggttgaaat    5760
tgttcgtcgt ttaaatacgc gagaacaaaa aggatgttca ctctcaatgg ccacgagcct    5820
gaaataaaag cagggcttaa tcatgatttt taattgcaag gttaaaaaag tcgaagcatc    5880
tgacagccat atttacaaag tgtttattaa gcctgacaaa tgctttgatt ttaaagcggg    5940
tcaatatgta attgtgtatc tcaatggaaa aaatttgccg ttttctattg ctaactgccc    6000
aacttgtaat gagctccttg aattacatgt aggaggttcg gtaaaagaat ccgccattga    6060
agctatttcg cactttatta atgcatttat ttatcaaaaa gaatttacaa tcgatgcacc    6120
acacggtgat gcatggctga gagatgaaag ccaatcacct ttactactta tagcaggagg    6180
gacaggttta tcatatatca atagcatttt aagttgttgt attagtaaac agttatctca    6240
gcctatctat ctttattggg gagtaaataa ctgtaatttta ctctatgctg atcaacaact    6300
aaaaacactc gccgcacaat acagaaatat aaattatatt cctgtggtag agaatttaaa    6360
tactgactgg cagggaaaaa ttggtaatgt tattgacgcg gttattgaag attttttcaga    6420 tttatctgac tttgatatct atgtctgcgg gccatttggt atgagccgga ctgcgaaaga    6480
tattctgatc tcacagaaaa aggcgaatat aggaaaaatg tattctgatg catttagcta    6540
tacgtaa                                                              6547
```

<210> SEQ ID NO 5
<211> LENGTH: 7130
<212> TYPE: DNA
<213> ORGANISM: Vibrio harveyi

<400> SEQUENCE: 5

```
caaaagagaa gctcttgata tggaaaaaca cttaccttta ataataaatg ggcaaatagt      60
ttctactaaa gaaaatcgat ttgagatcag ttttgaagaa aaaaaagtta agattgattc     120
ctttaatcat tttcatttaa tccagatggt gactcatgat tatttaaatg atctaaatat     180
taataacatc atcaattttc tttatacaac ggggcagcgt tggaagagcg aagaatattc     240
aagaagaagg gcatatattc ggtctcttat tacttatttg gggtattcac cacaaatggc     300
gaaactagaa gcaaattgga ttgcaatgat cctttgctct aagagtgcgc tctacgacat     360
tattgatacc gagcttggct caacgcatat acaagatgaa tggctaccgc agggtgagtg     420
ttatgtgagg gctttttccta aaggacgcac gatgcatttg cttgcgggga atgttcctct     480
ctccggtgtg acctcaatac tacgaggcat actgacgaga atcaatgta ttgtgagaat     540 gtcagcatcg gatcctttta ctgcccacgc gctagcgatg agctttattg acgtcgatcc     600
gaatcatcca atttctcgtt ctatctccgt attgtattgg cctcatgcat cggatacgac     660
actcgctgaa gagttactca gtcatatgga tgcagtggtt gcttgggggg gggcgggatg     720
ccattgattg gcggttaag cattctcctt cacatatcga tgttttgaag tttggtccaa     780
agaagagttt taccgtgtta gaccatccag ccgatctaga agaagccgcc tcgggtgttg     840
cccatgatat ttgctttttat gaccaaaatg cctgctttc tactcagaat atttactttt     900
ctggagataa gtatgaagaa tttaaattaa aacttgttga aaaactgaat ctctatcaag     960
aagttttacc aaaatcaaaa caagttttg atgacgaagc tttattttct atgactcgtc    1020
ttgagtgtca atttttctggg ttgaaagtta tatcagaacc ggaaaataac tggatgatca    1080
tcgagtcaga gcccgggggtt gaatataacc atccattaag tcgttgcgtt tatgtccaca    1140
aaataaataa ggttgatgat gttgttgaat atatagaaaa acatcaaaca caaacgattt    1200
```

```
cttttttatcc atgggaatct tccaagaaat atcgagatgc attcgccgca aaagggtag    1260 aaagaatcgt tgaatctggg atgaataata tatttagagc tggtggcgca catgatgcaa    1320
tgcgcccact tcaacgttta gttcgatttg tttctcatga agaccatat aacttcacca    1380 ctaaggatgt atctgtcgaa atagagcaaa cccgctttct tgaagaagat aaattcttgg    1440
ttttcgtccc ttaaataagg aaaattacaa tgaataatca atgcaagact attgcacacg    1500
tgttacgcgt gaacaatggt caggaacttc acgtctggga aacgccccca aaagaaaatg    1560
tgccttctaa aaataacacc attttaattg cttctggttt tgccagaaga atggatcact    1620
ttgctgggtt ggccgagtat ctatctgaaa atggtttcca tgtgttccgt tatgactctc    1680
ttcatcatgt ggggctcagc tcgggttcga ttgatgaatt caccatgacg acgggcaaaa    1740
atagtttgtg cactgtttat cactggctgc agaccaaggg cacacaaaac attggcttga    1800
ttgcggcaag tctctcagct cgtgtcgcct atgaagttat ctctgatctg agctgtctt    1860 ttctgattac tgcggttggt gtggtgaact tgcgtgacac actagaaaaa gcgcttggtt    1920
ttgattacct cagtttgcct atcgatgagc taccaaacga tcttgatttt gaaggtcata    1980
agcttggttc tgaagtgttc gttcgcgact gcttcgagca tcactgggat accttagatt    2040
ctactctcga caaagtagcc aatacctcgg ttccttaat cgcctttacc gctaacaacg    2100
atgattgggt taagcaagaa gaagtctatg acatgttagc gcatatccgc actgggcatt    2160
gcaagctcta ctccttgctt ggtagctctc atgacttggg cgaaaacttg gtcgtgttac    2220
gtaattttta ccaatccgtc accaaagccg ccatcgcaat ggatggaggc agcttagaaa    2280
tcgacgtcga ctttatcgag cctgattttg aacaactcac catcgcgact gtgaatgaac    2340
gtcgcttgaa agcggaaatt gaaagccgta cgccagaaat ggcttaggtc tcatcgtaat    2400
accaataaat aaggaaatgt tatgaaattt ggaaacttcc ttctcactta tcagccacct    2460
gagctatctc agaccgaagt gatgaagcga ttggttaatc tgggcaaagc gtctgaaggt    2520
tgtggtttcg acactgtttg gttactagag caccacttca ctgaatttgg gttgttaggg    2580
aatccttatg ttgctgccgc acatctatta ggtgcgacag aaaagctcaa tgttggcacc    2640
gcagccattg tattgccgac tgcccatccg gttcgacaag cagaagacgt aaacctactg    2700
gatcaaatgt cgaaaggacg attccgttt gggatttgtc gcggtttgta cgacaaagat    2760
ttccgtgtct ttggtacaga catggataac agccgagcct taatgactg ttggtatgac    2820 ttgatgaaag aaggcttcaa tgaaggctat atcgcggcgg ataacgaaca tattaagttc    2880
ccgaaaatcc aactgaatcc atcggcttac acacaaggtg gcgctcctgt ttatgtcgtc    2940
gcggagtcag catcaacgac agaatgggct gcagagcgtg gcctaccaat gattctaagc    3000
tggatcatca atactcacga gaagaaagcg cagcttgatc tttacaatga agtcgcgact    3060
gaacatggct acgatgtgac taagattgac cactgtttgt cttacatcac ctccgtcgat    3120
catgactcaa ataaagccaa agatatttgc cgcaacttct tgggtcattg gtacgactca    3180
tacgtgaatg ccaccaagat ttttgacgac tctgaccaaa caaaaggcta cgacttcaat    3240
aaaggccaat ggcgcgattt tgtgttgaaa ggccacaaag ataccaaccg ccgaattgat    3300
tacagctacg aaatcaaccc agtagggacg cctgaagagt gtatcgcgat tatccagcaa    3360
gatatcgatg caacgggtat tgacaatatt tgttgtggtt ttgaagcaaa cggttctgaa    3420
gaagaaatta tcgcatctat gaagctattc cagtccgatg tgatgccata tctcaaagaa    3480
aaacagtaat taatatttc taaaaggaaa gagacatgaa atttggatta ttcttcctca    3540
```

```
atttttatgaa ttcaaagcgt tcttctgatc aagtcatcga agaaatgtta gataccgcac    3600
attacgtaga tcagttgaag tttgacacgt tggctgttta cgaaaaccat ttctcgaaca    3660
atggtgtggt tggtgcccca ttaacagtgg ctggtttttt acttggtatg acaaagaacg    3720
ccaaagtggc ttcgttgaat cacgttatta acacacatca tccagtacgt gtggcggaag    3780
aagcgtgtct actcgaccaa atgagtgaag gccgttttgt ctttggcttt agtgattgtg    3840
aaaagagtgc agatatgcgc ttctttaatc gaccaacgga ttctcagttt cagttgttca    3900
gtgagtgtca caagatcatc aatgatgcat tcactactgg gtactgccat ccaaacaatg    3960 attttttatag ttttcctaaa atctctgtta acccacacgc ttacactgaa ggcggtcctg    4020
cgcaatttgt gaatgcgacg agcaaagaag tggttgaatg ggcggctaag ttagggcttc    4080
cactcgtgtt taaatgggac gactcaaacg cgcaaagaaa agaatacgcc ggtttgtacc    4140
acgaagttgc tcaggcacat agtgtcgatg ttagtcaggt tcgacacaag ctgacgctgt    4200
tggtcaacca aaatgtagat ggtgaagcag caagggcaga agcacgcctg tatttggaag    4260
agtttgtccg tgaatcttac ccaaataccg aatttgagca aaaaatggca gagctgttgt    4320
cagaaaatgc catcggtact tatgaagaaa gtactcaggc agcgcgagtt gcgattgagt    4380
gttgtggtgc cgcggaccta ttgatgtctt ttgagtcgat ggaagataaa gcgcagcaaa    4440
gagcggttat cgatgtggta aacgccaaca tcgtcaaata ccactcgtaa cgtttaactg    4500
atgctgaagg ggcagcgatg ccccttatat caccattctt ttcgcgcgat agcgctaact    4560
aatagaggca tttatatgga cgtactttca gcggttaagc aggaaaatat cgcagcgagc    4620
acagaaatcg atgacttgat tttcatggga actcctcagc aatggtcatt gcaggaacaa    4680
aaacagctga catctcgcct tgttaaaggg gcatatcaat accattacca caataatgat    4740
gactatcgtc agttctgcca aaggctggga gtcggagagg aggtcgaaga tctcaatgag    4800
atccccgttt tccctacttc tatttttaag ttgaagaccc tattaacact tgacgatgaa    4860
gaggtagaga atcgctttac tagcagcggt actagtggca tcaaaagtat tgtcgcacga    4920
gatagactca gtattgagcg acttcttggc tcagtaaatt tcggtatgaa ttacgttggt    4980
gattggtttg accatcagat ggagttggtg aacttaggcc cagatcgctt taatgccaac    5040
aatatttggt tcaagtacgt catgagctta gtcgagctcc tttatccgac cgcatttact    5100
gccactgagg atgagatcga cttgaggcg acgctagcta atatgaatcg tattaagcag    5160
tctggtaaaa ccatttgtct tatcggccct ccttatttta tctatctact gtgctgtttc    5220
atgcgcgagc aaggtcaaac tttcaatggt ggtcgcgatc tttacatcat cactggcggc    5280
ggctggaaaa acatcagga tcaatcgctc gatagagacg agttcaacca gcttttgtgt    5340
gagactttta ccttagaaag cgcagagcag attcgagaca catttaatcc agttgaactg    5400
aacacctgct ttttttgaaga tacagaacac aaaaagcgtg taccgccctg ggtctttgca    5460
agagctctgg atcctaaaac attaaagccg cttccgcatg ccagccagg actgatgagc    5520 tatatggatg cctcggcggt cagctatcca tgttttctag tgacggatga catcggcatc    5580
gtgcgagaag aagaaggcga tcgcccggga accactgttg agatcgttag aagagttaag    5640
acgcggggta tgaaggggtg tgctctcagt atgtctcaag catttacagc taagaatgaa    5700
ggaggcaact gacatgttat gttcgataga aaaaattgag ccgttaacta acctcatatt    5760
ccgagtattg ctcaagccag atcagccttt tgaatttagg gcagggcagt acattaacgt    5820
cagtttaagc tttggtagtt taccgttttc tatagcctca tgtccttcta atggtgcgtt    5880
tttagaactc catattggtg gctcagatat cagcaagaaa aatacgcttg tgatggaaga    5940
```

| | |
|---|---|
| actcaccaat tcatggggct gcggcaacat ggttgaagtc agtgaggcgc gaggtgaggc | 6000 |
| ttggttgcgt gatgagagtg tcaaacccctt gttattggtc gcaggcggga cgggaatgtc | 6060 |
| atacaccccta agtattttga aaaatagctt ggagcaaggg tttacccagc cgatttacgt | 6120 |
| ctattggggc gccaaggata tggataacct gtatgtacat gacgaactgg tggatattgc | 6180 |
| gcttgaaaac aaaaacgtca gttacgtgcc agtcactgaa atatcaacct gtccccaata | 6240 |
| cgctaagcaa ggaaaggtgt tggagtgtgt gatgagtgat ttccgtaact tatctgagtt | 6300 |
| cgatatctac ttgtgtggtc cttgcaaaat ggttgaagtg gctcgtgatt ggttctgtga | 6360 |
| caaaagaggg gcagaaccag agcaacttta cgcggacgcg ttcgcttatt tgtaatcatt | 6420 |
| atcaaggaga agaaactatg agctcaacgt cactactaga tgagtttggc actccagtac | 6480 |
| aaagggtaga aagagcgatt gaggctctga aaaatggcct tggtgttcta ttaatggatg | 6540 |
| atgaggatcg cgagaacgaa ggcgaccttta tcttctctgc acagcatctt accgaagcgc | 6600 |
| aaaatggcact catgattcgt gaatgcagtg gtatcgtgtg tttgtgctta acggaggaac | 6660 |
| gcgccaattg gttagagctt cctcctatgg tgaaagataa tcgcagtaaa aaccagaccg | 6720 |
| cttttacggt ttcgattgaa gcgaaagaag gggtgacgac aggagtctct gcgaaagatc | 6780 |
| gcgttacaac ggttaaaacg gctacttatt ttgatgctca accagaagat ttagcaagac | 6840 |
| caggccatgt ttttccgctg gttgcgaaaa caaatggcgt gttggcccgt cgaggtcata | 6900 |
| ccgaaggtac gatcgatttg atgtatctag caaacttagt cccatcaggg atcctttgcg | 6960 |
| aactgactaa ccgtgatgga accatggcga aactaccaga aaccattgag tttgcaagac | 7020 |
| gtcatggaat gccagtgctc actattgaag atatcgtcga ttatcggacg gtaattgaac | 7080 |
| tgagaaatga atatgagagt ggcttagtgt gtgaagtgag ttggtcttag | 7130 |

<210> SEQ ID NO 6
<211> LENGTH: 5820
<212> TYPE: DNA
<213> ORGANISM: Photorhabdus luminescens

<400> SEQUENCE: 6

| | |
|---|---|
| cattaaatgg atggctaata tgactaaaaa aatttcattc attattaacg gccaggttga | 60 |
| aattttttccc gaaagtgatg atttagtgca atccattaat tttggtgata atagtgttta | 120 |
| cctgccaata ttgaataatt ctcatgtaaa aaacattatt gattataatg aaaataataa | 180 |
| attacggttg cataatattg tcaattttct ctatacggta gggcaaagat ggaaaaatga | 240 |
| agaatattca agacgcagga catacattcg tgatttaaaa aaatatatgg gatattcaga | 300 |
| agcaatggcc aagttagagg ccaactggat atctatgatt ttatgttcta aaggtggcct | 360 |
| ttatgatgtt gtagaaaatg aacttggttc tcgccatatc atggatgaat ggctacctca | 420 |
| ggatgaaagt tatattaagg cttttccgaa aggtaagtct atacatctgt tggcaggtaa | 480 |
| tgttccatta tctgtgatca tgtctatatt acgcgcaatt ttaaccaaga atcagtgtat | 540 |
| tataaaaaca tcgtcaaccg atcccttta cgctaatgca ttagcgttaa gctttatcga | 600 |
| tgtagaccct aatcatccga taacgcgctc tttgtctgtt gtatattggc cacaccaagg | 660 |
| tgatacatca ctcgcaaaag aaattatgca acatatggat gttattgtcg cttggggagg | 720 |
| ggaagatgcg attaattggg ctgtagaaca tgcaccaccc tatgctgacg tgattaaatt | 780 |
| tggctctaaa aagagttttt gcattattga taatccagtt gatttaacgt cagcagctac | 840 |
| cggtgcgggct catgatattt gttttttacga tcagcgcgct tgttttttctg cccaaaacat | 900 |

```
atattacatg ggaaatcagt atgaggaatt taagttagcg ttgatagaaa aacttaatct    960
atatgcgcat atattaccaa acgccaaaaa agatttgat gaaaaggcgg cctattcttt   1020
agtccaaaaa gagagcttat ttgctggatt aaaagtagag gtggatgttc atcaacgttg   1080
gatgattatt gagtcaaatg cgggtgtgga atttaatcaa ccacttggca gatgtgtgta   1140
tcttcatcac gtcgataata ttgagcaagt attgccttat gttcaaaaaa ataagacaca   1200
aaccatatct attttccctt gggaatccgc atttaagtat cgagatgcgt tggcattaag   1260
aggtgcggaa aggattgtag aagcaggaat gaataatata tttcgagttg gtggatctca   1320
tgacggaatg aggccgttac aacgattagt gacatatatt tctcatgaga ggccatctca   1380
ttatactgct aaggatgttg cggttgaaat agaacagact cgattcctgg aagaagataa   1440
gttccttgta tttgtcccgt aataggtaaa aagtatggaa aataaatcca atataaaaac   1500
catcgaccat gttctttgtg ttgaaggaaa taaaaaaatt catgtttggg aaacgctgcc   1560
agaagaaacc agcccaaaga gaaagaatcc cattattatt gcgtcgggtt ttgcccgaag   1620
gatggatcat tttgctggtt tagcggaata tttatcgcgg aatgggtttc atgtgattcg   1680
ctatgattca cttcaccacg ttgggttgag ttcagggaca attgatgaat ttacaatgtc   1740
tataggaaaa cagagcctat tagccgtggt tgattggtta aatacacgaa aaataaataa   1800
ccgtggtatt ttggcttcaa gcttatctgc acggatagtt tatgcaagtc tatctgaaat   1860
taatgttca tttttaatca ccgcagtcgg tgttgttaac ttaagatata cgcttgaaag   1920
agctttagga tttgattatc tcagtttacc cattaatgaa ttgccgaata atttggattt   1980
tgaaggccat aaattgggtg ctgaagtctt tgcgagagat tgccttgatt ttggctggga   2040
agatttaact tctacaatca atagcatgat gtatcttgat ataccgttta ttgctttta   2100
tgcaaataac gacaattggg taaagcaaga tgaagttatc acattgttat caaatattcg   2160
tagtaatcga tgcaagatac attctttgtt aggaagttcg catgacttgt gtgttttctt   2220
agtggtcctg cgcaattttt atcaatcggt tacgaaggct gctatcgcga tggataatga   2280
tcgtctggat attgatgttg atattattga accatcattc gaacatctaa ctattgcgac   2340
agtcaatgaa cgtcgaatga aaattgagat tgaaaatcaa gcgatttcgc tgtcttaaaa   2400
cctattggga tagatattac cctatagatt tcaagatgga tcgcgacggc aagggagcga   2460
atcccgggag catagcaaac tatgtgaccg gggtgagtga gtgcagccaa caaagaagca   2520
acttgaaaga taacgggtat agttaattct atcactcaaa tataagggct ctctatgaaa   2580
tttggaaact ttttgcttac ataccaaccc ccccaatttt ctcaaacaga agtaatgaaa   2640
cgtttggtta aattaggtcg tatttctgag gagtgtggtt ttgatactgt atggttactg   2700
gagcatcatt tcacggagtt tggtttgctt ggtaaccctt atgtcgctgc tgcatattta   2760
cttggtgcaa ccaaaaaatt gaatgtaggg actgcggcta ttgttcttcc caccgctcat   2820
ccagtgcgcc aacttgaaga tgtgaattta ttggatcaaa tgtcaaaagg acgatttcgg   2880
tttggtattt gtcgggggct ttacaataaa gactttcgcg tatttggcac ggatatgaat   2940
aacagtcgcg ctttaacgga gtgctggtac gggttgataa aaaatggcat gacagaggga   3000
tatatggaag ctgataatga acatatcaag ttccataagg taaagtaaa cccgacagca   3060
tatagtaaag gtggagcccc tgtttatgtg gttgctgaat cagcctcgac aactgaatgg   3120
gccgctcaat ttggtttacc gatgatatta agttggatta taaatactaa cgaaaagaaa   3180
gcacagcttg agctttataa cgaggtggct caagaatatg ggcacgatat tcataatatc   3240
gaccattgct tatcatatat aacatctgta aattatgact caaataaagc gaaagagatt   3300
```

```
tgtcggaaat tctagggca ttggtatgat tcttatgtga atgccacgac cattttgat    3360
gattcagaca aaacaagagg ttatgatttc aataaagggc agtggcgtga ctttgtatta   3420
aagggacata gagatactaa tcgccgcatt gattacagtt acgaaatcaa tcccgtggga   3480
accccgcagg aatgcattga cataattcaa aaagacattg atgccacggg aatatcaaat   3540
atctgttgtg ggtttgaagc gaatggaaca gtagacgaaa ttattgcttc catgaagctc   3600
ttccagtctg atgtcatgcc gtttcttaaa gaaaaacaac gttcgctatt atagtagcta   3660
aggaaaaaga aatgaaattt ggattgttct tccttaactt catcaattca acaactgttc   3720
aagaacaaag tatagttcgc atgcaggaaa taacggagta tgttgataag ttgaattttg   3780
aacagatttt ggtgtatgaa atcattttt caggtaatgg tgttgtcggt gctcctctga    3840
ctgtttctgg ttttttgctc ggtttaacag aaaaaattaa aattggctca ttgaatcaca   3900
tcattacaac tcatcatcct gtccgaatag cggaggaggc ttgcttactg gatcaattaa   3960
gcgaagggag atttatttta gggtttagtg attgtgaaaa aaagatgaa atgcgtcttt     4020
ttaatcgccc tgttgaatat caacagcaac tatttgaaga gtgttatgaa atcattaacg   4080
atgctttaac aacaggctat tgtaatcccg ataatgattt ttatagtttc cctaaaaatat  4140
cggtaaaccc ccacgcttat acccaaggcg ggcctcggag atatattaca gcaaccagtc   4200
atcatattgt tgaatgggcg gctaaaaaag gcattcctct catctttaag tgggatgact   4260
ccaatgatgt tagatatgaa tatgctgaaa ggtataaagc cgttgctgat aaatatggca   4320
ttgacttatc agcgatagat catcagttaa tggtattggt taactataac gaagatagtc   4380
acaaagctaa acaagagacg cgtgcattta tccgtgatta tgttcttgaa atgtatccta   4440
atgaaaatct cgaaaataaa cttgaagaga taatcacaga aaacgctgtc ggagattata   4500
cggaatgtat agctgcggct aagctggcaa ttgaaaagtg cggtgcaaaa agggtattat   4560
tatcctttga accaatgaat gacttgatgc accaaaaaaa tgtaatcaat attgttgatg   4620
ataatattaa aaagtaccac atgtagtaaa agaatatggc agcaacgctg ccatattctc   4680
taaattattt ggagggtaa aacaggtatg acttcatatg ttgataaaca agagatcata   4740
gcaagctcag aaattgatga tttgatttt tccagcgatc cattagcttg gtcttacgat   4800
gaacaggaaa aaatcagaaa caaatttgtt cttgatgcat ttcgtaatca ctataaacat   4860
tgtcaagaat accgtcacta ctgtcaggta cacaaagtag acgacaatat tacgaaaatt   4920
gatgacatac ctgtattccc aacatcagtt tttaagttta ctcgcttatt aacttctcag   4980
gagaacgaga ttgaaagttg gtttaccagc agcggcacga gtggttttaaa aagtcaggtg   5040
gcgcgtgaca gactaagtat tgagagactc ttaggctctg tgagttatgg catgaaatat   5100
gttggtagtt ggtttgatca tcaaatagag ttggtcaact tagggccaga tagatttaat   5160
gctcataaca tttggtttaa atatgttatt agtttggtag aattattata tcccacgaca   5220
tttaccgtaa tggaagaacg aatagatttt gttaagacat tgaatagcct tgagcgaata   5280
aaaaatcaag ggaaagatat ttgtcttatc ggctcaccat actttattta tttgctctgc   5340
cagtatatga aagataaaaa catctcattt tatggggata aaaacctta tatcataacg    5400
gggggcggct ggaaaagtta tgaaaaagag tccctaaaac gcgatgattt caatcatctt   5460
ttattcgaca cgttcaacct caataatatt agtcaaatcc gcgatatatt taatcaagtt   5520
gaactcaaca cttgtttctt tgaggatgaa atgcaacgta acgtgttcc gccgtgggta   5580
tatgcgcgag cacttgatcc tgaaacattg aaacctgtac ctgatggaat gccgggtttg   5640
```

```
atgagttata tggatgcgtc atcaacgagt tatccggcat ttattgttac cgatgatgtc    5700
gggataatga gcagagaata tggtcaatat cctggtgtac ttgttgagat tttacgtcgc    5760
gtcaatacga gggcacagaa agggtgtgct ttaagcttaa accaagcatt taatagttga    5820

<210> SEQ ID NO 7
<211> LENGTH: 3191
<212> TYPE: DNA
<213> ORGANISM: Vibrio fischeri

<400> SEQUENCE: 7
aagataagtt tttagttttt gtcccatagt taaaaggaaa ttatatgaaa gatgaaagtg      60 cttttttac gattgatcac attatcaagc ttgataatgg tcagtctatc cgagtttggg     120
aaacactccc taaaaaaaac gtaccagaga aaaacatac aatacttatt gcttcgggtt     180
ttgctagaag aatggatcat tttgcaggtc ttgctgagta tttatctact aacggttttc     240
atgtcattcg ctacgattct ttgcatcatg ttggattaag cagtggatgt ataaatgaat     300
ttacgatgtc gattggaaaa atagcctgc ttacagtcgt agattggctt aaagagcatg     360
gtgtcgaacg aatagggctg attgctgcta gtttgtcagc gagaatcgct tatgaggtag     420
taaataaaat taaattatca tttttaatta cggccgtagg tgtcgttaat cttagagata     480
cattagaaaa agcattggag tatgactatt tgcaattacc tatttcagat ctaccagaag     540
atcttgactt tgaaggtcat aatttaggag ctgaggtctt tgttacagat tgctttaaac     600
ataaatggga cacattagac tcgacactta gtggtgttaa aggattaacg attccattta     660 ttgctttac tgcaaacgat gatagctggg taaagcaaag tgaagttata gagctcattg     720
atagtattga atctaataat tgtaagctct attcgctaat tggaagttca catgatcttg     780
gggaaaattt ggttgtatta agaaattttt atcaatcagt aacgaaggca gctttagcat     840
tagatgttgg tttattggat ttagatatag atattattga acctcgattt gaggacgtta     900
caagtattac tgttaaggag cgtagattaa aaatgaaat tgaaaatgaa ttattagaat     960
tagcttaatt aaataaaatc accaaaaagg aatagagtat gaagtttgga aatatttgtt    1020
tttcgtatca accaccaggt gaaactcata agcaagtaat ggatcgcttt gttcgacttg    1080
gtatcgcctc agaggaagta ggctttgata catattggac cttagaacat cattttacag    1140
agtttggtct cacgggaaat ttatttgttg ctgcggcaaa tctgttagga agaactaaaa    1200
cattaaatgt tggtactatg ggggttgtta ttccaacagc tcatcctgtt cgacaattag    1260
aagacgtttt attattagat caaatgtcga aagggcgttt taattttgga accgttcgag    1320
ggctatacca taaagatttt cgagtatttg tgttgatat ggaagagtct cgagcgatta    1380
ctcaaaattt ctaccagatg ataatggaaa gcttacaaac aggaacagtt agttctgata    1440
gtgattatat ccagttccct aatgtagatg tgtatcctaa agtatattct aaaaatgttc    1500
caacgtgtat gactgctgag tccgcaagta cgacagaatg gctagcaata caagggctac    1560
caatggttct tagttggatt attggtacta atgaaaaaaa agcacagatg gaactctata    1620
atgaaattgc gacagaatat ggccatgaca tatctaaaat agatcattgt atgacttata    1680
tttgctctgt tgatgatgat gcacaaaagg cgcaagatgt ttgtcgggag tttctgaaaa    1740
attggtatga ttcatatgta aatgcgacca atatctttaa tgatagcaat caaactcgtg    1800
gttatgatta tcataaaggc caatggcgtg attttgtttt acaaggacat acaaacacta    1860
atcgacgtgt tgattatagc aatggtatta accctgtagg cactcctgag cagtgtattg    1920
aaataattca acgtgatatt gatgcgacgg gtattacaaa cattacatgc ggatttgaag    1980
```

```
ctaatggaac tgaagatgaa ataatagctt ccatgcgacg ctttatgaca caagtcgctc    2040 cttcttaaa agaacctaaa taaattactt atttgatact agagataata aggaacaagt    2100
tatgaaattt ggattatttt ttctaaactt tcagaaagat ggaataacat ctgaagaaac    2160
gttggataat atggtaaaga ctgtcacgtt aattgattca actaaatatc attttaatac    2220
tgcctttgtt aatgagcatc atttttcaaa aatggtatt gttggagcac ctattaccgc    2280
agctggtttt ttattagggt taacaaataa attacatatt ggttcattaa atcaagtaat    2340
taccacccat caccctgtac gtgtagcaga agaagccagt ttattagatc aaatgtcaga    2400
ggggcgcttt attctcggtt ttagtgactg cgaaagtgat ttcgaaatgg agttttttaa    2460
acgtcacatt ccatcaaggc aacaacaatt tgaagcatgc tatgaaataa ttaatgacgc    2520
attaactaca ggttattgtc atccccaaaa tgattttat gatttccaa aggtttcaat     2580 taatccacac tgttacagtg ataatgggcc taagcaatat gtatccgcaa catcaaaaga    2640
agtcgtcatg tgggcagcga aaaaggcact gcctttaaca tttaagtggg aggataattt    2700
agaaaccaaa gagcgttatg caattctata taataaaaca gcacaacaat atggtgttga    2760
tatttcggat gttgatcatc aattaactgt aattgcgaac ttaaattctg atagaagtac    2820
ggctcaagaa gaagtgagag aatacttaaa agactatatc actgaaactt accctcaaat    2880
ggacagggat gaaaaaatta actgtattat tgaagagaat gcagtagggt ctcatgatga    2940
ctattatgaa tcgataaaat tagcggtgga aaaaacaggg tctaaaaata ttttattatc    3000
ctttgagtca atggctgatt ttaagggggt aaaagaaatt attgatatgt tgaaccaaaa    3060
aattgaaaag aatctaccct aataaaatta agggcaattt atatattaga ttgccttttt    3120
tgcatttctg ttgatattag gtgttattgg agaggggatg gtatgactgt tcatactgaa    3180 tataaagaa a                                                         3191
```

<210> SEQ ID NO 8
<211> LENGTH: 9585
<212> TYPE: DNA
<213> ORGANISM: Vibrio harveyi

<400> SEQUENCE: 8

```
gtgagcagcc cctattatta tggggtgaaa gctgttgttt tgtaaaaata ttgggcgttc     60
tcatggaagc tgagtctcac gattgcattc tctttccgtt tagcttagtc ctagaggaaa    120
tacatccgat gaatggtcca cgacatttgt aagccaacaa cgttgcggca gcataaacgc    180
tctgcataga ctgccgcgca ggctagttta tgaatgtccg actgcttaaa cgcttgcaaa    240
gtaaagagca tattggagag ttacctatga cagtacatga actagagtgc caccgcgcat    300
cagaaacaaa agacaatgct atcgtttcag ccaacgagaa ctttagcgcc gtcagagcgc    360
taagcgcatc atgaaggcga gagagactgc tgcgcagatc acgttgacca tgaacgactt    420
agtcgcgagc aagaacgaca caaaatgtta tatggacttc tctgacaaga acacaggaga    480
caaagtattt cgtgatgacg gtgaaaagat cgttatgcgc agcaaacaag cggacattaa    540
ccataccgca gccgcactaa tttggagtgg tgaaaattaa tggtccgaag gagttgaaag    600
agcaagtcat tgatgtggct gtgagcaagg gcttaaacct gcaagtgaca ataaacggga    660
agctgccaaa ccgttttgaa gaatccacgg tcgagcaaat tgtgaagaaa gatgctttct    720
tgaagcacta caccgttaaa gatgtgcagt tggtttgat agaccaaaag aaagcgtagg    780
gtgttcaacc agtgcctaag acgtatgatg ctcaagctaa cattatcgat gaaattggta    840
```

```
agcaaaaaca aagccgccat ataaaatgaa cactcggttt aatacgagca caaattgtcg    900
ctgttcaatt tcaaggttta gtcagatctt ataggttggt ctgactcatt ctgacctaaa    960
ttagttagat caaatcgctt aacgtattca aacgccctag tttcttgatc ccaaaactgc   1020
gtaattattc aagttttatt tttaagttac cttaaaagct caccttttatg attagtgtta  1080
agacatcatt aaaaaatcta tgcataaatt ataaatacta tttcttaact attggggtt    1140
attgatcggt taggtagtat aagtatctaa attaatgagc tttgtttagt gttttttctat  1200
ttataaataa ctttaattat aattaaagtt gatggtaatg attatcatta gcgtgatcct   1260
tttggcgtgt ttgattaaat taaattaatt ttcttttaaa ttgtaaattt aaacattacc   1320
gtgttttaa attcaaaaga gaagctcttg atatggaaaa cacttaccct ttaataataa    1380
atgggcaaat agtttctact aaagaaaatc gatttgagat cagttttgaa gaaaaaaaag   1440
ttaagattga ttcctttaat cattttcatt taatccagat ggtgactcat gattatttaa   1500
atgatctaaa tattaataac atcatcaatt ttctttatac aacggggcag cgttggaaga   1560
gcgaagaata ttcaagaaga agggcatata ttcggtctct tattacttat ttggggtatt   1620
caccacaaat ggcgaaacta gaagcaaatt ggattgcaat gatcctttgc tctaagagtg   1680
cgctctacga cattattgat accgagcttg gctcaacgca tatacaagat gaatggctac   1740
cgcagggtga gtgttatgtg agggcttttc ctaaaggacg cacgatgcat ttgcttgcgg   1800
ggaatgttcc tctctccggt gtgacctcaa tactacgagg catactgacg agaaatcaat   1860
gtattgtgag aatgtcagca tcggatcctt ttactgccca cgcgctagcg atgagcttta   1920
ttgacgtcga tccgaatcat ccaatttctc gttctatctc cgtattgtat tggcctcatg   1980
catcggatac gacactcgct gaagagttac tcagtcatat ggatgcagtg gttgcttggg   2040
gggggcggga tgccattga ttgggcggtt aagcattctc cttcacatat cgatgtttg    2100
aagtttggtc caaagaagag ttttaccgtg ttagaccatc cagccgatct agaagaagcc   2160
gcctcgggtg ttgcccatga tatttgcttt tatgaccaaa atgcctgctt ttctactcag   2220
aatatttact tttctggaga taagtatgaa gaattttaaat taaaacttgt tgaaaaactg   2280
aatctctatc aagaagtttt accaaaatca aacaaagtt ttgatgacga agctttatt    2340
tctatgactc gtcttgagtg tcaattttct gggttgaaag ttatatcaga accggaaaat   2400
aactggatga tcatcgagtc agagcccggg gttgaatata accatccatt aagtcgttgc   2460
gtttatgtcc acaaaataaa taaggttgat gatgttgttg aatatataga aaaacatcaa   2520
acacaaacga tttctttta tccatgggaa tcttccaaga aatatcgaga tgcattcgcc   2580
gcaaaagggg tagaaagaat cgttgaatct gggatgaata atatatttag agctggtggc   2640
gcacatgatg caatgcgccc acttcaacgt ttagttcgat tgttttctca tgaaagacca   2700
tataacttca ccactaagga tgtatctgtc gaaatagagc aaacccgctt tcttgaagaa   2760
gataaattct tggttttcgt cccttaaata aggaaaatta caatgaataa tcaatgcaag   2820
actattgcac acgtgttacg cgtgaacaat ggtcaggaac ttcacgtctg ggaaacgccc   2880
ccaaaagaaa atgtgccttc taaaaataac accattttaa ttgcttctgg ttttgccaga   2940
agaatggatc actttgctgg gttggccgag tatctatctg aaaatggttt ccatgtgttc   3000
cgttatgact ctcttcatca tgtggggctc agctcgggtt cgattgatga attcaccatg   3060
acgacgggca aaaatagttt gtgcactgtt tatcactggc tgcagaccaa gggcacacaa   3120
aacattggct tgattgcggc aagtctctca gctcgtgtcg cctatgaagt tatctctgat   3180
ctggagctgt cttttctgat tactgcggtt ggtgtggtga acttgcgtga cacactagaa   3240
```

```
aaagcgcttg gttttgatta cctcagtttg cctatcgatg agctaccaaa cgatcttgat    3300
tttgaaggtc ataagcttgg ttctgaagtg ttcgttcgcg actgcttcga gcatcactgg    3360
gataccttag attctactct cgacaaagta gccataacct cggttccttt aatcgccttt    3420
accgctaaca acgatgattg ggttaagcaa gaagaagtct atgacatgtt agcgcatatc    3480
cgcactgggc attgcaagct ctactccttg cttggtagct ctcatgactt gggcgaaaac    3540
ttggtcgtgt tacgtaattt ttaccaatcc gtcaccaaag ccgccatcgc aatggatgga    3600
ggcagcttag aaatcgacgt cgactttatc gagcctgatt ttgaacaact caccatcgcg    3660
actgtgaatg aacgtcgctt gaaagcggaa attgaaagcc gtacgccaga aatggcttag    3720
gtctcatcgt aataccaata aataaggaaa tgttatgaaa tttggaaact tccttctcac    3780
ttatcagcca cctgagctat ctcagaccga agtgatgaag cgattggtta atctgggcaa    3840
agcgtctgaa ggttgtggtt tcgacactgt ttggttacta gagcaccact tcactgaatt    3900
tgggttgtta gggaatcctt atgttgctgc cgcacatcta ttaggtgcga cagaaaagct    3960
caatgttggc accgcagcca ttgtattgcc gactgcccat ccggttcgac aagcagaaga    4020
cgtaaaccta ctggatcaaa tgtcgaaagg acgattccgt tttgggattt gtcgcggttt    4080
gtacgacaaa gatttccgtg tctttggtac agacatggat aacagccgag ccttaatgga    4140
ctgttggtat gacttgatga agaaggctt caatgaaggc tatatcgcgg cggataacga    4200
acatattaag ttcccgaaaa tccaactgaa tccatcggct tacacacaag gtggcgctcc    4260
tgtttatgtc gtcgcggagt cagcatcaac gacagaatgg gctgcagagc gtggcctacc    4320
aatgattcta agctggatca tcaatactca cgagaagaaa gcgcagcttg atctttacaa    4380
tgaagtcgcg actgaacatg gctacgatgt gactaagatt gaccactgtt tgtcttacat    4440
cacctccgtc gatcatgact caaataaagc caaagatatt tgccgcaact tcttgggtca    4500
ttggtacgac tcatacgtga atgccaccaa gattttgac gactctgacc aaacaaaagg    4560
ctacgacttc aataaaggcc aatggcgcga ttttgtgttg aaaggccaca agataccaa    4620 ccgccgaatt gattacagct acgaaatcaa cccagtaggg acgcctgaag agtgtatcgc    4680
gattatccag caagatatcg atgcaacggg tattgacaat atttgttgtg gttttgaagc    4740
aaacggttct gaagaagaaa ttatcgcatc tatgaagcta ttccagtccg atgtgatgcc    4800
atatctcaaa gaaaaacagt aattaatatt ttctaaaagg aaagagacat gaaatttgga    4860
ttattcttcc tcaattttat gaattcaaag cgttcttctg atcaagtcat cgaagaaatg    4920
ttagataccg cacattacgt agatcagttg aagtttgaca cgttggctgt ttacgaaaac    4980
catttctcga acaatggtgt ggttggtgcc ccattaacag tggctggttt tttacttggt    5040
atgacaaaga acgccaaagt ggcttcgttg aatcacgtta ttacaacaca tcatccagta    5100
cgtgtggcgg aagaagcgtg tctactcgac caaatgagtg aaggccgttt tgtctttggc    5160
tttagtgatt gtgaaaagag tgcagatatg cgcttcttta atcgaccaac ggattctcag    5220
tttcagttgt tcagtgagtg tcacaagatc atcaatgatg cattcactac tgggtactgc    5280
catccaaaca atgatttta tagttttcct aaaaatctctg ttaacccaca cgcttacact    5340
gaaggcggtc ctgcgcaatt tgtgaatgcg acgagcaaag aagtggttga atgggcggct    5400
aagttagggc ttccactcgt gtttaaatgg gacgactcaa acgcgcaaag aaaagaatac    5460
gccggtttgt accacgaagt tgctcaggca catagtgtcg atgttagtca ggttcgacac    5520
aagctgacgc tgttggtcaa ccaaaatgta gatggtgaag cagcaagggc agaagcacgc    5580
```

```
ctgtatttgg aagagtttgt ccgtgaatct tacccaaata ccgaatttga gcaaaaaatg    5640
gcagagctgt tgtcagaaaa tgccatcggt acttatgaag aaagtactca ggcagcgcga    5700
gttgcgattg agtgttgtgg tgccgcggac ctattgatgt cttttgagtc gatggaagat    5760
aaagcgcagc aaagagcggt tatcgatgtg gtaaacgcca acatcgtcaa ataccactcg    5820
taacgtttaa ctgatgctga aggggcagcg atgcccctta tatcaccatt cttttcgcgc    5880
gatagcgcta actaatagag gcatttatat ggacgtactt tcagcggtta agcaggaaaa    5940
tatcgcagcg agcacagaaa tcgatgactt gattttcatg ggaactcctc agcaatggtc    6000
attgcaggaa caaaaacagc tgacatctcg ccttgttaaa ggggcatatc aataccatta    6060
ccacaataat gatgactatc gtcagttctg ccaaaggctg ggagtcggag aggaggtcga    6120
agatctcaat gagatccccg ttttccctac ttctattttt aagttgaaga ccctattaac    6180
acttgacgat gaagaggtag agaatcgctt tactagcagc ggtactagtg gcatcaaaag    6240
tattgtcgca cgagatagac tcagtattga gcgacttctt ggctcagtaa atttcggtat    6300
gaattacgtt ggtgattggt ttgaccatca gatggagttg gtgaacttag gcccagatcg    6360
ctttaatgcc aacaatattt ggttcaagta cgtcatgagc ttagtcgagc tcctttatcc    6420
gaccgcattt actgccactg aggatgagat cgactttgag gcgacgctag ctaatatgaa    6480
tcgtattaag cagtctggta aaaccatttg tcttatcggc cctccttatt ttatctatct    6540
actgtgctgt ttcatgcgcg agcaaggtca aactttcaat ggtggtcgcg atctttacat    6600
catcactggc ggcggctgga aaaaacatca ggatcaatcg ctcgatagag acgagttcaa    6660
ccagcttttg tgtgagactt ttaccttaga aagcgcagag cagattcgag acacatttaa    6720
tccagttgaa ctgaacaccct gcttttttga agatacagaa cacaaaaagc gtgtaccgcc    6780 ctgggtctt gcaagagctc tggatcctaa aacattaaag ccgcttccgc atggccagcc    6840
aggactgatg agctatatgg atgcctcggc ggtcagctat ccatgttttc tagtgacgga    6900
tgacatcggc atcgtgcgag aagaagaagg cgatcgcccg ggaaccactg ttgagatcgt    6960
tagaagagtt aagacgcggg gtatgaaggg gtgtgctctc agtatgtctc aagcatttac    7020
agctaagaat gaaggaggca actgacatgt tatgttcgat agaaaaaatt gagccgttaa    7080
ctaacctcat attccgagta ttgctcaagc cagatcagcc ttttgaattt agggcagggc    7140
agtacattaa cgtcagttta agctttggta gtttaccgtt ttctatagcc tcatgtcctt    7200
ctaatggtgc gttttagaa ctccatattg gtggctcaga tatcagcaag aaaatacgc    7260 ttgtgatgga agaactcacc aattcatggg gctgcggcaa catggttgaa gtcagtgagg    7320
cgcgaggtga ggcttggttg cgtgatgaga gtgtcaaacc cttgttattg gtcgcaggcg    7380
ggacgggaat gtcatacacc ctaagtattt tgaaaaatag cttggagcaa gggtttaccc    7440
agccgattta cgtctattgg ggcgccaagg atatggataa cctgtatgta catgacgaac    7500
tggtggatat tgcgcttgaa aacaaaaacg tcagttacgt gccagtcact gaaatatcaa    7560 cctgtccccca atacgctaag caaggaaagg tgttggagtg tgtgatgagt gatttccgta    7620
acttatctga gttcgatatc tacttgtgtg gtccttgcaa aatggttgaa gtggctcgtg    7680
attggttctg tgacaaaaga ggggcagaac cagagcaact ttacgcggac gcgttcgctt    7740
atttgtaatc attatcaagg agaagaaact atgagctcaa cgtcactact agatgagttt    7800
ggcactccag tacaaagggt agaagagcg attgaggctc tgaaaaatgg ccttggtgtt    7860
ctattaatgg atgatgagga tcgcgagaac gaaggcgacc ttatcttctc tgcacagcat    7920
cttaccgaag cgcaaatggc actcatgatt cgtgaatgca gtggtatcgt gtgtttgtgc    7980
```

```
ttaacggagg aacgcgccaa ttggttagag cttcctccta tggtgaaaga taatcgcagt    8040
aaaaaccaga ccgcttttac ggtttcgatt gaagcgaaag aagggggtgac gacaggagtc    8100 tctgcgaaag atcgcgttac aacggttaaa acggctactt attttgatgc tcaaccagaa    8160
gatttagcaa gaccaggcca tgttttccg ctggttgcga aaacaaatgg cgtgttggcc    8220
cgtcgaggtc ataccgaagg tacgatcgat ttgatgtatc tagcaaactt agtcccatca    8280
gggatccttt gcgaactgac taaccgtgat ggaaccatgg cgaaactacc agaaccatt    8340 gagtttgcaa gacgtcatgg aatgccagtg ctcactattg aagatatcgt cgattatcgg    8400
acggtaattg aactgagaaa tgaatatgag agtggcttag tgtgtgaagt gagttggtct    8460
tagtatttaa agttcctttg tttgttcagt cgcctagctg actttccgcc cttatcgggc    8520 ggttttttg ttttgtagaa gtcaaaaata aacccgcaaa agcgggctta tttaagtaag    8580
gtagttggag cagttgacgt attacctgaa gtgttctgac tcagacctga tctgacagtt    8640
acccactttt cgactcggtg cctgtcaggt tatatctggg ctagattctt ttcagcccag    8700
attgatttcc catcctctaa tgtctctatt ggcgttcggc cgcagcacat ttttccttga    8760
tgagtacgat gattgttgtt gtagtccatc cattcgtcag atctttctgt aactcttcca    8820
ttgaatcata cagtttcttt ctgaaggcca cttggtagaa ctcatttaat atggccttgt    8880
ggaagtgttc gcagatacca tttgtctgtg gcgacatcgc tttagttttc gtgtggtcta    8940
tatcattgat ggcaagatag agttggtaat cgtgctgttt aacacggcca aagtatccgg    9000
agcctcggtc cagtcaaaat tctcagcatt agcagctcat gagtgtcgaa gtacggtagt    9060
cggtgattgg tgtttttgtc gtgtggagct tagcgaagcg actttgttgt aggtattagc    9120
gactgtcttc tgatagatgc gtccaatacc tttcaaatta ccaatataga acgtatcttg    9180
agagtcgaag taacctgagt gtgcagtttc tatctcgcca aaagcctaat catcgtcctt    9240
ctaacgctca aaggcagcga cttaccttcc tttagcta taccgttctc agcaatctgt    9300
tttctgagac aataaggcgt ttttgacttt ttctaagtca ttattaaacc aagtctaacg    9360
cacactactt ggagatgcga tagataagac ttatggagat cagcaggttg aacaaataag    9420
acaaaaaatg acatcgaaaa tcaatgatta ttcgccatcg gaacaggttt catcgaacct    9480
atcaggcaga aaggatgctt tggggaaaat agttcacgga gaactaccag caataaatag    9540
tgcactagat ggtacaaaat aacttttcaa tatcggtatt tttgt              9585
```

<210> SEQ ID NO 9
<211> LENGTH: 6782
<212> TYPE: DNA
<213> ORGANISM: Photorhabdus luminescens

<400> SEQUENCE: 9

```
ggaatatagg ggtcatcttc ttctaaatta accccaatac aatcaacatc atttaatcca      60
atttcccaag cccaccgaac gtctaacgta ctcatttcta tacctaaact atcttttgt     120 ggatgttcag gattaatatt ttttaacatc gcatcacatc ctagatagaa tttcttattc     180
agacaacgga caccgatttt gaactgactg gccttgctta cgacacaaaa ttcaatttaa     240
accacgaagt aaaactgttt tatgattcta actggtttga aattgtgcca gcttggcgta     300
cgttgccaat ctctgttacg ccgtgtatgg ggatactgcc agccagctac tatgatgctg     360
tacgacaagc cgcggcacac ctcaaaaagt agctaaattt attgctttaa ttggaggggc     420
gggctatata cacaaagagc tcaggtattt tgaacttgag ctcttcttct agaaatctgc     480
```

```
tggtggaaag cggcattgcc attcaatgta ttctctcggt attagagaaa tagcataagg      540
agttattaaa tgaataatca gtttaatcag tttcatgaat atttgtatat aaagaagagc      600
ttgatttctt taatttaaat ttttattaat aaaattttgt tgatataaaa gtttcctttt     660
gctattttac agacattaca aatggaacag gaattatatt tatgagcgcg aagttacatt      720
aatagttttg agcataaaat tcagggcgtt attatttcta cgaaactta tagattgaga      780 ttattataat aaaaaatctt attttctgga tattcttttt attttttatcg ttgtaacata     840 aaaatacaag aagcaaatat tggtacaacc agtttgcaag atgattaaac aataacttaa      900
gttgaagtta ccccattaaa tggatggcta atatgactaa aaaaatttca ttcattatta      960
acggccaggt tgaaattttt cccgaaagtg atgatttagt gcaatccatt aattttggtg     1020
ataatagtgt ttacctgcca atattgaata attctcatgt aaaaaacatt attgattata     1080
atgaaaataa taaattacgg ttgcataata ttgtcaattt tctctatacg gtagggcaaa     1140
gatggaaaaa tgaagaatat tcaagacgca ggacatacat tcgtgattta aaaaaatata     1200
tgggatattc agaagcaatg gccaagttag aggccaactg gatatctatg attttatgtt     1260
ctaaaggtgg cctttatgat gttgtagaaa atgaacttgg ttctcgccat atcatggatg     1320
aatggctacc tcaggatgaa agttatatta aggcttttcc gaaaggtaag tctatacatc     1380
tgttggcagg taatgttcca ttatctgtga tcatgtctat attacgcgca attttaacca     1440
agaatcagtg tattataaaa acatcgtcaa ccgatccctt taccgctaat gcattagcgt     1500
taagctttat cgatgtagac cctaatcatc cgataacgcg ctctttgtct gttgtatatt     1560
ggccacacca aggtgataca tcactcgcaa aagaaattat gcaacatatg gatgttattg     1620
tcgcttgggg aggggaagat gcgattaatt gggctgtaga acatgcacca ccctatgctg     1680
acgtgattaa atttggctct aaaaagagtt tttgcattat tgataatcca gttgatttaa     1740
cgtcagcagc taccggtgcg gctcatgata tttgttttta cgatcagcgc gcttgttttt     1800
ctgcccaaaa catatattac atgggaaatc agtatgagga atttaagtta gcgttgatag     1860
aaaaacttaa tctatatgcg catatattac caaacgccaa aaaagatttt gatgaaaagg     1920
cggcctattc tttagtccaa aaagagagct tatttgctgg attaaaagta gaggtggatg     1980
ttcatcaacg ttggatgatt attgagtcaa atgcgggtgt ggaatttaat caaccacttg     2040
gcagatgtgt gtatcttcat cacgtcgata atattgagca agtattgcct tatgttcaaa     2100
aaaataagac acaaaccata tctatttttc cttgggaatc cgcatttaag tatcgagatg     2160
cgttggcatt aagaggtgcg gaaaggattg tagaagcagg aatgaataat atatttcgag     2220
ttggtggatc tcatgacgga atgaggccgt tacaacgatt agtgacatat atttctcatg     2280
agaggccatc tcattatact gctaaggatg ttgcggttga aatagaacag actcgattcc     2340
tggaagaaga taagttcctt gtatttgtcc cgtaataggt aaaaagtatg gaaaataaat     2400
ccaaatataa aaccatcgac catgttcttt gtgttgaagg aaataaaaaa attcatgttt     2460
gggaaacgct gccagaagaa accagcccaa agagaaagaa tcccattatt attgcgtcgg     2520
gttttgcccg aaggatggat cattttgctg gtttagcgga atatttatcg cggaatgggt     2580
ttcatgtgat tcgctatgat tcacttcacc acgttgggtt gagttcaggg acaattgatg     2640
aatttacaat gtctatagga aaacagagcc tattagccgt ggttgattgg ttaaatacac     2700
gaaaaataaa taaccgtggt attttggctt caagcttatc tgcacggata gtttatgcaa     2760
gtctatctga aattaatgtt tcattttttaa tcaccgcagt cggtgttgtt aacttaagat     2820
atacgcttga aagagcttta ggatttgatt atctcagttt acccattaat gaattgccga     2880
```

```
ataatttgga ttttgaaggc cataaattgg gtgctgaagt ctttgcgaga gattgccttg    2940
attttggctg ggaagattta acttctacaa tcaatagcat gatgtatctt gatataccgt    3000
ttattgcttt tactgcaaat aacgacaatt gggtaaagca agatgaagtt atcacattgt    3060
tatcaaatat tcgtagtaat cgatgcaaga tacattcttt gttaggaagt tcgcatgact    3120
tgtgtgtttt cttagtggtc ctgcgcaatt tttatcaatc ggttacgaag gctgctatcg    3180
cgatggataa tgatcgtctg gatattgatg ttgatattat tgaaccatca ttcgaacatc    3240
taactattgc gacagtcaat gaacgtcgaa tgaaaattga gattgaaaat caagcgattt    3300
cgctgtctta aaacctattg ggatagatat taccctatag atttcaagat ggatcgcgac    3360
ggcaagggag cgaatcccgg gagcatagca aactatgtga ccggggtgag tgagtgcagc    3420
caacaaagaa gcaacttgaa agataacggg tatagttaat tctatcactc aaatataagg    3480
gctctctatg aaatttggaa acttttttgct tacataccaa ccccccccaat tttctcaaac    3540 agaagtaatg aaacgtttgg ttaaattagg tcgtatttct gaggagtgtg gttttgatac    3600
tgtatggtta ctggagcatc atttcacgga gtttggtttg cttggtaacc cttatgtcgc    3660
tgctgcatat ttacttggtg caaccaaaaa attgaatgta gggactgcgg ctattgttct    3720
tcccaccgct catccagtgc gccaacttga agatgtgaat ttattggatc aaatgtcaaa    3780
aggacgattt cggtttggta tttgtcgggg gctttacaat aaagactttc gcgtatttgg    3840
cacggatatg aataacagtc gcgctttaac ggagtgctgg tacgggttga taaaaaatgg    3900
catgacagag ggatatatgg aagctgataa tgaacatatc aagttccata aggtaaaagt    3960
aaacccgaca gcatatagta aaggtggagc ccctgtttat gtggttgctg aatcagcctc    4020
gacaactgaa tgggccgctc aatttggttt accgatgata ttaagttgga ttataaatac    4080
taacgaaaag aaagcacagc ttgagcttta taacgaggtg gctcaagaat atgggcacga    4140
tattcataat atcgaccatt gcttatcata taacatct gtaaattatg actcaaataa    4200
agcgaaagag atttgtcgga aatttctagg gcattggtat gattcttatg tgaatgccac    4260
gaccattttt gatgattcag acaaaacaag aggttatgat ttcaataaag ggcagtggcg    4320
tgactttgta ttaaagggac atagagatac taatcgccgc attgattaca gttacgaaat    4380
caatcccgtg ggaaccccgc aggaatgcat tgacataatt caaaaagaca ttgatgccac    4440
gggaatatca aatatctgtt gtgggtttga agcgaatgga acagtagacg aaattattgc    4500
ttccatgaag ctcttccagt ctgatgtcat gccgtttctt aaagaaaaac aacgttcgct    4560
attatagtag ctaaggaaaa agaaatgaaa tttggattgt tcttccttaa cttcatcaat    4620
tcaacaactg ttcaagaaca agtatagtt cgcatgcagg aaataacgga gtatgttgat    4680
aagttgaatt ttgaacagat tttggtgtat gaaaatcatt tttcaggtaa tggtgttgtc    4740
ggtgctcctc tgactgtttc tggtttttttg ctcggtttaa cagaaaaaat taaaattggc    4800
tcattgaatc acatcattac aactcatcat cctgtccgaa tagcggagga ggcttgctta    4860
ctggatcaat taagcgaagg gagatttatt ttagggttta gtgattgtga aaaaaaagat    4920
gaaatgcgtc ttttttaatcg ccctgttgaa tatcaacagc aactatttga agagtgttat    4980
gaaatcatta acgatgcttt aacaacaggc tattgtaatc ccgataatga ttttatagt    5040 ttccctaaaa tatcggtaaa ccccacgct tatacccaag gcgggcctcg agatatatt    5100 acagcaacca gtcatcatat tgttgaatgg gcggctaaaa aaggcattcc tctcatcttt    5160
aagtgggatg actccaatga tgttagatat gaatatgctg aaaggtataa agccgttgct    5220
```

```
gataaatatg gcattgactt atcagcgata gatcatcagt taatggtatt ggttaactat    5280
aacgaagata gtcacaaagc taaacaagag acgcgtgcat ttatccgtga ttatgttctt    5340
gaaatgtatc ctaatgaaaa tctcgaaaat aaacttgaag agataatcac agaaaacgct    5400
gtcggagatt atacgaatg tatagctgcg gctaagctgg caattgaaaa gtgcggtgca    5460
aaaagggtat tattatcctt tgaaccaatg aatgacttga tgcaccaaaa aaatgtaatc    5520
aatattgttg atgataatat taaaaagtac cacatgtagt aaaagaatat ggcagcaacg    5580
ctgccatatt ctctaaatta tttggagggg taaaacaggt atgacttcat atgttgataa    5640
acaagagatc atagcaagct cagaaattga tgatttgatt ttttccagcg atccattagc    5700
ttggtcttac gatgaacagg aaaaaatcag aaacaaattt gttcttgatg catttcgtaa    5760
tcactataaa cattgtcaag aataccgtca ctactgtcag gtacacaaag tagacgacaa    5820
tattacggaa attgatgaca tacctgtatt cccaacatca gttttttaagt ttactcgctt    5880 attaacttct caggagaacg agattgaaag ttggtttacc agcagcggca cgagtggttt    5940
aaaaagtcag gtggcgcgtg acagactaag tattgagaga ctcttaggct ctgtgagtta    6000
tggcatgaaa tatgttggta gttggtttga tcatcaaata gagttggtca acttagggcc    6060
agatagattt aatgctcata acatttggtt taaatatgtt attagtttgg tagaattatt    6120
atatcccacg acatttaccg taatggaaga acgaatagat tttgttaaga cattgaatag    6180
ccttgagcga ataaaaaatc aagggaaaga tatttgtctt atcggctcac catactttat    6240
ttatttgctc tgccagtata tgaaagataa aaacatctca ttttatgggg ataaaaacct    6300
ttatatcata acgggggggcg gctggaaaag ttatgaaaaa gagtccctaa acgcgatga    6360 tttcaatcat cttttattcg acacgttcaa cctcaataat attagtcaaa tccgcgatat    6420
atttaatcaa gttgaactca acacttgttt ctttggaggat gaaatgcaac gtaaacgtgt    6480
tccgccgtgg gtatatgcgc gagcacttga tcctgaaaca ttgaaacctg tacctgatgg    6540
aatgccgggt tgatgagtt atatggatgc gtcatcaacg agttatccgg catttattgt    6600
taccgatgat gtcgggataa tgagcagaga atatggtcaa tatcctggtg tacttgttga    6660
gattttacgt cgcgtcaata cgagggcaca gaaagggtgt gctttaagct taaaccaagc    6720
atttaatagt tgatatactc tatggatttt aagatgcatc gcgatggcaa gggagtgaat    6780
tc                                                                    6782
```

<210> SEQ ID NO 10
<211> LENGTH: 13760
<212> TYPE: DNA
<213> ORGANISM: Shewanella hanedai

<400> SEQUENCE: 10

```
tgtacccata cctcttgctg tatcttaatg atattaagca ggaggttatg atactcgtca      60
tattattcac atactgggtc gagtgatatt aactaagtgc ctgtatatga gctaagtcca     120
tgtgctcgta tttatttcg tattgcaatg ataaaaagat cgttaatact aaggtcttgt     180
tgaatgtatt gacgctgaca gtattttat ccaagtggct tctcattatt tacgtctagt     240
tgtttaacaa atttattaaa taaagctgca ctctttttg ggacttctac catgggaagg     300
tgcccaatat tcttcagtaa tacgacctga acattactga gtaaaggaca gatttttatcg    360 agtgcacttt tatctaaaat tctgtcttcc tccccccata caatcaatac tggaacctga     420
attttatcta agtaaggaag gagatcattg ttgtgaaaat cagcaaatat cttgtgatgt     480
aattgttttt tatgcgcctg aagtgctaaa tgtgtttgtt ttaaagattt gggaataagg     540
```

```
ccagatttat agaaagtgta attaaagtat tcaattggat tggtacaatc aatcaaaggg    600
ttggggcggt tagaggccaa gtcttgaaac atatcactct taattgggct gtcgattcca    660
gcattatcaa ataacgtgac cgataaaatc tcttctggaa atagagcagc ataggttgct    720
gcgatctgcc ctcccataga gctaccgagt atatgaaaag gagctaattt ttgctcggaa    780
acaaacaaat gcacacgctt aacctgagct tcaatgcagt agtctgcatc aagtggtgca    840
tcactctcac catgtccaag taaatctaat gcatgattc gatatttttt ctttaaaaat     900
aacgacattt gaagccagtt atctttattg gcggtaaagc catggagcat aaggagtatt    960
ggcttactgt ttatttgata gtgttcattt gcgttatcta gatatacata acgcttttca   1020
aggagagtga tctcttttcg gctgagccct gagagataac gagtggtgtg ggttaagagt   1080
tgatagagat acaatggagt aaaatagata agaattaagc taattagcag tactaaaatg   1140
aatgcggata taaaaaatga aaccatgaaa ctctccaaat gaaaatagat tttgtctaat   1200
aatatacggc cccaaaagaa cacttgatac agtagcacga tagttattaa agtgttgcgt   1260
aaaagtgtgc tgatttgctt agcctaaatt aggggtaatg attattaaga tgtcagcaaa   1320
cataatttga aattaaagat ttaagtggca cttggttttg aacatattta acggttggat   1380
cttcattcat ttgcactacc gcgccaatca taaatagaaa gccaataccc agtagtatta   1440
atcccatagc gcatttctct ggtgagttgg gttctttagc acctcaacgg atccagatag   1500
atgccgttaa gcggggcatt tgtttagca gtttcgctg caggtatagt atcaatatct     1560
cccaataatc ttttagcaaa acaaattgc accctatctt gtgattgcaa caaataacgc    1620
ttgatatgaa atagcgttgg ctaatgagta aaatcgtatt atgtcattac aatcaaactc   1680
aatggcaata actgcgcaaa atcattaaca attgggtgtg taattttttt aattattgaa   1740
cactgtgata ttaataaact cttaaattat ttaatgaatt ttgtgtttat gcgtatgggg   1800
gcggttataa ttatagtgtt tttttagtgt gatctattaa gtaagattat acaggattgt   1860
gatgaatagt atgaagtatt acaaagggaa tggattcatg acccctgtta ggatagattt   1920
tgagatactt tgactgcgat tatttgtacc aagtttagtt tgtaaattgg ttatatgaaa   1980
agatactgtt ctttcagagc aatctagtat tttagatatt tcccaggttg ttttcccctc   2040
acttatccaa gctaggcatt cttctctct tggtgttaac tgtgtgcaag tattgccaat    2100 attttatta attctttgat ggctgtctaa aagttcagga agaacgagta aaacataaga    2160
gtaagagttt gaatgtaaag atattaatgt tttttcatta tttgaattgg caaaactaat   2220
tactccaaag ctattatttt ttgtatgaac aggaaagcta atcctgatt taagatttga    2280 attttttgct tcttcaatta catttgtttt gttttatcc catttacttt gttccaacat    2340
actccaaatt attggagcgt aattagaagc gctataatca ataataggat cgtaatcaat   2400
tagtttctca tcgttgtaat attttttcca acatgaaggg taattatcta aaatatataa   2460
gtctgattta aatattgata ctggattcag tatagcaaat agatagtatt cacagtcaag   2520
gagaagggct aattttgtga ggcaagcgtt gaggtcatta tcattttcag ataaacgaag   2580
gttatcattg atttcatata cggcatccat tttgaaaaaa tccatttatt tcccttactt   2640
tttataatga tatagtattt ggtaactata gcatgtctag tttactaatc tgtatctgta   2700
tcttaatttt aaaactaaag tagtaggtgg tgtgaagtaa gtaatcgttt tataagagtt   2760
gtaaccctgt aatatcgtac aggcttaaaa gatatactcg cttgttatag tggttttgaa   2820
aggagtatat atgcaaatta tcataaagaa atcaaacttt atcactattc caagaatga    2880
```

```
ataccttggg ttgttaaagc tgcgctatca agtatttgtg ctaaggttgc aatgggggct   2940
ggcttctgta aatggtctgg agtcagataa ctatgacaat gtggatgctg catatatata   3000
tgcttgcgat gatactgaaa aaatttatgg ttgttggcgg ttactgccaa caacaggaga   3060
ttatatgtta agaacagtat ttttaaagtt gcttggtgac caagatatac ctaatgatcc   3120
tactattatt gaattaagtc ggtttgcagt tgaaaagcag agttcaacaa tgaatggagt   3180
aagcagtgag ataacaatga aacttttga agcaatatac attcatgcag taaaccatgg   3240
aataaaagaa tacgtttcgg tgacatctac agcgattgag cgatttctaa aacgaattaa   3300
aatcccttgt aatcgtattg gtgatcaaca agttcatttg ttgggatgta ctaagtcagt   3360
tgtattgtca atgcctatta atgacgattt taaacatgct gtcatgtgtt aatattaggt   3420
caaactatga cagttaacat tacattaata cgtatttaaa aacaccattt aataatggaa   3480
gtaaaaagtc acaacgtaaa tttatcaagg gctagtaata ttaacaatat agaactatca   3540
attatactga ggtatgttaa tgattaagta tgttccaatg ataatcggag gcgtcattca   3600
agatgatccc gataatgaaa ttagagagtt aacgttaaat aatgaacgta aagttcatct   3660
acctattatt gatagtagtc atgtggataa aataatagaa ataaaagtac agaacaattt   3720
gaatttaaat caagtcgtta actttttgta tacgttggga caacgttgga aaagtgaaga   3780
gtattcacgt cgtcgaactt atattagaga tctgaaaaac ttccttggat attcaaatga   3840
aatggcgaaa ctagaagcta attggattgc gatgttattg tgttcaaaaa gtgcattata   3900
tgacattgta aaaaatgatt tagggtcatt gcatattatt gatgagtgga tacctcaagg   3960
agattgttac gtcaaagcat tgccaaaagg taaatcagta catttacttg caggtaatgt   4020
gcccttatct ggagtgacat cgattcttag ggctatttta actaaaaatg aatgtattat   4080
taaaacatct gcggcagatc cattcacggc aaccgctttg atatctagtt ttatcgatgt   4140
caatgcgagt catattatta cgcgatcaat gtcggtgatg tattgggcac atagtgaaga   4200
tatttcgtta ccgaaaatca tcatgagtca ggctgatgtc gtagtcgctt ggggcggaga   4260
tgaggccatt aaatgggctg ttaaacatac accgtacaat atcgatattc taaagtttgg   4320
tccaaagcag agtctgagca ttgttgataa tccagaagat atggtccttg cggcaactgg   4380
agttgctcat gatatttgtt tttatgatca acaggcctgt ttttcaactc aaaatattta   4440
ttacatcggt aataaattag cttttgttcat tgatgagctt gagagacaat taacacttta   4500
tgcaaaaatt ttgcctaaag gttttcaaaa ttttgatgaa aaagcggctt ttagtcttac   4560
tgaaaaagaa tgcttatttg caggttatga cattagaagg ggagataatc aaagctggct   4620
aattattaca tccccttta attcatttgg aaatcaacct ttatcacgat ctgtttatgt   4680
tcatcatgtt tcaacactct ctgagatact accttttatt aataaaaatg ttactcagac   4740
tgtctcggta actccatggg gatcctcatt taagttcaga gaccaactgg cagaatatgg   4800
tgctgagcgt attgtcgagt caggtatgaa taatgtattt cgtgttggtg gtgcccatga   4860
tggtatgcgt cctctacaac atttagttaa ttatgtgtct caagagagac catccagtca   4920
tacaacaaaa gatgttgctg tggaaataga acaaacacgt tatttacaag aagataaatt   4980
tttagttttt gtcccataat ataaaaggaa atcatatgga atgttcaaat tcttgcttaa   5040
ctatagatca tgttattcag cttgatgatg ataaagaaat tagagtatgg gaaacgttac   5100
caaaggataa tacagcggta aggaataaca ctattcttat tgcttctggt tttgctcgga   5160
gaatggatca ttttgcaggc ttagctgaat acctatccag taatggtttt catgttatcc   5220
gttatgattc tcttcatcat gttggattga gcagtggtga tattaatgag tttacaatgt   5280
```

```
cgattggaaa agacagtttg cttatcgtaa tagaatggct caaaggacgt ggcgttaata    5340
aattaggttt gattgcagca agtttatccg ctcgtattgc ttatgaaata tcaaatgatg    5400
ttgatttatc attttttagtg actgctgtgg gagttgtaaa tttgagggat acgttagaga    5460
ggtcattaaa atatgactac ttacaattag aaattgaaga cttgcctgaa gatttagatt    5520
ttgaggggca caatttggga tctaaagttt ttgtgagaga ttgttttaaa cataactggg    5580
ttacgttaga ttcgacaaaa aacaaaatga aaaacctaga cattccatttt attgcattta    5640 cggctaatga tgatgattgg gttaagaaag ctgaagtatt ggagatgatg aatagtatca    5700
gttctacaaa gtgtaaactg tattcttaa tcggtagctc tcatgattta ggtgaaaacc    5760
ttgtcgtgtt aagaaatttt tatcagtcag ttactaaggc cgcaatatct ttagataatg    5820
attctgttga tctaaatgtt gaaatatttg aaccaaaatt tgaagaatta acgagtgtaa    5880
cagtacaaga gcgaagatta aaaaataaaa tcgaaagtga aattctagag ttaatgaatt    5940
aatagtcata cccggttata taaaataaag gaaataatta tgaagttcgg aaatatttgt    6000
ttttcatatc aaccgcctgg tgagactcat aaacaggtaa tggatcgttt tattcgactt    6060
ggcgttgctt cggaagaact tggctttgat acatactgga ctctggagca ccatttttact    6120 gagttcggtc ttactggtaa cctttttgtt gctgcagcaa atctacttgg ccgaactaaa    6180
acactgcaag ttgggacgat ggggggttgta ctccctacag ctcatccagt tcgacaacta    6240
gaagatgtat tgttattgga tcaaatgtct aaaggtcgtt ttaattttgg cgttgttcga    6300
ggtttatacc ataaagattt cagggtattt ggcgtcaata tggaagactc acgcgggata    6360
actcaaagct tccataccat gatcattgat ggcgtaaaaa cgggacgtat aagctcagat    6420
ggggaacata tagagttccc agaagttgag gtatatccaa cagcttattc aaaggagctc    6480
ccaacgtgta tgacagcgga gtcagctagc acaacggagt ggttagctga gcggggattg    6540
ccaatggtgc ttagctggat aattggaacc aacgagaaaa aagcgcaaat ggaactttat    6600
aatgaaattg cgatagagca tggtcatgat attactaaga ttgatcattg tatgacatttt    6660 atatgctcag tggataatga tagtaataag gcacgtgatg tatgccgtgc ttttcttgct    6720
aattggtatg actcttatgt taatgctacc aacatattca atgatagcaa ccaaactcgt    6780
ggctatgact atcacaaagg tcagtggaga gattttgtac taaaaggtca tacaaatagc    6840
aacagacgtg ttgattacag taatgaaatt aaccctgtag gcacacctga agaatgtatt    6900
tcaattattc aacgtgatat tgatgcgacc ggtattacta atatcacctg tgggtttgaa    6960
gcaaatggta gtgaagagga aatagtggct tctatgggac ggtttatgac acaagtggct    7020 cctttttttga aagaccctag ctagtcatta atacatttaa ttaaatatag taaggaaata    7080
ttatgaaatt tggattgttt ttcctcaact ttcagctaga tggtatgact tcagaaaaca    7140
ctttagataa tatggtgagc atggtgtctc ttgttgatgc tgatgaatat cattttgata    7200
cagtactcat atacgaacat cattttttcta aaagtggcat tatagcttca cctattacag    7260
cggctggttt tttacttgga ttgactaata ggctgcatat tggctcttta aatcaagtta    7320
ttacaactca ccatccagta cgtgttgccg aggaatcaag tttattagac cagatgtctg    7380
aaggtcgttt cattctggga ttcagcaata gtgaaaacga ctttgaaatg gatttcttta    7440
aacgtaattt agcatctcgg caacagcaat ttgaagcttg ttatgacatc attaatgagg    7500
cgttgacgac tggatattgc caccctcaaa atgatttttta cgatttccct aaagtgtcaa    7560
taaacccaca ttgttttagt aaaaatgggc ctaagcagta tgtagtagca acaagtaaaa    7620
```

```
gtgtcgttga atgggccgct aaaaatgcat tgtctctgac gtttaaatgg gatgatagtc      7680
ttgcagataa agaaagttat gcaatgcttt ataatgaaat tgcgatgcgt tatggtattg      7740
acatttcaaa tgtagagcac caacttacag tcattgtcaa tttgaatgct gatggtgatt      7800
tagctcgcga tgaagctaag gggtacttga aaaactatat tgttgaaaca tatccagaca      7860
tcgatcatgt ggctaaaata aattcaatca ttgcagagaa cgcgattggt actgatgccg      7920
agtattatga ccaaattaaa ctagcagttg aaaaaacagg agttaaaaaa attctgttat      7980
catttgaatc catgaaggat tcaaatgatg ttaaaaatat tattaatatg gcaaatgaca      8040
aaatatctaa aaatattaag gcatagtgtt cgttggtttt aaatggtggt agaaataatt      8100
taccactatt taaaataatg ttaataaccc ctgctattta ggttgtatat gaatactcaa      8160
tgtatagttg aagagtacca agttatagca agctcagaga tagatgatct tatttttatg      8220
agtaacccac aagagtggac atttgaagag caaaagaaa ttcaaaataa acttatcctt       8280
gaagcgttta actatcatta aatagaaat gaagttata ggaaatattg tattacacaa        8340
catgttaatg agaatatcac ttcaattgat gatattcctg tgtttccaac atctgttttt      8400
aaatatatga aactcatac tgctagtgaa gatgatattg agaattggta tacaagtagc       8460
ggtactagtg gtatgaaaag taatattgct cgtgatcgac taagtattga aaggttactt      8520
ggttcagtta atttttggcat gaaatatgtc ggtaattggt ttgaacacga atggaattg      8580 gttaatcttg gtccagaccg ttttaacact aataatatat ggtttaagta tgtaatgagt      8640
ttggttgaat tactttaccc aaccgaattc actgtcaata acgatgaaat tgatttagaa      8700
aaaacaatgc atcatttatt tcgtatttat aacactaaaa aagatatttg cttgattggt      8760
cctccttatt ttatttatct attatgtcag tacattaatg ccaatgatat tgaatttatt      8820
gcggggaata gattgcacat catcactggt ggtggttgga agttaaatca aagtgagtcc      8880
ttaagtcgtg atgattttaa tgctatgtta atggaagtat ttcatttgaa taacatcaat      8940
caaattagag acacttttaa tcaagtagag ttaaatacgt gttttttttga agatgaatat     9000 caaaggaagc atgttcctcc ttgggtttat gctcgcgctc ttgatcctga aacactacag      9060
ccagttattg acggtgaaca aggattatta agctatatgg atgcatcatc aacaggatac      9120
ccagcattta ttgttacaga tgatataggt attatccatc atgttaaaag ccctgatccc      9180
tatcctggta caaagttga dataatacga agattaaata cacgcgcaca gaaagggtgt       9240
gctatttcaa tgattaatac aatgaaagta aataattaat actgcgtggt ggatataata      9300
tatgaaagta aaatgcagcg tatcaaaaat agagttaata aataaaaata tatataaagt      9360
ttatattaaa ccttatgttc ctattgattt caaagctggg cagtatatat atataaattt      9420
aagtggtaat aaaaggcaac cattttctat tgctagttgt ccaacagata atagtgtgat      9480
tgaactgcat gttggcagtt caaatgaaaa cagttctta gatgtaatgg aatattttgg       9540
tgatgctcta ataaaaaata gtaccatcgt gatagatgct ccacatggag aggcgtggtt      9600
acgtgaaggc agtaataaac caatattgtt gattgccggt ggtacaggtt atcctatat      9660 tagcagtatt cttcgaaact gtttaaaccg aggtttcact caacctatt atgtttattg       9720 gggagtgaaa aatatagatt ttttgtatgc agatgaagaa ctacagttat tatgcagtca      9780
ccacagtaat ttacattaca ttccagtggt attagaagac agtaaatata cgtggttagg      9840
aaaaaaaggc acggttattg atgctgtcat ggatgatttt actgttctta cgcttttga     9900 tatttatgtc tgtgggccta atttgatgac taaggcagca aaagataaat tagttgcaaa      9960
aaagagtgct aaatcagaac aaatgttttc cgatgctttt gcatatatgt gatcttttaa    10020
```

```
atgtagtgta gatataataa acatcagtct aagaagcaat ctatttggtt cgttgtattt   10080
taagtggtga tttctgacat gacagtcata taaagtcatg tcagttctct atgaacctca   10140
cccattaaac attaaccaaa tacaaactct tcttcactgt cgagccaggt tgggtatttt   10200
atcattatgt cgatgaaagt agagctggct aaatgtttag ctaaccaggc ctgaacattg   10260
ggggtagggg atgtttcgaa ccacatttta tctacatggg caaattggcg tacaaaggga   10320
tagattgcat aatcagcgat actggctgta tgacagagca gattatcatg cttggctaag   10380
aggctttcca ggtgggagat gaatatcatg ccctgatcgc gataatgtgc tttagtgaat   10440
tcagggtatc tgtcggcgta cttgtatttg tctagccaag gtttaaagtt atcatcatta   10500
gtcttgatta atgccatggc tatctcttgt aactcaggct tatcggtcag caataaattc   10560
agaggatcct tctgcattag tgcccaacac atgatatcga tactctcatc gatcacttga   10620
ttatctgaag tgatgagtac gggtaccgtt cctttggggg atgaatataa catttgctga   10680
ggtttatttt ttaggattat ctctcttaac atgacttgag tgccagagag ggaaatgcca   10740
agtcgagcgc gcatggcata ggggcagcgt ctaaatgagt agagagtggc taaagacatg   10800
attttctctg gtaagttgct tgaattcttt attatgttgt ggcttttctt atcaaaaaac   10860
aatcaagatt taacttcaaa ttgaacttgg gagactaaag tcatcatatt ttcttaatac   10920
ccctactttt tgtctctgtt tgtgtttatg ttactcatgt atgattctcg ccgttttgc   10980
taactagctc actcacaatt gtgagccagt ctatcattga gtcaatatgc actggagatt   11040
aagctccagc aagcagtaga ggttagtatg tcccacgttg ttgtttgtgc cctttataag   11100
tttgtttccc ttcctgattt tgaactgatc cagaaacccc tattagccga gatggaaaaa   11160
tcaggcataa aaggcacttt gttgctggcc aacgaaggga ttaacggtac tgtcgcgggc   11220
tcacaagaag cgatagataa cctacttatc tggctggctg gacagccggg ccttgataac   11280
atagtgcata agttttcgtt cgatgaaacc atgcctttt atcgtaccaa ggtgaaatta   11340
aaaaagaga tcgtgacgat ggggatcgag ggtattgatc cactcaaagt cgttggcact   11400
tatgttaagc ctaaagattg gaatgcgctt atttcagatc ctgaggtgtt actggtcgac   11460
acccgcaatg aatacgaagt caaaatagga accttttaaaa atgctgtcga tcctaagacc   11520
gacacatttc gtgaattccc tgcttatgta aaagaacacc tcgatcctgc gaagcataaa   11580
aaagtggcca tgttttgtac gggtgggatc cgctgtgaaa aatccaccgc ttacctcaaa   11640
gagcaaggct tgatgaggt ttatcatctt gaaggcggcg tgcttaagta tcttgaagag   11700
gttaagcagg aagagagctt gtgggaaggt gagtgttttg tgtttgataa tcgcgttgcg   11760
gttaaccatg acttggaaaa aggtcaatac gatcaatgca acgcttgtcg tatgccaata   11820
acagaggctg aaaaagccag tgaagcattt gttcagggag tcagttgtcc tcattgtatc   11880
gacaccattt cagataagca gcgtcagcgc tttgaagaac gagagcgtca gatgcaactc   11940
gcagacaagc gtggtgaagc tcatatcggt agtgatgtcg gtgctgtgat tcaaaaccgc   12000
cgtgatcaca agaaaaacct taagaaagcg cagcttaagc ttaacagtaa aaaatagaaa   12060
taaatgagtt ggaggctaga atggcgtcta tactcattta gcaataagag aattattgat   12120
cctgtatcgg gcgattaata cctccatatt gttgaaaaag ccgtctttga cggcttttt   12180
tttgctttct gtcattgaat gatttatttc tcttgtttta tccactttga tgttcatcaa   12240
tgtatttta gattaactct atttagcgat tgatatcgaa ctgtttatat tctgccattg   12300
atttcttttt ctaatggtta cttgtttgca ttctattttt aagaatattc taaatagtat   12360
```

```
ttctgaattt acaaatttaa ttatgaatgt agttttgttc aaagaaacaa caaaaataat   12420
taaataggaa tagataatga aacagtgcaa agaaaaatta atagtatcaa tattatttgg   12480
atgttctgct ggtatagcca gttgtggtgt gcaagcaata gaaatacaag ctgatccatg   12540
gacgttaaat attaatggta atgttaatgg ccacctctct tacgtgcagt gtgataacag   12600
tactaatgtc gtcgcgggta atccattatt atgtataggc gatgatgcaa cctctgttgc   12660
gaatggatat ttaccaacag gtatcgattt cggtatttct agaacggtta atgattacca   12720
tgttgccgtg catttgctt atgaaggggg aaccgttact aatgggccat ttaatggcgg   12780
aggcacaacg gagtcattta gaggatattt aactgtcgca aatgaccatt acggtgaggt   12840
taaaattgga cgagactacg gtgtatttgg aatcgatgtc atattgtccg atatgtcttt   12900
attaggcgta ggtgcttcag ccattataaa atctccatta aacaccacat taggaagttc   12960
tgggtatggt tatatatttg tcgatcgcct cgcgcaaatt aactattcgt ttcctaccaa   13020
aaacggtctg agtgccactg ttggggtata tcaaccgcta gatccatcga ccctaggggc   13080
tgaaaacacc tttgtaggtg actcaggctc taaaacgcca ggttttcacg ggaaattaaa   13140
gtatgagttt gaaaaggggt ttatatctag cacttggtta acccagcaga ttgataataa   13200
tgaggtgaac gaaaccgctt tgcttgggga tgtcactggt aaaatgaatt ttggggcgct   13260
ttctcttgtg gcttcttatc atgatgcgaa aggtgtcggt cactcagggt tgttttcga   13320 tggtatcgat gcccaaggta atgcgagaaa ctcgaatggc tactttgtgc aggctatgta   13380
tagcttcaca gacactcgtg tcggcattaa ttatggaata tcaacattgg acagaaatgc   13440
caatgatccg ttagtgaacc ttaagcaaag tgaaaagcta acatttggcg cctatcatag   13500
cttgtttgaa ggactcacct tggtggctga agtgtccatg tatgaatctg aaaacaataa   13560
aaatcaaagt attgataatc taggactaaa cttaggcgct gtgtatttt tctagcgtag   13620 aagattaaac taaatgtaat attacgattc ataaccactt agttttatgg atgactaagt   13680 ggttttttg aggtgtttat ggattcagtt agagatcaag caatttcaaa tgttcaaatt   13740
gataatgaca gagtgttggt                                               13760
```

<210> SEQ ID NO 11
<211> LENGTH: 7385
<212> TYPE: DNA
<213> ORGANISM: Photobacterium leiognathi

<400> SEQUENCE: 11

```
tctagacttt gtatattttc aatttaatac caaacgataa atctaagagg attttagttt     60
tttaaagata aaatacaaaa tacggacaaa tttttttat tatcatcaca aatattttaa    120
tttaaaaaca taaagaacaa tcttgtattt attctaaaac accaataata ttctggtggg    180
agatagtaat atcattaatt acataccata tatagacaaa cactacctag cgataataaa    240
tcccatcata cccacaccaa aaaaaaataa aaaccaccca atataacaaa gacataacta    300
caaccagaaa gaattaaaat aaatttcacc attcatttaa gttatgttta ttccatcaat    360
aataaaaact ataaaaatac cattcaacct aatttaaaaa ttccggagta aattaaaaat    420
aaagataaaa agtaaagcca ataaataaaa tcacaaaaaa cataaaaaac gaattaataa    480
taaaaatttt tgtaatatat ttcacttata ccatcatcta tcatgaaaaa tgaaaaataa    540
aaaaatcaga aagattaaat ataaaaatat taaattaaaa actgatttta ttaatagtgt    600
gaccaaaatc tcgaatagaa aaaagaaaaa ataaattagt tatcacatcc atatttcttt    660
atctaatctg attcagctag ctcatgcggc atagtttata ccgaaactac atactcagca    720
```

```
tgtgcgaata ccaaaggaga ttacatgatt aagaagatcc caatgattat tgggggtgta       780
gttcaaaaca cgtctggata tggcatgcgt gaactaacgc tcaacaataa taaagtgaat       840
atccctatca tcacccaaag tgatgttgaa gctattcaat cactaaatat agaaaacaaa       900
ttgactataa atcagatagt taatttctta tatacagtgg gacaaaaatg gaagagcgaa       960
acttacagcc gacgactcac ttatattcga gatcttatta agttcctcgg ttactcacaa      1020
gagatggcaa aacttgaagc taactggatc tcaatgattc tgtgtagcaa aagtgcgttg      1080
tacgatattg ttgagaatga tcttagctca cggcatatta ttgatgagtg gatcccccaa      1140
ggtgaatgtt atgtcaaagc gctcccaaaa ggaaaatctg tacacctatt agctggtaac      1200
gtaccactat ctggtgtgac ttctattctt cgtgcgattt tgaccaaaaa cgagtgcatc      1260
ataaaaacgt catcagctga tccttttaca gctactgcgc tagttaatag ttttatcgat      1320
gtagatgcag aacacccgat cacacgttca atctcagtta tgtattggtc acatagcgag      1380
gatcttgcta ttccaaaaca aataatgagc tgtgctgatg tggttattgc atggggtggt      1440
gatgatgcaa ttaaatgggc tacagaacat gcaccatcac acgcagatat tctaaaattt      1500
ggtcccaaaa agagtatatc cattgttgac aacccaacag atattaaggc tgctgctatc      1560
ggtgtagcac atgatatctg tttttacgat cagcaagcat gtttctccac ccaagatatt      1620
tattatattg gcgatagcat agacatattt tttgatgaat tagctcagca attaaataaa      1680
tataaagaca tattgcctaa aggtgagcgg aattttgatg aaaaagcagc ttttctctta      1740
acggaaagag aatgtttgtt tgccaaatat aaagttcaaa aaggtgaaag ccaatcttgg      1800
ttattaacgc aatcacctgc gggatcattt ggtaatcagc cgttatcacg ctcggcttat      1860
attcatcaag taaatgacat ttcagaagtc attccattcg tgcataaggc ggtaacgcaa      1920
accgtcgcaa tagcgccgtg ggagtcgtct ttcaaatata gagatatatt agcagaacat      1980
ggtgcagaac gaattataga agccggaatg aataatatat ttcgagtagg tggcgcccat      2040
gatgggatgc gtccccttca acggcttgtt aactatatat cacatgaaag gccgtcaaca      2100
tataccacta aagatgtctc ggtgaaaatc gaacagactc gttatcttga ggaagataag      2160
ttcctcgtat ttgtaccgta gaaagagata tatcatggaa aatacacaac attcattacc      2220
tattgatcac gtaattgata ttggtgataa ccgttatatt cgagtatggg aaaccaagcc      2280
gaaaaataaa gaaccaagcc gtaataatac catcgttatc gcctcaggct ttgctcgacg      2340
catggatcat tttgctggtc ttgccgaata tttagcaaat aatggttttc gtgttattcg      2400
ttatgattcg ttaaatcatg tcggtcttag tagcggagag atcaaacagt tctcgatgtc      2460
agtaggtaaa cacagtttgc taactgttat tgattggcta aaagaacgaa atattaacaa      2520
tataggtctt attgcttcga gtctttctgc tcgaattgct tatgaagtgg cagcagaaat      2580
tgatttgtca ttttaatta ccgccgtcgg tgttgtcaat ttaagaagta cgctagaaaa      2640
agcactgaaa tatgattatc tacaaatgga agtaaatact attcctgaag atttaatttt      2700
tgaaggacac aatctaggtt caaaagtctt tgtgacagat tgttttgaaa ataattggga      2760
ctcattagat tcgacaataa ataaaattg tgaactagat attccattta ttgctttcac      2820
ttcagatggc gatgattggg tttgccaaca tgaagtaaaa catttagtca gtaacgttaa      2880
atctgacaaa aagaaaattt actcactcgt tggctcatct catgatttgg gcgaaaacct      2940
agtggtgctt cgtaacttct atcaatcaat gacgaaagct gctgtgagct tagatcgtca      3000
attagtagag cttgttgatg aaattattga accaaatttt gaagacctaa cagttattac      3060
```

```
ggtaaatgaa cggcgcctca aaaataaaat cgaaaatgaa attattaata gattagctga    3120
tcgcgtattg gctagtgtct aaatagtact tacctaagta cagccaaaag gaagaaataa    3180
tgaaaattag taatatctgt ttctcatacc aaccaccagg tgaatcacat caagaggtaa    3240
tggagcgctt tattcgttta ggcgttgcat cagaagagct caactttgat ggtttctata    3300
cacttgaaca ccatttcact gagtttggta ttacaggtaa cctttatatt gcctgtgcca    3360
atattcttgg tcgaaccaaa aggatccaag tcggtaccat ggggatagtg ttaccgacag    3420
agcacccagc acgacatgta gaaagtcttc tcgttttaga tcaactgtct aaagggcgct    3480
ttaactacgg tactgttcgc ggactctacc ataaagattt tcgtgttttt ggtacatcac    3540
aggaagattc tcgtaagacc gcagaaaatt tctactctat gatcttggat gcatcaaaaa    3600
caggtgtgct acatactgac ggtgaagtag tagagttccc agatgtcaat gtttatccag    3660
aagcttacag caaaaaacaa cccacctgca tgacagccga atcatccgag accatcactt    3720
atttagctga acgtggttta ccaatggtgt taagttggat tattccggtc agtgagaaag    3780
tctcacaaat ggaattgtac aatgaagttg cggcagagca tggtcatgac attaacaaca    3840
ttgaacatat cctaactttc atttgctctg taaatgaaga cggtgaaaaa gcagacagcg    3900
tatgccgtaa tttcctagaa aattggtacg actcttacaa aaatgcaacc aacatcttca    3960
acgacagtaa ccaaactcgt ggctacgatt acctcaaagc tcagtggcgt gagtgggtaa    4020
tgaaggggtt ggctgatcct cgtcgccgac ttgattacag taacgaatta aaccctgtcg    4080
gcacgccaga acgatgcatt gagatcattc aaagtaatat tgatgccact ggaattaagc    4140
atattactgt tggatttgaa gcgaatggtt ctgaacaaga aattcgtgaa tccatggagc    4200
tatttatgga aaaagtagcg ccacacttaa aagatcctca gtaagctgtt ctttttaaac    4260
tattcaatat caaggcataa ggaataaaat atgaatttcg ggttattttt cctaaatttc    4320
cagcctgaag gtatgacttc agaaatggtt ttagacaaca tggtagatac tgtcgcatta    4380
gtggataaag atgattacca ctttaaaaga gtgctcgtca gcgagcatca tttttctaaa    4440
aacggcatta tcggagaacc tttgacagcg attagcttct tacttggttt gactaaacgt    4500
atagaaattg gttctttaaa tcaagtgatt accacccatc atcctgtacg tatcggagaa    4560
caaacgggct tacttgatca aatgtcttac ggtcgtttcg ttttaggctt aagtgactgt    4620
gtcaatgact tcgaaatgga tttctttaag agaaaacgta gctctcaaca gcaacaattc    4680
gaagcatgtt acgaaatttt aaatgaagcg ctgacgacaa actattgtca ggcagatgat    4740
gacttcttta acttcccacg tatttctgtt aacccgcatt gtattagcga agtaaaacaa    4800
tatatttag cttcaagcat gggcgtggtt gaatgggcag caagaaaagg attgccactc    4860
acttaccgct ggagtgacag cctagcagaa aaagaaaaat actatcagcg ttatctcgct    4920
gttgctaaag agaataatat tgatgtatca aatattgacc accaattccc actgctcgtt    4980
aatatcaatg aaaatcgtcg tattgctcga gatgaagtaa gggagtatat acaaagttat    5040
gtgagtgaag cctaccctac tgaccccaac attgagctaa gagtagaaga gcttattgag    5100
cagcatgctg tcggcaaagt ggatgagtac tacgactcaa caatgcacgc agtaaaagtt    5160
acaggttcaa aaaatttatt actctctttt gaatcaatga aaaataaaga cgatgttacc    5220
aagcttataa atatgtttaa tcaaaaaatc aaagataacc ttattaaata atttaattac    5280
ggatagatat tttcgatata tctaagtctt actaccattt atataaacta tttatacaga    5340
taacgtttca tttgattaag tcagtaaata attgccatta ttaatggca gtgcagatcc    5400
ttacactgcc atttataaat taaataaggg ttaacatgtc aacattatta aatatagatg    5460
```

```
caactgaaat taaggtgagt acagaaatag atgatattat ttttacatca tcaccgctaa    5520
cgttactatt tgaagatcaa gaaaaaatac agaaagaact tattttggag tctttccatt    5580
atcattacaa tcataataaa gattataagt actattgtaa tatacaaggc gtagatgaga    5640
atatacagtc cattgacgat attcctgttt ttcctacttc aatgttcaag tactcaagat    5700
tacatactgc tgatgaatca aatattgaaa attggtttac tagtagtggt acaaagggag    5760
tcaaaagtca tatagctcga gatcggcaga gtattgaacg cttgctaggt tctgttaatt    5820
acggcatgaa atacttgggt gaatttcacg agcatcaatt agaactagtg aatatggggc    5880
cagatcgttt cagtgcgtca aatgtttggt ttaaatatgt aatgagctta gttcaattac    5940
tttacccaac aacatttacc gttgaaaacg atgaaatcga ttttgaacaa accatcttag    6000
cgttaaaagc aattcagcgt aaaggaaaag gaatttgttt aattggccct ccgtatttta    6060
tttatttgtt atgccactac atgaaagagc ataatatcga atttaatgct ggtgcacata    6120
tgtttatcat tacaggtggg ggatggaaaa ccaaacaaaa agaagcgcta aaccgacaag    6180
atttcaatca actattgatg gagactttta gccttttcca tgaaagtcaa attcgagata    6240
tctttaacca agtagagcta aacacttgtt tctttgaaga cagcctacag cgtaaacatg    6300
taccaccgtg ggtatatgct cgtgcgcttg atcctgtcac tttaacgccc gtagaagatg    6360
gccaagaggg cttgatgagt tatatggatg cctcatctac cagctacccg acatttattg    6420
ttaccgacga tattggtatt gttcgccatc taaaagaacc agatccattc caaggaacaa    6480
cggttgaaat tgttcgtcgt ttaaatacgc gagaacaaaa aggatgttca ctctcaatgg    6540
ccacgagcct gaaataaaag cagggcttaa tcatgatttt taattgcaag gttaaaaaag    6600
tcgaagcatc tgacagccat atttacaaag tgtttattaa gcctgacaaa tgctttgatt    6660
ttaaagcggg tcaatatgta attgtgtatc tcaatggaaa aaatttgccg ttttctattg    6720
ctaactgccc aacttgtaat gagctccttg aattacatgt aggaggttcg gtaaaagaat    6780
ccgccattga agctatttcg cactttatta atgcatttat ttatcaaaaa gaatttacaa    6840
tcgatgcacc acacggtgat gcatggctga gagatgaaag ccaatcacct ttactactta    6900
tagcaggagg gacaggttta tcatatatca atagcatttt aagttgttgt attagtaaac    6960
agttatctca gcctatctat ctttattggg gagtaaataa ctgtaattta ctctatgctg    7020
atcaacaact aaaaacactc gccgcacaat acagaaatat aaattatatt cctgtggtag    7080
agaatttaaa tactgactgg cagggaaaaa ttggtaatgt tattgacgcg gttattgaag    7140
atttttcaga tttatctgac tttgatatct atgtctgcgg gccatttggt atgagccgga    7200
ctgcgaaaga tattctgatc tcacagaaaa aggcgaatat aggaaaaatg tattctgatg    7260
catttagcta tacgtaatta aaatcattat ttaactctaa ataaaccgt tattaatttt    7320 tcgacctact tattctgggt actgataatt agtacccaat agatagttct atttataggg    7380
atatt                                                                7385
```

<210> SEQ ID NO 12
<211> LENGTH: 10364
<212> TYPE: DNA
<213> ORGANISM: Photobacterium phosphoreum

<400> SEQUENCE: 12

```
ataataatct ccttctgtag gtaatatat ttaaatgaag ttattcattt tttaattagt      60
ctagtggtaa aaaaataaaa ttcaacagta aataatgttt tttgatttta aatctgtttt     120
```

```
taataaaataa attattgatt tttaagttct gttttttgttt gtttcattta aatatttata    180
tttaaattga tgttttttaat tacagtctat gcttgataag aagatgattt ataagaaaat    240
gtatacttaa tgattactgt tttatattta tactgatttt tatgtattat tgattttta     300 tctatttata atgtccaaat ttacttgttg accaattttc attgtaatat ttattatttt    360
acttgaaatc taaacttcta atattatatg taataaaatg ctcctgtttt atattttag     420 atgtttaaaa atagttataa attaataaat aacaaagtta gatgctaaaa gtgtgatatt    480
tacctcataa aattaataat gcgtgaatac tttacatatt aaccttacat gcccaataaa    540
aattagctag gctatgtaca tgcttatgaa gcaggtttgt atgcttgctg ggtatgtgca    600
gcagggtaat ttaaggagat tgtatgataa agaaaatccc aatgattatt ggtggcgcag    660
agagggatac ttcagaacat gaatatcgtg agctcacact caatagctat aaagttagta    720
tacctatcat aaatcaagat gatgttgagg cgattaaatc acaaaacgtt gaaaataact    780
taaatatcaa tcagatagta aacttcttat acactgttgg ccaaaaatgg aaaagtgaga    840
attattctcg tcgactcacc tatattcgag atttgataag atttctcgga tattcttctg    900
aaatggccaa actagaagcc aactggatct caatgatctt gagttcaaaa agtgccttat    960
acgatattgt tgaaacagat ttaggttctc gtcatattgt agatgaatgg ttacctcagg   1020
gggattgtta tgtcaaggct atgtcaaaag gaaaatccgt tcatttgtta gcaggtaatg   1080
tgcctctatc tggtgttact tctattatta gagcaatttt gactaaaaat gaatgtatca   1140
ttaaaacatc atcggctgat ccatttacgg caatagcatt agcttcaagt tttattgata   1200
cagatgagca ccatccaatt agtcgttcaa tgtcggtaat gtattggtct catagcgaag   1260
atattgtaat cccacaacaa attatgaatt gtgctgatgt tgttgttagt tggggtggac   1320
atgatgcaat taaatgggca acagaacata caccagtaaa cgtcgacata ttaaaatttg   1380
ggccgaagaa aagtattgcg attgttgatg atcctgtaga tattacagct tctgctattg   1440
gcgtcgctca tgatatttgt ttttatgatc agcaggcctg ttttttcaacc caagatatct   1500 attatatagg cgataacatt gatgcgtttt ttgatgagct tgtagaacaa ttagatatat   1560
atatggagat attaccaaaa ggcgatcaaa catttgatga aaaggcatca ttttcattaa   1620
ttgaaaaaga gtgtcaattc gcaaaatata aagttgaaaa aggtgataat caatcttggt   1680
tattggttaa atcaccgcta ggatcttttg gtaatcaacc attagctaga tctacatata   1740
ttcatcacgt ctcggatata tcagaaataa cgccttatat agaaaacaga attactcaaa   1800
ctgtaactgt tactccttgg gagtcatcat ttaaatatag agatgttcta gcctctcatg   1860
gtgcagagcg tattgttgaa tctgggatga ataatatctt ccgtgtcggt ggtgcgcatg   1920
atggtatgag gcctcttcaa cgtttagtta aatatatttc acatgaaaga ccttctacat   1980
atacaaccaa agatgtggca gtaaaaatcg aacaaacacg ttacctagaa gaagataagt   2040
ttttagtctt tgtaccataa aaaggaatta atatgaaaag tgaaacaat tctgtgccaa    2100 ttgatcatgt tataaaagtt gataatgacc aatatatacg tgtttgggaa caatccctta   2160
aaaatcaagg tgataaaaga aataatacta ttgttattgc ttctggtttt gctcgaagaa   2220
tggaccattt tgcaggttta gcagaatatt tatcgaccaa tggatttcat gttattcggt   2280
atgattcact taatcatgtt ggattaagta gcggtgaaat tgatcagttc tcaatgtcag   2340
tcggcaagaa aagttttatta accgttattg attggttgaa atcagagcat ggtattgatc   2400
aaattggttt aattgcatca agccttctg ctcgaattgc ttatgatatt gttgctgatg   2460
ttaatttgtc ttttttaatt accgccgttg gtgtggttaa tttacgaaac actcttgaac   2520
```

```
aagcacttaa atatgattac ttgaagatgg aaattgatga aataccagaa gatctaaatt    2580
ttgatggata taatttaggt tcaaaagtat ttgttacaga ttgctttgaa aataactggg    2640
atacattaga ttcaactata aataaaacga agaatttaaa tttcccttt atcgcttttg     2700 tcgccaatga tgacagttgg gtacaacagc acgaagttga agaattaatg aataatatta    2760
attcagataa aaccaagatt tactctttaa taggttcatc acatgattta ggtgaaaatc    2820
taatagtgct aagaaatttc tatcaatcaa ttacgaaagc tgcgattgca ttagatagta    2880
atttattagg gttagcgagt gagattgttg agccacaatt tgaagctctt acaattgcta    2940
cagtaaatga acgccgcttg aaaaacacaa taaaagtaa gtcattagtt taattacaac     3000
tgatacataa accaaccaaa ggaatatatt atgaaatttg gaaatatttg tttctcatat    3060
cagcccccag gtgagtcaca taaacaagtc atggatcgct ttgttcgttt aggtgttgca    3120
tcagaagagc taaattttaa tacttactgg actctagagc atcattttac tgaatttggt    3180
ctaacaggta accttttgt tgcttgtgct aacttacttg gtcgaaccac aaaattacat      3240
gttggcacaa tgggaattgt acttcctact gctcaccctg cgcgtcaaat ggaagactta    3300
ctacttttag atcaaatgtc aaaggtcgt tttaattttg gtgttgtacg tggcttgtac      3360
cataaagatt ttcgcgtctt tggtgtaaca atggaagatt ctcgtgccat tactgaagat    3420
tttcatacca tgattatgga tggcacaaaa acgggtacac ttcatactga tgggaaaaac    3480
atcgagttcc cagatgttaa cgtttatcca gaggcgtatt tagataaaat tccaacatgt    3540
atgactgcgg aatcagcagt aacaacgact tggcttgctg agcgtggttt accgatggtg    3600
cttagctgga ttattacaac cagtgaaaag aaagctcaaa tggaactcta taatgctgtt    3660
gctagagata gtggttacag tgaagagtat attaaaaacg ttgatcacag tatgacctc     3720 atctgttctg tagatgaaga tgctaaaaaa gctgaagatg tatgccgtga gtttttggga   3780
aattggtatg actcatacgt aaatgcgacc aatatcttta gtgaaagtaa ccagactcgt    3840
ggttatgatt atcataaagg tcaatggaaa gatttcgttc ttcagggaca tactaatacg    3900
aaacgtcgag ttgactatag ccacgattta aaccctgtcg gtacacctga aaatgtatt     3960 gaaattattc aacgtgatat tgatgcaaca ggtattacta atattacctt tggttttgaa    4020
gcgaatggtt cagaggaaga aatcattgcc tctatgaaac gtttcatgac acaagttgca    4080
ccattcttaa aagatccaaa ataaatcact tagattaacg ttaataaata atataaggaa    4140
tataacatga ttttggatt attcttcctc aactttcagc ctgaaaacac atcgtcagaa      4200 actgtttag ataatatgat caatatggtg tctctggttg ataaagatta taaaaacttt      4260
acaactattt tagtcaatga gcaccattt tctaaaatg gtattgtcgg tgccccgatc       4320
actgctgcga gcttcctatt agggttaact gaacgtttac acattggttc tttaaatcaa    4380
gttattacaa ctcatcaccc ggttcgtatt gcagaagaag caagtttact tgaccaaatg    4440
tcagatagtc gtttattct aggtttaagt gattgtatta tgattttga gatggatttc      4500 tttaaacgtc agcgtgattc acagcagcta caatttgaag cttgttatga gatcattaat    4560
gaagcaatca caaccaatta ttgccaagcg aataatgatt tttataactt ccctcgcatc    4620
tcaattaatc ctcattgcct gagtaaagag aatatgaagc aatatatttt agcttctagt    4680
gtgagtgttg ttgagtgggc ggctaaaaaa gcgctgccac tgacatatcg ttggagcgat    4740
agccttgaag ataagagat tctttataag cgttatttag acgttgcagc aaatcataat     4800
attgacgttt ctaatgtcga gcatcagttc ccactgcttg taaattaa tcatgatcgt      4860
```

```
gatgttgctc atcaagaagc aacaacctat ttagcaagtt atattgccga ggtatatccg    4920
catctaaatc agcaacaaaa aatggctgaa cttattagcc aacatgcgat tggtactgat    4980
aatgattact atgaatcaac attaaatgcg ttagagcgta caggttcaaa aatgtatta     5040 ctttctttg aatcaatgaa aaatcatgat gatgttgtaa acgtgattaa tatggtcaat     5100
gagaaaattc aaaagaattt accaagctcg taaacataaa ggtggcggtg ttattatgaa    5160
taaatggaat tacggaattt tcttcgttaa cttttatagt aaaggcgaac aagagtcatc    5220
aaaaatgatg aataatgcgt tagaaacatt acgcattatt gatgaagata catctattta    5280
tgatgtggtt aatattaatg atcactatct tgtaaagaaa gatagtgaag ataataagtt    5340
agcgcctttt attgcactag ggtctaaatt atatgtgctt gctaccagtg aaaacacagt    5400
tgatagcgca gcaaaatatg cattaccgct agttttttaaa tgggatgata caaacgagga    5460
acgacttaaa ttattgagtt cctataatac atccgcaagt aaatataatc agaatataga    5520
ttcggttcga caccagctta tgttacatgt caatgttaat gaggcagaag ctgtagcaaa    5580
agaagagcta aaattatatt ttgaaaacta tgtagcatgt acacaaccta gtaattttaa    5640
tggctcgatt gatagtatta ttcagagtaa tgtgacaggg tgttataacg attgtttgtc    5700
atatgtagcg aatcttgctg gtaaatttaa taatactgtg gacttcttac tttgctttga    5760
gtcaatgcaa gataaaaata agaaaaaatc agtaatgata gaacttaata atcaagttat    5820
taagtttcgc caagataaca atctaatcta atctacaatc attgccgctt ataatggcag    5880
tgctaattta aagttctgcc attatattta attatatctt aaataggatt aaacatgact    5940
attatattag atacttgcga aaaagatatt attgtaagtt cagagatcga cgatattatt    6000
tttacatcct cacctcttga tattacttat gatgaacaag aaagaataaa gcataaatta    6060
atattagaat catttcgtta tcattataac aataatgaag attataagtt tttctgtaat    6120 gctcagggg ttgacggaaa tatttcatca cttgacgata tccctgtttt tccgacttca    6180
atgtttaagt atgcaaaaat atgtacagca gatgagtcta acattgaaga ctggtttaca    6240
agtagtggta ctagtggtgt aaaaagttat attgctcgtg atcgtgtaag tattgaacgt    6300
ttactgggtt ctgtaaatta tggaatgaaa tatcttggct catttcatga aaatcagtta    6360
gagcttgtta atatggggcc cgatcgtttt aatgctaaaa atgtttggtt taagtatgta    6420
atgagtcttg ttgaattatt atatccaacc acatttacgg tgaataatga tgaaatagat    6480
tttgaactta ccattaaaag tttaaaagaa atctataata aaggtaaagg catttgtctc    6540
attggtcctc catattttat ttacttatta tgccagtaca tgaaagagaa tgatattgag    6600
tttaatgctg gtaatcgaat ctttattatt actggtggtg gttggaaaac taagcaaaaa    6660
caagcgctaa accgtcaaga ttttaatcaa ctattgatgg ataccttcca cttagcacat    6720
gaaagtcaga ttcgagatac atttaatcaa gttgaattaa atacctgttt ctttgaagat    6780
aatcgtcagc gtaagcatgt tccgccatgg gtttatgcac gtgcacttga tcctgtgaca    6840
ctaaaacctg ttgaagatgg tcaagagggt cttattagtt atatggatgc atcatcaacg    6900
agttacccaa catttatcgt tactgatgat atcggtatta ttcatactat taaagcgcca    6960
gatccactcc aagtactac gattgatatc gtccgccgtt tgaataccag agaacaaaaa    7020
gggtgttcat tatcaatgtc atcaggttta aaatagatca taaggaagat gtatgatttt    7080
aaattgtaaa ataattaaaa ttgaagcttc tgaatgtaat atttttaaag tatttattaa    7140
gcctgataag tgtctcaatt tcaaagctgg gcaaatgtt ttagcgtatt tagatggtaa    7200
aaaattacct ttttcaattg ctaattgtcc aacatgtaat gagcttatag agttacatgt    7260
```

```
tggaagttcg gtaaaagaaa cagcagttaa atctatttct tactttgtag atgcttttgt    7320
gaatagcgat gacatacaaa tagatgcacc tcatggtaat gcttggttac gtgagggcag    7380
taattcgcca ttattactta ttgctggagg tacaggacta tcatatatca atagtattct    7440
tagtaattgt gtaaatagga atttacctcg ttctatttat gtttactggg gagttaataa    7500
tattgattta ttatatgcag acactcaatt aaaaacactt tctagcgact ttagtaatgt    7560
taaatacgtg cctgttctag aaaactttga taatagttgg tatggaaaaa aaggtaatgt    7620
tattgatgca ataatagaag attttttgtga tttatcagat tttgatattt atgtttgcgg    7680
ccctcaaggc atgacttata gtgttcgaga aaaattaaca tcacttaaaa aagcgaatgc    7740
tgataaaatg tttgctgatg cttttgcata tatgtgatct taatttaagt aataaaaat     7800
taaaaaaact ttaaattcgc tatgaggtta tatttatatg aattgatttt taactctatt    7860
ttttggtttg taatattatt attctctcaa taaatagagt tattactaaa tttgtaatta    7920
acgttaagtt caagtttttg atatgtttgt tagggatttt gaaaaatatt aataagatat    7980
tacctgtaac ttcagtaatt tttattcaat aggaaataat aaaggaatga ttatgacgtt    8040
aagtacagcc caagaaatca ttgaggatat tcgccaaggg aaaatggtta tattaatgga    8100
tgatgaggat cgtgaaaatg agggcgatct tattattgca tcagataaaa tcacgcctga    8160
agcaataaat tttatggcaa cttacggtcg tggtttaatt tgtctgacat aaacaaagc     8220
ccgttgcctg caattaaaat tacctttgat ggtgaagaac aataccgata aatttgcaac    8280
cccgtttact ctttctatag aagcggcttc tggggttaca accggtattt cagtaaaaga    8340
tagagcgcgc actgttcaag cggctgtagc ggcaatggcg acatcggaag atattgttat    8400
gcctggacac attttttccat taatggctca agatggcggt gtattaactc gcgcaggcca    8460
tactgaagct ggttgtgatg tcgcgcgatt agcaggatta gagccatcca gtgttattgt    8520
tgaaatattg aatgatgacg gtacgatggc gagacggccg cagttagaag tctttgctaa    8580
taagcatggc ttaaggttag gtactgtcgc tgatcttatt gaatatcgaa ataaatatga    8640
aaccatgatt gaacgtattt ctgagtgtaa attgaagact gaatatggtg aattcaatat    8700
gatcacttat cgagataaaa ttaatcatca aattcattat gcgctacaaa aagtaatat     8760
tgagccgaat tctcaaacct tagtgcgagt gcatttacaa gatacattta agatattct     8820
gcaaacagga tcgaatcgat ggacattacc cgccgcgatg agtcgtatta gttctgaaaa    8880
tggcgttctt gttatagtaa ctaaaccaga agatcctgaa attgtaatca gtaaaattca    8940
gaatctagct ttgggtaatc aagaaacgcc agtgattaat agtcaatcac gtcaggttgg    9000
attaggttcg caaatattat cagatcttgg cgttagaaaa atgcgtttat tatcatctag    9060
tcgtcagctt tatcattcat tatctggttt cggtcttgaa atagttgagt atgtgtgtga    9120
ttaagtttcg atacagtaat aagactagcc gttatttata ctaaaattaa ttataaatat    9180
tataggagta cccatgaagc taattgaagg tgccaccgta gcacctaatg ctaaagttgc    9240
tattgtaatt gcacgtttta atagtttat taatgacagt ttattatctg gcgcgcttga    9300
tgcgttgcaa cgtcaaggtc aagttagcga tgataatatt actataattc gttgccctgg    9360
agcttatgag ttacctcttg ttgcccagtt tacggccaaa actgatcgtt atgatgcaat    9420
tatagcttta ggtgctgtta ttcgaggtgg tacaccgcat tttgaatatg tggctggtga    9480
atgtaataaa ggtcttgcgc aagtcgcatt agattataat attccagttg cttttggtgt    9540
gttgactgtt gattcaattg aacaagcgat tgaacgtgct ggcactaaag cgggaaataa    9600
```

| aggtgcagag gctgcattaa gtgtacttga gatggttaat gttttggctc aagttgaatc | 9660 |
| ttaactatat aacggtttat taaaattaag ttacgagtgt ttaattacac tcgtttataa | 9720 |
| atacaatacc gaatagttat taagtaatga atattagtca tattcgttga ttaagtttgt | 9780 |
| tgttatcgaa agagaataaa tacttcttta tttcacatgg aaatatttag gaatattatg | 9840 |
| gtcaatgtta gggaaagagt acctttaaac gtgggtatta atagtgatat tcctgccgag | 9900 |
| ttgctttcgt ttaatggtct tgaatcggga aaagaacata tagcacttat ttttaaagaa | 9960 |
| gcagataaaa tattggttcc tttagttcgt atgcattctg agtgtttaac gggcgatgtt | 10020 |
| tttcattcat cacgctgtga ttgtggagag cagttagttg aaactattga aaaaatgact | 10080 |
| gagcaaggtg gtattatttt atatttgcgt caggaaggtc gcggtattgg gctctataat | 10140 |
| aagatcgatg cttataagct acaaagtcaa ggaatgaata cttatgaagc gaataattat | 10200 |
| ttaggttttg atgacgactt acgagagttt tctgaagcag ctcaaatgct tactgctctt | 10260 |
| ggtattcaga atatacattt agtgacgaac aatcctaaga aaattttga tttacaacaa | 10320 |
| aacggtataa atattgtaga agttgttgga actaacgttc attt | 10364 |

<210> SEQ ID NO 13
<211> LENGTH: 1065
<212> TYPE: DNA
<213> ORGANISM: Photobacterium leiognathi

<400> SEQUENCE: 13

| atgaaaatta gtaatatctg tttctcatac caaccaccag gtgaatcaca tcaagaggta | 60 |
| atggagcgct ttattcgttt aggcgttgca tcagaagagc tcaactttga tggtttctat | 120 |
| acacttgaac accatttcac tgagtttggt attacaggta acctttatat tgcctgtgcc | 180 |
| aatattcttg gtcgaaccaa aaggatccaa gtcggtacca tggggatagt gttaccgaca | 240 |
| gagcacccag cacgacatgt agaaagtctt ctcgttttag atcaactgtc taaagggcgc | 300 |
| tttaactacg gtactgttcg cggactctac cataaagatt ttcgtgtttt tggtacatca | 360 |
| caggaagatt ctcgtaagac cgcagaaaat ttctactcta tgatcttgga tgcatcaaaa | 420 |
| acaggtgtgc tacatactga cggtgaagta gtagagttcc cagatgtcaa tgtttatcca | 480 |
| gaagcttaca gcaaaaaaca acccacctgc atgacagccg aatcatccga gaccatcact | 540 |
| tatttagctg aacgtggttt accaatggtg ttaagttgga ttattccggt cagtgagaaa | 600 |
| gtctcacaaa tggaattgta caatgaagtt gcggcagagc atggtcatga cattaacaac | 660 |
| attgaacata tcctaacttt catttgctct gtaaatgaag acggtgaaaa agcagacagc | 720 |
| gtatgccgta atttcctaga aaattggtac gactcttaca aaaatgcaac caacatcttc | 780 |
| aacgacagta accaaactcg tggctacgat tacctcaaag ctcagtggcg tgagtgggta | 840 |
| atgaaggggt tggctgatcc tcgtcgccga cttgattaca gtaacgaatt aaaccctgtc | 900 |
| ggcacgccag aacgatgcat tgagatcatt caaagtaata ttgatgccac tggaattaag | 960 |
| catattactg ttggatttga agcgaatggt tctgaacaag aaattcgtga atccatggag | 1020 |
| ctatttatgg aaaaagtagc gccacactta aaagatcctc agtaa | 1065 |

<210> SEQ ID NO 14
<211> LENGTH: 981
<212> TYPE: DNA
<213> ORGANISM: Photobacterium leiognathi

<400> SEQUENCE: 14

| atgaatttcg ggttattttt cctaaatttc cagcctgaag gtatgacttc agaaatggtt | 60 |

```
ttagacaaca tggtagatac tgtcgcatta gtggataaag atgattacca ctttaaaaga    120
gtgctcgtca gcgagcatca tttttctaaa aacggcatta tcggagaacc tttgacagcg    180
attagcttct tacttggttt gactaaacgt atagaaattg gttctttaaa tcaagtgatt    240
accacccatc atcctgtacg tatcggagaa caaacgggct tacttgatca aatgtcttac    300
ggtcgtttcg ttttaggctt aagtgactgt gtcaatgact tcgaaatgga tttctttaag    360
agaaaacgta gctctcaaca gcaacaattc gaagcatgtt acgaaatttt aaatgaagcg    420
ctgacgacaa actattgtca ggcagatgat gacttcttta acttcccacg tatttctgtt    480
aacccgcatt gtattagcga agtaaaacaa tatattttag cttcaagcat gggcgtggtt    540
gaatgggcag caagaaaagg attgccactc acttaccgct ggagtgacag cctagcagaa    600
aaagaaaaat actatcagcg ttatctcgct gttgctaaag agaataatat tgatgtatca    660
aatattgacc accaattccc actgctcgtt aatatcaatg aaaatcgtcg tattgctcga    720
gatgaagtaa gggagtatat acaaagttat gtgagtgaag cctaccctac tgaccccaac    780
attgagctaa gagtagaaga gcttattgag cagcatgctg tcggcaaagt ggatgagtac    840
tacgactcaa caatgcacgc agtaaaagtt acaggttcaa aaaatttatt actctctttt    900
gaatcaatga aaaataaaga cgatgttacc aagcttataa atatgtttaa tcaaaaaatc    960
aaagataacc ttattaaata a                                              981

<210> SEQ ID NO 15
<211> LENGTH: 1437
<212> TYPE: DNA
<213> ORGANISM: Photobacterium leiognathi

<400> SEQUENCE: 15
atgattaaga agatcccaat gattattggg ggtgtagttc aaaacacgtc tggatatggc     60
atgcgtgaac taacgctcaa caataataaa gtgaatatcc ctatcatcac ccaaagtgat    120
gttgaagcta ttcaatcact aaatatagaa aacaaattga ctataaatca gatagttaat    180
ttcttatata cagtgggaca aaaatggaag agcgaaactt acagccgacg actcacttat    240
attcgagatc ttattaagtt cctcggttac tcacaagaga tggcaaaact tgaagctaac    300
tggatctcaa tgattctgtg tagcaaaagt gcgttgtacg atattgttga gaatgatctt    360
agctcacggc atattattga tgagtggatc ccccaaggtg aatgttatgt caaagcgctc    420
ccaaaaggaa aatctgtaca cctattagct ggtaacgtac cactatctgg tgtgacttct    480
attcttcgtg cgattttgac caaaaacgag tgcatcataa aaacgtcatc agctgatcct    540
tttacagcta ctgcgctagt taatagtttt atcgatgtag atgcagaaca cccgatcaca    600
cgttcaatct cagttatgta ttggtcacat agcgaggatc ttgctattcc aaaacaaata    660
atgagctgtg ctgatgtggt tattgcatgg ggtggtgatg atgcaattaa atgggctaca    720
gaacatgcac catcacacgc agatattcta aaatttggtc ccaaaagag tatatccatt    780 gttgacaacc caacagatat taaggctgct gctatcggtg tagcacatga tatctgtttt    840
tacgatcagc aagcatgttt ctccacccaa gatatttatt atattggcga tagcatagac    900 atatttttg atgaattagc tcagcaatta aataaatata aagacatatt gcctaaaggt    960
gagcggaatt ttgatgaaaa agcagctttt tctttaacgg aaagagaatg tttgtttgcc   1020
aaatataaag ttcaaaaagg tgaaagccaa tcttggttat aacgcaatc acctgcggga   1080 tcatttggta atcagccgtt atcacgctcg gcttatattc atcaagtaaa tgacatttca   1140
```

```
gaagtcattc cattcgtgca taaggcggta acgcaaaccg tcgcaatagc gccgtgggag   1200
tcgtctttca aatatagaga tatattagca gaacatggtg cagaacgaat tatagaagcc   1260
ggaatgaata atatatttcg agtaggtggc gcccatgatg ggatgcgtcc ccttcaacgg   1320
cttgttaact atatatcaca tgaaaggccg tcaacatata ccactaaaga tgtctcggtg   1380
aaaatcgaac agactcgtta tcttgaggaa gataagttcc tcgtatttgt accgtag      1437
```

<210> SEQ ID NO 16
<211> LENGTH: 948
<212> TYPE: DNA
<213> ORGANISM: Photobacterium leiognathi

<400> SEQUENCE: 16

```
atggaaaata cacaacattc attacctatt gatcacgtaa ttgatattgg tgataaccgt     60
tatattcgag tatgggaaac caagccgaaa aataaagaaa ccaagcgtaa taataccatc    120
gttatcgcct caggctttgc tcgacgcatg gatcattttg ctggtcttgc cgaatattta    180
gcaaataatg gttttcgtgt tattcgttat gattcgttaa atcatgtcgg tcttagtagc    240
ggagagatca aacagttctc gatgtcagta ggtaaacaca gtttgctaac tgttattgat    300
tggctaaaag aacgaaatat taacaatata ggtcttattg cttcgagtct ttctgctcga    360
attgcttatg aagtggcagc agaaattgat ttgtcatttt taattaccgc cgtcggtgtt    420
gtcaatttaa gaagtacgct agaaaaagca ctgaaatatg attatctaca aatggaagta    480
aatactattc ctgaagattt aatttttgaa ggacacaatc taggttcaaa agtctttgtg    540
acagattgtt tgaaaataa ttgggactca ttagattcga caataaataa aatttgtgaa    600
ctagatattc catttattgc tttcacttca gatggcgatg attgggtttg ccaacatgaa    660
gtaaaacatt tagtcagtaa cgttaaatct gacaaaaaga aaatttactc actcgttggc    720
tcatctcatg atttgggcga aaacctagtg gtgcttcgta acttctatca atcaatgacg    780
aaagctgctg tgagcttaga tcgtcaatta gtagagcttg ttgatgaaat tattgaacca    840
aattttgaag acctaacagt tattacggta aatgaacggc gcctcaaaaa taaaatcgaa    900
aatgaaatta ttaatagatt agctgatcgc gtattggcta gtgtctaa                 948
```

<210> SEQ ID NO 17
<211> LENGTH: 1122
<212> TYPE: DNA
<213> ORGANISM: Photobacterium leiognathi

<400> SEQUENCE: 17

```
atgtcaacat tattaaatat agatgcaact gaaattaagg tgagtacaga aatagatgat     60
attattttta catcatcacc gctaacgtta ctatttgaag atcaagaaaa aatacagaaa    120
gaacttattt tggagtcttt ccattatcat tacaatcata taaagatta taagtactat     180 tgtaatatac aaggcgtaga tgagaatata cagtccattg acgatattcc tgtttttcct    240
acttcaatgt tcaagtactc aagattacat actgctgatg aatcaaatat tgaaaattgg    300
tttactagta gtggtacaaa gggagtcaaa agtcatatag ctcgagatcg gcagagtatt    360
gaacgcttgc taggttctgt taattacggc atgaaatact gggtgaatt tcacgagcat    420 caattagaac tagtgaatat ggggccagat cgtttcagtg cgtcaaatgt ttggtttaaa    480
tatgtaatga gcttagttca attactttac ccaacaacat ttaccgttga aaacgatgaa    540
atcgattttg aacaaaccat cttagcgtta aaagcaattc agcgtaaagg aaaaggaatt    600
tgtttaattg gccctccgta ttttatttat ttgttatgcc actacatgaa agagcataat    660
```

```
atcgaattta atgctggtgc acatatgttt atcattacag gtgggggatg gaaaaccaaa    720 caaaagaag cgctaaaccg acaagatttc aatcaactat tgatggagac ttttagcctt    780
ttccatgaaa gtcaaattcg agatatcttt aaccaagtag agctaaacac ttgtttcttt    840
gaagacagcc tacagcgtaa acatgtacca ccgtgggtat atgctcgtgc gcttgatcct    900
gtcactttaa cgcccgtaga agatggccaa gagggcttga tgagttatat ggatgcctca    960
tctaccagct acccgacatt tattgttacc gacgatattg gtattgttcg ccatctaaaa   1020
gaaccagatc cattccaagg aacaacggtt gaaattgttc gtcgtttaaa tacgcgagaa   1080
caaaaaggat gttcactctc aatggccacg agcctgaaat aa                     1122
```

<210> SEQ ID NO 18
<211> LENGTH: 705
<212> TYPE: DNA
<213> ORGANISM: Photobacterium leiognathi

<400> SEQUENCE: 18

```
atgatttta attgcaaggt taaaaagtc gaagcatctg acagccatat ttacaaagtg      60
tttattaagc ctgacaaatg ctttgatttt aaagcgggtc aatatgtaat tgtgtatctc    120
aatggaaaaa atttgccgtt ttctattgct aactgcccaa cttgtaatga gctccttgaa    180
ttacatgtag gaggttcggt aaaagaatcc gccattgaag ctatttcgca ctttattaat    240
gcatttattt atcaaaaaga atttacaatc gatgcaccac acggtgatgc atggctgaga    300
gatgaaagcc aatcaccttt actacttata gcaggaggga caggtttatc atatatcaat    360 agcatttaa gttgttgtat tagtaaacag ttatctcagc ctatctatct ttattgggga    420
gtaaataact gtaatttact ctatgctgat caacaactaa aaacactcgc cgcacaatac    480
agaaatataa attatattcc tgtggtagag aatttaaata ctgactggca gggaaaaatt    540
ggtaatgtta ttgacgcggt tattgaagat ttttcagatt tatctgactt tgatatctat    600
gtctgcgggc catttggtat gagccggact gcgaaagata ttctgatctc acagaaaaag    660
gcgaatatag gaaaaatgta ttctgatgca tttagctata cgtaa                    705
```

<210> SEQ ID NO 19
<211> LENGTH: 745
<212> TYPE: DNA
<213> ORGANISM: Vibrio fischeri

<400> SEQUENCE: 19

```
ataaggatt aagttatgat tgttgatggc agagtttcaa agatagtttt agcatcgata      60
aaaaataata tatataaggt atttattact gtaaattcac caataaagtt catcgctgga    120
caatttgtaa tggtcacgat taatgggaaa aaatgtcctt tttcaattgc gaattgcccg    180
acaaaaaatc acgaaataga attgcatatt ggtagttcga ataaagactg ctcattggat    240
attatcgaat attttgtcga tgctcttgtt gaggaagtcg caattgagtt agatgctccc    300
catggaaacg cttggttacg gtctgaaagt aataacccat tgctattaat tgcgggaggt    360
acaggtttat catatataaa tagcattcta accaattgct aaatcggaa tatacctcaa    420 gatatttatc tttactgggg agtaaaaaac agttctcttt tgtatgaaga cgaagagtta    480
ttggaattat cactaaataa caaaaatctt cattatattc ctgttatcga agataaaagt    540
gaagaatgga taggaaaaaa aggtacggtt cttgatgctg taatgaaga ttttacggat    600 ctagcccatt ttgatattta tgtttgtggg cccttcatga tggctaaaac agcaaaagaa    660
```

```
aaattaattg aagagaaaaa agcaaagtca gaacagatgt ttgccgatgc ttttgcatac    720
gtataaagag aatataaaaa gccag                                         745

<210> SEQ ID NO 20
<211> LENGTH: 687
<212> TYPE: DNA
<213> ORGANISM: Photobacterium leiognathi

<400> SEQUENCE: 20
atgacaaaat ggaattatgg cgtcttcttc cttaattttt accatgtagg acagcaagag     60
ccatcattaa ccatgagcaa tgcgttagaa acattacgta ttatagatga agatacatct    120
atctatgatg ttgttgcatt tagcgaacac cacatagata aaagctacaa tgatgaaacg    180
aaattagcgc catttgttag ccttggcaaa caaattcata ttttagccac cagccctgaa    240
acggttgtaa agcggctaaa atatgggatg ccactactgt ttaaatggga tgatagtcaa    300
caaaagcgta tcgaattatt aaaccattac caagcagctg cggctaaatt taatgtcgat    360
attgcaggtg ttcgtcatcg attaatgtta tttgtcaatg ttaatgacaa cccaacgcaa    420
gccaaagctg agcttagcat ttacttagaa gattacctct cttacaccca agcagaaaca    480
tccattgatg aaatcatcaa tagcaatgct gcaggcaact tcgatacgtg tttacatcac    540
gttgctgaaa tggctcaagg tttaaataat aaagtcgatt tcttattttg ctttgaatcg    600
atgaaagatc aagagaataa aaaatcacta atgattaact tgataaacg cgttattaat     660 tatagaaaag aacacaacct taactaa                                        687

<210> SEQ ID NO 21
<211> LENGTH: 585
<212> TYPE: DNA
<213> ORGANISM: Artificial Sequence
<220> FEATURE:
<223> OTHER INFORMATION: Aliivibrio fischeri yellow fluorescent protein

<400> SEQUENCE: 21
atgtttaaag gtatagtaga aggtatagga atcattgaaa aaattgatat atatactgac     60
ctagataagt atgcaattcg atttcctgaa aatatgttga atggaattaa aaaggagtcg    120
tcaataatgt ttaacggatg cttcttaacg gtaactagcg tgaattcaaa cattgtctgg    180
tttgatatat ttgaaaaaga agcacgtaag cttgatactt ttcgggaata taaggtaggt    240
gaccgagtaa atttaggaac attcccaaaa tttggcgctg catctggtgg gcatatatta    300
tcagcaagga tttcatgtgt agcaagtatt attgaaataa tagaaaatga ggattatcaa    360
caaatgtgga ttcaaattcc tgaaaatttt acagagtttc ttattgataa agactatatt    420
gctgtggatg gtattagctt aactattgac actataaaaa acaaccaatt tttcattagt    480
ttacccttaa aaatagcaca aaatacaaat atgaaatggc gaaaaaaagg tgataaggta    540
aatgttgagt tatcaaacaa aattaatgct aaccagtgtt ggtaa                    585

<210> SEQ ID NO 22
<211> LENGTH: 693
<212> TYPE: DNA
<213> ORGANISM: Artificial Sequence
<220> FEATURE:
<223> OTHER INFORMATION: Synthetic nucleotide sequence: Vibrio sp.
      BCB494 LUX H

<400> SEQUENCE: 22
atgagctcaa cgtcactact agatgagttt ggcactccac tacaaagagt agaaagagcg     60
```

```
attgaagctc tacaaaatgg ccttggcgtt ctattaatgg atgatgagga gcgtgagaac    120
gaaggcgacc ttattttctc tgcacagcat cttaccgaag cgcaaatggc actcatgatt    180
cgtgaatgca gtggcatcgt gtgtttgtgc ttaacggaag aacgcgccaa ttggttggag    240
cttcctccta tggtgaaaga taattgcagt aaaaaccaga ccgcttttac ggtttcgatt    300
gaagcgaaag aagggggtgac gacaggggtc tctgcgaaag atcgcgtgac aacggtcaaa    360
```

<210> SEQ ID NO 26
<211> LENGTH: 4553
<212> TYPE: DNA
<213> ORGANISM: Artificial Sequence
<220> FEATURE:
<223> OTHER INFORMATION: Synthetic nucleotide sequence: pSAT1-EGFP-C1

<400> SEQUENCE: 26

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcggggctgg | cttaactatg | cggcatcaga | gcagattgta | ctgagagtgc | 180 |
| accatatgcg | gtgtgaaata | ccgcacagat | gcgtaaggag | aaaataccgc | atcaggcgcc | 240 |
| attcgccatt | caggctgcgc | aactgttggg | aagggcgatc | ggtgcgggcc | tcttcgctat | 300 |
| tacgccagct | ggcgaaaggg | ggatgtgctg | caaggcgatt | aagttgggta | acgccagggt | 360 |
| tttcccagtc | acgacgttgt | aaaacgacgg | ccagtgccgg | cgcgccaccg | gtcaacatgt | 420 |
| ggagcacgac | acacttgtct | actccaaaaa | tatcaaagat | acagtctcag | aagaccaaag | 480 |
| ggcaattgag | acttttcaac | aaagggtaat | atccggaaac | ctcctcggat | tccattgccc | 540 |
| agctatctgt | cactttattg | tgaagatagt | ggaaaaggaa | ggtggctcct | acaaatgcca | 600 |
| tcattgcgat | aaaggaaagg | ccatcgttga | agatgcctct | gccgacagtg | gtcccaaaga | 660 |
| tggacccca | cccacgagga | gcatcgtgga | aaaagaagac | gttccaacca | cgtcttcaaa | 720 |
| gcaagtggat | tgatgtgata | acatggtgga | gcacgacaca | cttgtctact | ccaaaaatat | 780 |
| caaagataca | gtctcagaag | accaaagggc | aattgagact | tttcaacaaa | gggtaatatc | 840 |
| cggaaacctc | ctcggattcc | attgcccagc | tatctgtcac | tttattgtga | agatagtgga | 900 |
| aaaggaaggt | ggctcctaca | aatgccatca | ttgcgataaa | ggaaaggcca | tcgttgaaga | 960 |
| tgcctctgcc | gacagtggtc | ccaaagatgg | accccaccc | acgaggagca | tcgtggaaaa | 1020 |
| agaagacgtt | ccaaccacgt | cttcaaagca | agtggattga | tgtgatatct | ccactgacgt | 1080 |
| aagggatgac | gcacaatccc | actatccttc | gcaagaccct | tcctctatat | aaggaagttc | 1140 |
| atttcatttg | gagaggacgt | cgagagttct | caacacaaca | tatacaaaac | aaacgaatct | 1200 |
| caagcaatca | agcattctac | ttctattgca | gcaatttaaa | tcatttctt | taaagcaaaa | 1260 |
| gcaattttct | gaaaattttc | accatttacg | aacgatagcc | atggtgagca | agggcgagga | 1320 |
| gctgttcacc | ggggtggtgc | ccatcctggt | cgagctggac | ggcgacgtaa | acggccacaa | 1380 |
| gttcagcgtg | tccggcgagg | gcgagggcga | tgccacctac | ggcaagctga | ccctgaagtt | 1440 |
| catctgcacc | accggcaagc | tgcccgtgcc | ctggcccacc | ctcgtgacca | ccctgaccta | 1500 |
| cggcgtgcag | tgcttcagcc | gctacccga | ccacatgaag | cagcacgact | tcttcaagtc | 1560 |
| cgccatgccc | gaaggctacg | tccaggagcg | caccatcttc | ttcaaggacg | acggcaacta | 1620 |
| caagacccgc | gccgaggtga | agttcgaggg | cgacaccctg | gtgaaccgca | tcgagctgaa | 1680 |
| gggcatcgac | ttcaaggagg | acggcaacat | cctggggcac | aagctggagt | acaactacaa | 1740 |
| cagccacaac | gtctatatca | tggccgacaa | gcagaagaac | ggcatcaagg | tgaacttcaa | 1800 |
| gatccgccac | aacatcgagg | acggcagcgt | gcagctcgcc | gaccactacc | agcagaacac | 1860 |
| ccccatcggc | gacggccccg | tgctgctgcc | cgacaaccac | tacctgagca | cccagtccgc | 1920 |
| cctgagcaaa | gaccccaacg | agaagcgcga | tcacatggtc | ctgctggagt | tcgtgaccgc | 1980 |
| cgccgggatc | actctcggca | tggacgagct | gtacaagtcc | ggactcagat | ctcgagctca | 2040 |
| agcttcgaat | tctgcagtcg | acggtaccgc | gggcccggga | tccacctagt | ctagagtccg | 2100 |

```
caaaaatcac cagtctctct ctacaaatct atctctctct atttttctcc agaataatgt    2160
gtgagtagtt cccagataag ggaattaggg ttcttatagg gtttcgctca tgtgttgagc    2220
atataagaaa cccttagtat gtatttgtat ttgtaaaata cttctatcaa taaaatttct    2280
aattcctaaa accaaaatcc agtgacgcgg ccgcggcgcg ccgtaatcat ggtcatagct    2340
gtttcctgtg tgaaattgtt atccgctcac aattccacac aacatacgag ccggaagcat    2400
aaagtgtaaa gcctggggtg cctaatgagt gagctaactc acattaattg cgttgcgctc    2460
actgcccgct ttccagtcgg gaaacctgtc gtgccagctg cattaatgaa tcggccaacg    2520
cgcggggaga ggcggtttgc gtattgggcg ctcttccgct tcctcgctca ctgactcgct    2580
gcgctcggtc gttcggctgc ggcgagcggt atcagctcac tcaaaggcgg taatacggtt    2640
atccacagaa tcaggggata acgcaggaaa gaacatgtga gcaaaaggcc agcaaaaggc    2700
caggaaccgt aaaaaggccg cgttgctggc gtttttccat aggctccgcc cccctgacga    2760
gcatcacaaa aatcgacgct caagtcagag gtggcgaaac ccgacaggac tataaagata    2820
ccaggcgttt ccccctggaa gctccctcgt gcgctctcct gttccgaccc tgccgcttac    2880
cggatacctg tccgcctttc tcccttcggg aagcgtggcg ctttctcaat gctcacgctg    2940
taggtatctc agttcggtgt aggtcgttcg ctccaagctg ggctgtgtgc acgaaccccc    3000
cgttcagccc gaccgctgcg ccttatccgg taactatcgt cttgagtcca acccggtaag    3060
acacgactta tcgccactgg cagcagccac tggtaacagg attagcagag cgaggtatgt    3120
aggcggtgct acagagttct tgaagtggtg gcctaactac ggctacacta aaggacagt    3180 atttggtatc tgcgctctgc tgaagccagt taccttcgga aaaagagttg gtagctcttg    3240
atccggcaaa caaccaccg ctggtagcgg tggttttttt gtttgcaagc agcagattac    3300
gcgcagaaaa aaaggatctc aagaagatcc tttgatcttt tctacggggt ctgacgctca    3360
gtggaacgaa aactcacgtt aagggatttt ggtcatgaga ttatcaaaaa ggatcttcac    3420
ctagatcctt ttaaattaaa aatgaagttt taaatcaatc taaagtatat atgagtaaac    3480
ttggtctgac agttaccaat gcttaatcag tgaggcacct atctcagcga tctgtctatt    3540
tcgttcatcc atagttgcct gactccccgt cgtgtagata actacgatac gggagggctt    3600
accatctggc cccagtgctg caatgatacc gcgagaccca cgctcaccgg ctccagattt    3660
atcagcaata aaccagccag ccggaagggc cgagcgcaga agtggtcctg caactttatc    3720
cgcctccatc cagtctatta attgttgccg ggaagctaga gtaagtagtt cgccagttaa    3780
tagtttgcgc aacgttgttg ccattgctac aggcatcgtg gtgtcacgct cgtcgtttgg    3840
tatggcttca ttcagctccg gttcccaacg atcaaggcga gttacatgat cccccatgtt    3900
gtgcaaaaaa gcggttagct ccttcggtcc tccgatcgtt gtcagaagta agttggccgc    3960
agtgttatca ctcatggtta tggcagcact gcataattct cttactgtca tgccatccgt    4020
aagatgcttt tctgtgactg gtgagtactc aaccaagtca ttctgagaat agtgtatgcg    4080
gcgaccgagt tgctcttgcc cggcgtcaat acgggataat accgcgccac atagcagaac    4140
tttaaaagtg ctcatcattg gaaaacgttc ttcgggggcga aaactctcaa ggatcttacc    4200
gctgttgaga tccagttcga tgtaacccac tcgtgcaccc aactgatctt cagcatcttt    4260
tactttcacc agcgtttctg ggtgagcaaa aacaggaagg caaaatgccg caaaaagggg    4320
aataagggcg acacggaaat gttgaatact catactcttc cttttcaat attattgaag    4380 catttatcag ggttattgtc tcatgagcgg atacatattt gaatgtattt agaaaaataa    4440
```

-continued

| | |
|---|---|
| acaaataggg gttccgcgca catttccccg aaaagtgcca cctgacgtct aagaaaccat | 4500 |
| tattatcatg acattaacct ataaaaatag gcgtatcacg aggcccttc gtc | 4553 |

<210> SEQ ID NO 27
<211> LENGTH: 4560
<212> TYPE: DNA
<213> ORGANISM: Artificial Sequence
<220> FEATURE:
<223> OTHER INFORMATION: Synthetic nucleotide sequence: pSAT2-EGFP-C1

<400> SEQUENCE: 27

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgccgc taccttaaga gagaccggtc | 420 |
| aacatgtgga gcacgacaca cttgtctact ccaaaaatat caaagataca gtctcagaag | 480 |
| accaaagggc aattgagact tttcaacaaa gggtaatatc cggaaacctc ctcggattcc | 540 |
| attgcccagc tatctgtcac tttattgtga agatagtgga aaaggaaggt ggctcctaca | 600 |
| aatgccatca ttgcgataaa ggaaaggcca tcgttgaaga tgcctctgcc gacagtggtc | 660 |
| ccaaagatgg acccccaccc acgaggagca tcgtggaaaa agaagacgtt ccaaccacgt | 720 |
| cttcaaagca agtggattga tgtgataaca tggtggagca cgacacactt gtctactcca | 780 |
| aaaatatcaa agatacagtc tcagaagacc aaagggcaat tgagactttt caacaaaggg | 840 |
| taatatccgg aaacctcctc ggattccatt gcccagctat ctgtcacttt attgtgaaga | 900 |
| tagtggaaaa ggaaggtggc tcctacaaat gccatcattg cgataaagga aaggccatcg | 960 |
| ttgaagatgc ctctgccgac agtggtccca agatggaccc ccacccacg aggagcatcg | 1020 |
| tggaaaaaga agacgttcca accacgtctt caaagcaagt ggattgatgt gatatctcca | 1080 |
| ctgacgtaag ggatgacgca caatcccact atccttcgca agacccttcc tctatataag | 1140 |
| gaagttcatt tcatttggag aggacgtcga gagttctcaa cacaacatat acaaaacaaa | 1200 |
| cgaatctcaa gcaatcaagc attctacttc tattgcagca atttaaatca tttcttttaa | 1260 |
| agcaaaagca atttttctgaa aattttcacc atttacgaac gatagccatg gtgagcaagg | 1320 |
| gcgaggagct gttcaccggg gtggtgccca tcctggtcga gctggacggc gacgtaaacg | 1380 |
| gccacaagtt cagcgtgtcc ggcgagggcg agggcgatgc cacctacggc aagctgaccc | 1440 |
| tgaagttcat ctgcaccacc ggcaagctgc ccgtgccctg gccccacctc gtgaccaccc | 1500 |
| tgacctacgg cgtgcagtgc ttcagccgct accccgacca catgaagcag cacgacttct | 1560 |
| tcaagtccgc catgcccgaa ggctacgtcc aggagcgcac catcttcttc aaggacgacg | 1620 |
| gcaactacaa gacccgcgcc gaggtgaagt tcgagggcga caccctggtg aaccgcatcg | 1680 |
| agctgaaggg catcgacttc aaggaggacg gcaacatcct ggggcacaag ctggagtaca | 1740 |
| actacaacag ccacaacgtc tatatcatgg ccgacaagca gaagaacggc atcaaggtga | 1800 |
| acttcaagat ccgccacaac atcgaggacg gcagcgtgca gctcgccgac cactaccagc | 1860 |
| agaacacccc catcggcgac ggccccgtgc tgctgcccga caaccactac ctgagcaccc | 1920 |
| agtccgccct gagcaaagac cccaacgaga agcgcgatca catggtcctg ctggagttcg | 1980 |

```
tgaccgccgc cgggatcact ctcggcatgg acgagctgta caagtccgga ctcagatctc   2040
gagctcaagc ttcgaattct gcagtcgacg gtaccgcggg cccgggatcc acctagtcta   2100
gagtccgcaa aaatcaccag tctctctcta caaatctatc tctctctatt tttctccaga   2160
ataatgtgtg agtagttccc agataaggga attagggttc ttatagggtt tcgctcatgt   2220
gttgagcata taagaaaccc ttagtatgta tttgtatttg taaaatactt ctatcaataa   2280
aatttctaat tcctaaaacc aaaatccagt gacgcggccg cggcgcgccg taatcatggt   2340
catagctgtt tcctgtgtga aattgttatc cgctcacaat tccacacaac atacgagccg   2400
gaagcataaa gtgtaaagcc tggggtgcct aatgagtgag ctaactcaca ttaattgcgt   2460
tgcgctcact gcccgctttc cagtcgggaa acctgtcgtg ccagctgcat taatgaatcg   2520
gccaacgcgc ggggagaggc ggtttgcgta ttgggcgctc ttccgcttcc tcgctcactg   2580
actcgctgcg ctcggtcgtt cggctgcggc gagcggtatc agctcactca aaggcggtaa   2640
tacggttatc cacagaatca ggggataacg caggaaagaa catgtgagca aaaggccagc   2700
aaaaggccag gaaccgtaaa aaggccgcgt tgctggcgtt tttccatagg ctccgccccc   2760
ctgacgagca tcacaaaaat cgacgctcaa gtcagaggtg gcgaaacccg acaggactat   2820
aaagatacca ggcgtttccc cctggaagct ccctcgtgcg ctctcctgtt ccgaccctgc   2880
cgcttaccgg atacctgtcc gcctttctcc cttcgggaag cgtggcgctt tctcaatgct   2940
cacgctgtag gtatctcagt tcggtgtagg tcgttcgctc caagctgggc tgtgtgcacg   3000
aaccccccgt tcagcccgac cgctgcgcct tatccggtaa ctatcgtctt gagtccaacc   3060
cggtaagaca cgacttatcg ccactggcag cagccactgg taacaggatt agcagagcga   3120
ggtatgtagg cggtgctaca gagttcttga agtggtggcc taactacggc tacactagaa   3180
ggacagtatt tggtatctgc gctctgctga agccagttac cttcggaaaa agagttggta   3240
gctcttgatc cggcaaacaa accaccgctg gtagcggtgg ttttttttgtt tgcaagcagc   3300 agattacgcg cagaaaaaaa ggatctcaag aagatccttt gatcttttct acggggtctg   3360
acgctcagtg gaacgaaaac tcacgttaag ggattttggt catgagatta tcaaaaagga   3420
tcttcaccta gatccttttta aattaaaaat gaagttttaa atcaatctaa agtatatatg   3480
agtaaacttg gtctgacagt taccaatgct taatcagtga ggcacctatc tcagcgatct   3540
gtctatttcg ttcatccata gttgcctgac tccccgtcgt gtagataact acgatacggg   3600
agggcttacc atctggcccc agtgctgcaa tgataccgcg agacccacgc tcaccggctc   3660
cagatttatc agcaataaac cagccagccg aagggccga gcgcagaagt ggtcctgcaa   3720
ctttatccgc ctccatccag tctattaatt gttgccggga agctagagta agtagttcgc   3780
cagttaatag tttgcgcaac gttgttgcca ttgctacagg catcgtggtg tcacgctcgt   3840
cgtttggtat ggcttcattc agctccggtt cccaacgatc aaggcgagtt acatgatccc   3900
ccatgttgtg caaaaaagcg gttagctcct tcggtcctcc gatcgttgtc agaagtaagt   3960
tggccgcagt gttatcactc atggttatgg cagcactgca taattctctt actgtcatgc   4020
catccgtaag atgcttttct gtgactggtg agtactcaac caagtcattc tgagaatagt   4080
gtatgcggcg accgagttgc tcttgcccgg cgtcaatacg ggataatacc gcgccacata   4140
gcagaacttt aaaagtgctc atcattggaa aacgttcttc ggggcgaaaa ctctcaagga   4200
tcttaccgct gttgagatcc agttcgatgt aacccactcg tgcacccaac tgatcttcag   4260
catcttttac tttcaccagc gtttctgggt gagcaaaaac aggaaggcaa aatgccgcaa   4320
```

```
aaaagggaat aagggcgaca cggaaatgtt gaatactcat actcttcctt tttcaatatt    4380
attgaagcat ttatcagggt tattgtctca tgagcggata catatttgaa tgtatttaga    4440
aaaataaaca aatagggtt ccgcgcacat ttccccgaaa agtgccacct gacgtctaag    4500
aaaccattat tatcatgaca ttaacctata aaaataggcg tatcacgagg ccctttcgtc    4560
```

<210> SEQ ID NO 28
<211> LENGTH: 4567
<212> TYPE: DNA
<213> ORGANISM: Artificial Sequence
<220> FEATURE:
<223> OTHER INFORMATION: Synthetic nucleotide sequence: pSAT3-EGFP-C1

<400> SEQUENCE: 28

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgccgc taccttaaga gagaccggtc     420
aacatgtgga gcacgacaca cttgtctact ccaaaaatat caaagataca gtctcagaag     480
accaaagggc aattgagact tttcaacaaa gggtaatatc cggaaacctc ctcggattcc     540
attgcccagc tatctgtcac tttattgtga agatagtgga aaaggaaggt ggctcctaca     600
aatgccatca ttgcgataaa ggaaaggcca tcgttgaaga tgcctctgcc gacagtggtc     660
ccaaagatgg acccccaccc acgaggagca tcgtggaaaa agaagacgtt ccaaccacgt     720
cttcaaagca agtggattga tgtgataaca tggtggagca cgacacactt gtctactcca     780
aaaatatcaa agatacagtc tcagaagacc aaagggcaat tgagactttt caacaaaggg     840
taatatccgg aaacctcctc ggattccatt gcccagctat ctgtcacttt attgtgaaga     900
tagtggaaaa ggaaggtggc tcctacaaat gccatcattg cgataaagga aaggccatcg     960
ttgaagatgc ctctgccgac agtggtccca agatggaccc ccacccacg aggagcatcg    1020 tggaaaaaga agacgttcca accacgtctt caaagcaagt ggattgatgt gatatctcca    1080
ctgacgtaag ggatgacgca caatcccact atccttcgca agacccttcc tctatataag    1140
gaagttcatt tcatttggag aggacgtcga gagttctcaa cacaacatat acaaaacaaa    1200
cgaatctcaa gcaatcaagc attctacttc tattgcagca atttaaatca tttcttttaa    1260
agcaaaagca atttttctgaa aatttttcacc atttacgaac gatagccatg gtgagcaagg    1320
gcgaggagct gttcaccggg gtggtgccca tcctggtcga gctggacggc gacgtaaacg    1380
gccacaagtt cagcgtgtcc ggcgagggcg agggcgatgc cacctacggc aagctgaccc    1440
tgaagttcat ctgcaccacc ggcaagctgc ccgtgccctg gcccaccctc gtgaccaccc    1500
tgacctacgg cgtgcagtgc ttcagccgct accccgacca catgaagcag cacgacttct    1560
tcaagtccgc catgcccgaa ggctacgtcc aggagcgcac catcttcttc aaggacgacg    1620
gcaactacaa gacccgcgcc gaggtgaagt tcgagggcga caccctggtg aaccgcatcg    1680
agctgaaggg catcgacttc aaggaggacg gcaacatcct ggggcacaag ctggagtaca    1740
actacaacag ccacaacgtc tatatcatgg ccgacaagca gaagaacggc atcaaggtga    1800
acttcaagat ccgccacaac atcgaggacg gcagcgtgca gctcgccgac cactaccagc    1860
```

```
agaacacccc catcggcgac ggccccgtgc tgctgcccga caaccactac ctgagcaccc    1920
agtccgccct gagcaaagac cccaacgaga agcgcgatca catggtcctg ctggagttcg    1980
tgaccgccgc cgggatcact ctcggcatgg acgagctgta caagtccgga ctcagatctc    2040
gagctcaagc ttcgaattct gcagtcgacg gtaccgcggg cccgggatcc acctagtcta    2100
gagtccgcaa aaatcaccag tctctctcta caaatctatc tctctctatt tttctccaga    2160
ataatgtgtg agtagttccc agataaggga attagggttc ttatagggtt tcgctcatgt    2220
gttgagcata taagaaaccc ttagtatgta tttgtatttg taaaatactt ctatcaataa    2280
aatttctaat tcctaaaacc aaaatccagt gacgcggccg cgctacctta agagaggtaa    2340
tcatggtcat agctgtttcc tgtgtgaaat tgttatccgc tcacaattcc acacaacata    2400
cgagccggaa gcataaagtg taaagcctgg ggtgcctaat gagtgagcta actcacatta    2460
attgcgttgc gctcactgcc cgctttccag tcgggaaacc tgtcgtgcca gctgcattaa    2520
tgaatcggcc aacgcgcggg gagaggcggt ttgcgtattg ggcgctcttc cgcttcctcg    2580
ctcactgact cgctgcgctc ggtcgttcgg ctgcggcgag cggtatcagc tcactcaaag    2640
gcggtaatac ggttatccac agaatcaggg gataacgcag gaaagaacat gtgagcaaaa    2700
ggccagcaaa aggccaggaa ccgtaaaaag gccgcgttgc tggcgttttt ccataggctc    2760
cgcccccctg acgagcatca caaaaatcga cgctcaagtc agaggtggcg aaacccgaca    2820
ggactataaa gataccaggc gtttccccct ggaagctccc tcgtgcgctc tcctgttccg    2880
accctgccgc ttaccggata cctgtccgcc tttctccctt cgggaagcgt ggcgctttct    2940
caatgctcac gctgtaggta tctcagttcg gtgtaggtcg ttcgctccaa gctgggctgt    3000
gtgcacgaac cccccgttca gcccgaccgc tgcgccttat ccggtaacta tcgtcttgag    3060
tccaacccgg taagacacga cttatcgcca ctggcagcag ccactggtaa caggattagc    3120
agagcgaggt atgtaggcgg tgctacagag ttcttgaagt ggtggcctaa ctacggctac    3180
actagaagga cagtatttgg tatctgcgct ctgctgaagc cagttacctt cggaaaaaga    3240
gttggtagct cttgatccgg caaacaaacc accgctggta gcggtggttt ttttgtttgc    3300
aagcagcaga ttacgcgcag aaaaaaagga tctcaagaag atcctttgat cttttctacg    3360
gggtctgacg ctcagtggaa cgaaaactca cgttaaggga ttttggtcat gagattatca    3420
aaaaggatct tcacctagat ccttttaaat taaaaatgaa gttttaaatc aatctaaagt    3480
atatatgagt aaacttggtc tgacagttac caatgcttaa tcagtgaggc acctatctca    3540
gcgatctgtc tatttcgttc atccatagtt gcctgactcc ccgtcgtgta gataactacg    3600
atacgggagg gcttaccatc tggccccagt gctgcaatga taccgcgaga cccacgctca    3660
ccggctccag atttatcagc aataaaccag ccagccggaa gggccgagcg cagaagtggt    3720
cctgcaactt tatccgcctc catccagtct attaattgtt gccgggaagc tagagtaagt    3780
agttcgccag ttaatagttt cgcaacgtt gttgccattg ctacaggcat cgtggtgtca    3840
cgctcgtcgt ttggtatggc ttcattcagc tccggttccc aacgatcaag gcgagttaca    3900
tgatccccca tgttgtgcaa aaaagcggtt agctccttcg gtcctccgat cgttgtcaga    3960
agtaagttgg ccgcagtgtt atcactcatg gttatgcag cactgcataa ttctcttact    4020
gtcatgccat ccgtaagatg cttttctgtg actggtgagt actcaaccaa gtcattctga    4080
gaatagtgta tgcggcgacc gagttgctct tgcccggcgt caatacggga taataccgcg    4140
ccacatagca gaactttaaa agtgctcatc attggaaaac gttcttcggg gcgaaaactc    4200
```

```
tcaaggatct taccgctgtt gagatccagt tcgatgtaac ccactcgtgc acccaactga    4260
tcttcagcat cttttacttt caccagcgtt tctgggtgag caaaaacagg aaggcaaaat    4320
gccgcaaaaa agggaataag ggcgacacgg aaatgttgaa tactcatact cttccttttt    4380
caatattatt gaagcattta tcagggttat tgtctcatga gcggatacat atttgaatgt    4440
atttagaaaa ataaacaaat aggggttccg cgcacatttc cccgaaaagt gccacctgac    4500
gtctaagaaa ccattattat catgacatta acctataaaa ataggcgtat cacgaggccc    4560
tttcgtc                                                              4567

<210> SEQ ID NO 29
<211> LENGTH: 4573
<212> TYPE: DNA
<213> ORGANISM: Artificial Sequence
<220> FEATURE:
<223> OTHER INFORMATION: Synthetic nucleotide sequence: pSAT4-EGFP-C1

<400> SEQUENCE: 29
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgccat taccctgtta tccctaaccg     420
gtcaacatgt ggagcacgac acacttgtct actccaaaaa tatcaaagat acagtctcag     480
aagaccaaag ggcaattgag acttttcaac aaagggtaat atccggaaac ctcctcggat     540
tccattgccc agctatctgt cactttattg tgaagatagt ggaaaggaa ggtggctcct     600 acaaatgcca tcattgcgat aaaggaaagg ccatcgttga agatgcctct gccgacagtg     660
gtcccaaaga tggaccccca cccacgagga gcatcgtgga aaaagaagac gttccaacca     720
cgtcttcaaa gcaagtggat tgatgtgata acatggtgga gcacgacaca cttgtctact     780
ccaaaaatat caaagataca gtctcagaag accaaagggc aattgagact tttcaacaaa     840
gggtaatatc cggaaacctc ctcggattcc attgcccagc tatctgtcac tttattgtga     900
agatagtgga aaggaaggt ggctcctaca atgccatca ttgcgataaa ggaaaggcca     960
tcgttgaaga tgcctctgcc gacagtggtc ccaaagatgg acccccaccc acgaggagca    1020
tcgtggaaaa agaagacgtt ccaaccacgt cttcaaagca agtggattga tgtgatatct    1080
ccactgacgt aagggatgac gcacaatccc actatccttc gcaagaccct tcctctatat    1140
aaggaagttc atttcatttg gagaggacgt cgagagttct caacacaaca tatacaaaac    1200
aaacgaatct caagcaatca agcattctac ttctattgca gcaatttaaa tcatttcttt    1260
taaagcaaaa gcaattttct gaaaattttc accatttacg aacgatagcc atggtgagca    1320
agggcgagga gctgttcacc ggggtggtgc ccatcctggt cgagctggac ggcgacgtaa    1380
acggccacaa gttcagcgtg tccggcgagg gcgaggcga tgccacctac ggcaagctga    1440
ccctgaagtt catctgcacc accggcaagc tgcccgtgcc ctggcccacc ctcgtgacca    1500
ccctgaccta cggcgtgcag tgcttcagcc gctaccccga ccacatgaag cagcacgact    1560
tcttcaagtc cgccatgccc gaaggctacg tccaggagcg caccatcttc ttcaaggacg    1620
acggcaacta caagacccgc gccgaggtga agttcgaggg cgacaccctg gtgaaccgca    1680
```

-continued

```
tcgagctgaa gggcatcgac ttcaaggagg acggcaacat cctggggcac aagctggagt    1740
acaactacaa cagccacaac gtctatatca tggccgacaa gcagaagaac ggcatcaagg    1800
tgaacttcaa gatccgccac aacatcgagg acggcagcgt gcagctcgcc gaccactacc    1860
agcagaacac ccccatcggc gacggccccg tgctgctgcc cgacaaccac tacctgagca    1920
cccagtccgc cctgagcaaa gaccccaacg agaagcgcga tcacatggtc ctgctggagt    1980
tcgtgaccgc cgccgggatc actctcggca tggacgagct gtacaagtcc ggactcagat    2040
ctcgagctca agcttcgaat tctgcagtcg acggtaccgc gggcccggga tccacctagt    2100
ctagagtccg caaaaatcac cagtctctct ctacaaatct atctctctct attttctcc     2160
agaataatgt gtgagtagtt cccagataag ggaattaggg ttcttatagg gtttcgctca    2220
tgtgttgagc atataagaaa cccttagtat gtatttgtat ttgtaaaata cttctatcaa    2280
taaaatttct aattcctaaa accaaaatcc agtgacgcgg ccgcattacc ctgttatccc    2340
tagtaatcat ggtcatagct gtttcctgtg tgaaattgtt atccgctcac aattccacac    2400
aacatacgag ccggaagcat aaagtgtaaa gcctggggtg cctaatgagt gagctaactc    2460
acattaattg cgttgcgctc actgcccgct ttccagtcgg gaaacctgtc gtgccagctg    2520
cattaatgaa tcggccaacg cgcggggaga ggcggtttgc gtattgggcg ctcttccgct    2580
tcctcgctca ctgactcgct gcgctcggtc gttcggctgc ggcgagcggt atcagctcac    2640
tcaaaggcgg taatacggtt atccacagaa tcaggggata acgcaggaaa gaacatgtga    2700
gcaaaaggcc agcaaaaggc caggaaccgt aaaaaggccg cgttgctggc gtttttccat    2760
aggctccgcc cccctgacga gcatcacaaa aatcgacgct caagtcagag gtggcgaaac    2820
ccgacaggac tataaagata ccaggcgttt ccccctggaa gctccctcgt gcgctctcct    2880
gttccgaccc tgccgcttac cggatacctg tccgcctttc tcccttcggg aagcgtggcg    2940
ctttctcaat gctcacgctg taggtatctc agttcggtgt aggtcgttcg ctccaagctg    3000
ggctgtgtgc acgaaccccc cgttcagccc gaccgctgcg ccttatccgg taactatcgt    3060
cttgagtcca acccggtaag acacgactta tcgccactgg cagcagccac tggtaacagg    3120
attagcagag cgaggtatgt aggcggtgct acagagttct tgaagtggtg gcctaactac    3180
ggctacacta aaggacagt atttggtatc tgcgctctgc tgaagccagt taccttcgga    3240
aaaagagttg gtagctcttg atccggcaaa caaaccaccg ctggtagcgg tggtttttt     3300
gtttgcaagc agcagattac gcgcagaaaa aaaggatctc aagaagatcc tttgatcttt    3360
tctacggggt ctgacgctca gtggaacgaa aactcacgtt aagggatttt ggtcatgaga    3420
ttatcaaaaa ggatcttcac ctagatcctt ttaaattaaa aatgaagttt taaatcaatc    3480
taaagtatat atgagtaaac ttggtctgac agttaccaat gcttaatcag tgaggcacct    3540
atctcagcga tctgtctatt tcgttcatcc atagttgcct gactccccgt cgtgtagata    3600
actacgatac gggagggctt accatctggc cccagtgctg caatgatacc gcgagaccca    3660
cgctcaccgg ctccagattt atcagcaata aaccagccag ccggaagggc cgagcgcaga    3720
agtggtcctg caactttatc cgcctccatc cagtctatta attgttgccg ggaagctaga    3780
gtaagtagtt cgccagttaa tagtttgcgc aacgttgttg ccattgctac aggcatcgtg    3840
gtgtcacgct cgtcgtttgg tatggcttca ttcagctccg gttcccaacg atcaaggcga    3900
gttacatgat cccccatgtt gtgcaaaaaa gcggttagct ccttcggtcc tccgatcgtt    3960
gtcagaagta agttggccgc agtgttatca ctcatggtta tggcagcact gcataattct    4020
```

| | |
|---|---|
| cttactgtca tgccatccgt aagatgcttt tctgtgactg gtgagtactc aaccaagtca | 4080 |
| ttctgagaat agtgtatgcg gcgaccgagt tgctcttgcc cggcgtcaat acgggataat | 4140 |
| accgcgccac atagcagaac tttaaaagtg ctcatcattg gaaaacgttc ttcggggcga | 4200 |
| aaactctcaa ggatcttacc gctgttgaga tccagttcga tgtaacccac tcgtgcaccc | 4260 |
| aactgatctt cagcatcttt tactttcacc agcgtttctg ggtgagcaaa aacaggaagg | 4320 |
| caaaatgccg caaaaaaggg aataagggcg acacggaaat gttgaatact catactcttc | 4380 |
| ctttttcaat attattgaag catttatcag ggttattgtc tcatgagcgg atacatattt | 4440 |
| gaatgtattt agaaaaataa acaaataggg gttccgcgca catttccccg aaaagtgcca | 4500 |
| cctgacgtct aagaaaccat tattatcatg acattaacct ataaaaatag gcgtatcacg | 4560 |
| aggccctttc gtc | 4573 |

<210> SEQ ID NO 30
<211> LENGTH: 4589
<212> TYPE: DNA
<213> ORGANISM: Artificial Sequence
<220> FEATURE:
<223> OTHER INFORMATION: Synthetic nucleotide sequence: pSAT5-EGFP-C1

<400> SEQUENCE: 30

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctggc ttaactatgc ggcatcagag cagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgcctc gctaccttag gaccgttata | 420 |
| gttaaccggt caacatgtgg agcacgcac acttgtctac tccaaaaata tcaaagatac | 480 |
| agtctcagaa gaccaaaggg caattgagac ttttcaacaa agggtaatat ccggaaacct | 540 |
| cctcggattc cattgcccag ctatctgtca ctttattgtg aagatagtgg aaaaggaagg | 600 |
| tggctcctac aaatgccatc attgcgataa aggaaaggcc atcgttgaag atgcctctgc | 660 |
| cgacagtggt cccaaagatg gacccccacc cacgaggagc atcgtggaaa agaagacgt | 720 |
| tccaaccacg tcttcaaagc aagtggattg atgtgataac atggtggagc acgacacact | 780 |
| tgtctactcc aaaaatatca agatacagt ctcagaagac caagggcaa ttgagacttt | 840 |
| tcaacaaagg gtaatatccg gaaacctcct cggattccat tgcccagcta tctgtcactt | 900 |
| tattgtgaag atagtggaaa aggaaggtgg ctcctacaaa tgccatcatt gcgataaagg | 960 |
| aaaggccatc gttgaagatg cctctgccga cagtggtccc aaagatggac ccccacccac | 1020 |
| gaggagcatc gtggaaaaag aagacgttcc aaccacgtct tcaaagcaag tggattgatg | 1080 |
| tgatatctcc actgacgtaa gggatgacgc acaatcccac tatccttcgc aagacccttc | 1140 |
| ctctatataa ggaagttcat ttcatttgga gaggacgtcg agagttctca acacaacata | 1200 |
| tacaaaacaa acgaatctca agcaatcaag cattctactt ctattgcagc aatttaaatc | 1260 |
| atttctttta aagcaaaagc aattttctga aaatttttcac catttacgaa cgatagccat | 1320 |
| ggtgagcaag ggcgaggagc tgttcaccgg ggtggtgccc atcctggtcg agctggacgg | 1380 |
| cgacgtaaac ggccacaagt tcagcgtgtc cggcgagggc gagggcgatg ccacctacgg | 1440 |
| caagctgacc ctgaagttca tctgcaccac cggcaagctg cccgtgccct ggcccaccct | 1500 |

```
cgtgaccacc ctgacctacg gcgtgcagtg cttcagccgc tacccgacc acatgaagca    1560 gcacgacttc ttcaagtccg ccatgcccga aggctacgtc caggagcgca ccatcttctt    1620
caaggacgac ggcaactaca agacccgcgc cgaggtgaag ttcgagggcg acaccctggt    1680
gaaccgcatc gagctgaagg gcatcgactt caaggaggac ggcaacatcc tggggcacaa    1740
gctggagtac aactacaaca gccacaacgt ctatatcatg gccgacaagc agaagaacgg    1800
catcaaggtg aacttcaaga tccgccacaa catcgaggac ggcagcgtgc agctcgccga    1860
ccactaccag cagaacaccc ccatcggcga cggccccgtg ctgctgcccg acaaccacta    1920
cctgagcacc cagtccgccc tgagcaaaga ccccaacgag aagcgcgatc acatggtcct    1980
gctggagttc gtgaccgccg ccgggatcac tctcggcatg gacgagctgt acaagtccgg    2040
actcagatct cgagctcaag cttcgaattc tgcagtcgac ggtaccgcgg gcccgggatc    2100
cacctagtct agagtccgca aaaatcacca gtctctctct acaaatctat ctctctctat    2160
ttttctccag aataatgtgt gagtagttcc cagataaggg aattagggtt cttatagggt    2220
ttcgctcatg tgttgagcat ataagaaacc cttagtatgt atttgtattt gtaaaatact    2280
tctatcaata aaatttctaa ttcctaaaac caaaatccag tgacgcggcc gctcgctacc    2340
ttaggaccgt tatagttagt aatcatggtc atagctgttt cctgtgtgaa attgttatcc    2400
gctcacaatt ccacacaaca tacgagccgg aagcataaag tgtaaagcct ggggtgccta    2460
atgagtgagc taactcacat taattgcgtt gcgctcactg cccgctttcc agtcgggaaa    2520
cctgtcgtgc cagctgcatt aatgaatcgg ccaacgcgcg gggagaggcg gtttgcgtat    2580
tgggcgctct tccgcttcct cgctcactga ctcgctgcgc tcggtcgttc ggctgcggcg    2640
agcggtatca gctcactcaa aggcggtaat acggttatcc acagaatcag gggataacgc    2700
aggaaagaac atgtgagcaa aaggccagca aaaggccagg aaccgtaaaa aggccgcgtt    2760
gctggcgttt ttccataggc tccgcccccc tgacgagcat cacaaaaatc gacgctcaag    2820
tcagaggtgg cgaaacccga caggactata aagataccag gcgtttcccc ctggaagctc    2880
cctcgtgcgc tctcctgttc cgaccctgcc gcttaccgga tacctgtccg cctttctccc    2940
ttcgggaagc gtggcgcttt ctcaatgctc acgctgtagg tatctcagtt cggtgtaggt    3000
cgttcgctcc aagctgggct gtgtgcacga accccccgtt cagcccgacc gctgcgcctt    3060
atccggtaac tatcgtcttg agtccaaccc ggtaagacac gacttatcgc cactggcagc    3120
agccactggt aacaggatta gcagagcgag gtatgtaggc ggtgctacag agttcttgaa    3180
gtggtggcct aactacggct acactagaag gacagtattt ggtatctgcg ctctgctgaa    3240
gccagttacc ttcggaaaaa gagttggtag ctcttgatcc ggcaaacaaa ccaccgctgg    3300
tagcggtggt ttttttgttt gcaagcagca gattacgcgc agaaaaaaag gatctcaaga    3360
agatcctttg atcttttcta cggggtctga cgctcagtgg aacgaaaact cacgttaagg    3420
gattttggtc atgagattat caaaaaggat cttcacctag atccttttaa attaaaaatg    3480
aagttttaaa tcaatctaaa gtatatatga gtaaacttgg tctgacagtt accaatgctt    3540
aatcagtgag gcacctatct cagcgatctg tctatttcgt tcatccatag ttgcctgact    3600
ccccgtcgtg tagataacta cgatacggga gggcttacca tctggcccca gtgctgcaat    3660
gataccgcga gacccacgct caccggctcc agatttatca gcaataaacc agccagccgg    3720
aagggccgag cgcagaagtg gtcctgcaac tttatccgcc tccatccagt ctattaattg    3780
ttgccgggaa gctagagtaa gtagttcgcc agttaatagt ttgcgcaacg ttgttgccat    3840
```

| | |
|---|---|
| tgctacaggc atcgtggtgt cacgctcgtc gtttggtatg gcttcattca gctccggttc | 3900 |
| ccaacgatca aggcgagtta catgatcccc catgttgtgc aaaaaagcgg ttagctcctt | 3960 |
| cggtcctccg atcgttgtca gaagtaagtt ggccgcagtg ttatcactca tggttatggc | 4020 |
| agcactgcat aattctctta ctgtcatgcc atccgtaaga tgcttttctg tgactggtga | 4080 |
| gtactcaacc aagtcattct gagaatagtg tatgcggcga ccgagttgct cttgcccggc | 4140 |
| gtcaatacgg gataataccg cgccacatag cagaacttta aaagtgctca tcattggaaa | 4200 |
| acgttcttcg gggcgaaaac tctcaaggat cttaccgctg ttgagatcca gttcgatgta | 4260 |
| acccactcgt gcacccaact gatcttcagc atcttttact ttcaccagcg tttctgggtg | 4320 |
| agcaaaaaca ggaaggcaaa atgccgcaaa aaagggaata agggcgacac ggaaatgttg | 4380 |
| aatactcata ctcttccttt ttcaatatta ttgaagcatt tatcagggtt attgtctcat | 4440 |
| gagcggatac atatttgaat gtatttagaa aaataaacaa ataggggttc cgcgcacatt | 4500 |
| tccccgaaaa gtgccacctg acgtctaaga accattatt atcatgacat aacctataa | 4560 |
| aaataggcgt atcacgaggc cctttcgtc | 4589 |

<210> SEQ ID NO 31
<211> LENGTH: 4597
<212> TYPE: DNA
<213> ORGANISM: Artificial Sequence
<220> FEATURE:
<223> OTHER INFORMATION: Synthetic nucleotide sequence: pSAT6-EGFP-C1

<400> SEQUENCE: 31

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgccac cataataccc ataatagct | 420 |
| gtttgccaac cggtcaacat gtggagcacg acacacttgt ctactccaaa aatatcaaag | 480 |
| atacagtctc agaagaccaa agggcaattg agacttttca acaaagggta atatccggaa | 540 |
| acctcctcgg attccattgc ccagctatct gtcactttat tgtgaagata gtggaaaagg | 600 |
| aaggtggctc ctacaaatgc catcattgcg ataaaggaaa ggccatcgtt gaagatgcct | 660 |
| ctgccgacag tggtcccaaa gatggacccc cacccacgag gagcatcgtg gaaaagaag | 720 |
| acgttccaac cacgtcttca agcaagtgg attgatgtga acatggtg gagcacgaca | 780 |
| cacttgtcta ctccaaaaat atcaaagata cagtctcaga agaccaaagg caattgaga | 840 |
| cttttcaaca aagggtaata tccggaaacc tcctcggatt ccattgccca gctatctgtc | 900 |
| actttattgt gaagatagtg gaaaggaag gtggctccta caaatgccat cattgcgata | 960 |
| aaggaaaggc catcgttgaa gatgcctctg ccgacagtgg tcccaaagat ggaccccac | 1020 |
| ccacgaggag catcgtggaa aaagaagacg ttccaaccac gtcttcaaag caagtggatt | 1080 |
| gatgtgatat ctccactgac gtaagggatg acgcacaatc ccactatcct cgcaagacc | 1140 |
| cttcctctat ataaggaagt tcatttcatt tggagaggac gtcgagagtt ctcaacacaa | 1200 |
| catatacaaa acaaacgaat ctcaagcaat caagcattct acttctattg cagcaattta | 1260 |
| aatcatttct tttaaagcaa aagcaatttt ctgaaaattt tcaccattta cgaacgatag | 1320 |

```
ccatggtgag caagggcgag gagctgttca ccggggtggt gcccatcctg gtcgagctgg   1380
acggcgacgt aaacggccac aagttcagcg tgtccggcga gggcgagggc gatgccacct   1440
acggcaagct gaccctgaag ttcatctgca ccaccggcaa gctgcccgtg ccctggccca   1500
cccctcgtgac caccctgacc tacggcgtgc agtgcttcag ccgctacccc gaccacatga   1560
agcagcacga cttcttcaag tccgccatgc ccgaaggcta cgtccaggag cgcaccatct   1620
tcttcaagga cgacggcaac tacaagaccc gcgccgaggt gaagttcgag ggcgacaccc   1680
tggtgaaccg catcgagctg aagggcatcg acttcaagga ggacggcaac atcctggggc   1740
acaagctgga gtacaactac aacagccaca acgtctatat catggccgac aagcagaaga   1800
acggcatcaa ggtgaacttc aagatccgcc acaacatcga ggacggcagc gtgcagctcg   1860
ccgaccacta ccagcagaac acccccatcg gcgacggccc cgtgctgctg cccgacaacc   1920
actacctgag cacccagtcc gccctgagca agacccccaa cgagaagcgc gatcacatgg   1980
tcctgctgga gttcgtgacc gccgccggga tcactctcgg catggacgag ctgtacaagt   2040
ccggactcag atctcgagct caagcttcga attctgcagt cgacggtacc gcgggcccgg   2100
gatccaccta gtctagagtc cgcaaaaatc accagtctct ctctacaaat ctatctctct   2160
ctatttttct ccagaataat gtgtgagtag ttcccagata agggaattag ggttcttata   2220
gggtttcgct catgtgttga gcatataaga aaccttagt atgtatttgt atttgtaaaa   2280
tacttctatc aataaaattt ctaattccta aaaccaaaat ccagtgacgc ggccgcaccc   2340
ataatacccca taatagctgt ttgccagtaa tcatggtcat agctgtttcc tgtgtgaaat   2400
tgttatccgc tcacaattcc acacaacata cgagccggaa gcataaagtg taaagcctgg   2460
ggtgcctaat gagtgagcta actcacatta attgcgttgc gctcactgcc cgctttccag   2520
tcgggaaacc tgtcgtgcca gctgcattaa tgaatcggcc aacgcgcggg gagaggcggt   2580
ttgcgtattg ggcgctcttc cgcttcctcg ctcactgact cgctgcgctc ggtcgttcgg   2640
ctgcggcgag cggtatcagc tcactcaaag gcggtaatac ggttatccac agaatcaggg   2700
gataacgcag gaaagaacat gtgagcaaaa ggccagcaaa aggccaggaa ccgtaaaaag   2760
gccgcgttgc tggcgttttt ccataggctc cgcccccctg acgagcatca caaaaatcga   2820
cgctcaagtc agaggtggcg aaacccgaca ggactataaa gataccaggc gtttccccct   2880
ggaagctccc tcgtgcgctc tcctgttccg accctgccgc ttaccggata cctgtccgcc   2940
tttctccctt cgggaagcgt ggcgctttct caatgctcac gctgtaggta tctcagttcg   3000
gtgtaggtcg ttcgctccaa gctgggctgt gtgcacgaac cccccgttca gcccgaccgc   3060
tgcgccttat ccggtaacta tcgtcttgag tccaacccgg taagacacga cttatcgcca   3120
ctggcagcag ccactggtaa caggattagc agagcgaggt atgtaggcgg tgctacagag   3180
ttcttgaagt ggtggcctaa ctacggctac actagaagga cagtatttgg tatctgcgct   3240
ctgctgaagc cagttacctt cggaaaaaga gttggtagct cttgatccgg caaacaaacc   3300
accgctggta gcggtggttt ttttgtttgc aagcagcaga ttacgcgcag aaaaaagga   3360
tctcaagaag atcctttgat cttttctacg gggtctgacg ctcagtggaa cgaaaactca   3420
cgttaaggga ttttggtcat gagattatca aaaaggatct tcacctagat ccttttaaat   3480
taaaaatgaa gttttaaatc aatctaaagt atatatgagt aaacttggtc tgacagttac   3540
caatgcttaa tcagtgaggc acctatctca gcgatctgtc tatttcgttc atccatagtt   3600
gcctgactcc ccgtcgtgta gataactacg atacgggagg gcttaccatc tggccccagt   3660
```

```
gctgcaatga taccgcgaga cccacgctca ccggctccag atttatcagc aataaaccag    3720
ccagccggaa gggccgagcg cagaagtggt cctgcaactt tatccgcctc catccagtct    3780
attaattgtt gccgggaagc tagagtaagt agttcgccag ttaatagttt gcgcaacgtt    3840
gttgccattg ctacaggcat cgtggtgtca cgctcgtcgt ttggtatggc ttcattcagc    3900
tccggttccc aacgatcaag gcgagttaca tgatccccca tgttgtgcaa aaaagcggtt    3960
agctccttcg gtcctccgat cgttgtcaga agtaagttgg ccgcagtgtt atcactcatg    4020
gttatggcag cactgcataa ttctcttact gtcatgccat ccgtaagatg cttttctgtg    4080
actggtgagt actcaaccaa gtcattctga gaatagtgta tgcggcgacc gagttgctct    4140
tgcccggcgt caatacggga taataccgcg ccacatagca gaactttaaa agtgctcatc    4200
attggaaaac gttcttcggg gcgaaaactc tcaaggatct taccgctgtt gagatccagt    4260
tcgatgtaac ccactcgtgc acccaactga tcttcagcat cttttacttt caccagcgtt    4320
tctgggtgag caaaaacagg aaggcaaaat gccgcaaaaa agggaataag ggcgacacgg    4380
aaatgttgaa tactcatact cttcctttt caatattatt gaagcattta tcagggttat    4440
tgtctcatga gcggatacat atttgaatgt atttagaaaa ataaacaaat aggggttccg    4500
cgcacatttc cccgaaaagt gccacctgac gtctaagaaa ccattattat catgacatta    4560
acctataaaa ataggcgtat cacgaggccc tttcgtc                            4597

<210> SEQ ID NO 32
<211> LENGTH: 4599
<212> TYPE: DNA
<213> ORGANISM: Artificial Sequence
<220> FEATURE:
<223> OTHER INFORMATION: Synthetic nucleotide sequence: pSAT7-EGFP-C1

<400> SEQUENCE: 32
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgccca taaagccgtc agtgtccgca     420
taaagaacca ccggtcaaca tgtggagcac gacacacttg tctactccaa aaatatcaaa     480
gatacagtct cagaagacca aagggcaatt gagacttttc aacaaagggt aatatccgga     540
aacctcctcg gattccattg cccagctatc tgtcacttta ttgtgaagat agtggaaaag     600
gaaggtggct cctacaaatg ccatcattgc gataaaggaa aggccatcgt tgaagatgcc     660
tctgccgaca gtggtcccaa agatggaccc cacccacga ggagcatcgt ggaaaaagaa     720
gacgttccaa ccacgtcttc aaagcaagtg gattgatgtg ataacatggt ggagcacgac     780
acacttgtct actccaaaaa tatcaaagat acagtctcag aagaccaaag gcaattgag     840 acttttcaac aaagggtaat atccggaaac ctcctcggat tccattgccc agctatctgt     900
cactttattg tgaagatagt ggaaaaggaa ggtggctcct acaaatgcca tcattgcgat     960
aaaggaaagg ccatcgttga agatgcctct gccgacagtg gtcccaaaga tggacccccca   1020 cccacgagga gcatcgtgga aaaagaagac gttccaacca cgtcttcaaa gcaagtggat   1080
tgatgtgata tctccactga cgtaagggat gacgcacaat cccactatcc ttcgcaagac   1140
```

```
ccttcctcta tataaggaag ttcatttcat ttggagagga cgtcgagagt tctcaacaca    1200
acatatacaa aacaaacgaa tctcaagcaa tcaagcattc tacttctatt gcagcaattt    1260
aaatcatttc ttttaaagca aaagcaattt tctgaaaatt ttcaccattt acgaacgata    1320
gccatggtga gcaagggcga ggagctgttc accggggtgg tgcccatcct ggtcgagctg    1380
gacggcgacg taaacggcca caagttcagc gtgtccggcg agggcgaggg cgatgccacc    1440
tacggcaagc tgaccctgaa gttcatctgc accaccggca agctgcccgt gccctggccc    1500
accctcgtga ccaccctgac ctacggcgtg cagtgcttca gccgctaccc cgaccacatg    1560
aagcagcacg acttcttcaa gtccgccatg cccgaaggct acgtccagga gcgcaccatc    1620
ttcttcaagg acgacggcaa ctacaagacc cgcgccgagg tgaagttcga gggcgacacc    1680
ctggtgaacc gcatcgagct gaagggcatc gacttcaagg aggacggcaa catcctgggg    1740
cacaagctgg agtacaacta caacagccac aacgtctata tcatggccga caagcagaag    1800
aacggcatca aggtgaactt caagatccgc cacaacatcg aggacggcag cgtgcagctc    1860
gccgaccact accagcagaa cacccccatc ggcgacggcc ccgtgctgct gcccgacaac    1920
cactacctga gcacccagtc cgccctgagc aaagaccccca acgagaagcg cgatcacatg    1980
gtcctgctgg agttcgtgac cgccgccggg atcactctcg gcatggacga gctgtacaag    2040
tccggactca gatctcgagc tcaagcttcg aattctgcag tcgacggtac cgcgggcccg    2100
ggatccacct agtctagagt ccgcaaaaat caccagtctc tctctacaaa tctatctctc    2160 tctattttc tccagaataa tgtgtgagta gttcccagat aagggaatta gggttcttat    2220
agggtttcgc tcatgtgttg agcatataag aaacccttag tatgtatttg tatttgtaaa    2280
atacttctat caataaaatt tctaattcct aaaaccaaaa tccagtgacg cggccgccat    2340
aaagccgtca gtgtccgcat aaagaaccgt aatcatggtc atagctgttt cctgtgtgaa    2400
attgttatcc gctcacaatt ccacacaaca tacgagccgg aagcataaag tgtaaagcct    2460
ggggtgccta atgagtgagc taactcacat taattgcgtt gcgctcactg cccgctttcc    2520
agtcgggaaa cctgtcgtgc cagctgcatt aatgaatcgg ccaacgcgcg gggagaggcg    2580
gtttgcgtat tgggcgctct tccgcttcct cgctcactga ctcgctgcgc tcggtcgttc    2640
ggctgcggcg agcggtatca gctcactcaa aggcggtaat acggttatcc acagaatcag    2700
gggataacgc aggaaagaac atgtgagcaa aaggccagca aaaggccagg aaccgtaaaa    2760
aggccgcgtt gctggcgttt ttccataggc tccgcccccc tgacgagcat cacaaaaatc    2820
gacgctcaag tcagaggtgg cgaaacccga caggactata agataccagg cgtttccccc    2880
tggaagctcc ctcgtgcgc tctcctgttc cgaccctgcc gcttaccgga tacctgtccg    2940
cctttctccc ttcgggaagc gtggcgcttt ctcaatgctc acgctgtagg tatctcagtt    3000
cggtgtaggt cgttcgctcc aagctgggct gtgtgcacga accccccgtt cagcccgacc    3060
gctgcgcctt atccggtaac tatcgtcttg agtccaaccc ggtaagacac gacttatcgc    3120
cactggcagc agccactggt aacaggatta gcagagcgag gtatgtaggc ggtgctacag    3180
agttcttgaa gtggtggcct aactacggct acactagaag gacagtattt ggtatctgcg    3240
ctctgctgaa gccagttacc ttcggaaaaa gagttggtag ctcttgatcc ggcaaacaaa    3300
ccaccgctgg tagcggtggt ttttttgttt gcaagcagca gattacgcgc agaaaaaaag    3360
gatctcaaga agatcctttg atcttttcta cggggtctga cgctcagtgg aacgaaaact    3420
cacgttaagg gattttggtc atgagattat caaaaaggat cttcacctag atccttttaa    3480
```

```
attaaaaatg aagttttaaa tcaatctaaa gtatatatga gtaaacttgg tctgacagtt      3540
accaatgctt aatcagtgag gcacctatct cagcgatctg tctatttcgt tcatccatag      3600
ttgcctgact ccccgtcgtg tagataacta cgatacggga gggcttacca tctggcccca      3660
gtgctgcaat gataccgcga gacccacgct caccggctcc agatttatca gcaataaacc      3720
agccagccgg aagggccgag cgcagaagtg gtcctgcaac tttatccgcc tccatccagt      3780
ctattaattg ttgccgggaa gctagagtaa gtagttcgcc agttaatagt ttgcgcaacg      3840
ttgttgccat tgctacaggc atcgtggtgt cacgctcgtc gtttggtatg gcttcattca      3900
gctccggttc ccaacgatca aggcgagtta catgatcccc catgttgtgc aaaaaagcgg      3960
ttagctcctt cggtcctccg atcgttgtca gaagtaagtt ggccgcagtg ttatcactca      4020
tggttatggc agcactgcat aattctctta ctgtcatgcc atccgtaaga tgcttttctg      4080
tgactggtga gtactcaacc aagtcattct gagaatagtg tatgcggcga ccgagttgct      4140
cttgcccggc gtcaatacgg gataataccg cgccacatag cagaacttta aaagtgctca      4200
tcattggaaa acgttcttcg ggcgaaaac tctcaaggat cttaccgctg ttgagatcca      4260
gttcgatgta acccactcgt gcacccaact gatcttcagc atctttact tcaccagcg      4320 tttctgggtg agcaaaaaca ggaaggcaaa atgccgcaaa aaagggaata agggcgacac      4380
ggaaatgttg aatactcata ctcttccttt ttcaatatta ttgaagcatt tatcagggtt      4440
attgtctcat gagcggatac atatttgaat gtatttagaa aaataaacaa ataggggttc      4500
cgcgcacatt tccccgaaaa gtgccacctg acgtctaaga aaccattatt atcatgacat      4560
taacctataa aaataggcgt atcacgaggc cctttcgtc                            4599
```

<210> SEQ ID NO 33
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 33

```
agttgtaggg agggatttat g                                                 21
```

<210> SEQ ID NO 34
<211> LENGTH: 395
<212> TYPE: DNA
<213> ORGANISM: Artificial Sequence
<220> FEATURE:
<223> OTHER INFORMATION: Synthetic nucleotide sequence

<400> SEQUENCE: 34

```
gatcctggcc tagtctatag gaggttttga aagaaagga gcaataatca ttttcttgtt       60
ctatcaagag ggtgctattg ctcctttctt ttttctttt tatttattta ctagtatttt      120
acttacatag acttttttgt ttacattata gaaaagaag gagaggttat ttcttgcat       180 ttattcatga ttgagtattc tattttgatt ttgtatttgt ttaaaattgt agaaatagaa      240
cttgtttctc ttcttgctaa tgttactata tcttttttgat ttttttttc caaaaaaaaa     300 atcaaatttt gacttcttct tatctcttat ctttgaatat ctcttatctt tgaaataata     360
atatcattga aataagaaag aagagctata ttcga                                395
```

<210> SEQ ID NO 35
<211> LENGTH: 161
<212> TYPE: DNA
<213> ORGANISM: Artificial Sequence

```
<220> FEATURE:
<223> OTHER INFORMATION: Synthetic nucleotide sequence

<400> SEQUENCE: 35
accgaaattc aattaaggaa ataaattaag gaaatacaaa aagggggta gtcatttgta      60 tataactttg tatgactttt ctcttctatt tttttgtatt tcctcccttt ccttttctat    120
ttgtattttt ttatcattgc ttccattgaa ttccgtgttc t                        161

<210> SEQ ID NO 36
<211> LENGTH: 24
<212> TYPE: DNA
<213> ORGANISM: Artificial Sequence
<220> FEATURE:
<223> OTHER INFORMATION: Synthetic nucleotide sequence

<400> SEQUENCE: 36
ttcttccccg aattcgggga agaa                                            24

<210> SEQ ID NO 37
<211> LENGTH: 30
<212> TYPE: DNA
<213> ORGANISM: Artificial Sequence
<220> FEATURE:
<223> OTHER INFORMATION: Synthetic nucleotide sequence: PI-PspI

<400> SEQUENCE: 37
tggcaaacag ctattatggg tattatgggt                                      30

<210> SEQ ID NO 38
<211> LENGTH: 26
<212> TYPE: DNA
<213> ORGANISM: Artificial Sequence
<220> FEATURE:
<223> OTHER INFORMATION: Synthetic nucleotide sequence: I-CeuI

<400> SEQUENCE: 38
taactataac ggtcctaagg tagcga                                          26

<210> SEQ ID NO 39
<211> LENGTH: 18
<212> TYPE: DNA
<213> ORGANISM: Artificial Sequence
<220> FEATURE:
<223> OTHER INFORMATION: Synthetic nucleotide sequence: I-SceI

<400> SEQUENCE: 39
tagggataac agggtaat                                                   18

<210> SEQ ID NO 40
<211> LENGTH: 23
<212> TYPE: DNA
<213> ORGANISM: Artificial Sequence
<220> FEATURE:
<223> OTHER INFORMATION: Synthetic nucleotide sequence: I-Ppol

<400> SEQUENCE: 40
atgactctct taaggtagcc aaa                                             23

<210> SEQ ID NO 41
<211> LENGTH: 3490
<212> TYPE: DNA
<213> ORGANISM: Photobacterium leiognathi

<400> SEQUENCE: 41
```

-continued

```
agggatagta tgtttacagg aataatagaa gcagtgggaa atatcagcgc cattattcgt      60
aataacgacg atatttcaat ggttatcaat accaatcggc ttgatatttc ggatgtaaaa     120
cttggcgata gcattgctag caatggcgtt tgtttaaccg tatctaaatt aacgccaact     180
ggatttgttg ccgatctttc aacagagaca ttaaagcgta ccgcttttca cagttaccac     240
gttggacaaa aaatcaattt agaaaaagcc atgttaccca ccacacgctt tggtggtcat     300
atcgtttctg ggcatgttga tggtattggc gacattattg agctaaagcg aaaaggtcgc     360
acccttgata tgtggataac cgtgcctatt cacctaaaga aattcgtttc cgagaaaggt     420
tcagtttgca ttgatggaac cagtttaacc atcaacgctg tgtatcagaa tgtcattaaa     480
ttaaccataa tccctcatac gttagctaac acgacacttg ccaatgccac cattgatcaa     540
aaagtcaata ttgaagccga catgatggcg cgctacctcg aacgattaat cagtattgat     600
aaacaagaat ctaaaaaaaa cactaacgtc tctatgtctt tgttagagaa gcacggcttt     660
atcgtataac tcacttacac tgttgataat aaaggaccca ttatgacttt aagtagcgcc     720
caagaaatca ttaatgatat ccgtctgggt aaaatggtga tcttaatgga tgatgaaaat     780
cgcgaaaatg aaggcgattt gatcatcgcc gctgacatga tcacccctga agcgattaat     840
ttcatggcga cctatggacg cgggttgatc tgcttaacgt taaccaaaga tcgctgccag     900
accttaaatt taccgcttat ggtgcaaaat aatcacgata agttctcaac tgcatttacc     960
gtttcaatag aagccgccgc cgatgttacg accgggatct ctgcctatga tcgtgcaaaa    1020
acagtacaag ccgccattgg cccaaatgcc agtgctgatg atattgtgat gccaggtcat    1080
attttccct taatggcgca agatggtggc gtattaattc gtgccggcca cactgaagct    1140
ggctgtgatg ttgcacgttt agctggactt gaagcctcta gtgttattgt ggaaattctt    1200
aatgaagacg gcacgatggc acgccgacct caactcgaag tctttgctca aaaacacggt    1260
ttaaaactgg gaacgattgc tgatttaatt gagtatcgta cccaacgaga aagccatatt    1320
gaacgtttat cagaaagtga attatgcact gagtatggcg tttttaactt aatcacctac    1380
cgtgacacca ttgataacca actgcattac gcattatgta aggtgatat aaaccctgat    1440
agtgagacct tagtccgtgt tcatgttaaa gatacactga aagatatttt acatactggc    1500
gcaacgcaat ggtctctaca agcggccatg cagcgcattc aagccgacgg tggcatatta    1560
gtgatcataa gccaaattga gccctcagcg atgatcctaa atcaaataaa ccacttagat    1620
tcagagcacc aagcgagttt acctttacct atcacaccgc aatcccgaca aattggttta    1680
ggatcgcaaa ttctgtctga attagggcta tgcaaaattc gtttactgtc ttctcagagc    1740
caacaatatc gttctttatc aggatttgat cttgaggttg tggaatatat tgtaactag     1800
taaacactta gatattattg attcatcatt ctttttttaca aatacactta ggaagctcca    1860
tgaatattat tgaaggtgca atcacagcac cccatgccaa tgtcgcgatc atcgtttctc    1920
gtttcaatag ttttatcaat gacagcttat tgtctggtgc attagatgcc ctacaacgcc    1980
aaggtcttgt taaagaaagt aatattaccg ttgtacgttg ccctggagca tacgagctac    2040
ctttactggc gcaacaactg gcaaaaaaag gcagttatga tgccattatc gctttaggct    2100
cagtgatacg tggcggtact ccacattttg aatatgttgc aggtgaatgt aataaaggtt    2160
tagcgcaaat tgcgttagag catcaaattc cagtcgcgtt cggtgtcctt actgtggatt    2220
caatcgaaca agccattgaa cgtgcaggaa caaaaatggg aaataaaggt gcagaagcgg    2280
cattaagtgc actagaaatg attaacgtgc tagcagaaat cgagccttaa tttccttata    2340
ttttcacccg tcatgatggc tatgatgccc tacgtcatca tagccattgc ccttctaaag    2400
```

```
caatgaactc aaatagaatt attaggaata ttatgatcac ggtaagagcc cgggtgcctt      2460
ttaaaatcgg gcaaaaaagt cagatcccag cggagttatt gtcgtttcat ggctttaatt      2520
caggtaaaga gcatatcgca attattttta acaagcaga taccacaacc gcccctttag       2580
ttcgcttaca ttcagaatgc ttaaccggtg atgtctttca ttcttcgcgc tgtgattgtg      2640
gcgagcagct caatgaaaca atagaaaaaa tgcatcaatt cggtgggatc attttgtatc     2700
tacgtcaaga aggacgtggc attggtttat acaataaaat cgatgcctat cacttacaaa     2760
gccaaggcat gaatacctat gaagccaata accatttagg tttcgctgat gatctacgcg     2820
attttagtga agctgcaaaa gcattaatgg cattaggcat aaacaagatc cgcttaatca     2880
ctaacaaccc aaagaaaatc aatgaacttc aacaacatgg cattgagatc atagatgtgg     2940
ttaacactca ggtacacatc aaacaagaca acgaagatta tctaaaaaca aaagcgttac     3000
acggccatca caacctctct ttatgatcag atctgctcaa cgcttatatt gagctatctt     3060
agccagaaga ttaactctta ccaatattgc gccatttaac agtactcccc cttatgttaa     3120
atggcgaaaa acaaccgcc ctcaaaaatc cacagctaag agttacccac taaatttgtg     3180
gataacacaa tattaccttt attttcaac atattatgtt tttcaataga aatacataat      3240
aatctcgact attttcaaaa atataaatac gtccttaaaa cgtaaaaagc cgcactattg      3300
cagtgcggct tggtgttgct attagtgtac ttactcggca caccaatatt gttacgcttc      3360
gccactcatt acgttgagct tgccgtgttc gacatagtag gttcgaaccg ctatttattg      3420
gcgaagaagc aaattttaa aaggtgtcac ttaccaaatt gttaacaact aagttttcac       3480
ttagaagctt                                                              3490

<210> SEQ ID NO 42
<211> LENGTH: 1133
<212> TYPE: DNA
<213> ORGANISM: Photorhabdus luminescens

<400> SEQUENCE: 42
gtcgacaaaa tctgggatga attagatatt ttaggaccat aagagggaac gcatgacaac        60
actgagctgt aaagtaacct ctgtagaggc tattactgat acggtttatc gggtacggtt       120
gcttcccgat tctccgttct tattccgcgc cggtcagtat ctgatggtgg taatggatga       180
gagagataaa cgtccgtttt caatggcgtc aacgccttca gaaaaggagt ttattgaatt       240
acatattggt gcttctgaac tgaatttgta tgcaatggct gtgatggata gaattctgga       300
tcagaaagtg atcaatattg atatccctca tggcaaagct tggttccgta aaagcagcgc       360
taatccgttg ttattaattg ctggcggtac ggggttttct tacacccgtt caatattatt       420
gacagcgttg gaagaacaac caaaacgtca tatctctatg tattgggggg cagagaatc       480 acaacattta tatgatcttg ctgaattacg gttacttaca gaacgctatc ctaatttgaa      540
ggttattcca gttgttgaac agtcagataa tggttggtgt ggacgtacag aacagtgct      600 taaagcagta ctagaggatt ttggtagttt ggccaattat gatatctaca ttgcagggcg       660
attcgaaatg gcaaaaattg ctcgcgagcg cttttgtagt gagcgtgatg cttctgctga       720
cagcatgtat ggtgatgctt tcgaattcat ttagaataat aaaaaaaccc gcccctgaca       780
ggcgggaatt acggcaacaa cgactcagtt ataataattc ttatataccc gtcatctttc      840
aagttgcctc tttgttggct gcactcactc accccggtta catagttttc tatgctcctg      900
gggattcatt cacttgccgc cgcgctgcaa ctcgaaatct attaggtata gataagttct       960
```

| taatccattc tttctataat ggtggcgata ccttggccta aaccgataca catggttgct | 1020 |
| aggccaaact gaacatcgcg gcgttccatt aagttcaaca acgttgttgt gatgcgagcg | 1080 |
| cctgagcagc ctaaaggatg acccagagca attgcgccac cattcaggtt aac | 1133 |

<210> SEQ ID NO 43
<211> LENGTH: 1121
<212> TYPE: DNA
<213> ORGANISM: Vibrio fischeri

<400> SEQUENCE: 43

| ctcgaggcgg gaattaatta tccaaaccga tgccaagtcg gcgcatgtgc tatgtgctta | 60 |
| tgcaaaaaat tagagggtga aattgaatac gatttagagc ctcttcttac cgataaagaa | 120 |
| caacaagaag ggtgggtatt tgcgtgtcag gcaacagcaa aaagtgattt agtgctgttg | 180 |
| ttagaataaa tcctccccgt ataattagag tttaatgctc aatacacata ataatgacag | 240 |
| cgtacaaatg ccatattaaa aaggcatcag ctgaaaaagg aaagtcatgc caatcaattg | 300 |
| caaagtaaag tctatcgagc cattggcttg taatactttt cgaattttac ttcacccaga | 360 |
| acagcctgtt gcttttaaag caggccaata cctaacggtt gttatgggtg aaaaagacaa | 420 |
| acgcccattc tcaatcgcaa gtagtccttg tcgccacgaa ggtgaaattg agttacatat | 480 |
| tggtgccgca gagcacaatg cttatgccgg agaagtggtt gaatcaatga atcggcact | 540 |
| agaaacgggt ggtgatattt taattgatgc gcctcatggt gaagcgtgga tccgtgaaga | 600 |
| cagcgatcgt tcaatgttat tgattgctgg cggtacaggt tttagttacg tacgttcaat | 660 |
| tcttgatcac tgtattagcc aacagattca aaaaccaatt tacctatact ggggtggtcg | 720 |
| tgatgaatgc caactgtatg caaaagcaga attagagagc attgctcaag cgcatagcca | 780 |
| tattacgttt gtgccagtgg ttgagaaaag tgaaggctgg acaggtaaaa cgggtaatgt | 840 |
| gttagaagcg gtaaaagccg attttaactc actagcagat atggatattt acatcgcagg | 900 |
| tcgctttgaa atggctggtg cagcacgtga gcagttcacc actgaaaaac aagcgaagaa | 960 |
| agagcagctg tttggtgatg cattcgcatt tatctaattt agagcactaa aaagacaaat | 1020 |
| aaaaatgcca ctcaataatg agtggcattt ttttatggat gttataaaaa atgaattagc | 1080 |
| ctttatcatc aaccatagtc agtgctttac gagaaagatc t | 1121 |

<210> SEQ ID NO 44
<211> LENGTH: 702
<212> TYPE: DNA
<213> ORGANISM: Escherichia coli

<400> SEQUENCE: 44

| atgacaacct taagctgtaa agtgacctcg gtagaagcta tcacggatac cgtatatcgt | 60 |
| gtccgcatcg tgccagacgc ggccttttct tttcgtgctg gtcagtattt gatggtagtg | 120 |
| atggatgagc gcgacaaacg tccgttctca atggcttcga cgccggatga aaagggttt | 180 |
| atcgagctgc atattggcgc ttctgaaatc aacctttacg cgaaagcagt catggaccgc | 240 |
| atcctcaaag atcatcaaat cgtggtcgac attccccacg agaagcgtg gctgcgcgat | 300 |
| gatgaagagc gtccgatgat tttgattgcg ggcggcaccg ggttctctta tgcccgctcg | 360 |
| attttgctga cagcgttggc gcgtaaccca accgtgata tcaccattta ctggggcggg | 420 |
| cgtgaagagc agcatctgta tgatctctgc gagcttgagg cgctttcgtt gaagcatcct | 480 |
| ggtctgcaag tggtgccggt ggttgaacaa ccggaagcgg ctggcgtgg gcgtactggc | 540 |
| accgtgttaa cggcggtatt gcaggatcac ggtacgctgg cagagcatga tatctatatt | 600 |

| | |
|---|---|
| gccggacgtt ttgagatggc gaaaattgcc cgcgatctgt tttgcagtga gcgtaatgcg | 660 |
| cgggaagatc gcctgtttgg cgatgcgttt gcatttatct ga | 702 |

<210> SEQ ID NO 45
<211> LENGTH: 2218
<212> TYPE: DNA
<213> ORGANISM: Arabidopsis thaliana

<400> SEQUENCE: 45

| | |
|---|---|
| cgtcttctcc gcccttctta ttcatttcta ctctgctgcg ttatttctcc gtcgtcctca | 60 |
| actcatcgcc ggcgtttacc atccgctaga tccgtcgcct ctccggtcga ctatttatat | 120 |
| ggaatcgtaa atttacagac actaataaga atagtttgac aaaatctgta gctggaataa | 180 |
| tgtcgatgag caattccttg aaaaagctct cttcttgtgt tcttattgat ctcgatggta | 240 |
| ccttaatcaa cacaggtaac ttaaaacctc aatagattgt ttcaatttct gtttatatag | 300 |
| cttggaattc gaatttgatg ttttttttaaa attcattgta gatggtgttg ttggtgacat | 360 |
| tttgaggaaa tacttgtgta aatatggtaa acagtgggat ggaagagaat cattgaaaat | 420 |
| agttggcaaa actccagtag aagctgctac tactattgtt gaagattatg aacttccttg | 480 |
| taaagttgat gaattcaatt ctgaattcta cccttgttc tctgctcagt aagttaccat | 540 |
| aaaaaaaatc gatctttgtc cttattgttg taatcttcat attgttgatt acctccggtt | 600 |
| tgtaggatg gacaaaatca aatctcttcc tggtgccaat aggttgattc gacatttgaa | 660 |
| gtgtcatgga gtacctgtgg ctttggcttc caattcttca agagcaaata ttgaatccaa | 720 |
| aatttcatat catgaaggtt tgttttatat gaaatgttgt tactcaatgc ataagcttgt | 780 |
| atagaggtaa acttgtttta tgaaaatggt ttcacttttg tgtagggtgg aaggaatgct | 840 |
| tctcggttat tgttggtagt gatgaagtct ctaaaggaaa gccttctcct gatatgtaag | 900 |
| atccatctct tgtcacccat ttgtggtttc atctattgat tccaattaaa caatgtctgg | 960 |
| ttaatgacaa tgatcatatt tgtaaaaagt tttctcgaag cagcgaaaag attgaagaaa | 1020 |
| gatccagctg actgtttggt tattgaagat tctgtgtaag tcttacttct agagtatcgt | 1080 |
| tttgctgttg tgtgtttgat tcattctcac taatagttgt ttgaaatggt aggcctggtg | 1140 |
| ttatggctgg taaagctgct gggacaaaag tgattgctgt tccttctctg cctaagcaaa | 1200 |
| cacatcttta tacatctgca gatgaagtca tcaattctct actcgacata agacttgaaa | 1260 |
| aatgggggact tcctccattc caagactgta aaaattcact catgaactct gttcaatact | 1320 |
| cctcttcctt gataacatgt tcatctcggt aatgagactt ttataccttg taatttgtat | 1380 |
| ttgcagggat agagaacact ttaccaattg atccatggca tattggaggt ccagtcatca | 1440 |
| aaggatttgg ccgtggctct aaagtactcg gaatccccac cggtcagtgt acaaacctca | 1500 |
| ttgaactcag ctctttttaca tcattatata tggcttcttt tcttatcgct gcatttgttt | 1560 |
| tgttttcagc taacttgtca acaaaggatt atgcggatga gctagtggaa catccttcgg | 1620 |
| gagtgtactt tggttgggca ggcttggcaa agagaggtgt ctttaaaatg gtcatgagca | 1680 |
| ttggttggaa tccttatttc aataacaagg agaaaactat tgtgagttca taaaaagttc | 1740 |
| aaacaaaatt cttactccag tggttgcttc tttaacttta gcttttgtta tataggaacc | 1800 |
| atggctgctt cacgatttca ctgaggattt ctacggagaa gagctacgtc ttattatcgt | 1860 |
| tggctatata cgccctgagg ttattataac gttatcatca ttcattcttc atatgactcc | 1920 |
| tttgtgtaat gcaatattcc ttgtttgctc atattgtttg tgtttgctag gctaatttct | 1980 |

| | |
|---|---|
| cttcactgga gagtctcatt gcaaagattc acgaggacag ggaagttgca gagaaagctc | 2040 |
| ttgatcttcc ttcgtatgct aagtttaagg gtgatcctta tctgactaaa tgatagaagc | 2100 |
| ttttatgaaa agaattcaaa cacttggatt tgtaatttca taactcaaat cagacttgca | 2160 |
| ttgttcttta gtactatcag cctctttgat tgattaact agataacaac tttcgtta | 2218 |

<210> SEQ ID NO 46
<211> LENGTH: 942
<212> TYPE: DNA
<213> ORGANISM: Escherichia coli

<400> SEQUENCE: 46

| | |
|---|---|
| atgaagctga tacgcggcat acataatctc agccaggccc cgcaagaagg gtgtgtgctg | 60 |
| actattggta atttcgacgg cgtgcatcgc ggtcatcgcg cgctgttaca gggcttgcag | 120 |
| gaagaagggc gcaagcgcaa cttaccggtg atggtgatgc tttttgaacc tcaaccactg | 180 |
| gaactgtttg ctaccgataa agccccggca cggctgaccc ggctgcggga aaaactgcgt | 240 |
| taccttgcag agtgtggcgt tgattacgtg ctgtgcgtgc gtttcgacag cgtttcgcg | 300 |
| gcgttaaccg cgcaaaattt catcagcgat cttctggtga agcatttgcg cgtaaaattt | 360 |
| cttgccgtag gtgatgattt ccgctttggc gctggtcgtg aaggcgattt cttgttatta | 420 |
| cagaaagctg gcatggaata cggcttcgat atcaccagta cgcaaacttt ttgcgaaggt | 480 |
| ggcgtgcgta tcagcagcac cgctgtgcgt caggcgctgg cggatgacaa tctggctctg | 540 |
| gcagaaagtt tactggggca cccgtttgcc atctccgggc gtgtagtcca cggtgatgaa | 600 |
| ttagggcgca ctataggttt cccgacggcg aatgtaccgc tacgccgtca ggtttccccg | 660 |
| gtgaaagggg tttatgcggt agaagtgctg ggcctcggtg aaaagccgtt acccggcgtg | 720 |
| gcaaacattg aacacgcccc aacgttgccg gtattcgcc agcagctgga agtgcatttg | 780 |
| ttagatgttg caatggacct ttacggtcgc catatacaag tagtgctgcg taaaaaaata | 840 |
| cgcaatgagc agcgatttgc gtcgctggac gaactgaaag cgcagattgc gcgtgatgaa | 900 |
| ttaaccgccc gcgaattttt tgggctaaca aaaccggctt aa | 942 |

<210> SEQ ID NO 47
<211> LENGTH: 6006
<212> TYPE: DNA
<213> ORGANISM: Bacillus subtilis

<400> SEQUENCE: 47

| | |
|---|---|
| aaaagtggac gaaccttatt tggcggctaa taaaaagaga gcgaaacagg acgttttgac | 60 |
| catttgaccg atgatttcgg cccggttaaa gtgcctgata caagtatttt gtgatgggt | 120 |
| gacaatcgtc gcaattccat ggacagccgt aacggccttg gcctcttcac gaaaaaacaa | 180 |
| attgcgggta cgtcaaagtt tgttttctac ccgtttaacg aaatgcgcaa acaaattag | 240 |
| gatcaagcag cttcccattg gggctgcttt ttttatatct ttttacggt catcccctaa | 300 |
| aaacagaaca taaattcgta tatctataga aaagaaattt ttgcagaaat gtgaaacata | 360 |
| ttcccgttat gcatcgttat attaataatt tacgagaatt tacggttttt tattcatgaa | 420 |
| aaaaaggaat aactctatatg aatgaataga ttcatattgg ctggaggttt agaaatggga | 480 |
| agaataaaaa ccaagattac cattctgtta gtgcttttgc ttttacttgc aggcggttat | 540 |
| atgtacataa atgatattga gctgaaggat gttccgacag caattggaca aaccttgtcc | 600 |
| tcggaagaag aggaatacac catccaggaa tataaagtga cgaaaattga cggctcagag | 660 |
| tatcatggag tagcagaaaa cggaacgaaa atcatcttca acggaaaaaa attaaatcag | 720 |

```
gatttatctg atataaaaga aggtgacaag attaaggctt acttcagcaa atcaaagcgg      780
atcgacggat taatcaaggt tgcaaaagtg aatgattaaa aaacatcact ttcggatcga      840
agggtgatgt tttgtttttc tcaaattgta agtttatttc attgcgtact ttaaaaagga      900
tcgctataat aaccaataag gacaaatgaa taaagattgt atccttcggg gcagggtgga      960
aatcccgacc ggcggtagta aagcacattt gctttagagc ccgtgacccg tgtgcataag     1020
cacgcggtgg attcagttta agctgaagcc gacagtgaaa gtctggatgg agaaggatg      1080 atgagccgct atgcaaaatg tttaaaaatg catagtgtta tttcctattg cgtaaaatac     1140
ctaaagcccc gaattttta taaattcggg gctttttga cggtaaataa caaagaggg       1200 gagggaaaca aatggaagag tattatatga agctggcctt agatcttgcg aagcagggcg     1260
aaggacagac cgaatccaat ccgctcgtcg gcgctgttgt cgtaaaggac ggacaaattg     1320
tcggaatggg cgcccattta aaatatggtg aagctcatgc agaagttcat gccatccata     1380
tggctggagc acatgcagag ggtgccgaca tttacgttac actcgaaccg tgcagccatt     1440
acggaaaaac accgccatgt gcagaattga ttatcaactc tggtatcaaa agagtgttcg     1500
tggcgatgag agatcctaat ccgcttgtgg ctggaagagg gatcagcatg atgaaagaag     1560
ctggcattga ggtaagggaa ggcatcctgg cagaccaggc ggagaggctg aatgaaaaat     1620
ttctgcactt tatgaggaca ggccttccgt acgtcacgct aaaagcggct gccagccttg     1680
acggcaagat agctaccagc acgggtgaca gcaaatggat cacgtcagag gctgcaagac     1740
aggatgctca gcaatacagg aaaacacacc aaagcatttt agtcggagtt ggcacagtga     1800
aagccgacaa tccgagctta acctgcagac tgccgaatgt aacaaaacag ccggttcggg     1860
tcatacttga taccgtactc tcgattcctg aggacgctaa agtgatttgc gatcaaatag     1920
cgccgacatg gatttttacg acggcacgcg cagacgagga aaagaaaaaa cggctttcag     1980
ctttcggagt gaacatattt acacttgaaa ccgagcgcat tcaaattcct gatgttttga     2040
agatcctagc ggaagaaggc atcatgtcgg tgtatgtgga aggcggttca gctgttcacg     2100
gaagctttgt caaagaaggc tgttttcaag aaatcatctt ctattttgcc cctaaactaa     2160
tcggaggaac gcatgctccc agcttaatct ccggtgaagg ttttcaatca atgaaagatg     2220
tccccttatt acaattcact gatataaccc aaatcggccg tgatatcaaa ctgacggcaa     2280
aaccgacaaa ggaataggat ggtgaccatg tttacaggaa ttatcgaaga acaggcaca     2340 atcgaatcca tgaaaaaagc agggcatgca atggccttaa ctattaaatg ctcaaagatt     2400
ttagaggatg ttcatcttgg cgacagcatt gcagtgaacg gcatttgtct gactgtcact     2460
gattttacaa aaaatcaatt cacagtggat gttatgcctg aaacagtcaa agctacgtca     2520
ctgaatgatt taacaaaagg aagcaaagta aatctggaaa gagcgatggc ggcaaacggc     2580
cgtttcggag gccatttcgt ctcaggccat gtcgacggaa ctgcggaaat cacacgaatt     2640
gaagagaaaa gcaacgcagt ttactatgat ttaaaaatgg acccgtcatt aacaaaaaca     2700
ttggttttaa agggatcaat tactgtggat ggcgtgagct taaccatatt cggcctgaca     2760
gaagacacag tgacgatctc cttaataccg catacgatca gcgaaacgat cttttcagaa     2820
aaaacgatcg gctctaaagt gaatatcgaa tgcgatatga tcgaaaata tatgtatcga     2880 tttttgcata agccaatga aaataagacc caacaaacca ttacaaaagc cttcttaagc     2940
gaaaacggct tttagagagg aagatttgca tgtttcatcc gatagaagaa gcactggacg     3000 cttaaaaaa aggcgaagtc atcatcgttg tagatgatga agacagagaa aatgaaggag     3060
```

```
actttgtggc tcttgccgag catgcaacgc cggaagtcat taactttatg gcgacacatg    3120
ggagaggact gatctgcacg ccgctcagtg aggaaatcgc agacaggctt gatcttcacc    3180
ctatggttga gcataataca gactctcacc acactgcatt taccgtaagc atagaccatc    3240
gtgaaacgaa gacaggtatc agcgctcaag aaagatcttt taccgttcaa gcattgctgg    3300
acagcaaatc cgtgccatct gattttcagc gtccggggca cattttttcca ctgattgcga    3360 aaaaaggagg tgtcctgaaa agagcgggcc atacagaagc tgctgttgat cttgctgaag    3420
cttgcggatc tccaggagcc ggcgtcattt gtgaaattat gaatgaagac ggaacgatgg    3480
cgagagtgcc tgagctcatt gaaattgcga aaaagcatca attaaaaatg atcaccatta    3540
aggatttgat tcaataccgt tacaatctga caacacttgt cgagcgtgaa gttgacatta    3600
cgctgcctac tgattttggg acatttaagg tttatggata cacaaatgag gtagatggaa    3660
aagagcatgt cgcatttgtg atgggagatg tgccgttcgg agaagaaccg gtattggtcc    3720
gggtgcattc agaatgtctc acaggtgacg tgtttggctc tcatcgctgt gattgcggac    3780
cgcagctgca cgccgcgctg aaccaaattg ccgcagaagg ccgtggagtg ctcctgtact    3840
tgcgccaaga aggacgaggc atcggtttaa tcaataaatt aaaagcttat aagcttcagg    3900
aacaaggcta tgacaccgta gaagccaatg aggcgcttgg attcttgccg gatcttcgca    3960
actatggcat cggagcacaa attttacgcg acctcggtgt ccggaatatg aagcttttga    4020
cgaataatcc gcgaaaaatc gcaggccttg aaggctacgg actcagtatt tcagaaagag    4080
tgccgcttca aatggaggcg aaagaacaca ataaaaaata tttgcaaacc aaaatgaaca    4140
agctaggtca tttacttcat ttctaatcac aaatatcaca aaaaggatg ggaatcatat    4200 gaatatcata caaggaaatt tagttggtac aggtcttaaa atcggaatcg tagtaggaag    4260
atttaatgat tttattacga gcaagctgct gagcggagca gaagatgcgc tgctcagaca    4320
tggcgtagac acaaatgaca ttgatgtggc ttgggttcca ggcgcatttg aaataccgtt    4380
tgctgcgaaa aaaatggcgg aaacaaaaaa atatgatgct attatcacat ggggcactgt    4440
catcagaggc gcaacgacac attacgatta tgtctgcaat gaagctgcaa aaggcatcgc    4500
gcaagcagca aacactactg gtgtacctgt catctttgga attgtaacaa ctgaaaacat    4560
cgaacaggct atcgagcgtg ccggcacaaa agcgggcaac aaaggtgtag attgtgctgt    4620
ttctgccatt gaaatggcaa atttaaaccg ctcatttgaa taatttgctg aaaacagttt    4680
aaaaatatgg cgaaaatgat ataatgtgag aaaacggatc acctattcgt atccgttaat    4740
agcagactgg acattttgga tatagagggg ttttatgtt aattcgttat aaaaaatcgt    4800
ttgaaaagat tgcgatgggg cttctttcgt ttatgccgaa tgaaaaagac cttaagcagc    4860
ttcagcagac aattaaggac tacgaaacgg atacagaccg ccagctcttt ctttggaaag    4920
aggacgagga tatcgtcgga gcaatcggag tcgaaaaaaa ggattctgag gttgagatcc    4980
ggcatatcag tgtgaatcct tctcatcgcc atcaaggaat cggaaaacag atgatggatg    5040 cttaaagca tttattcaaa acgcaagtac tggttccaaa tgaattaacg cagagctttt    5100
tcgaacgttg tcaaggtcag caggatcaag acatttcata caataattaa gcagaggctg    5160
tgatcagtct ctgctttttt ttctgcgttc tatttctttt tcacgttcac ggatgacgtc    5220
agtccgatcc cgcaaacggt gtttgtcgat aagaaatatg ttgctgagtg cactgggctg    5280
cccccatgta tacttttttt tcctgcattc gatcctgcat gcttcctcca gtttctcatc    5340
tttgattgga agtataatgc ttttataggc agagacggtt tcgatttgtt cgtaaaccga    5400
ttgcataagt tcgagcaaac ggccatgatc aagccctaag tcttcgactg cccggtgttc    5460
```

```
tgcttgaaga atccggatgc tgttcgccat cagtcttttt gccccggctg tattctgcct    5520
tctgtgatga tataaagcca ctgcaagctg aataaagccc acccaatagc gttttcgttt    5580
ctttggcgga tcttccttcc aatattcttc taatatttca tggcattcaa ataatcccg    5640 tgtcgcatga aactcaacga gataatctat ataagctttc ggatacaagg tgcttcctcc    5700
tttaatgtgc ttttagtgta ccatagaagg gataaaagga aaaagaacg cccggcctct    5760 agtgcttctt agaaaggaaa accagaagca aaggcttttt ctcccgcttc tgcgctccga    5820
gcaaacacct cttgtgtttt gaatattctg tacaaactcc ttcaaaacag gatatgaaat    5880
agtattggac gagagctttt tggtggctta ctataggg tagccagttt ttccggcaat      5940
gagagtgata cttgaaaatg gtgagatgat ggaagaatat caagtgaaaa ttgatacgtt    6000
tgagca                                                                6006

<210> SEQ ID NO 48
<211> LENGTH: 591
<212> TYPE: DNA
<213> ORGANISM: Escherichia coli

<400> SEQUENCE: 48
atgcagctta acgtgtggc agaagccaaa ctgccaaccc catggggcga tttcctgatg       60
gtgggatttg aagaactggc aaccggacac gatcatgtcg cgctagtcta tggcgatatt     120
tccgggcata ccccggtact tgcgcgcgtc cattccgaat gtctgaccgg tgacgccctg     180
ttcagcttgc gctgcgattg tggcttccag ctcgaagcgg cattgacgca aattgccgag     240
gaaggccgtg gtatttttgct gtatcaccgt caggaaggtc gtaacattgg tctgctgaat    300
aaaatccgcg cttacgcact gcaggatcaa ggttacgata ccgtagaggc taaccaccag     360
ttaggcttcg ccgctgatga gcgcgacttc actctttgcg ctgatatgtt caaactcctt    420
ggcgtcaatg aagtccgctt gttaaccaat aacccgaaaa agtcgaaat tctgaccgaa     480 gcagggatta atattgttga acgcgtacca ttgattgtag gtcgtaaccc caataacgaa     540
cattatctcg ataccaaagc cgagaaaatg ggccatttgc tgaacaaata a              591

<210> SEQ ID NO 49
<211> LENGTH: 642
<212> TYPE: DNA
<213> ORGANISM: Escherichia coli

<400> SEQUENCE: 49
atgtttacgg ggattgtaca gggcaccgca aaactggtgt cgattgacga gaaaccaaat      60
tttcgtacgc atgtggtgga gttacccgac cacatgctgg acggcctgga aaccggtgct    120
tccgtggcgc ataacggttg ctgcctgacc gtgacggaaa ttaacggcaa ccatgtcagt    180
tttgacctga tgaaagaaac gttacgcatt accaatcttg gcgatttaaa agtgggggat    240
tgggtaaacg ttgagcgtgc ggcgaaattc agtgatgaaa ttggcggaca cttaatgtca    300
ggtcatatta tgaccactgc tgaagtggcg aaaatattaa cctcagaaaa taatcgccag    360
atctggttta agtccagga tagtcagttg atgaaatata ttctgtacaa aggatttatt    420
ggcatcgacg gtattagcct gaccgtcggc gaagtcacgc aacgcgtttt tgcgtccat    480 ttaattccgg aaacactgga acgcacgact cttgggaaga aaaaacttgg cgcacgcgtc    540
aacattgaaa tcgatccaca aactcaggca gtggtagata cggtagaacg tgtgctggcg    600
gcacgagaaa atgccatgaa tcaaccaggc acagaagcct ga                        642
```

<210> SEQ ID NO 50
<211> LENGTH: 3490
<212> TYPE: DNA
<213> ORGANISM: Photobacterium leiognathi

<400> SEQUENCE: 50

| | | | | | |
|---|---|---|---|---|---|
| agggatagta | tgtttacagg | aataatagaa | gcagtgggaa | atatcagcgc | cattattcgt | 60 |
| aataacgacg | atatttcaat | ggttatcaat | accaatcggc | ttgatatttc | ggatgtaaaa | 120 |
| cttggcgata | gcattgctag | caatggcgtt | tgtttaaccg | tatctaaatt | aacgccaact | 180 |
| ggatttgttg | ccgatctttc | aacagagaca | ttaaagcgta | ccgcttttca | cagttaccac | 240 |
| gttggacaaa | aaatcaattt | agaaaaagcc | atgttaccca | ccacacgctt | tggtggtcat | 300 |
| atcgtttctg | ggcatgttga | tggtattggc | gacattattg | agctaaagcg | aaaaggtcgc | 360 |
| acccttgata | tgtggataac | cgtgcctatt | cacctaaaga | aattcgtttc | cgagaaaggt | 420 |
| tcagtttgca | ttgatggaac | cagtttaacc | atcaacgctg | tgtatcagaa | tgtcattaaa | 480 |
| ttaaccataa | tccctcatac | gttagctaac | acgacacttg | ccaatgccac | cattgatcaa | 540 |
| aaagtcaata | ttgaagccga | catgatggcg | cgctacctcg | aacgattaat | cagtattgat | 600 |
| aaacaagaat | ctaaaaaaaa | cactaacgtc | tctatgtctt | tgttagagaa | gcacggcttt | 660 |
| atcgtataac | tcacttacac | tgttgataat | aaaggaccca | ttatgacttt | aagtagcgcc | 720 |
| caagaaatca | ttaatgatat | ccgtctgggt | aaaatggtga | tcttaatgga | tgatgaaaat | 780 |
| cgcgaaaatg | aaggcgattt | gatcatcgcc | gctgacatga | tcacccctga | agcgattaat | 840 |
| ttcatggcga | cctatggacg | cgggttgatc | tgcttaacgt | taaccaaaga | tcgctgccag | 900 |
| accttaaatt | taccgcttat | ggtgcaaaat | aatcacgata | agttctcaac | tgcatttacc | 960 |
| gtttcaatag | aagccgccgc | cgatgttacg | accgggatct | ctgcctatga | tcgtgcaaaa | 1020 |
| acagtacaag | ccgccattgg | cccaaatgcc | agtgctgatg | atattgtgat | gccaggtcat | 1080 |
| attttttccct | taatggcgca | agatggtggc | gtattaattc | gtgccggcca | cactgaagct | 1140 |
| ggctgtgatg | ttgcacgttt | agctggactt | gaagcctcta | gtgttattgt | ggaaattctt | 1200 |
| aatgaagacg | gcacgatggc | acgccgacct | caactcgaag | tctttgctca | aaaacacggt | 1260 |
| ttaaaactgg | gaacgattgc | tgatttaatt | gagtatcgta | cccaacgaga | aagccatatt | 1320 |
| gaacgtttat | cagaaagtga | attatgcact | gagtatggcg | tttttaactt | aatcacctac | 1380 |
| cgtgacacca | ttgataacca | actgcattac | gcattatgta | aaggtgatat | aaaccctgat | 1440 |
| agtgagacct | tagtccgtgt | tcatgttaaa | gatacactga | aagatatttt | acatactggc | 1500 |
| gcaacgcaat | ggtctctaca | agcggccatg | cagcgcattc | aagccgacgg | tggcatatta | 1560 |
| gtgatcataa | gccaaattga | gccctcagcg | atgatcctaa | atcaaataaa | ccacttagat | 1620 |
| tcagagcacc | aagcgagttt | acctttacct | atcacaccgc | aatcccgaca | aattggttta | 1680 |
| ggatcgcaaa | ttctgtctga | attagggcta | tgcaaaattc | gtttactgtc | ttctcagagc | 1740 |
| caacaatatc | gttctttatc | aggatttgat | cttgaggttg | tggaatatat | ttgtaactag | 1800 |
| taaacactta | gatattattg | attcatcatt | ctttttttaca | aatacactta | ggaagctcca | 1860 |
| tgaatattat | tgaaggtgca | atcacagcac | cccatgccaa | tgtcgcgatc | atcgtttctc | 1920 |
| gtttcaatag | ttttatcaat | gacagcttat | tgtctggtgc | attagatgcc | ctacaacgcc | 1980 |
| aaggtcttgt | taaagaaagt | aatattaccg | ttgtacgttg | ccctggagca | tacgagctac | 2040 |
| ctttactggc | gcaacaactg | gcaaaaaaag | gcagttatga | tgccattatc | gctttaggct | 2100 |
| cagtgatacg | tggcggtact | ccacatttg | aatatgttgc | aggtgaatgt | aataaaggtt | 2160 |

```
tagcgcaaat tgcgttagag catcaaattc cagtcgcgtt cggtgtcctt actgtggatt    2220
caatcgaaca agccattgaa cgtgcaggaa caaaaatggg aaataaaggt gcagaagcgg    2280
cattaagtgc actagaaatg attaacgtgc tagcagaaat cgagccttaa tttccttata    2340
ttttcacccg tcatgatggc tatgatgccc tacgtcatca tagccattgc ccttctaaag    2400
caatgaactc aaatagaatt attaggaata ttatgatcac ggtaagagcc cgggtgcctt    2460
ttaaaatcgg gcaaaaaagt cagatcccag cggagttatt gtcgtttcat ggctttaatt    2520
caggtaaaga gcatatcgca attattttta aacaagcaga taccacaacc gccccttag     2580 ttcgcttaca ttcagaatgc ttaaccggtg atgtctttca ttcttcgcgc tgtgattgtg    2640
gcgagcagct caatgaaaca atagaaaaaa tgcatcaatt cggtgggatc attttgtatc    2700
tacgtcaaga aggacgtggc attggtttat acaataaaat cgatgcctat cacttacaaa    2760
gccaaggcat gaatacctat gaagccaata accatttagg tttcgctgat gatctacgcg    2820
attttagtga agctgcaaaa gcattaatgg cattaggcat aaacaagatc cgcttaatca    2880
ctaacaaccc aaagaaaatc aatgaacttc aacaacatgg cattgagatc atagatgtgg    2940
ttaacactca ggtacacatc aaacaagaca acgaagatta tctaaaaaca aaagcgttac    3000
acggccatca caacctctct ttatgatcag atctgctcaa cgcttatatt gagctatctt    3060
agccagaaga ttaactctta ccaatattgc gccatttaac agtactcccc cttatgttaa    3120
atggcgaaaa acaaccgcc ctcaaaaatc cacagctaag agttacccac taaatttgtg    3180
gataacacaa tattaccttt attttcaac atattatgtt tttcaataga aatacataat    3240
aatctcgact attttcaaaa atataaatac gtccttaaaa cgtaaaaagc cgcactattg    3300
cagtgcggct tggtgttgct attagtgtac ttactcggca caccaatatt gttacgcttc    3360
gccactcatt acgttgagct tgccgtgttc gacatagtag gttcgaaccg ctatttattg    3420
gcgaagaagc aaattttaa aaggtgtcac ttaccaaatt gttaacaact aagttttcac    3480
ttagaagctt                                                          3490
```

<210> SEQ ID NO 51
<211> LENGTH: 1438
<212> TYPE: DNA
<213> ORGANISM: Arabidopsis thaliana
<220> FEATURE:
<221> NAME/KEY: misc_feature
<222> LOCATION: (39)..(39)
<223> OTHER INFORMATION: n is a, c, g, or t

<400> SEQUENCE: 51

```
cgtcaataga ataaaaaaaa ctgtatgaat agaataatnc gtttaaattg gcacgtgaaa      60
tgcgaaatgg gctgagtcat tcattatgga agcccatgt gattggtagg gaacgacgtc      120
gggtgaaggg aggggaagag cttataaatg aaagcagcaa gcagagcagt tcacgctctt     180
tgtacactcc gccctctctc cccatctctt tcgacagatc tcttctctct ctcgtgtttc     240
acgaaacaat ggcgactcaa ttcagcgctt ctgtctcatt gcaaacttct tgtctggtaa     300
tcaaatcttc ttcttcatt ttaacaattg ccttagagat cgctttgatc ttacgattca      360 tgatcattc ccgttgttc catgcctgct cttgttatcg tatataaact cctgacgcat       420
gtttattatg tgtaacatag aagatcttcg ctttagtaat gatcagtttt atgttttgt      480 tccaatgatt ttatttctag tttcaaattc tgtgatcggc aacacatgga attaaaatcc     540
gtggttttgt gttctggttg taatctagat ctacagtcaa ttgaatttat gattgtggaa     600
```

```
gtgaatgctt acttttggct gtgaataatt gtgcatggac attcattggc taagaatttg    660
gcttgagtta tgaaaattca gaacaaagtt cttatgaatg caatgctttt ttttttttgtg   720 tgtgtttgat gaaacaaata ggcaacaaca aggattagtt tccaaaagcc agctttgatt   780
tccaaccatg gaaagactaa tctatccttc aacctccgcc gttcaatccc atctcgccgc   840
ctctctgttt cttgcgcggt atgagcattt tttttcaagt ttgttaatct atatatatag   900
ggctcaaagt tttaaaagac attatatttg gtttataggc aaaacaagag acgatagaga   960
aagtgtctgc tatagttaag aagcaactat cacttacacc ggataaaaaa gtcgttgcag  1020
aaaccaaatt tgctgacctt ggagcagatt ctctcgacac gtatccattc actcaagtgg  1080
caattaacac aaattcttaa ttttcttgat actgatcaac tgagtgtttt tcttcaggtt  1140
gagatagtaa tgggtttaga ggaagagttt aacatccaaa tggccgaaga gaaagcacag  1200
aagattgcca cagttgagca agctgctgaa ctcattgaag agctcatcaa cgagaagaag  1260
taattttagc tttataaaat gcccttaaat aaactaaaaa agaaaacgac aaaaaaaaac  1320
agggcgttga gtttgttttc attatgtttg atttctctgt cattttcttt aatgtgtcta  1380
gcgagtctgc ctttgtccca atggtttagt atctgcatgt atccacggat ctctattt    1438
```

<210> SEQ ID NO 52
<211> LENGTH: 255
<212> TYPE: DNA
<213> ORGANISM: Artificial Sequence
<220> FEATURE:
<223> OTHER INFORMATION: Synthetic nucleotide sequence: Photobacterium
      sp. SKA34 ACP

<400> SEQUENCE: 52

```
atgacagaag cgaatcgtaa ccaagttttt gaccaagtaa aaaatgttct tgttgaactg    60
tttgagcttg acgcagatga cattcaaccg caaaccaatc tatacactga acttgattta   120
gacagtattg atgccgttga tttagtcgtt cacttacaaa acatgaccgg tcagaaaatc   180
aaaccagaag agttcaaagc tgtccgtacc gttgatgacg tggtcgatgc agtgatcgag   240
cttgttaagg aataa                                                    255
```

<210> SEQ ID NO 53
<211> LENGTH: 705
<212> TYPE: DNA
<213> ORGANISM: Photobacterium leiognathi

<400> SEQUENCE: 53

```
atgatttta attgcaaggt taaaaaagtc gaagcatctg acagccatat ttacaaagtg    60
tttattaagc ctgacaaatg ctttgatttt aaagcgggtc aatatgtaat tgtgtatctc   120
aatggaaaaa atttgccgtt ttctattgct aactgcccaa cttgtaatga gctccttgaa   180
ttacatgtag gaggttcggt aaaagaatcc gccattgaag ctatttcgca ctttattaat   240
gcatttattt atcaaaaaga atttacaatc gatgcaccac acggtgatgc atggctgaga   300
gatgaaagcc aatcaccttt actacttata gcaggaggga caggtttatc atatatcaat   360
agcattttaa gttgttgtat tagtaaacag ttatctcagc ctatctatct ttattgggga   420
gtaaataact gtaatttact ctatgctgat caacaactaa aaacactcgc cgcacaatac   480
agaaatataa attatattcc tgtggtagag aatttaaata ctgactggca gggaaaaatt   540
ggtaatgtta ttgacgcggt tattgaagat tttttcagatt tatctgactt tgatatctat   600
gtctgcgggc catttggtat gagccggact gcgaaagata ttctgatctc acagaaaaag   660
```

```
gcgaatatag gaaaaatgta ttctgatgca tttagctata cgtaa            705
```

<210> SEQ ID NO 54
<211> LENGTH: 705
<212> TYPE: DNA
<213> ORGANISM: Photobacterium phosphoreum

<400> SEQUENCE: 54

```
atgattttaa attgtaaaat aattaaaatt gaagcttctg aatgtaatat ttttaaagta   60
tttattaagc ctgataagtg tctcaatttc aaagctgggc aatatgtttt agcgtattta  120
gatggtaaaa aattacccttt tcaattgct aattgtccaa catgtaatga gcttatagag  180
ttacatgttg gaagttcggt aaaagaaaca gcagttaaat ctatttctta ctttgtagat  240
gcttttgtga atagcgatga catacaaata gatgcacctc atggtaatgc ttggttacgt  300
gagggcagta attcgccatt attacttatt gctggaggta caggactatc atatatcaat  360
agtattctta gtaattgtgt aaataggaat ttacctcgtt ctatttatgt ttactgggga  420
gttaataata ttgattattt atatgcagac actcaattaa aaacactttc tagcgacttt  480
agtaatgtta aatacgtgcc tgttctagaa aactttgata atagttggta tggaaaaaaa  540
ggtaatgtta ttgatgcaat aatagaagat ttttgtgatt tatcagattt tgatatttat  600
gtttgcggcc ctcaaggcat gacttatagt gttcgagaaa aattaacatc acttaaaaaa  660
gcgaatgctg ataaaatgtt tgctgatgct tttgcatata tgtga              705
```

<210> SEQ ID NO 55
<211> LENGTH: 702
<212> TYPE: DNA
<213> ORGANISM: Photobacterium phosphoreum

<400> SEQUENCE: 55

```
atgttatgtt cgatagaaaa aattgagccg ttaactaacc tcatattccg agtattgctc   60
aagccagatc agcctttga atttagggca gggcagtaca ttaacgtcag tttaagcttt  120
ggtagtttac cgttttctat agcctcatgt ccttctaatg gtgcgttttt agaactccat  180
attggtggct cagatatcag caagaaaaat acgcttgtga tggaagaact caccaattca  240
tggggctgcg gcaacatggt tgaagtcagt gaggcgcgag gtgaggcttg gttgcgtgat  300
gagagtgtca aacccttgtt attggtcgca ggcgggacgg gaatgtcata caccctaagt  360
attttgaaaa atagcttgga gcaagggttt acccagccga tttacgtcta ttggggcgcc  420
aaggatatgg ataaccgtgta tgtacatgac gaactggtgg atattgcgct tgaaaacaaa  480
aacgtcagtt acgtgccagt cactgaaata tcaacctgtc cccaatacgc taagcaagga  540
aaggtgttgg agtgtgtgat gagtgatttc cgtaacttat ctgagttcga tatctacttg  600
tgtggtcctt gcaaaatggt tgaagtggct cgtgattggt tctgtgacaa agagggcca  660
gaaccagagc aactttacgc ggacgcgttc gcttatttgt aa                 702
```

<210> SEQ ID NO 56
<211> LENGTH: 711
<212> TYPE: DNA
<213> ORGANISM: Vibrio fischeri

<400> SEQUENCE: 56

```
atgattgttg atggcagagt ttcaaagata gttttagcat cgataaaaaa taatatatat   60
aaggtatta ttactgtaaa ttcaccaata aagttcatcg ctggacaatt tgtaatggtc  120
acgattaatg ggaaaaaatg tccttttca attgcgaatt gcccgacaaa aaatcacgaa  180
```

```
atagaattgc atattggtag ttcgaataaa gactgctcat tggatattat cgaatatttt    240
gtcgatgctc ttgttgagga agtcgcaatt gagttagatg ctccccatgg aaacgcttgg    300
ttacggtctg aaagtaataa cccattgcta ttaattgcgg gaggtacagg tttatcatat    360
ataaatagca ttctaaccaa ttgcttaaat cggaatatac ctcaagatat ttatctttac    420
tggggagtaa aaacagttc tcttttgtat gaagacgaag agttattgga attatcacta     480
aataacaaaa atcttcatta tattcctgtt atcgaagata aaagtgaaga atggatagga    540
aaaaaaggta cggttcttga tgctgtaatg aagattttta cggatctagc ccatttgat    600 atttatgttt gtgggccctt catgatggct aaaacagcaa aagaaaaatt aattgaagag    660
aaaaaagcaa agtcagaaca gatgtttgcc gatgcttttg catacgtata a             711

<210> SEQ ID NO 57
<211> LENGTH: 711
<212> TYPE: DNA
<213> ORGANISM: Shewanella hanedai

<400> SEQUENCE: 57
atgaaagtaa aatgcagcgt atcaaaaata gagttaataa ataaaaatat atataaagtt     60
tatattaaac cttatgttcc tattgatttc aaagctgggc agtatatata tataaattta    120
agtggtaata aaaggcaacc attttctatt gctagttgtc caacagataa tagtgtgatt    180
gaactgcatg ttggcagttc aaatgaaaac agttctttag atgtaatgga atattttggt    240
gatgctctaa taaaaatag taccatcgtg atagatgctc cacatggaga ggcgtggtta    300
cgtgaaggca gtaataaacc aatattgttg attgccggtg gtacaggttt atcctatatt    360
agcagtattc ttcgaaactg tttaaaccga ggtttcactc aacctatta tgtttattgg    420 ggagtgaaaa atatagattt tttgtatgca gatgaagaac tacagttatt atgcagtcac    480
cacagtaatt tacattacat tccagtggta ttagaagaca gtaaatatac gtggttagga    540
aaaaaaggca cggttattga tgctgtcatg gatgattta ctgttcttac gcttttgat     600 atttatgtct gtgggcctaa tttgatgact aaggcagcaa aagataaatt agttgcaaaa    660
aagagtgcta aatcagaaca aatgttttcc gatgcttttg catatatgtg a             711

<210> SEQ ID NO 58
<211> LENGTH: 98
<212> TYPE: DNA
<213> ORGANISM: Artificial Sequence
<220> FEATURE:
<223> OTHER INFORMATION: Synthetic nucleotide sequence

<400> SEQUENCE: 58
ggcgcgccta actataacgg tcctaaggta gcgatggcaa acagctatta tgggtattat     60
gggtttaatt aatagggata acagggtaat ggccggcc                              98

<210> SEQ ID NO 59
<211> LENGTH: 98
<212> TYPE: DNA
<213> ORGANISM: Artificial Sequence
<220> FEATURE:
<223> OTHER INFORMATION: Synthetic nucleotide sequence

<400> SEQUENCE: 59
ggccggccat taccctgtta tccctattaa ttaaacccat aatacccata atagctgttt      60
gccatcgcta ccttaggacc gttatagtta ggcgcgcc                              98
```

<210> SEQ ID NO 60
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 60
cttcgctatt acgccagctg g                                              21

<210> SEQ ID NO 61
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 61
gttagctcac tcattaggca c                                              21

<210> SEQ ID NO 62
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 62
ctggcgcgcc gccttgtaca caccgcccgt cac                                 33

<210> SEQ ID NO 63
<211> LENGTH: 49
<212> TYPE: DNA
<213> ORGANISM: Artificial Sequence
<220> FEATURE:
<223> OTHER INFORMATION: Synthetic nucleotide sequence

<400> SEQUENCE: 63
tcgctacctt aggaccgtta tagttagcag ctgggccatc ctggacttg                49

<210> SEQ ID NO 64
<211> LENGTH: 45
<212> TYPE: DNA
<213> ORGANISM: Artificial Sequence
<220> FEATURE:
<223> OTHER INFORMATION: Synthetic nucleotide sequence

<400> SEQUENCE: 64
aatagggata acagggtaat ctccacttgg ctcgggggga tatag                    45

<210> SEQ ID NO 65
<211> LENGTH: 35
<212> TYPE: DNA
<213> ORGANISM: Artificial Sequence
<220> FEATURE:
<223> OTHER INFORMATION: Synthetic nucleotide sequence

<400> SEQUENCE: 65
tatggccggc cagctttgta tcggctaagt tcacg                               35

<210> SEQ ID NO 66
<211> LENGTH: 29
<212> TYPE: DNA
<213> ORGANISM: Artificial Sequence
<220> FEATURE:
<223> OTHER INFORMATION: Synthetic nucleotide sequence

```
<400> SEQUENCE: 66
tcaccggtgg gcaacccact agcatatcg                                    29

<210> SEQ ID NO 67
<211> LENGTH: 30
<212> TYPE: DNA
<213> ORGANISM: Artificial Sequence
<220> FEATURE:
<223> OTHER INFORMATION: Synthetic nucleotide sequence

<400> SEQUENCE: 67
aaccatggta aaatcttggt ttatttaatc                                   30

<210> SEQ ID NO 68
<211> LENGTH: 29
<212> TYPE: DNA
<213> ORGANISM: Artificial Sequence
<220> FEATURE:
<223> OTHER INFORMATION: Synthetic nucleotide sequence

<400> SEQUENCE: 68
cctctagaga tcctggccta gtctatagg                                    29

<210> SEQ ID NO 69
<211> LENGTH: 39
<212> TYPE: DNA
<213> ORGANISM: Artificial Sequence
<220> FEATURE:
<223> OTHER INFORMATION: Synthetic nucleotide sequence

<400> SEQUENCE: 69
ttatgcggcc gctcgaatat agctcttctt tcttatttc                         39

<210> SEQ ID NO 70
<211> LENGTH: 29
<212> TYPE: DNA
<213> ORGANISM: Artificial Sequence
<220> FEATURE:
<223> OTHER INFORMATION: Synthetic nucleotide sequence

<400> SEQUENCE: 70
aaccatgggg gaagcggtga tcgccgaag                                    29

<210> SEQ ID NO 71
<211> LENGTH: 34
<212> TYPE: DNA
<213> ORGANISM: Artificial Sequence
<220> FEATURE:
<223> OTHER INFORMATION: Synthetic nucleotide sequence

<400> SEQUENCE: 71
tggagatctt tatttgccga ctaccttggt gatc                              34

<210> SEQ ID NO 72
<211> LENGTH: 30
<212> TYPE: DNA
<213> ORGANISM: Artificial Sequence
<220> FEATURE:
<223> OTHER INFORMATION: Synthetic nucleotide sequence

<400> SEQUENCE: 72
tcaccggtcg ccgtcgttca atgagaatgg                                   30

<210> SEQ ID NO 73
```

<210> SEQ ID NO 73
<211> LENGTH: 29
<212> TYPE: DNA
<213> ORGANISM: Artificial Sequence
<220> FEATURE:
<223> OTHER INFORMATION: Synthetic nucleotide sequence

<400> SEQUENCE: 73
aaccatggat attcgcccgg agttcgctc                                29

<210> SEQ ID NO 74
<211> LENGTH: 30
<212> TYPE: DNA
<213> ORGANISM: Artificial Sequence
<220> FEATURE:
<223> OTHER INFORMATION: Synthetic nucleotide sequence

<400> SEQUENCE: 74
cctctagaac cgaaattcaa ttaaggaaat                               30

<210> SEQ ID NO 75
<211> LENGTH: 35
<212> TYPE: DNA
<213> ORGANISM: Artificial Sequence
<220> FEATURE:
<223> OTHER INFORMATION: Synthetic nucleotide sequence

<400> SEQUENCE: 75
ttatgcggcc gcagaacacg catttcaatg gaagc                         35

<210> SEQ ID NO 76
<211> LENGTH: 42
<212> TYPE: DNA
<213> ORGANISM: Artificial Sequence
<220> FEATURE:
<223> OTHER INFORMATION: Synthetic nucleotide sequence

<400> SEQUENCE: 76
ccactcgaga ggagggattt atggtgagca agggcgagga gc                 42

<210> SEQ ID NO 77
<211> LENGTH: 35
<212> TYPE: DNA
<213> ORGANISM: Artificial Sequence
<220> FEATURE:
<223> OTHER INFORMATION: Synthetic nucleotide sequence

<400> SEQUENCE: 77
gggaattctt acttgtacag ctcgtccatg ccgag                         35

<210> SEQ ID NO 78
<211> LENGTH: 48
<212> TYPE: DNA
<213> ORGANISM: Artificial Sequence
<220> FEATURE:
<223> OTHER INFORMATION: Synthetic nucleotide sequence

<400> SEQUENCE: 78
ttccatggag ttgtagggag ggatttatgg tgagcaaggg cgaggagc           48

<210> SEQ ID NO 79
<211> LENGTH: 32
<212> TYPE: DNA
<213> ORGANISM: Artificial Sequence
<220> FEATURE:
<223> OTHER INFORMATION: Synthetic nucleotide sequence

<400> SEQUENCE: 79
acagaattcc caaaggagat tacatgatta ag                                          32

<210> SEQ ID NO 80
<211> LENGTH: 32
<212> TYPE: DNA
<213> ORGANISM: Artificial Sequence
<220> FEATURE:
<223> OTHER INFORMATION: Synthetic nucleotide sequence

<400> SEQUENCE: 80
ttggaattct tacgtatagc taaatgcatc ag                                          32

<210> SEQ ID NO 81
<211> LENGTH: 41
<212> TYPE: DNA
<213> ORGANISM: Artificial Sequence
<220> FEATURE:
<223> OTHER INFORMATION: Synthetic nucleotide sequence

<400> SEQUENCE: 81
ccactcgaga ggagggattt atgttacgtc ctgtagaaac c                                41

<210> SEQ ID NO 82
<211> LENGTH: 47
<212> TYPE: DNA
<213> ORGANISM: Artificial Sequence
<220> FEATURE:
<223> OTHER INFORMATION: Synthetic nucleotide sequence

<400> SEQUENCE: 82
aaccatggag ttgtagggag ggatttatgg gggaagcggt gatcgcc                          47

<210> SEQ ID NO 83
<211> LENGTH: 34
<212> TYPE: DNA
<213> ORGANISM: Artificial Sequence
<220> FEATURE:
<223> OTHER INFORMATION: Synthetic nucleotide sequence

<400> SEQUENCE: 83
ttgctcgagt tatttgccga ctaccttggt gatc                                        34

<210> SEQ ID NO 84
<211> LENGTH: 30
<212> TYPE: DNA
<213> ORGANISM: Artificial Sequence
<220> FEATURE:
<223> OTHER INFORMATION: Synthetic nucleotide sequence

<400> SEQUENCE: 84
gggaattctc attgtttgcc tccctgctgc                                             30

<210> SEQ ID NO 85
<211> LENGTH: 20
<212> TYPE: DNA
<213> ORGANISM: Artificial Sequence
<220> FEATURE:
<223> OTHER INFORMATION: Synthetic nucleotide sequence

<400> SEQUENCE: 85
atgaaaatta gtaatatctg                                                        20

<210> SEQ ID NO 86
<211> LENGTH: 28
<212> TYPE: DNA

<213> ORGANISM: Artificial Sequence
<220> FEATURE:
<223> OTHER INFORMATION: Synthetic nucleotide sequence

<400> SEQUENCE: 86
gaagatctat gaaaattagt aatatctg                28

<210> SEQ ID NO 87
<211> LENGTH: 20
<212> TYPE: DNA
<213> ORGANISM: Artificial Sequence
<220> FEATURE:
<223> OTHER INFORMATION: Synthetic nucleotide sequence

<400> SEQUENCE: 87
acttaaaaga tcctcagtaa                20

<210> SEQ ID NO 88
<211> LENGTH: 28
<212> TYPE: DNA
<213> ORGANISM: Artificial Sequence
<220> FEATURE:
<223> OTHER INFORMATION: Synthetic nucleotide sequence

<400> SEQUENCE: 88
acttaaaaga tcctcagtaa gaattccg                28

<210> SEQ ID NO 89
<211> LENGTH: 28
<212> TYPE: DNA
<213> ORGANISM: Artificial Sequence
<220> FEATURE:
<223> OTHER INFORMATION: Synthetic nucleotide sequence

<400> SEQUENCE: 89
cggaattctt actgaggatc ttttaagt                28

<210> SEQ ID NO 90
<211> LENGTH: 20
<212> TYPE: DNA
<213> ORGANISM: Artificial Sequence
<220> FEATURE:
<223> OTHER INFORMATION: Synthetic nucleotide sequence

<400> SEQUENCE: 90
atgaaaatta gtaatatctg                20

<210> SEQ ID NO 91
<211> LENGTH: 28
<212> TYPE: DNA
<213> ORGANISM: Artificial Sequence
<220> FEATURE:
<223> OTHER INFORMATION: Synthetic nucleotide sequence

<400> SEQUENCE: 91
gaagatctat gaaaattagt aatatctg                28

<210> SEQ ID NO 92
<211> LENGTH: 20
<212> TYPE: DNA
<213> ORGANISM: Artificial Sequence
<220> FEATURE:
<223> OTHER INFORMATION: Synthetic nucleotide sequence

<400> SEQUENCE: 92
acttaaaaga tcctcagtaa                20

<210> SEQ ID NO 93
<211> LENGTH: 28
<212> TYPE: DNA
<213> ORGANISM: Artificial Sequence
<220> FEATURE:
<223> OTHER INFORMATION: Synthetic nucleotide sequence

<400> SEQUENCE: 93
acttaaaaga tcctcagtaa gaattccg                                28

<210> SEQ ID NO 94
<211> LENGTH: 28
<212> TYPE: DNA
<213> ORGANISM: Artificial Sequence
<220> FEATURE:
<223> OTHER INFORMATION: Synthetic nucleotide sequence

<400> SEQUENCE: 94
cggaattctt actgaggatc ttttaagt                                28

<210> SEQ ID NO 95
<211> LENGTH: 22
<212> TYPE: DNA
<213> ORGANISM: Artificial Sequence
<220> FEATURE:
<223> OTHER INFORMATION: Synthetic nucleotide sequence

<400> SEQUENCE: 95
atgaatttcg ggttattttt cc                                      22

<210> SEQ ID NO 96
<211> LENGTH: 30
<212> TYPE: DNA
<213> ORGANISM: Artificial Sequence
<220> FEATURE:
<223> OTHER INFORMATION: Synthetic nucleotide sequence

<400> SEQUENCE: 96
gaagatctat gaatttcggg ttattttcc                              30

<210> SEQ ID NO 97
<211> LENGTH: 22
<212> TYPE: DNA
<213> ORGANISM: Artificial Sequence
<220> FEATURE:
<223> OTHER INFORMATION: Synthetic nucleotide sequence

<400> SEQUENCE: 97
caaagataac cttattaaat aa                                      22

<210> SEQ ID NO 98
<211> LENGTH: 30
<212> TYPE: DNA
<213> ORGANISM: Artificial Sequence
<220> FEATURE:
<223> OTHER INFORMATION: Synthetic nucleotide sequence

<400> SEQUENCE: 98
caaagataac cttattaaat aagaattccg                              30

<210> SEQ ID NO 99
<211> LENGTH: 30
<212> TYPE: DNA
<213> ORGANISM: Artificial Sequence
<220> FEATURE:

<223> OTHER INFORMATION: Synthetic nucleotide sequence

<400> SEQUENCE: 99
cggaattctt atttaataag gttatctttg                                      30

<210> SEQ ID NO 100
<211> LENGTH: 22
<212> TYPE: DNA
<213> ORGANISM: Artificial Sequence
<220> FEATURE:
<223> OTHER INFORMATION: Synthetic nucleotide sequence

<400> SEQUENCE: 100
atgattaaga agatcccaat ga                                              22

<210> SEQ ID NO 101
<211> LENGTH: 31
<212> TYPE: DNA
<213> ORGANISM: Artificial Sequence
<220> FEATURE:
<223> OTHER INFORMATION: Synthetic nucleotide sequence

<400> SEQUENCE: 101
ccgctcgaga tgattaagaa gatcccaatg a                                    31

<210> SEQ ID NO 102
<211> LENGTH: 22
<212> TYPE: DNA
<213> ORGANISM: Artificial Sequence
<220> FEATURE:
<223> OTHER INFORMATION: Synthetic nucleotide sequence

<400> SEQUENCE: 102
gttcctcgta tttgtaccgt ag                                              22

<210> SEQ ID NO 103
<211> LENGTH: 30
<212> TYPE: DNA
<213> ORGANISM: Artificial Sequence
<220> FEATURE:
<223> OTHER INFORMATION: Synthetic nucleotide sequence

<400> SEQUENCE: 103
gttcctcgta tttgtaccgt aggaattccg                                      30

<210> SEQ ID NO 104
<211> LENGTH: 30
<212> TYPE: DNA
<213> ORGANISM: Artificial Sequence
<220> FEATURE:
<223> OTHER INFORMATION: Synthetic nucleotide sequence

<400> SEQUENCE: 104
cggaattcct acggtacaaa tacgaggaac                                      30

<210> SEQ ID NO 105
<211> LENGTH: 20
<212> TYPE: DNA
<213> ORGANISM: Artificial Sequence
<220> FEATURE:
<223> OTHER INFORMATION: Synthetic nucleotide sequence

<400> SEQUENCE: 105
atggaaaata cacaacattc                                                 20

```
<210> SEQ ID NO 106
<211> LENGTH: 28
<212> TYPE: DNA
<213> ORGANISM: Artificial Sequence
<220> FEATURE:
<223> OTHER INFORMATION: Synthetic nucleotide sequence

<400> SEQUENCE: 106
gaagatctat ggaaaataca caacattc                                        28

<210> SEQ ID NO 107
<211> LENGTH: 20
<212> TYPE: DNA
<213> ORGANISM: Artificial Sequence
<220> FEATURE:
<223> OTHER INFORMATION: Synthetic nucleotide sequence

<400> SEQUENCE: 107
gcgtattggc tagtgtctaa                                                 20

<210> SEQ ID NO 108
<211> LENGTH: 28
<212> TYPE: DNA
<213> ORGANISM: Artificial Sequence
<220> FEATURE:
<223> OTHER INFORMATION: Synthetic nucleotide sequence

<400> SEQUENCE: 108
gcgtattggc tagtgtctaa gaattccg                                        28

<210> SEQ ID NO 109
<211> LENGTH: 28
<212> TYPE: DNA
<213> ORGANISM: Artificial Sequence
<220> FEATURE:
<223> OTHER INFORMATION: Synthetic nucleotide sequence

<400> SEQUENCE: 109
cggaattctt agacactagc caatacgc                                        28

<210> SEQ ID NO 110
<211> LENGTH: 22
<212> TYPE: DNA
<213> ORGANISM: Artificial Sequence
<220> FEATURE:
<223> OTHER INFORMATION: Synthetic nucleotide sequence

<400> SEQUENCE: 110
atgtcaacat tattaaatat ag                                              22

<210> SEQ ID NO 111
<211> LENGTH: 30
<212> TYPE: DNA
<213> ORGANISM: Artificial Sequence
<220> FEATURE:
<223> OTHER INFORMATION: Synthetic nucleotide sequence

<400> SEQUENCE: 111
gaagatctat gtcaacatta ttaaatatag                                      30

<210> SEQ ID NO 112
<211> LENGTH: 22
<212> TYPE: DNA
<213> ORGANISM: Artificial Sequence
<220> FEATURE:
<223> OTHER INFORMATION: Synthetic nucleotide sequence
```

```
<400> SEQUENCE: 112
aatggccacg agcctgaaat aa                                              22

<210> SEQ ID NO 113
<211> LENGTH: 30
<212> TYPE: DNA
<213> ORGANISM: Artificial Sequence
<220> FEATURE:
<223> OTHER INFORMATION: Synthetic nucleotide sequence

<400> SEQUENCE: 113
aatggccacg agcctgaaat aagaattccg                                      30

<210> SEQ ID NO 114
<211> LENGTH: 30
<212> TYPE: DNA
<213> ORGANISM: Artificial Sequence
<220> FEATURE:
<223> OTHER INFORMATION: Synthetic nucleotide sequence

<400> SEQUENCE: 114
cggaattctt atttcaggct cgtggccatt                                      30

<210> SEQ ID NO 115
<211> LENGTH: 23
<212> TYPE: DNA
<213> ORGANISM: Artificial Sequence
<220> FEATURE:
<223> OTHER INFORMATION: Synthetic nucleotide sequence

<400> SEQUENCE: 115 atgatttta attgcaaggt taa                                              23

<210> SEQ ID NO 116
<211> LENGTH: 31
<212> TYPE: DNA
<213> ORGANISM: Artificial Sequence
<220> FEATURE:
<223> OTHER INFORMATION: Synthetic nucleotide sequence

<400> SEQUENCE: 116
gaagatctat gatttttaat tgcaaggtta a                                    31

<210> SEQ ID NO 117
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 117
gatgcattta gctatacgta a                                               21

<210> SEQ ID NO 118
<211> LENGTH: 29
<212> TYPE: DNA
<213> ORGANISM: Artificial Sequence
<220> FEATURE:
<223> OTHER INFORMATION: Synthetic nucleotide sequence

<400> SEQUENCE: 118
gatgcattta gctatacgta agaattccg                                       29

<210> SEQ ID NO 119
<211> LENGTH: 29
```

```
<212> TYPE: DNA
<213> ORGANISM: Artificial Sequence
<220> FEATURE:
<223> OTHER INFORMATION: Synthetic nucleotide sequence

<400> SEQUENCE: 119
cggaattctt acgtatagct aaatgcatc                                          29

<210> SEQ ID NO 120
<211> LENGTH: 32
<212> TYPE: DNA
<213> ORGANISM: Artificial Sequence
<220> FEATURE:
<223> OTHER INFORMATION: Synthetic nucleotide sequence

<400> SEQUENCE: 120
acagaattcc caaaggagat tacatgatta ag                                      32

<210> SEQ ID NO 121
<211> LENGTH: 32
<212> TYPE: DNA
<213> ORGANISM: Artificial Sequence
<220> FEATURE:
<223> OTHER INFORMATION: Synthetic nucleotide sequence

<400> SEQUENCE: 121
ctgatgcatt tagctatacg taagaattcc aa                                      32

<210> SEQ ID NO 122
<211> LENGTH: 32
<212> TYPE: DNA
<213> ORGANISM: Artificial Sequence
<220> FEATURE:
<223> OTHER INFORMATION: Synthetic nucleotide sequence

<400> SEQUENCE: 122
ttggaattct tacgtatagc taaatgcatc ag                                      32

<210> SEQ ID NO 123
<211> LENGTH: 31
<212> TYPE: DNA
<213> ORGANISM: Artificial Sequence
<220> FEATURE:
<223> OTHER INFORMATION: Synthetic nucleotide sequence

<400> SEQUENCE: 123
aactcgagca aaagagaagc tcttgatatg g                                       31

<210> SEQ ID NO 124
<211> LENGTH: 30
<212> TYPE: DNA
<213> ORGANISM: Artificial Sequence
<220> FEATURE:
<223> OTHER INFORMATION: Synthetic nucleotide sequence

<400> SEQUENCE: 124
gtgtgaagtg agttggtctt agctcgagaa                                         30

<210> SEQ ID NO 125
<211> LENGTH: 30
<212> TYPE: DNA
<213> ORGANISM: Artificial Sequence
<220> FEATURE:
<223> OTHER INFORMATION: Synthetic nucleotide sequence

<400> SEQUENCE: 125
```

```
ttctcgagct aagaccaact cacttcacac                                       30

<210> SEQ ID NO 126
<211> LENGTH: 32
<212> TYPE: DNA
<213> ORGANISM: Artificial Sequence
<220> FEATURE:
<223> OTHER INFORMATION: Synthetic nucleotide sequence

<400> SEQUENCE: 126
atggatccca ttaaatggat ggctaatatg ac                                    32

<210> SEQ ID NO 127
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 127
cttaaaccaa gcatttaata gttgaggatc cat                                   33

<210> SEQ ID NO 128
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 128
atggatcctc aactattaaa tgcttggttt aag                                   33

<210> SEQ ID NO 129
<211> LENGTH: 678
<212> TYPE: DNA
<213> ORGANISM: Artificial Sequence
<220> FEATURE:
<223> OTHER INFORMATION: Synthetic nucleotide sequence

<400> SEQUENCE: 129
atggacaaca ccgaggacgt catcaaggag ttcatgcagt tcaaggtgcg catggagggc      60
tccgtgaacg gccactactt cgagatcgag ggcgagggcg agggcaagcc ctacgagggc     120
acccagaccg ccaagctgca ggtgaccaag ggcggccccc tgcccttcgc ctgggacatc     180
ctgtcccccc agttccagta cggctccaag gcctacgtga agcaccccgc cgacatcccc     240
gactacatga gctgtccttt ccccgagggc ttcacctggg agcgctccat gaacttcgag     300
gacggcggcg tggtggaggt gcagcaggac tcctccctgc aggacggcac cttcatctac     360
aaggtgaagt tcaagggcgt gaacttcccc gccgacggcc ccgtaatgca gaagaagact     420
gccggctggg agccctccac cgagaagctg taccccagg acggcgtgct gaagggcgag     480
atctcccacg ccctgaagct gaaggacggc ggccactaca cctgcgactt caagaccgtg     540
tacaaggcca agaagcccgt gcagctgccc ggcaaccact acgtggactc caagctggac     600
atcaccaacc acaacgagga ctacaccgtg gtggagcagt acgagcacgc cgaggcccgc     660
cactccggct cccagtag                                                  678
```